US011450816B2

(12) United States Patent
Li et al.

(10) Patent No.: US 11,450,816 B2
(45) Date of Patent: *Sep. 20, 2022

(54) DONOR-ACCEPTOR TYPE THERMALLY ACTIVATED DELAYED FLUORESCENT MATERIALS BASED ON IMIDAZO[1,2-F]PHENANTHRIDINE AND ANALOGUES

(71) Applicant: Arizona Board of Regents on behalf of Arizona State University, Scottsdale, AZ (US)

(72) Inventors: Jian Li, Tempe, AZ (US); Zhi-Qiang Zhu, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 103 days.

This patent is subject to a terminal disclaimer.

(21) Appl. No.: 16/834,193

(22) Filed: Mar. 30, 2020

(65) Prior Publication Data

US 2020/0227656 A1 Jul. 16, 2020

Related U.S. Application Data

(63) Continuation of application No. 15/984,157, filed on May 18, 2018, now Pat. No. 10,615,349.

(60) Provisional application No. 62/508,518, filed on May 19, 2017.

(51) Int. Cl.

| C07D 471/14 | (2006.01) |
|---|---|
| H01L 51/00 | (2006.01) |
| C09K 11/06 | (2006.01) |
| C07D 471/22 | (2006.01) |
| C07D 495/22 | (2006.01) |
| C07D 495/14 | (2006.01) |
| C07D 491/147 | (2006.01) |
| C07D 471/20 | (2006.01) |
| C07D 491/22 | (2006.01) |
| H01L 51/50 | (2006.01) |

(52) U.S. Cl.
CPC ........ *H01L 51/0072* (2013.01); *C07D 471/14* (2013.01); *C07D 471/20* (2013.01); *C07D 471/22* (2013.01); *C07D 491/147* (2013.01); *C07D 491/22* (2013.01); *C07D 495/14* (2013.01); *C07D 495/22* (2013.01); *C09K 11/06* (2013.01); *H01L 51/0071* (2013.01); *C09K 2211/1018* (2013.01); *H01L 51/5012* (2013.01)

(58) Field of Classification Search
CPC .. C07D 471/14; C07D 495/22; C07D 471/20; C07D 491/147; C07D 491/22; C07D 471/22; C07D 495/14; H01L 51/0072; H01L 51/0071
USPC ......................................................... 544/230
See application file for complete search history.

(56) References Cited

U.S. PATENT DOCUMENTS

| 8,106,199 B2 | 1/2012 | Jabbour |
|---|---|---|
| 8,389,725 B2 | 3/2013 | Li |
| 8,669,364 B2 | 3/2014 | Li |
| 8,816,080 B2 | 8/2014 | Li |
| 8,846,940 B2 | 9/2014 | Li |
| 8,927,713 B2 | 1/2015 | Li |
| 8,946,417 B2 | 2/2015 | Jian |
| 9,076,974 B2 | 7/2015 | Li |
| 9,082,989 B2 | 7/2015 | Li |
| 9,203,039 B2 | 12/2015 | Li |
| 9,221,857 B2 | 12/2015 | Li |
| 9,224,963 B2 | 12/2015 | Li |
| 9,238,668 B2 | 1/2016 | Li |
| 9,312,502 B2 | 4/2016 | Li |
| 9,318,725 B2 | 4/2016 | Li |
| 9,324,957 B2 | 4/2016 | Li |
| 9,382,273 B2 | 7/2016 | Li |
| 9,385,329 B2 | 7/2016 | Li |
| 9,425,415 B2 | 8/2016 | Li |
| 9,502,671 B2 | 11/2016 | Li |
| 9,550,801 B2 | 1/2017 | Li |
| 9,598,449 B2 | 3/2017 | Li |
| 9,617,291 B2 | 4/2017 | Li |
| 9,673,409 B2 | 6/2017 | Li |
| 9,698,359 B2 | 7/2017 | Li |
| 9,711,739 B2 | 7/2017 | Li |
| 9,711,741 B2 | 7/2017 | Li |
| 9,711,742 B2 | 7/2017 | Li |
| 9,755,163 B2 | 9/2017 | Li |
| 9,818,959 B2 | 11/2017 | Li |
| 9,865,825 B2 | 1/2018 | Li |
| 9,879,039 B2 | 1/2018 | Li |
| 9,882,150 B2 | 1/2018 | Li |
| 9,899,614 B2 | 2/2018 | Li |

(Continued)

FOREIGN PATENT DOCUMENTS

| KR | 20110066763 | 6/2011 |
|---|---|---|
| KR | 20130043460 A | 4/2013 |

(Continued)

OTHER PUBLICATIONS

STN Abstract of KR 2013043460 A (Year: 2013).

(Continued)

*Primary Examiner* — Kahsay Habte
(74) *Attorney, Agent, or Firm* — Riverside Law LLP

(57) ABSTRACT

Donor-acceptor type thermally activated delayed fluorescent emitters based on imidazo[1,2-F]phenanthridine and analogues for full color displays and lighting applications.

12 Claims, 1 Drawing Sheet

(56) References Cited

U.S. PATENT DOCUMENTS

| | | | |
|---|---|---|---|
| 9,920,242 B2 | 3/2018 | Li | |
| 9,923,155 B2 | 3/2018 | Li | |
| 9,941,479 B2 | 4/2018 | Li | |
| 9,947,881 B2 | 4/2018 | Li | |
| 9,985,224 B2 | 5/2018 | Li | |
| 10,020,455 B2 | 7/2018 | Li | |
| 10,033,003 B2 | 7/2018 | Li | |
| 10,056,564 B2 | 8/2018 | Li | |
| 10,056,567 B2 | 8/2018 | Li | |
| 10,158,091 B2 | 12/2018 | Li | |
| 10,177,323 B2 | 1/2019 | Li | |
| 10,211,411 B2 | 2/2019 | Li | |
| 10,211,414 B2 | 2/2019 | Li | |
| 10,263,197 B2 | 4/2019 | Li | |
| 10,294,417 B2 | 5/2019 | Li | |
| 10,392,387 B2 | 8/2019 | Li | |
| 10,411,202 B2 | 9/2019 | Li | |
| 10,414,785 B2 | 9/2019 | Li | |
| 10,516,117 B2 | 12/2019 | Li | |
| 10,566,553 B2 | 2/2020 | Li | |
| 10,566,554 B2 | 2/2020 | Li | |
| 10,615,349 B2 * | 4/2020 | Li | ........................ C07D 471/14 |
| 10,622,571 B2 | 4/2020 | Li | |
| 10,727,422 B2 | 7/2020 | Li | |
| 10,745,615 B2 | 8/2020 | Li | |
| 10,790,457 B2 | 9/2020 | Li | |
| 10,793,546 B2 | 10/2020 | Li | |
| 10,804,476 B2 | 10/2020 | Li | |
| 10,822,363 B2 | 11/2020 | Li | |
| 10,836,785 B2 | 11/2020 | Li | |
| 10,851,106 B2 | 12/2020 | Li | |
| 10,886,478 B2 | 1/2021 | Li | |
| 10,930,865 B2 | 2/2021 | Li | |
| 10,937,976 B2 | 3/2021 | Li | |
| 10,944,064 B2 | 3/2021 | Li | |
| 10,964,897 B2 | 3/2021 | Li | |
| 10,991,897 B2 | 4/2021 | Li | |
| 10,995,108 B2 | 5/2021 | Li | |
| 11,011,712 B2 | 5/2021 | Li | |
| 11,063,228 B2 | 7/2021 | Li | |
| 11,101,435 B2 | 8/2021 | Li | |
| 11,114,626 B2 | 9/2021 | Li | |
| 11,121,328 B2 | 9/2021 | Li | |
| 11,145,830 B2 | 10/2021 | Li | |
| 2008/0269491 A1 | 10/2008 | Jabbour | |
| 2009/0136779 A1 | 5/2009 | Cheng | |
| 2011/0028723 A1 | 2/2011 | Li | |
| 2011/0066763 A1 | 3/2011 | Minot | |
| 2011/0301351 A1 | 12/2011 | Li | |
| 2012/0095232 A1 | 4/2012 | Li | |
| 2012/0108806 A1 | 5/2012 | Li | |
| 2012/0202997 A1 | 8/2012 | Parham | |
| 2012/0215001 A1 | 8/2012 | Li | |
| 2012/0264938 A1 | 10/2012 | Li | |
| 2012/0302753 A1 | 11/2012 | Li | |
| 2013/0137870 A1 | 5/2013 | Li | |
| 2013/0203996 A1 | 8/2013 | Li | |
| 2013/0237706 A1 | 9/2013 | Li | |
| 2014/0066628 A1 | 3/2014 | Li | |
| 2014/0073798 A1 | 3/2014 | Li | |
| 2014/0114072 A1 | 4/2014 | Li | |
| 2014/0147996 A1 | 5/2014 | Vogt | |
| 2014/0148594 A1 | 5/2014 | Li | |
| 2014/0249310 A1 | 9/2014 | Li | |
| 2014/0330019 A1 | 11/2014 | Li | |
| 2014/0364605 A1 | 12/2014 | Li | |
| 2015/0008419 A1 | 1/2015 | Li | |
| 2015/0018558 A1 | 1/2015 | Li | |
| 2015/0105556 A1 | 4/2015 | Li | |
| 2015/0162552 A1 | 6/2015 | Li | |
| 2015/0194616 A1 | 7/2015 | Li | |
| 2015/0207086 A1 | 7/2015 | Li | |
| 2015/0228914 A1 | 8/2015 | Li | |
| 2015/0274762 A1 | 10/2015 | Li | |
| 2015/0287938 A1 | 10/2015 | Li | |
| 2015/0311456 A1 | 10/2015 | Li | |
| 2015/0318500 A1 | 11/2015 | Li | |
| 2015/0349279 A1 | 12/2015 | Li | |
| 2016/0028028 A1 | 1/2016 | Li | |
| 2016/0028029 A1 | 1/2016 | Li | |
| 2016/0043331 A1 | 2/2016 | Li | |
| 2016/0133861 A1 | 5/2016 | Li | |
| 2016/0133862 A1 | 5/2016 | Li | |
| 2016/0194344 A1 | 7/2016 | Li | |
| 2016/0197291 A1 | 7/2016 | Li | |
| 2016/0285015 A1 | 9/2016 | Li | |
| 2016/0359120 A1 | 12/2016 | Li | |
| 2016/0359125 A1 | 12/2016 | Li | |
| 2017/0005278 A1 | 1/2017 | Li | |
| 2017/0012224 A1 | 1/2017 | Li | |
| 2017/0040555 A1 | 2/2017 | Li | |
| 2017/0047533 A1 | 2/2017 | Li | |
| 2017/0066792 A1 | 3/2017 | Li | |
| 2017/0069855 A1 | 3/2017 | Li | |
| 2017/0077420 A1 | 3/2017 | Li | |
| 2017/0125708 A1 | 5/2017 | Li | |
| 2017/0267923 A1 | 9/2017 | Li | |
| 2017/0271611 A1 | 9/2017 | Li | |
| 2017/0301871 A1 | 10/2017 | Li | |
| 2017/0305881 A1 | 10/2017 | Li | |
| 2017/0331056 A1 | 11/2017 | Li | |
| 2017/0342098 A1 | 11/2017 | Li | |
| 2017/0373260 A1 | 12/2017 | Li | |
| 2018/0006246 A1 | 1/2018 | Li | |
| 2018/0053904 A1 | 2/2018 | Li | |
| 2018/0130960 A1 | 5/2018 | Li | |
| 2018/0138428 A1 | 5/2018 | Li | |
| 2018/0148464 A1 | 5/2018 | Li | |
| 2018/0159051 A1 | 6/2018 | Li | |
| 2018/0166655 A1 | 6/2018 | Li | |
| 2018/0175329 A1 | 6/2018 | Li | |
| 2018/0194790 A1 | 7/2018 | Li | |
| 2018/0219161 A1 | 8/2018 | Li | |
| 2018/0226592 A1 | 8/2018 | Li | |
| 2018/0226593 A1 | 8/2018 | Li | |
| 2018/0277777 A1 | 9/2018 | Li | |
| 2018/0301641 A1 | 10/2018 | Li | |
| 2018/0312750 A1 | 11/2018 | Li | |
| 2018/0331307 A1 | 11/2018 | Li | |
| 2018/0334459 A1 | 11/2018 | Li | |
| 2018/0337345 A1 | 11/2018 | Li | |
| 2018/0337349 A1 | 11/2018 | Li | |
| 2018/0337350 A1 | 11/2018 | Li | |
| 2019/0013485 A1 | 1/2019 | Li | |
| 2019/0067602 A1 | 2/2019 | Li | |
| 2019/0109288 A1 | 4/2019 | Li | |
| 2019/0194536 A1 | 6/2019 | Li | |
| 2019/0259963 A1 | 8/2019 | Li | |
| 2019/0276485 A1 | 9/2019 | Li | |
| 2019/0312217 A1 | 10/2019 | Li | |
| 2019/0367546 A1 | 12/2019 | Li | |
| 2019/0389893 A1 | 12/2019 | Li | |
| 2020/0006678 A1 | 1/2020 | Li | |
| 2020/0071330 A1 | 3/2020 | Li | |
| 2020/0075868 A1 | 3/2020 | Li | |
| 2020/0119288 A1 | 4/2020 | Li | |
| 2020/0152891 A1 | 5/2020 | Li | |
| 2020/0239505 A1 | 7/2020 | Li | |
| 2020/0243776 A1 | 7/2020 | Li | |
| 2021/0104687 A1 | 4/2021 | Li | |
| 2021/0111355 A1 | 4/2021 | Li | |
| 2021/0126208 A1 | 4/2021 | Li | |
| 2021/0193936 A1 | 6/2021 | Li | |
| 2021/0193947 A1 | 6/2021 | Li | |
| 2021/0217973 A1 | 7/2021 | Li | |
| 2021/0230198 A1 | 7/2021 | Li | |
| 2021/0261589 A1 | 8/2021 | Li | |
| 2021/0273182 A1 | 9/2021 | Li | |

FOREIGN PATENT DOCUMENTS

| | | |
|---|---|---|
| KR | 20140027030 | 3/2014 |
| KR | 20140065357 A * | 5/2014 |
| WO | 2009086209 | 7/2009 |

(56) References Cited

FOREIGN PATENT DOCUMENTS

| | | |
|---|---|---|
| WO | 2009111299 | 9/2009 |
| WO | 2010050778 | 5/2010 |
| WO | 2010105141 | 9/2010 |
| WO | 2010118026 | 10/2010 |
| WO | 2011137429 | 11/2011 |
| WO | 2011137431 | 11/2011 |
| WO | 2012074909 | 6/2012 |
| WO | 2012112853 | 8/2012 |
| WO | 2012142387 | 10/2012 |
| WO | 2012162488 | 11/2012 |
| WO | 2013130483 | 9/2013 |
| WO | 2014009310 | 1/2014 |
| WO | 2014031977 | 2/2014 |
| WO | 2014047616 | 3/2014 |
| WO | 2014109814 | 7/2014 |
| WO | 2015027060 | 2/2015 |
| WO | 2015099507 | 7/2015 |
| WO | 2015131158 | 9/2015 |
| WO | 2016025921 | 2/2016 |
| WO | 2016029137 | 2/2016 |
| WO | 2016029186 | 2/2016 |
| WO | 2016197019 | 12/2016 |
| WO | 2018071697 | 4/2018 |
| WO | 2018140765 | 8/2018 |
| WO | 2019079505 | 4/2019 |
| WO | 2019079508 | 4/2019 |
| WO | 2019079509 | 4/2019 |
| WO | 2019236541 | 12/2019 |
| WO | 2020018476 | 1/2020 |

OTHER PUBLICATIONS

U.S. Appl. No. 16/668,010, filed Oct. 30, 2019, has not yet published. Inventor: Li et al.
U.S. Appl. No. 16/739,480, filed Jan. 10, 2020, has not yet published. Inventors: Li et al.
U.S. Appl. No. 16/751,561, filed Jan. 24, 2020, has not yet published. Inventor: Li.
U.S. Appl. No. 16/751,586, filed on Jan. 24, 2020, has not yet published. Inventor: Li et al.
Uoyama et al., "Highly efficient organic light-emitting diodes from delayed fluorescence" Nature, 492:234-238, (2012).
Yan, et al. Organic & Biomolecular Chemistry, 11(45), 2013, 7966-7977.

\* cited by examiner

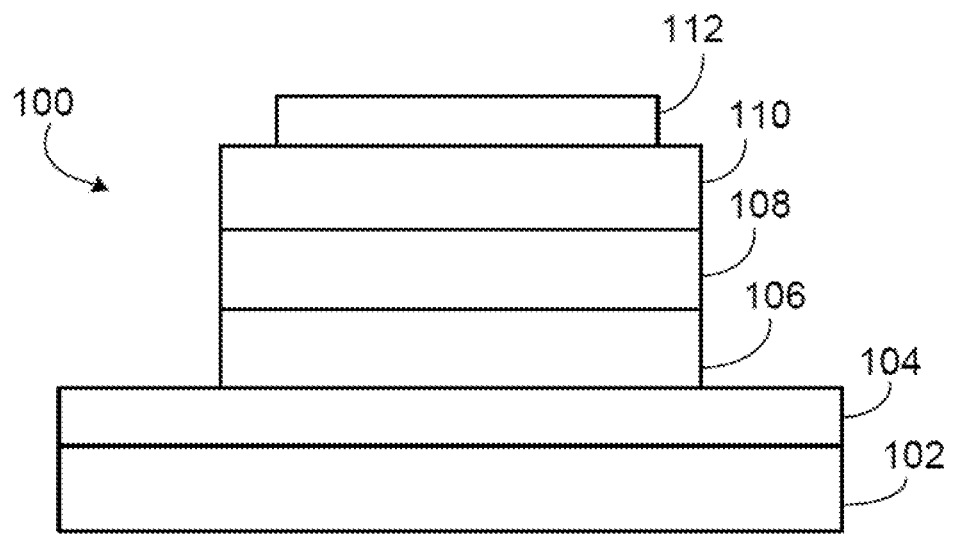

DONOR-ACCEPTOR TYPE THERMALLY ACTIVATED DELAYED FLUORESCENT MATERIALS BASED ON IMIDAZO[1,2-F]PHENANTHRIDINE AND ANALOGUES

CROSS-REFERENCE TO RELATED APPLICATION

The present application is a divisional of U.S. patent application Ser. No. 15/984,157, filed May 18, 2018, now allowed, which claims the benefit of U.S. Provisional Patent Application No. 62/508,518, filed May 19, 2017, all of which applications are incorporated herein by reference in their entireties.

TECHNICAL FIELD

This invention relates to donor-acceptor type thermally activated delayed fluorescent materials based on imidazo[1,2-F]phenanthridine and analogues for full color displays and lighting applications.

BACKGROUND

Compounds capable of absorbing or emitting light can be used in a variety of optical and electro-optical devices, including photo-absorbing devices (e.g., solar- and photo-sensitive devices), photo-emitting devices, organic light-emitting diodes (OLEDs), and devices capable of photo-absorption and photo-emission. Much research has been devoted to the discovery and optimization of organic and organometallic materials for use in optical and electro-optical devices. Metal complexes can be used for many applications, such as emitters for OLEDs. Despite advances in research devoted to optical and electro-optical materials, many currently available materials exhibit a number of disadvantages, including poor processing ability, inefficient emission or absorption, and insufficient stability.

SUMMARY

General Formulas I-IV include donor-acceptor type thermally activated delayed fluorescent materials based on imidazo[1,2-f]phenanthridine and analogues for organic light emitting diodes (OLEDS) suitable for full color displays and lighting applications.

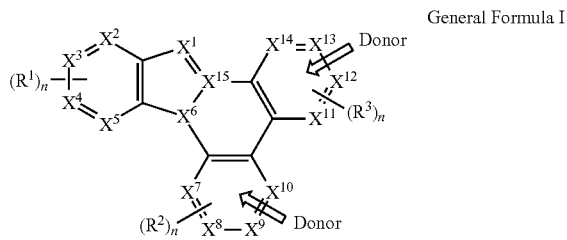

General Formula I

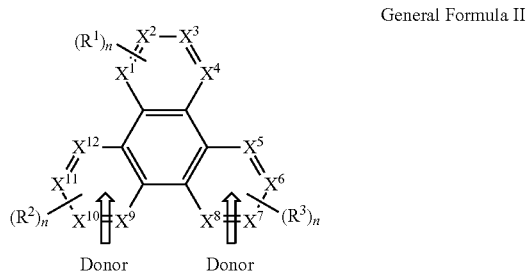

General Formula II

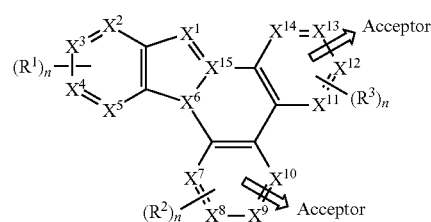

General Formula III

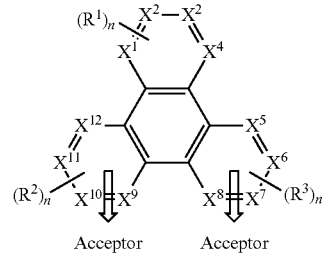

General Formula IV

In General Formulas I-IV:

$R^1$, $R^2$, and $R^3$ each independently represents hydrogen, cyanide, halogen, hydroxy, amino, nitro, thiol, or substituted or unsubstituted $C_1$-$C_4$ alkyl, alkoxy, or aryl, and $X^1$, $X^2$, $X^3$, $X^4$, $X^5$, $X^6$, $X^8$, $X^{10}$, $X^{11}$, $X^{12}$, $X^{13}$, $X^{14}$, and $X^{15}$ each independently represents substituted or unsubstituted C, N, Si, O, or S, valency permitting, and each n is independently an integer as permitted by valence.

These general and specific aspects may be implemented using a device, system or method, or any combination of devices, systems, or methods. The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1 depicts a cross-sectional view of an organic light emitting device.

DETAILED DESCRIPTION

General Formulas I-IV include donor-acceptor type thermally activated delayed fluorescent materials based on imidazo[1,2-f]phenanthridine and analogues for organic light emitting diodes (OLEDS) suitable for full color displays and lighting applications.

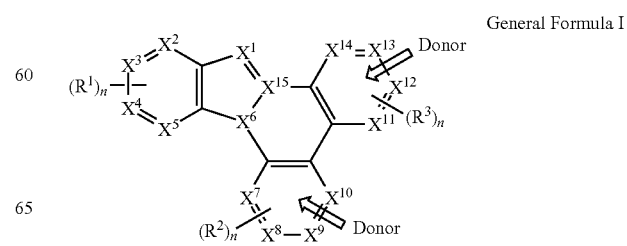

General Formula I

General Formula II

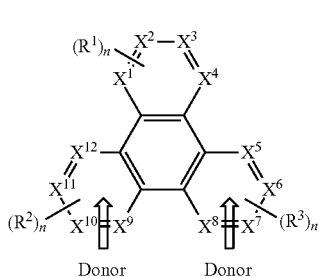

General Formula III

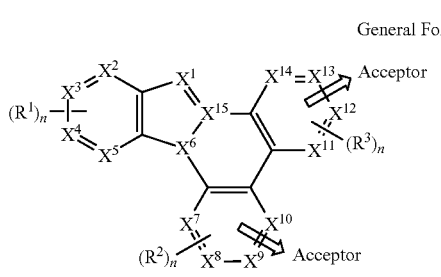

General Formula IV

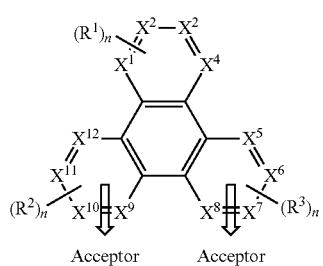

In General Formulas I-IV:

R$^1$, R$^2$, and R$^3$ each independently represents hydrogen, cyanide, halogen, hydroxy, amino, nitro, thiol, or substituted or unsubstituted C$_1$-C$_4$ alkyl, alkoxy, or aryl, and X$^1$, X$^2$, X$^3$, X$^4$, X$^5$, X$^6$, X$^8$, X$^{10}$, X$^{11}$, X$^{12}$, X$^{13}$, X$^{14}$, and X$^{15}$ each independently represents substituted or unsubstituted C, N, Si, O, or S, valency permitting, and each n is independently an integer as permitted by valence.

Implementations of General Formulas I-IV are shown below.

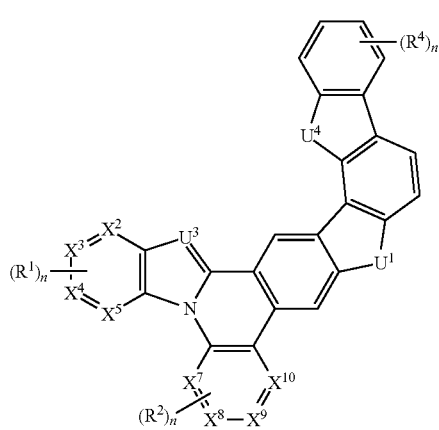

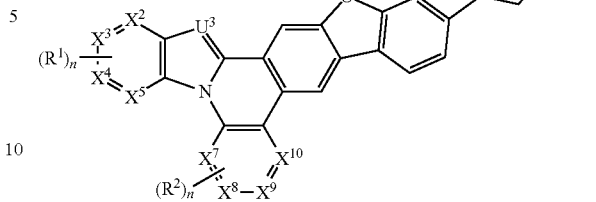

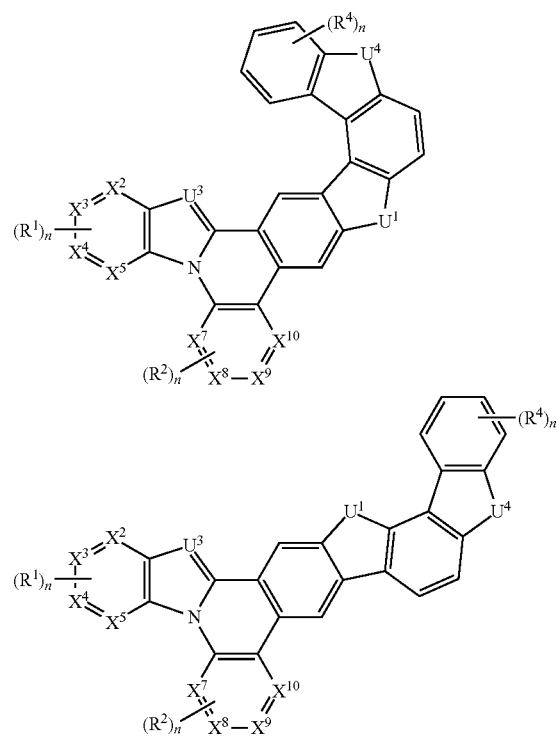

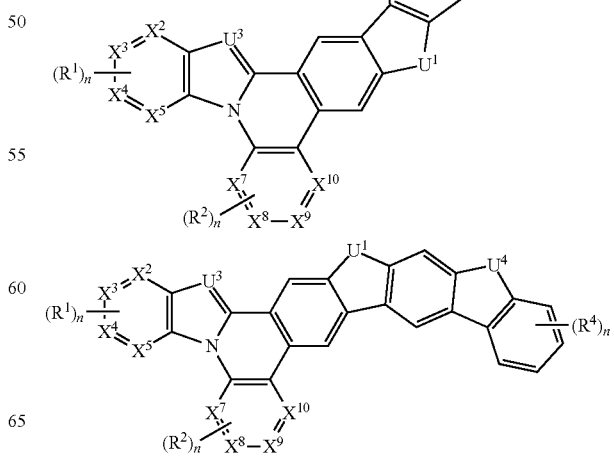

-continued
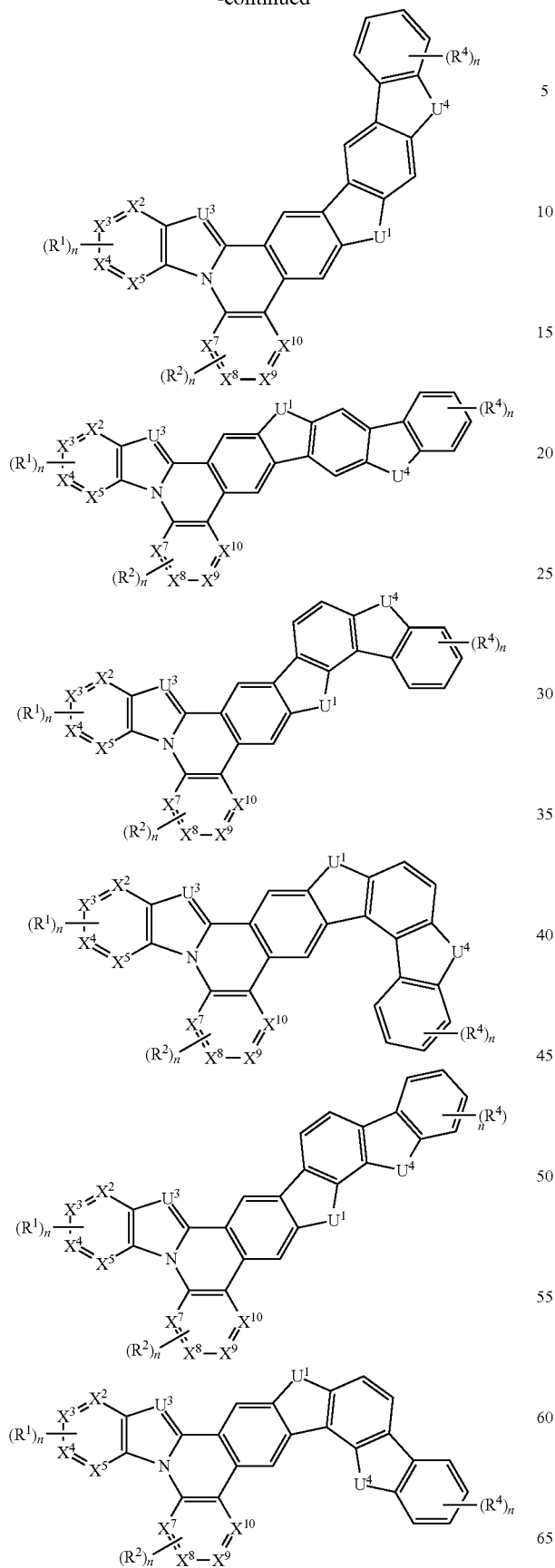
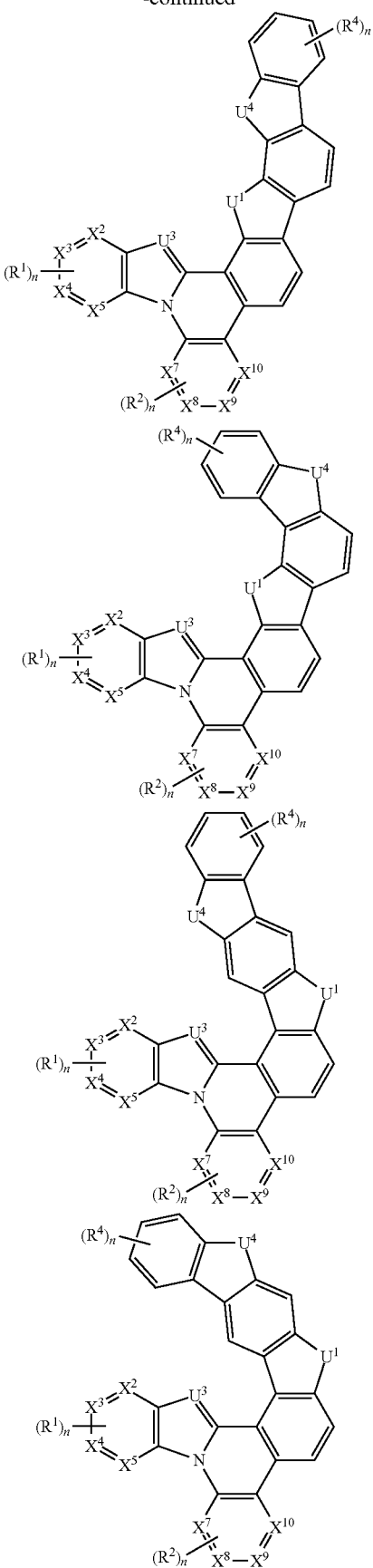

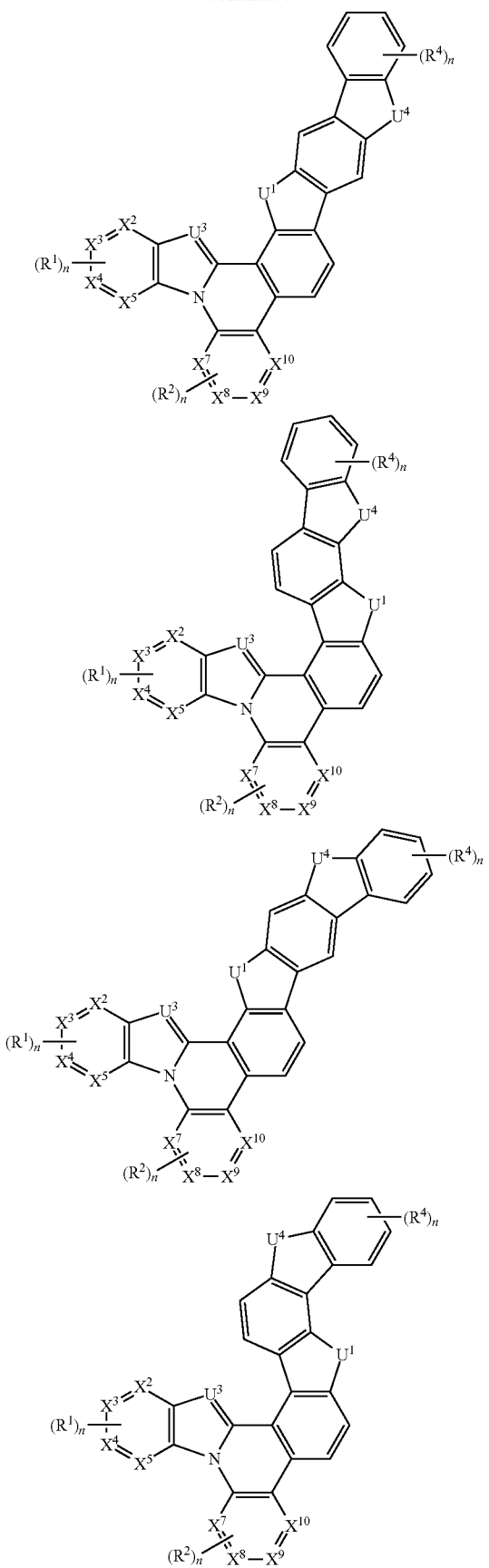
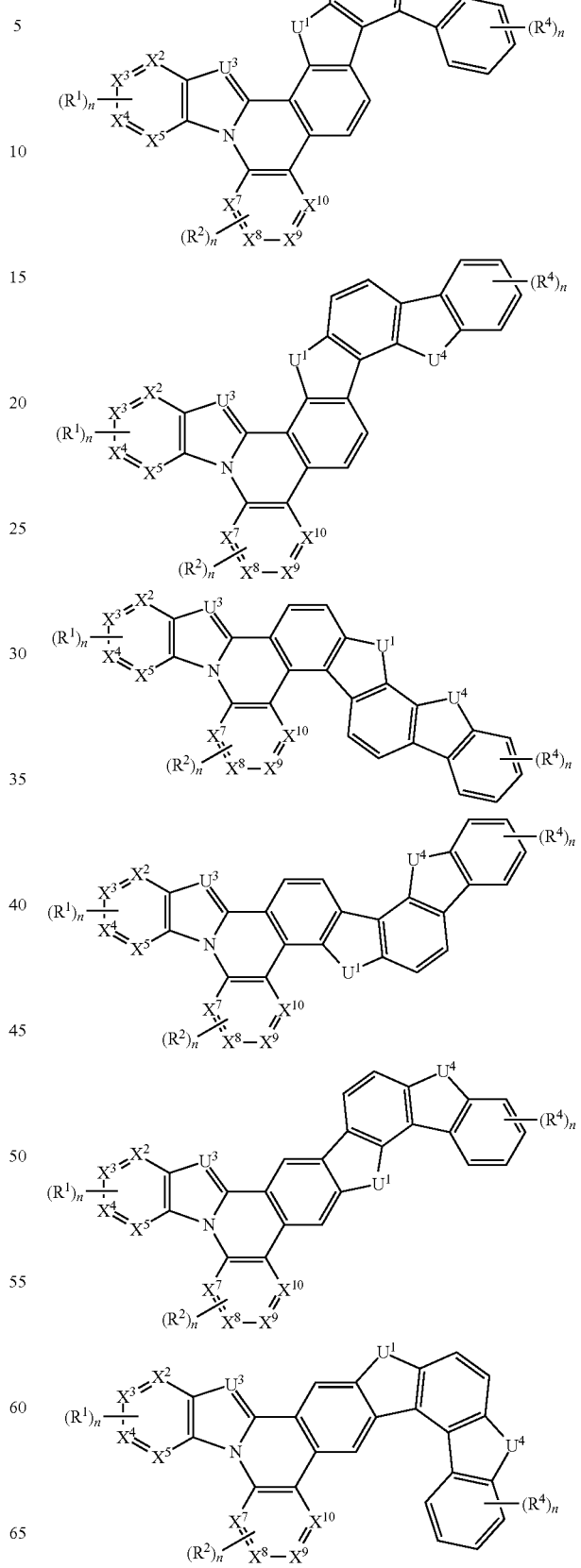

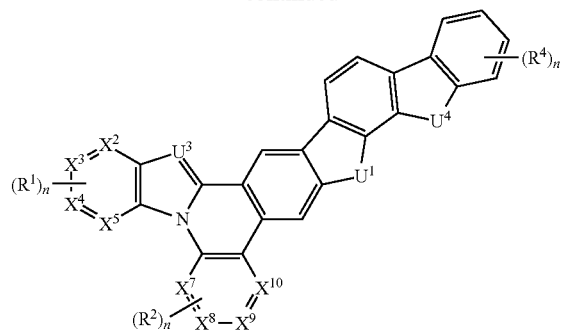
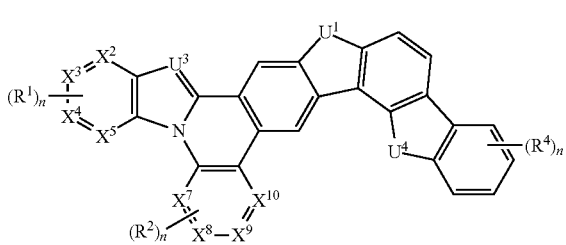
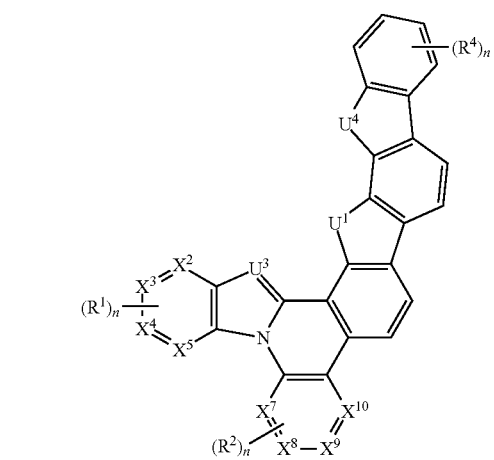
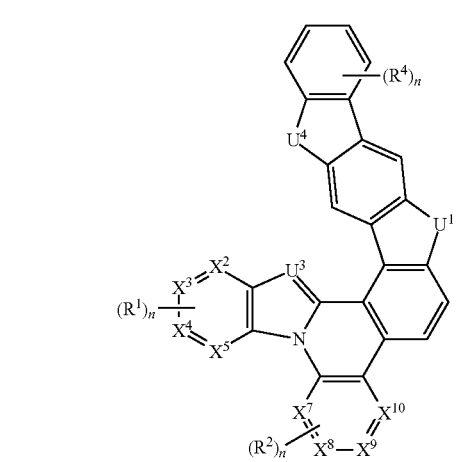
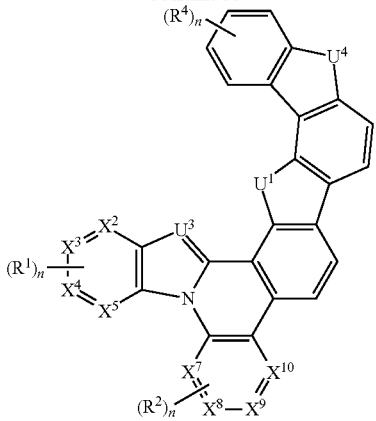
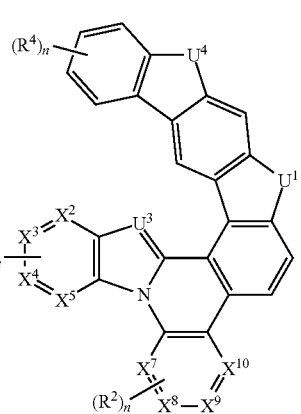

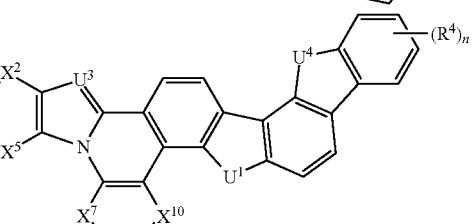
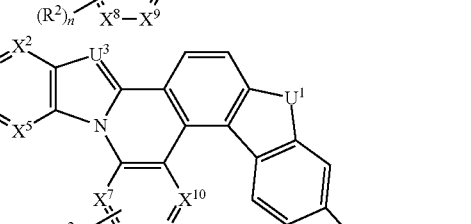

-continued
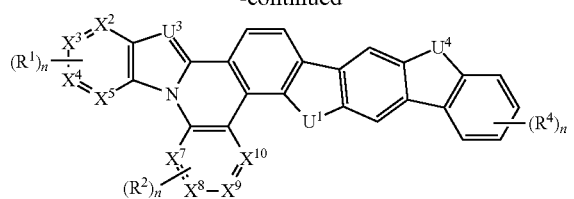
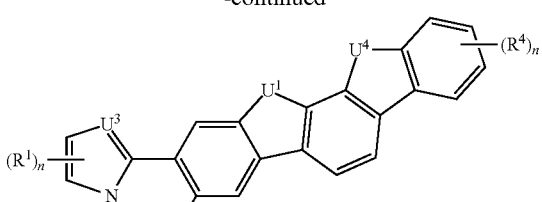
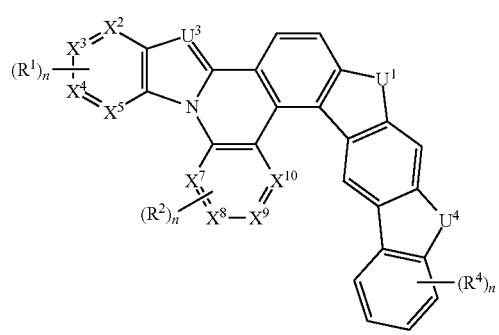
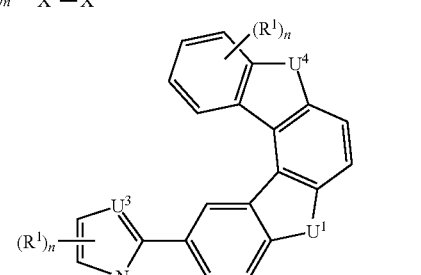
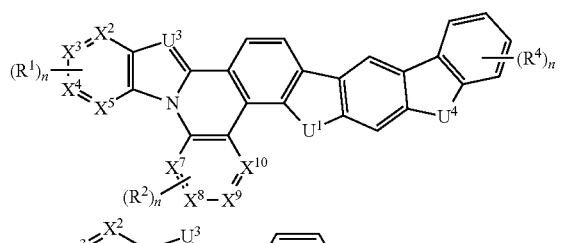
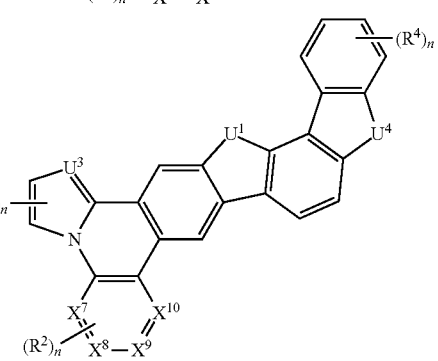
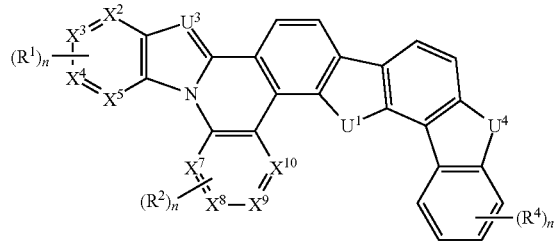
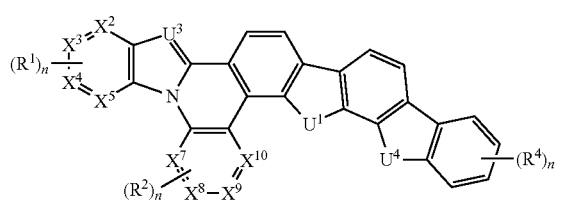
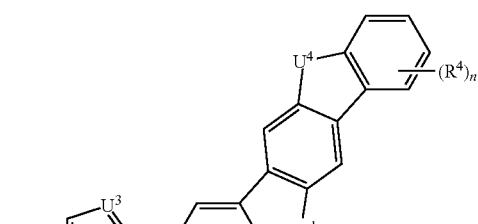
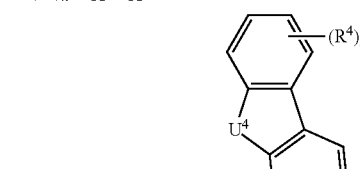
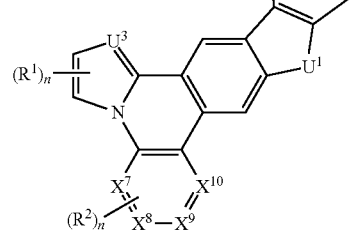
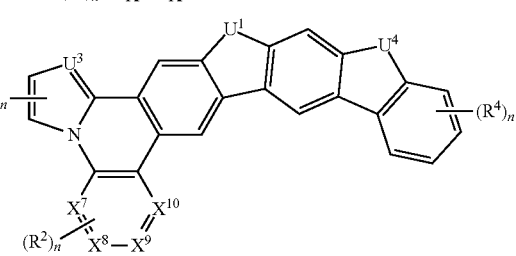

-continued
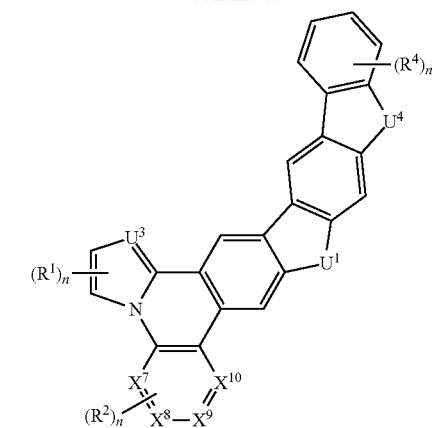
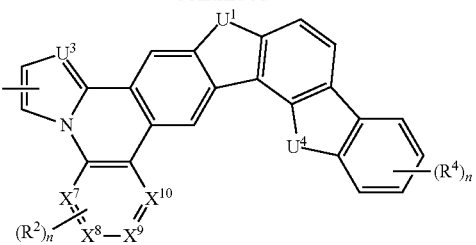
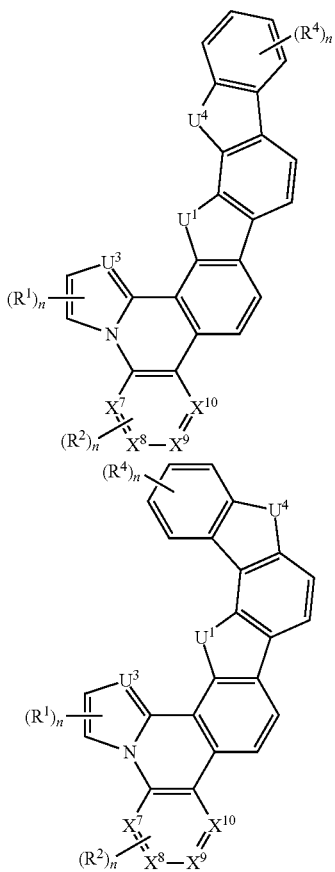
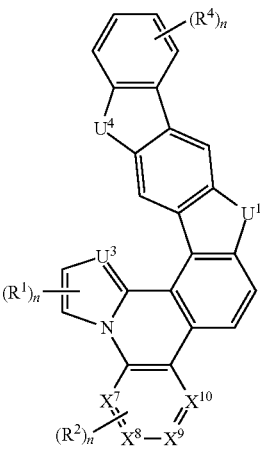

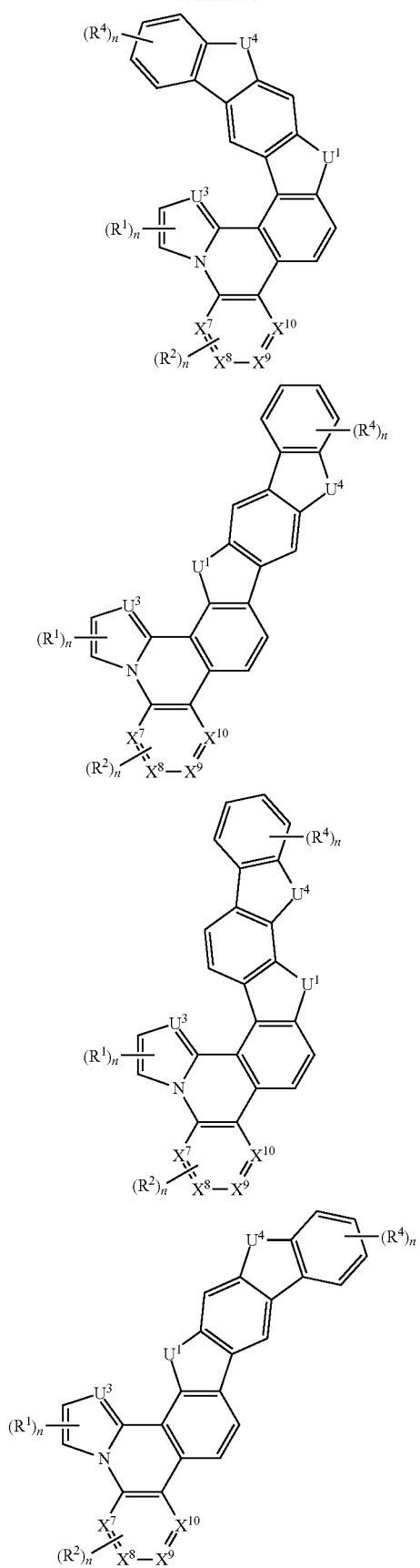
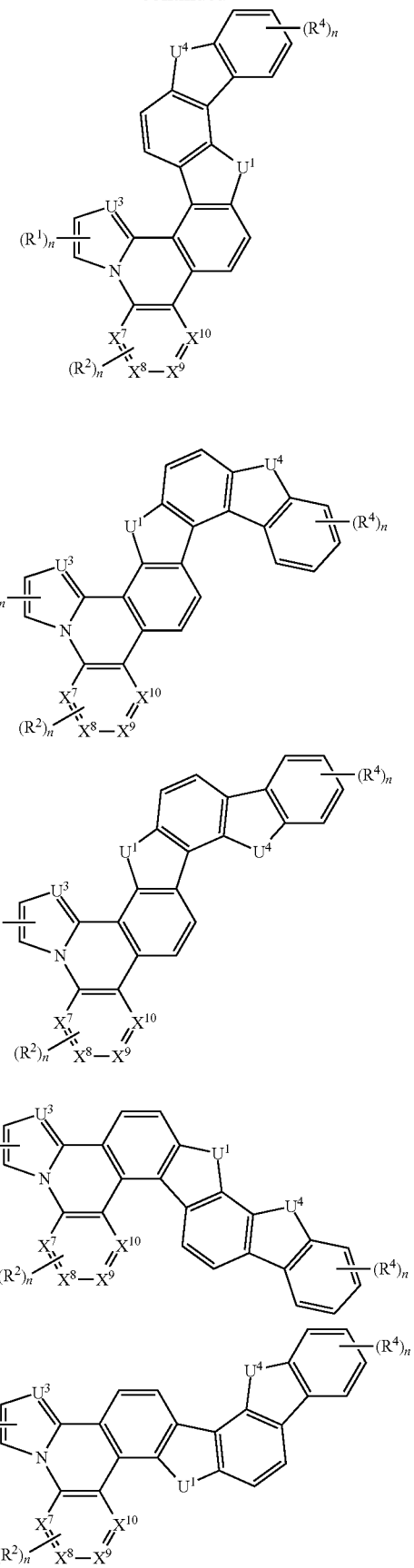

-continued
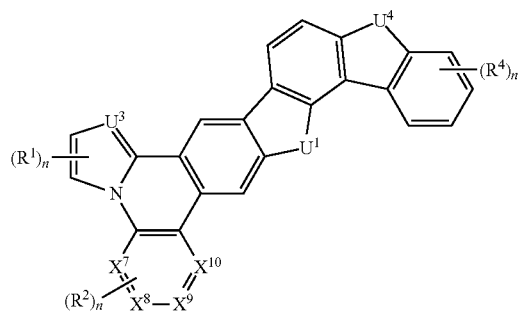
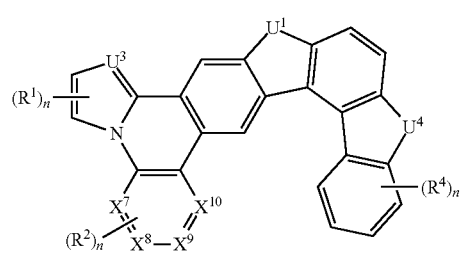
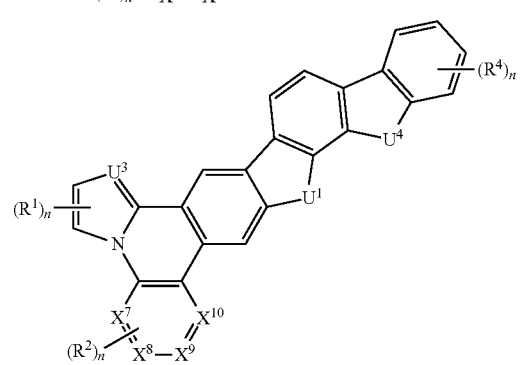
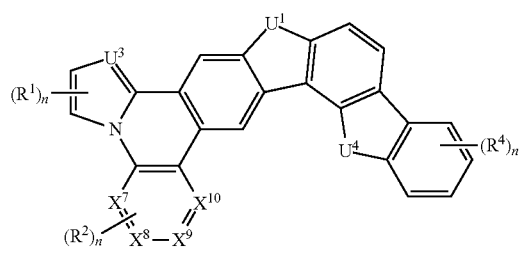
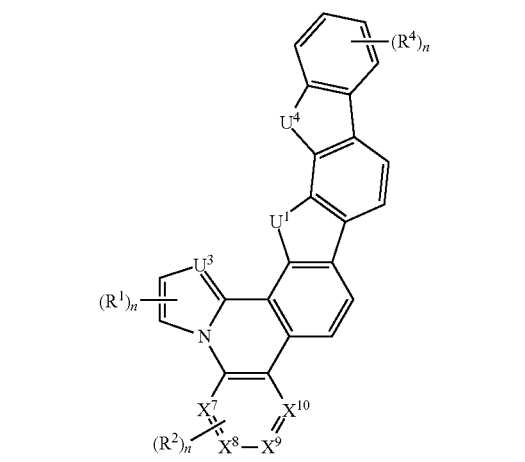
-continued
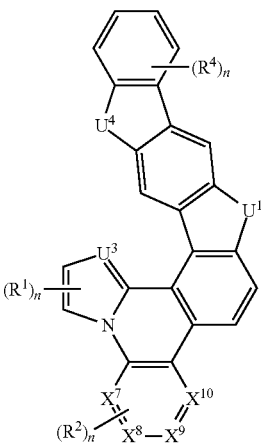
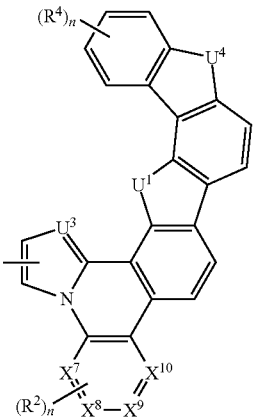
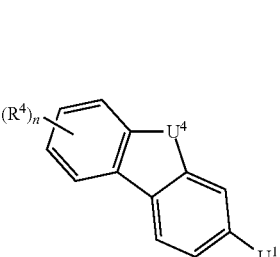
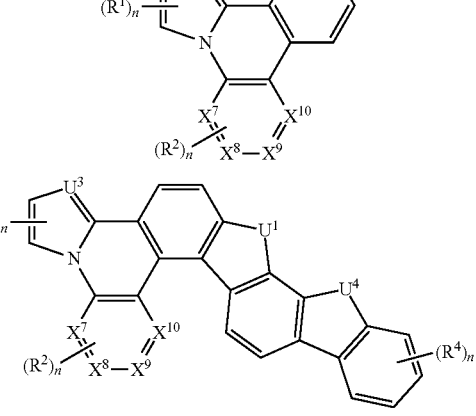

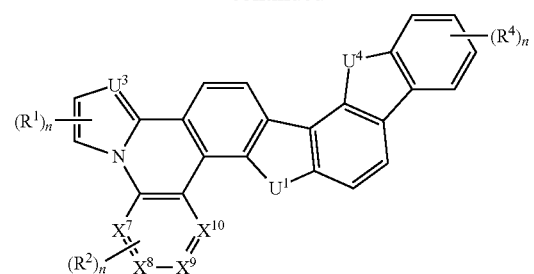
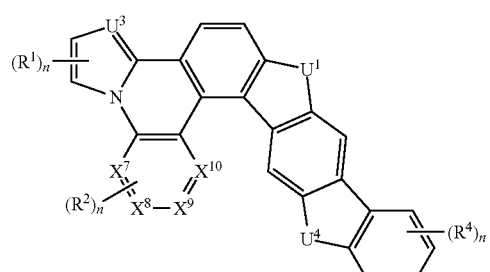
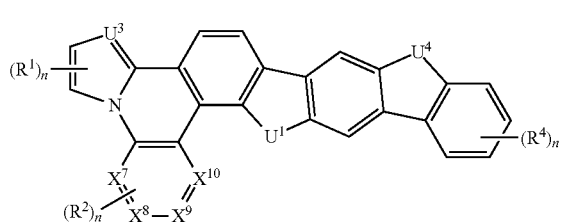
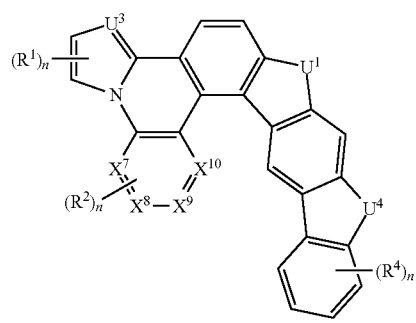
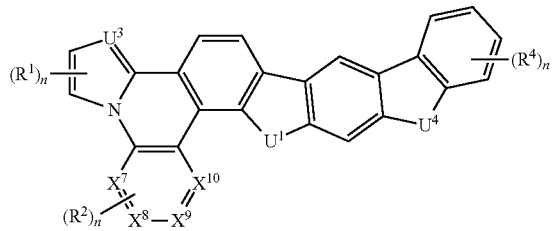
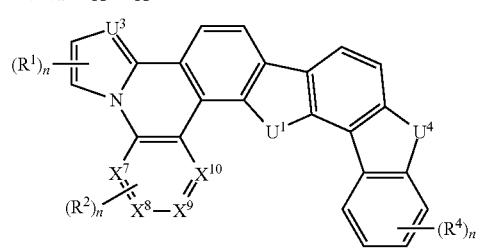
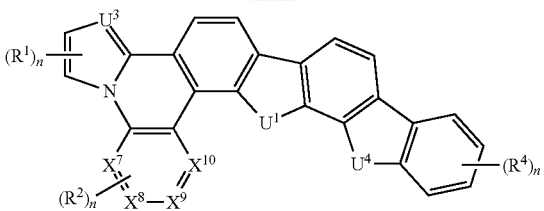
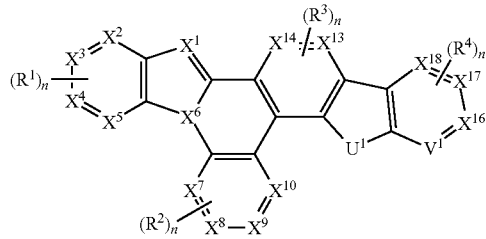
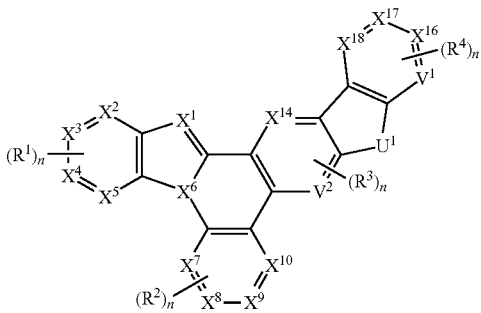
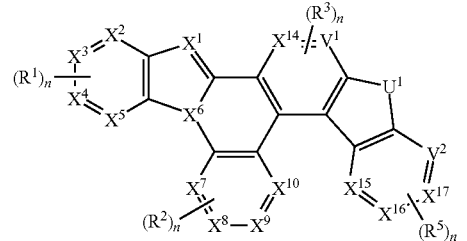
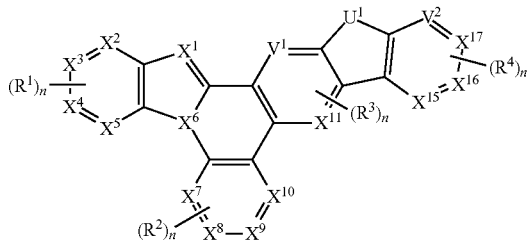
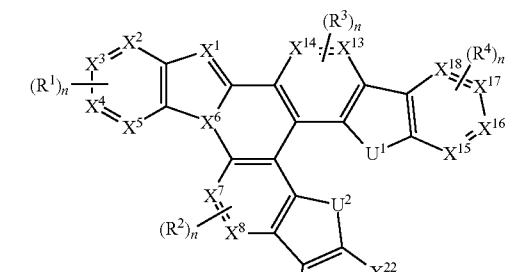

-continued
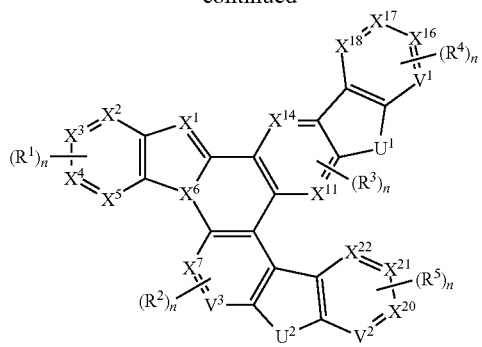
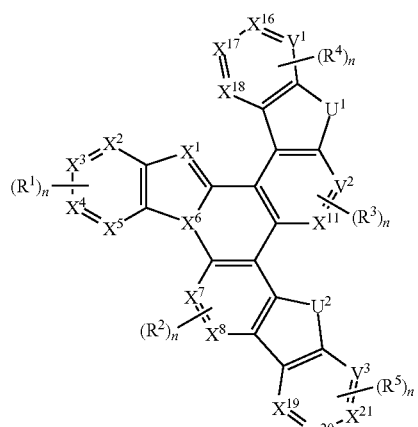
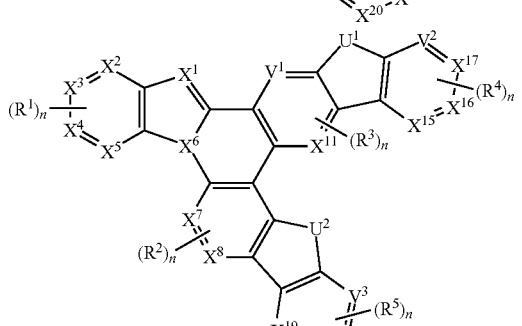
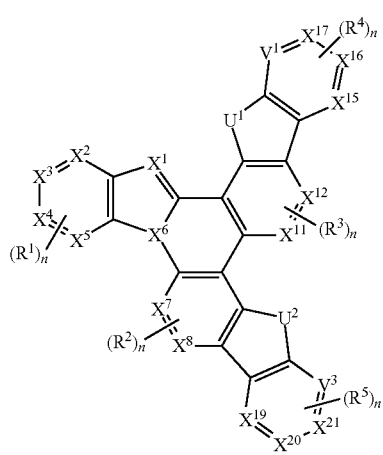
-continued
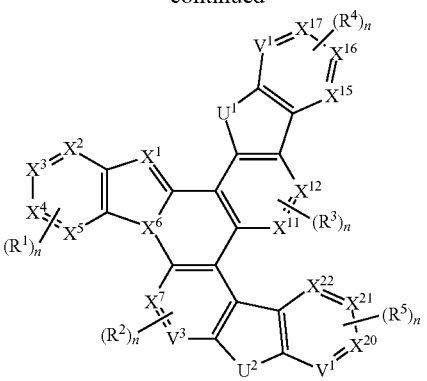
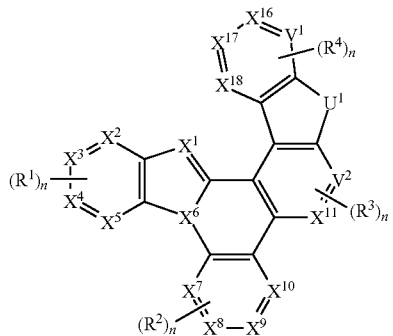
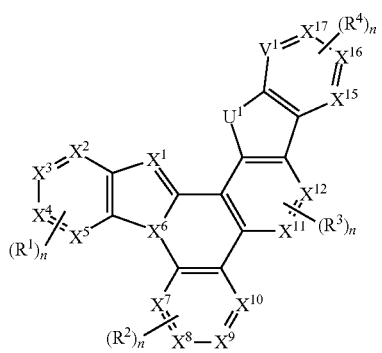
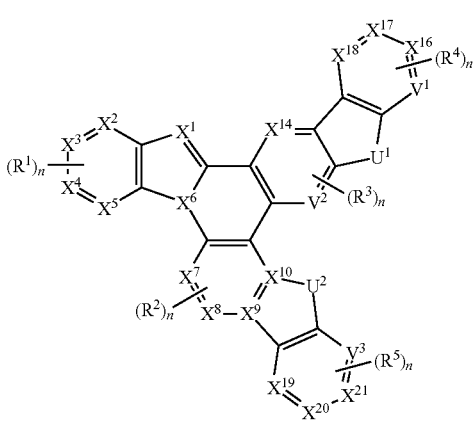

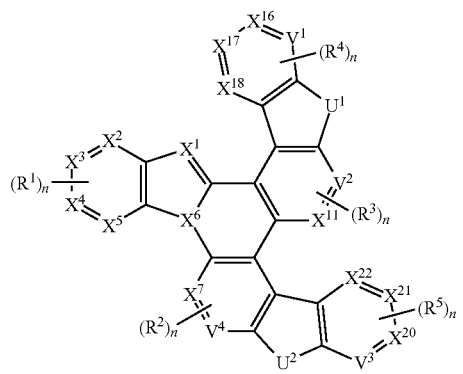
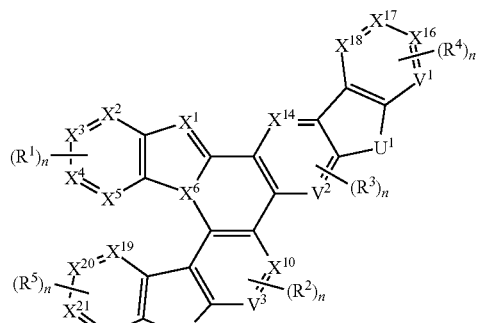
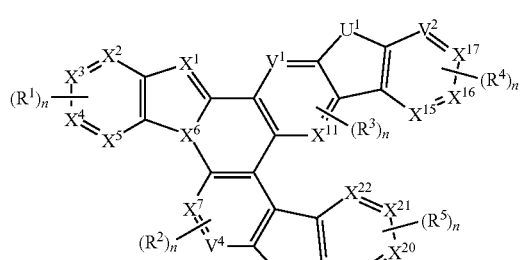
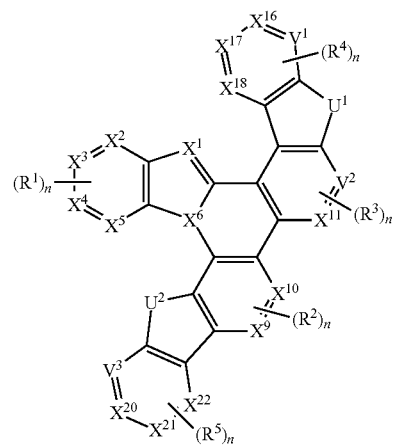
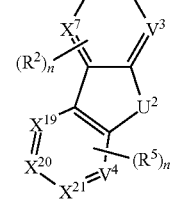
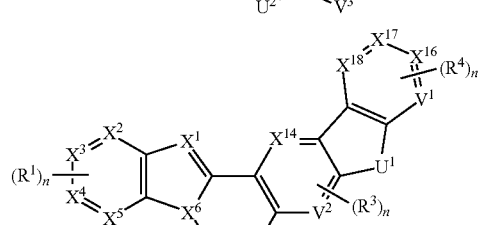
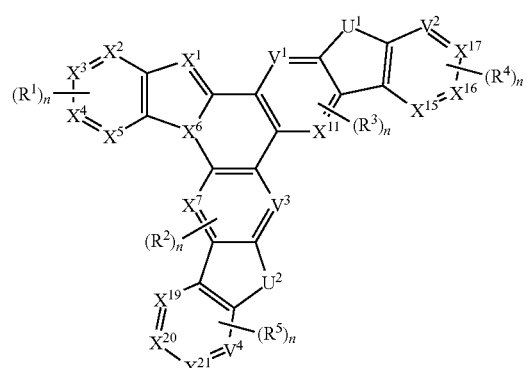
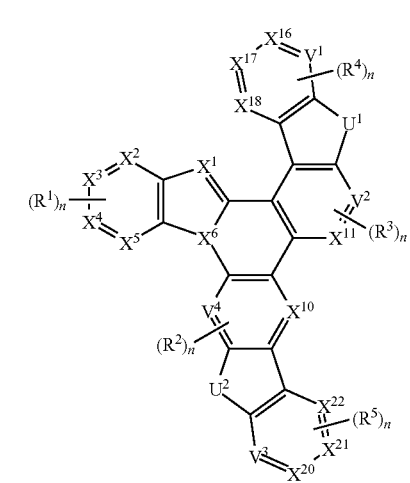
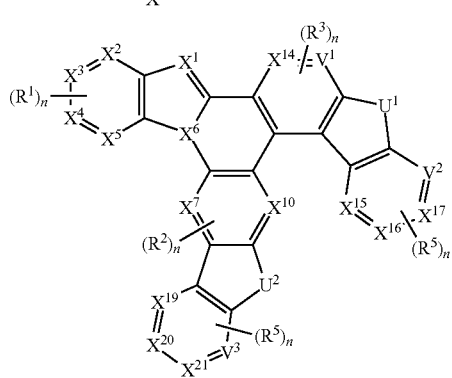

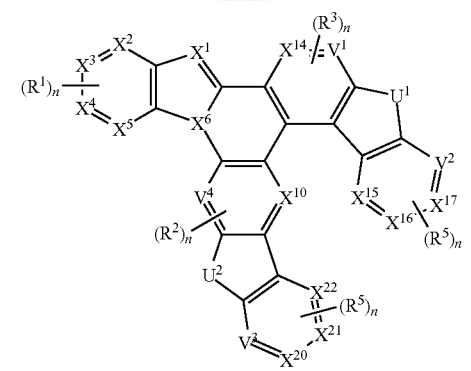
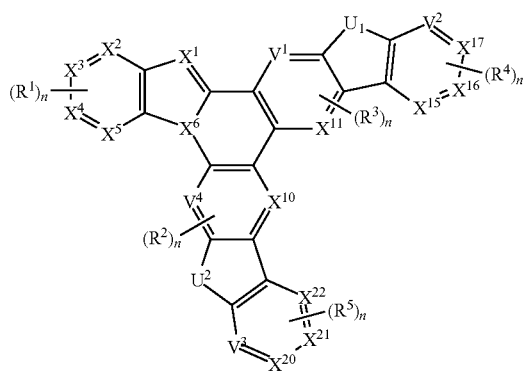
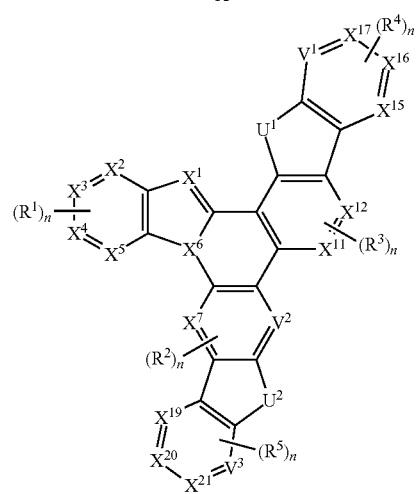
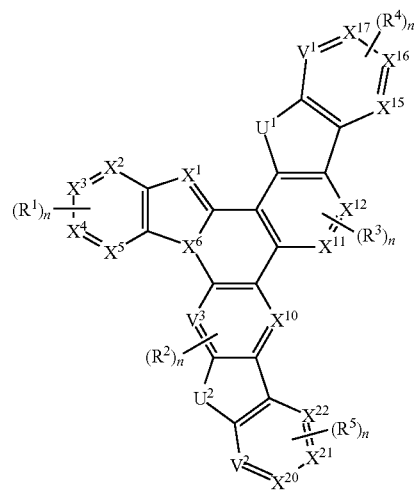
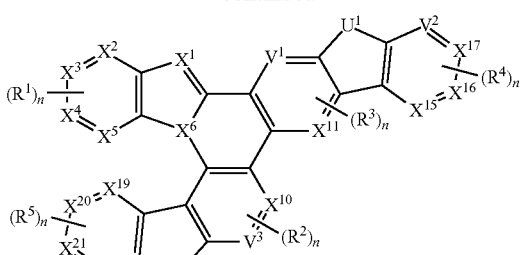
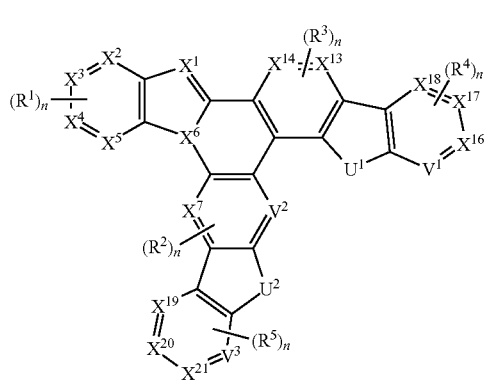
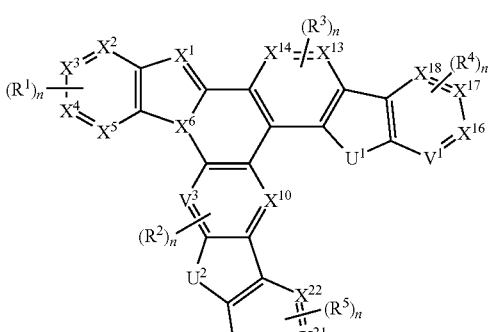
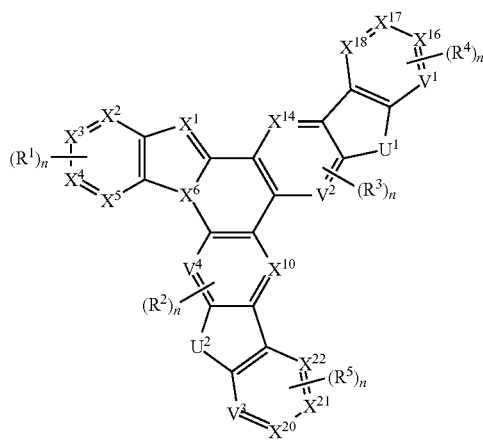

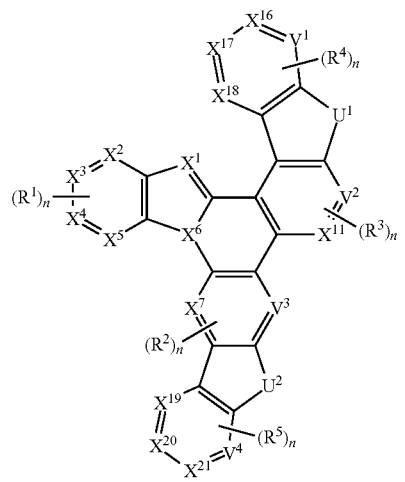
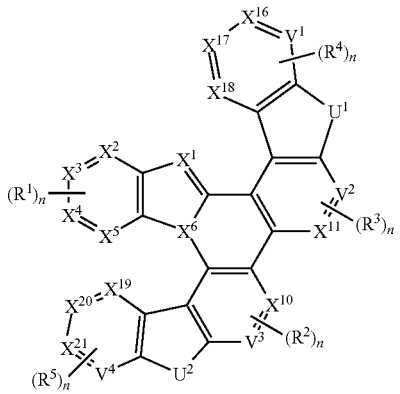
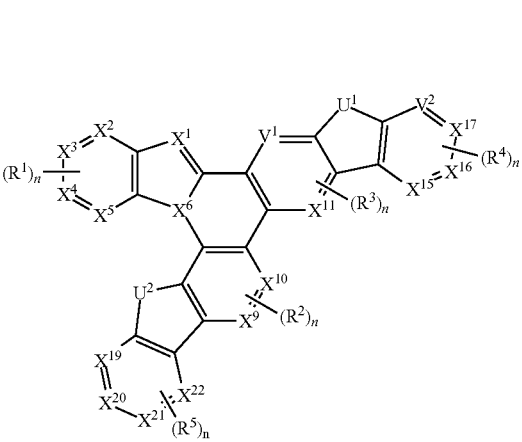

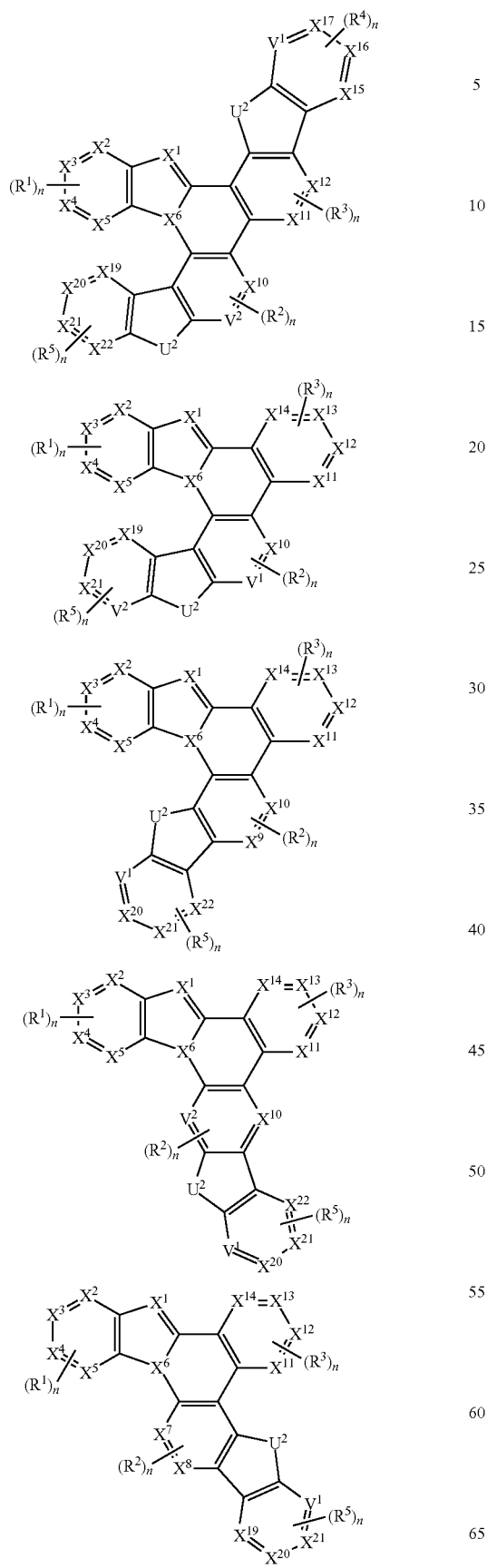
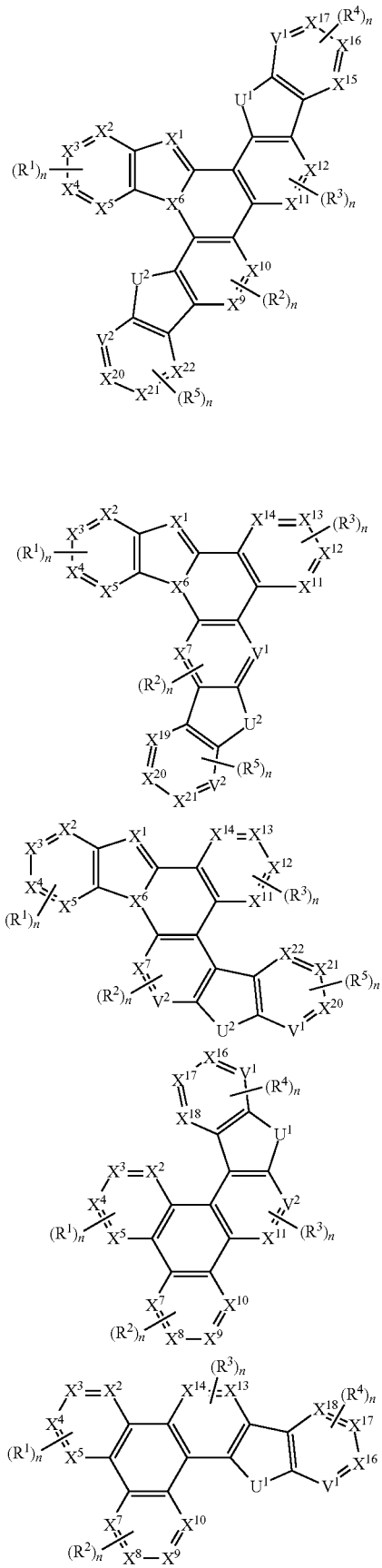

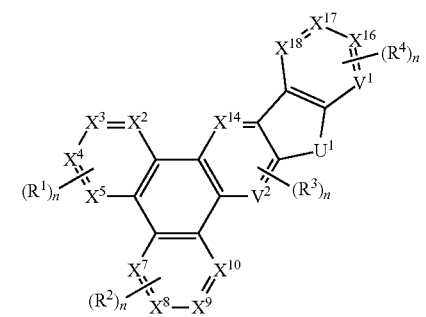
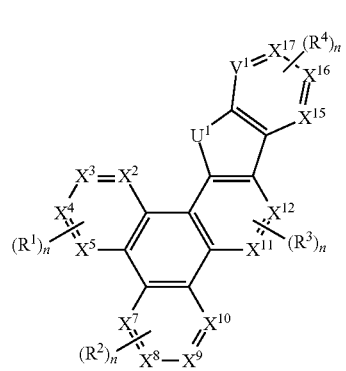
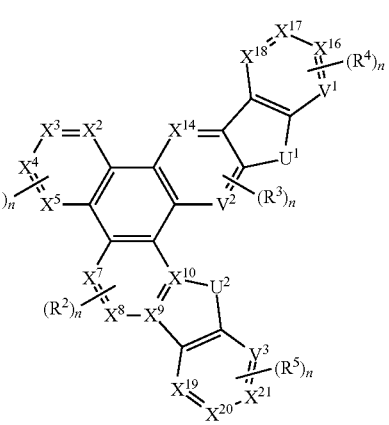
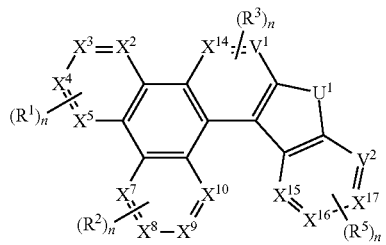
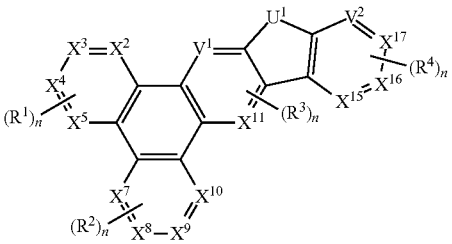
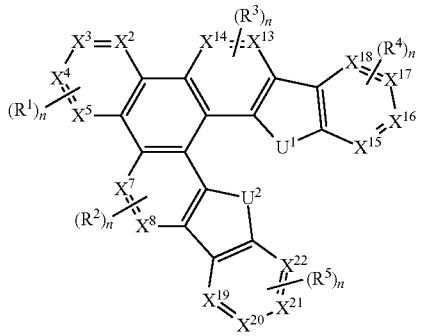
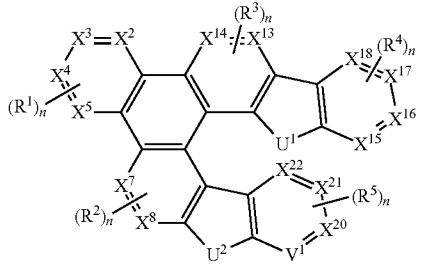
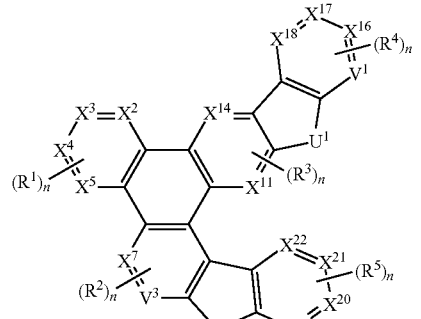
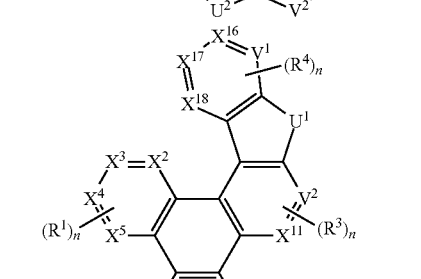
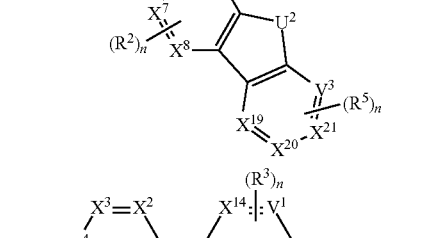
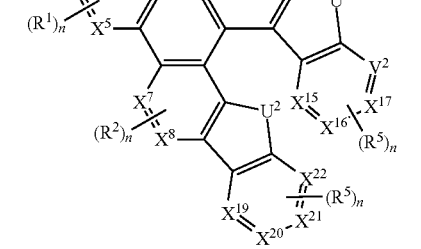

-continued
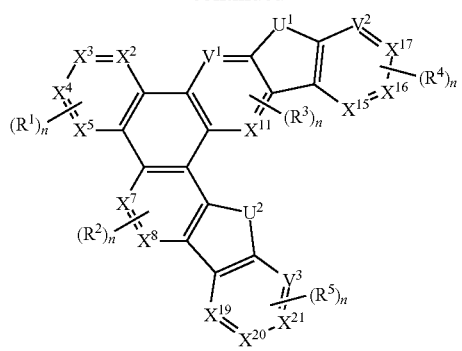
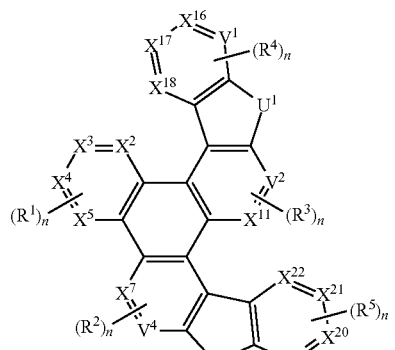
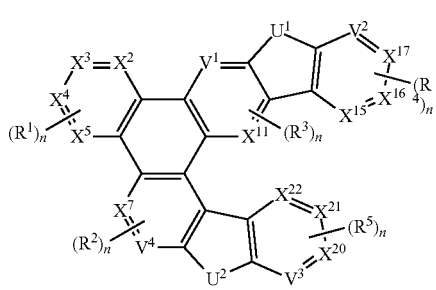
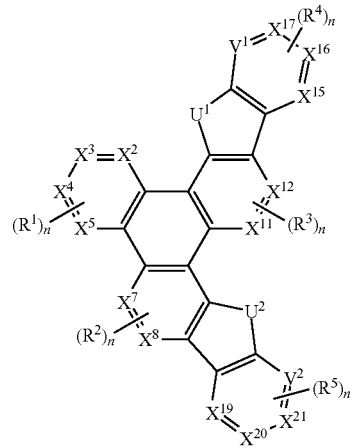
-continued
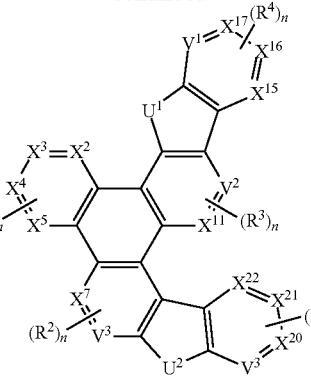
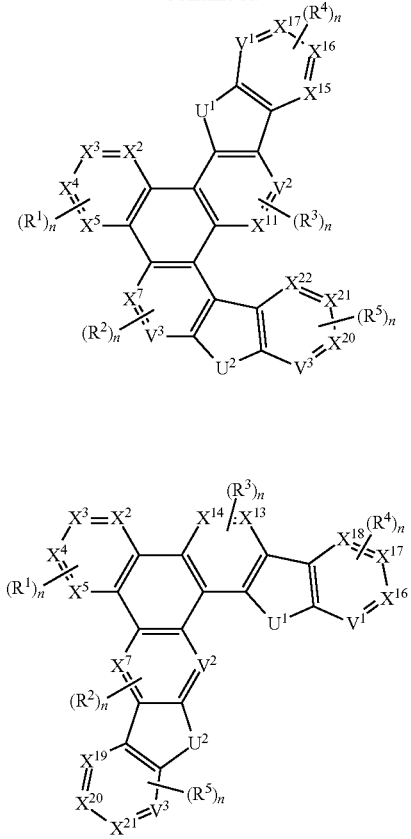
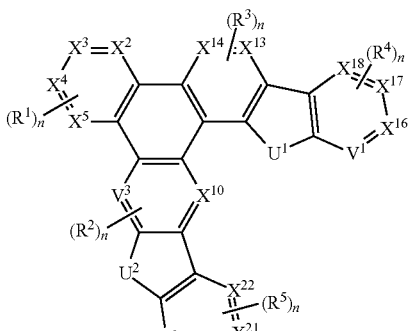
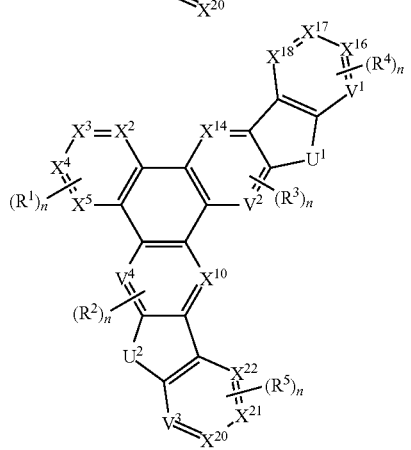

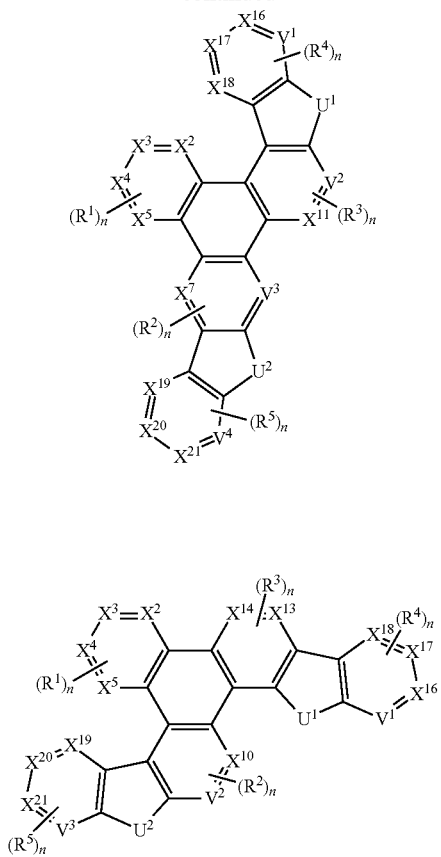
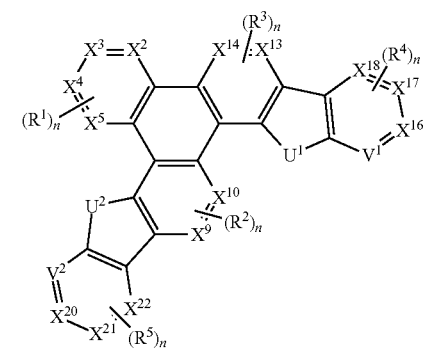
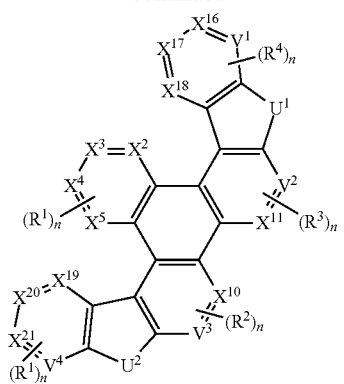
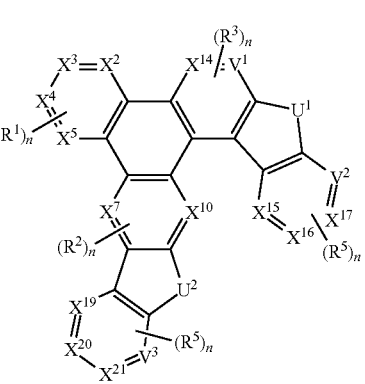
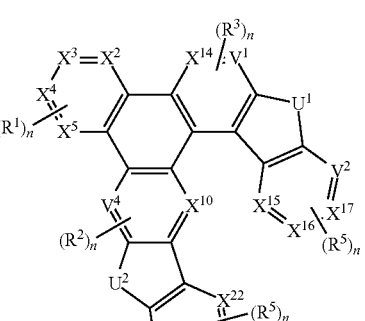
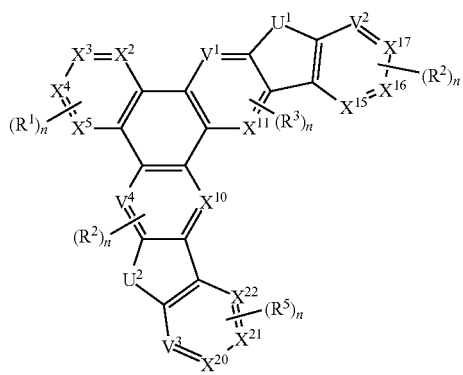

37
-continued
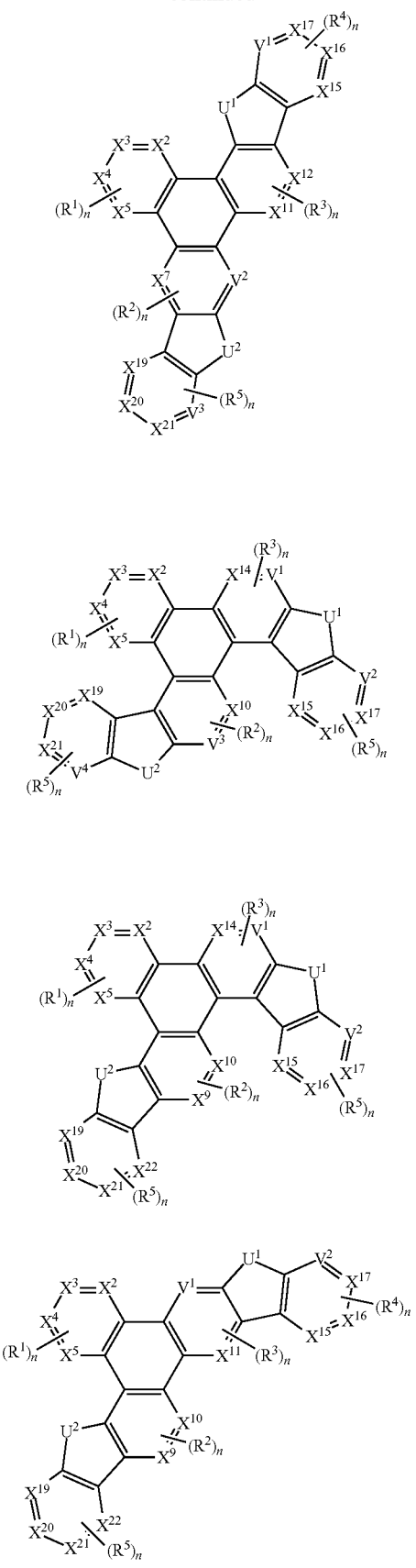
38
-continued
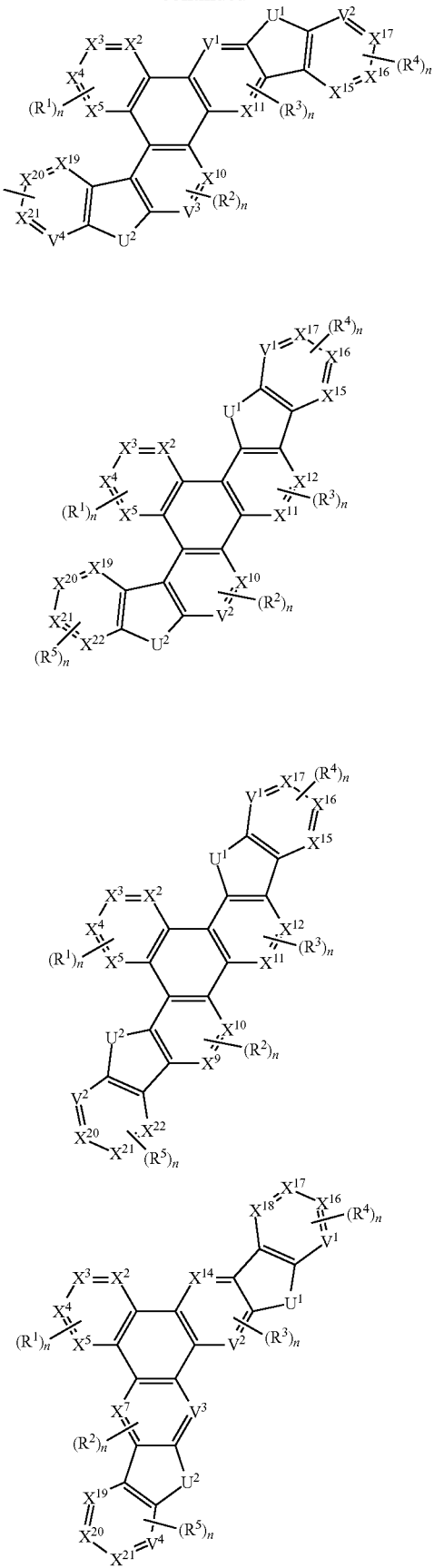

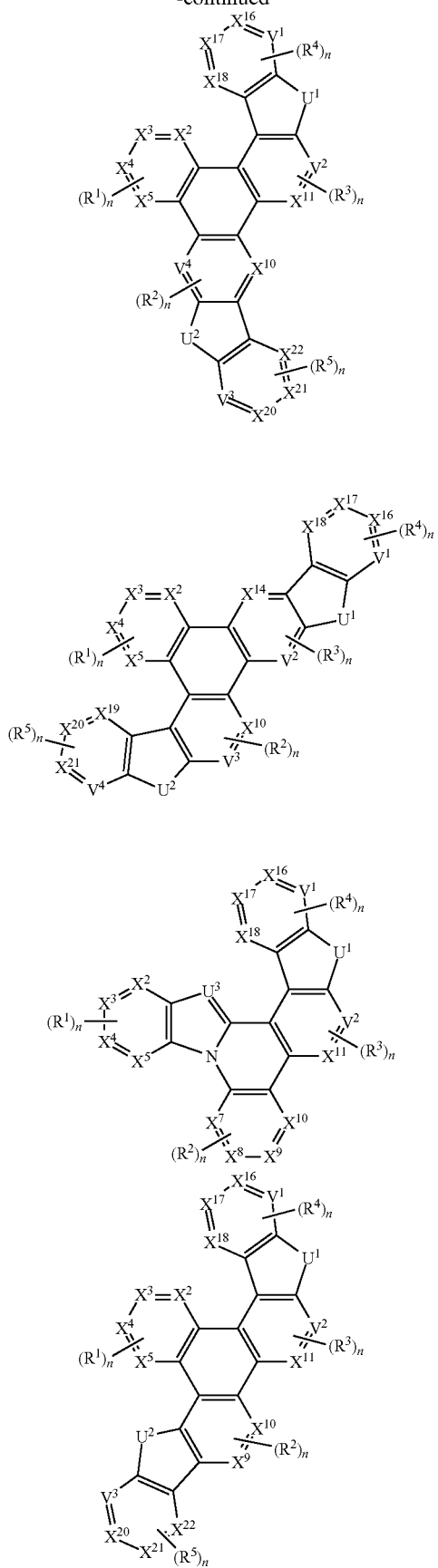
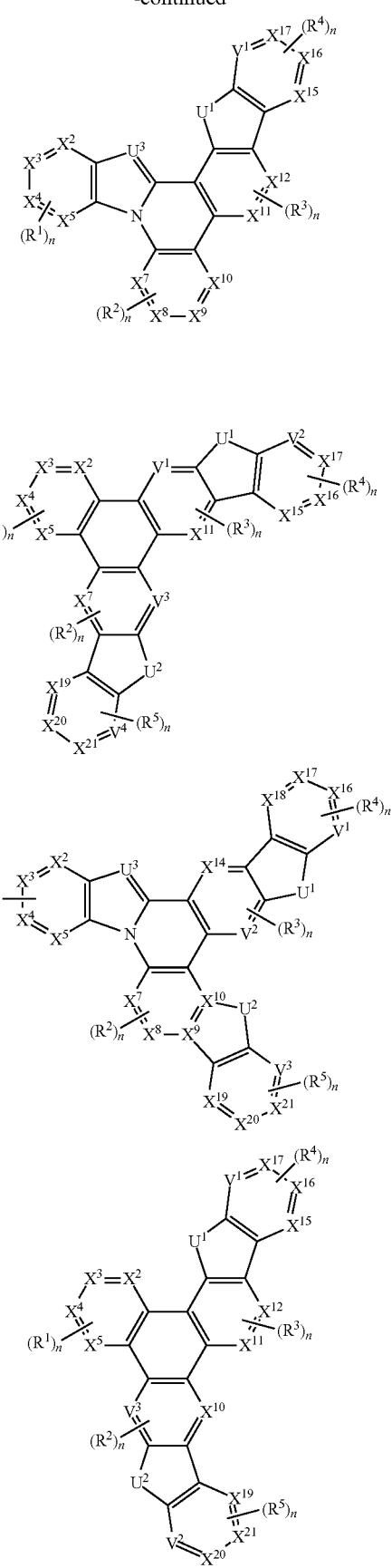

-continued
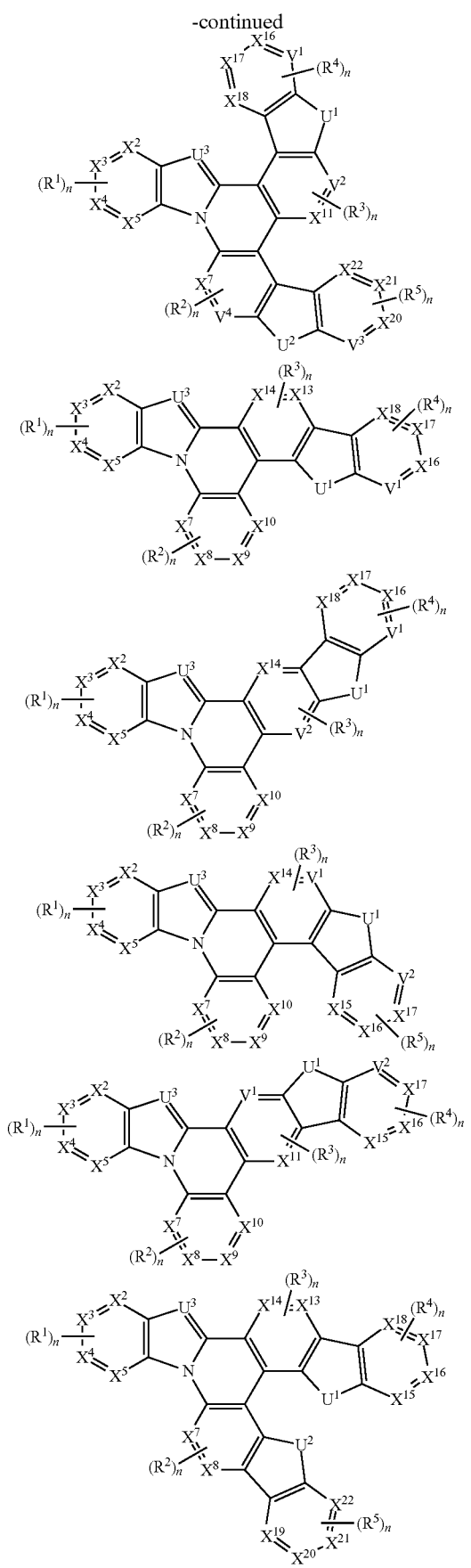
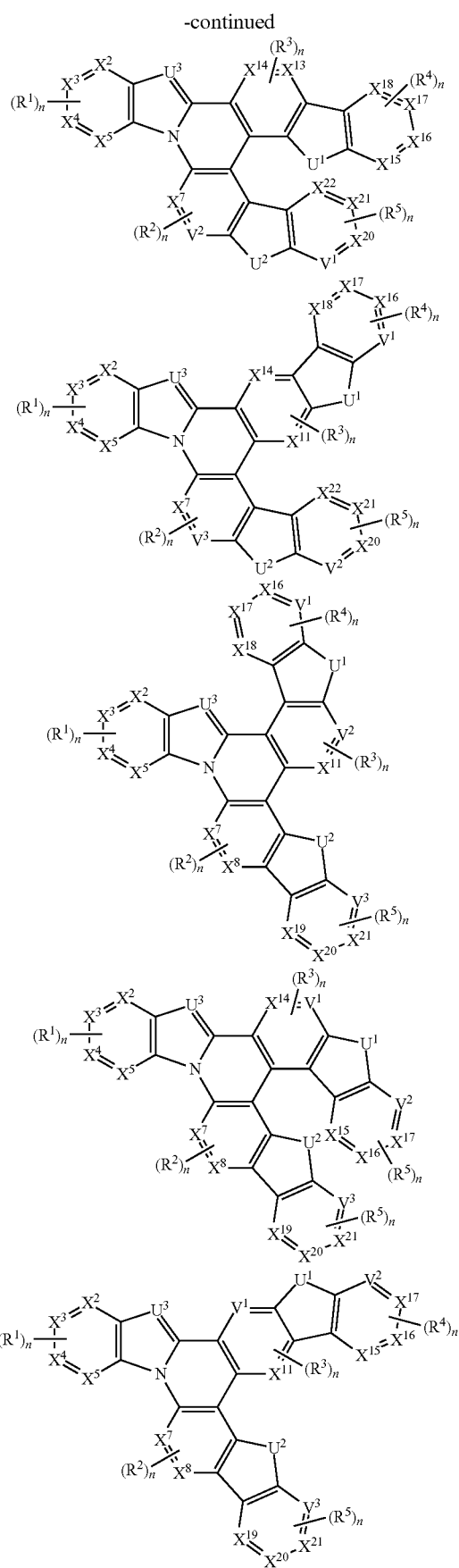

-continued
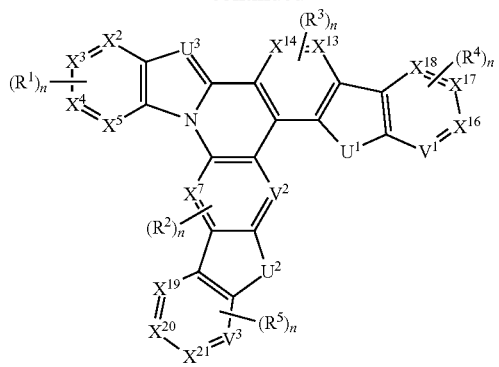
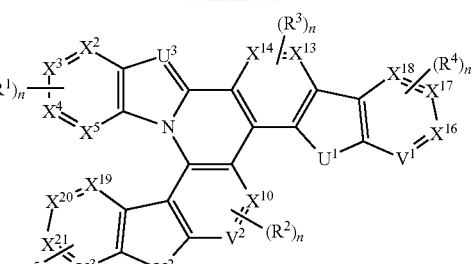
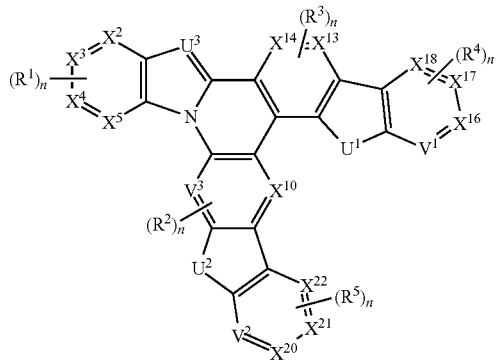
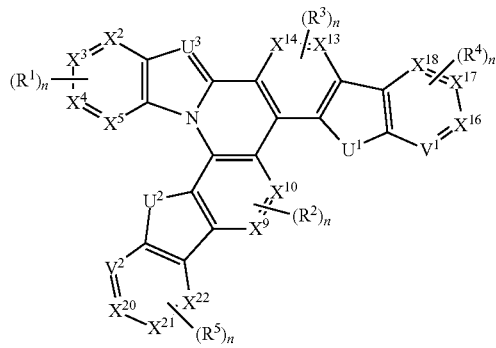
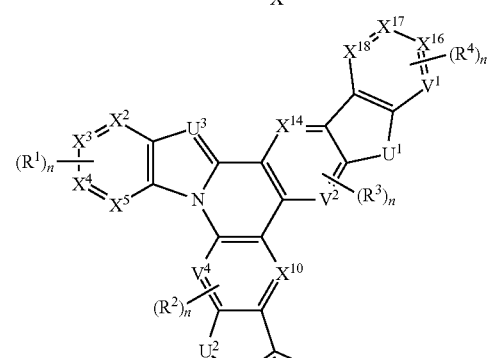
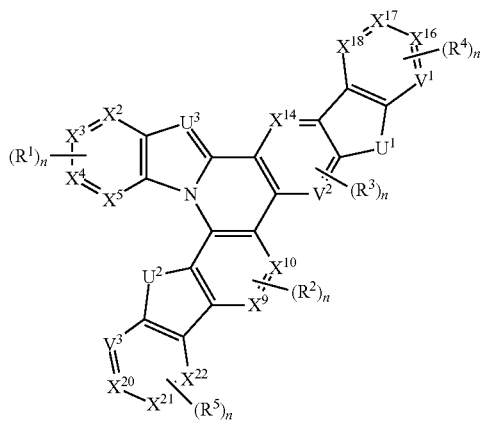
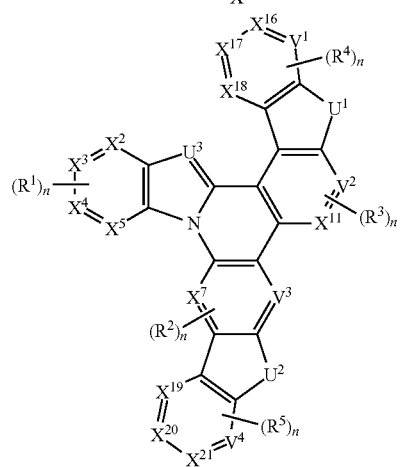
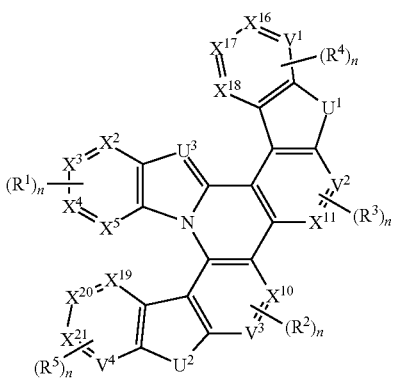

-continued
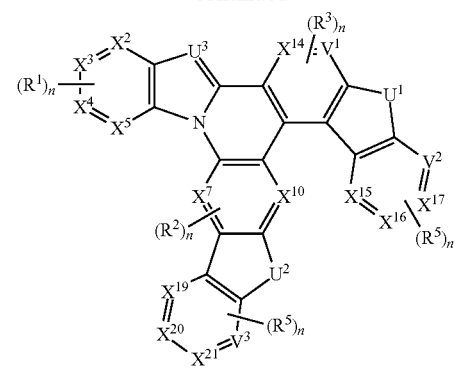
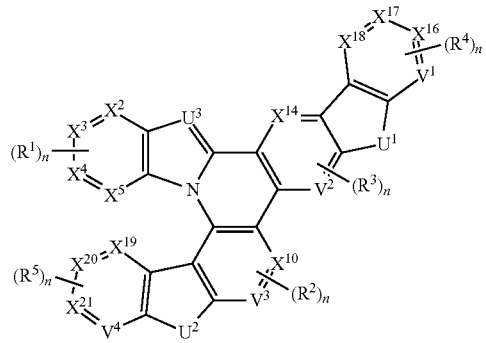
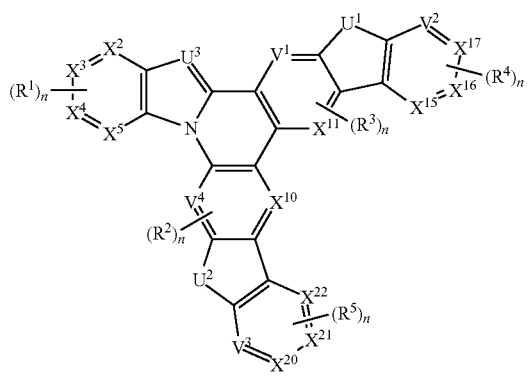
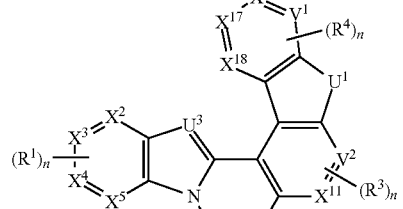
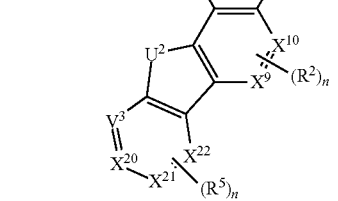
-continued
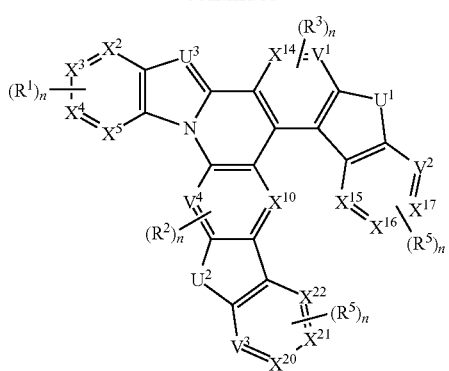
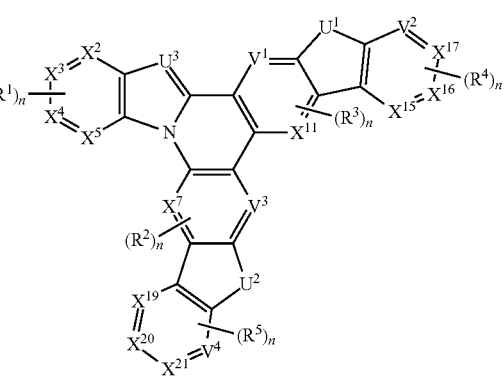
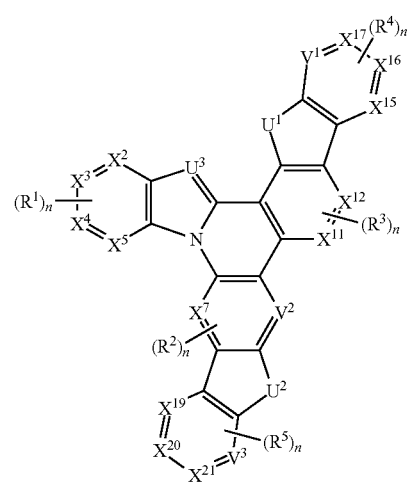
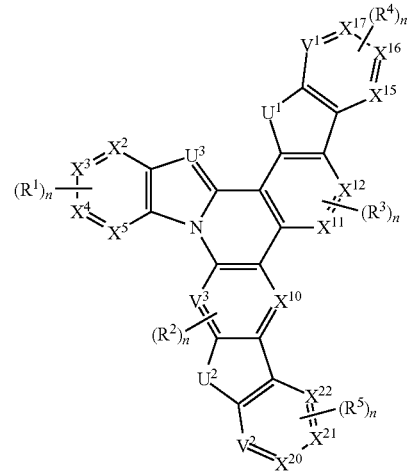

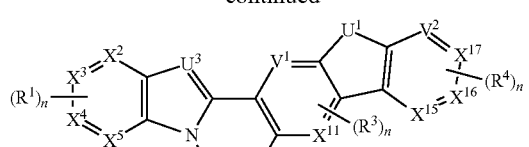
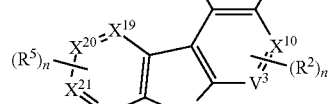
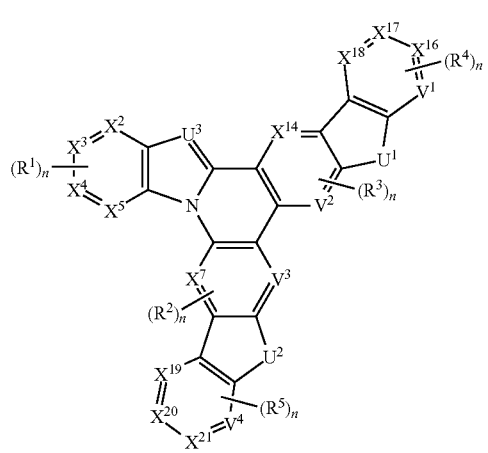
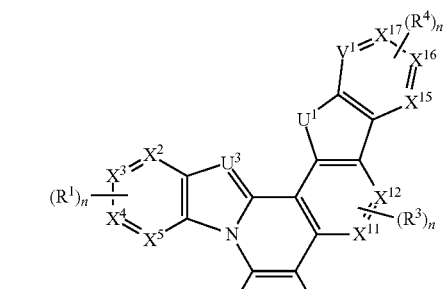
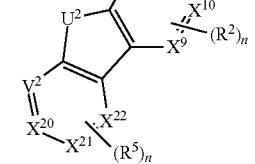
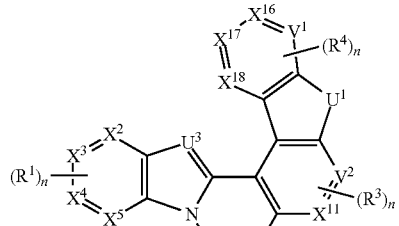
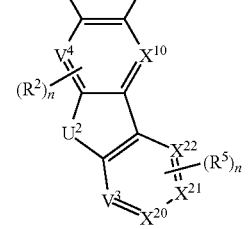
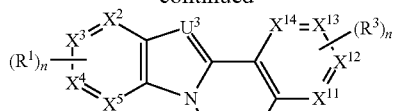
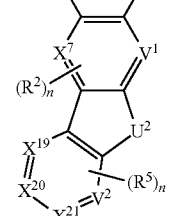
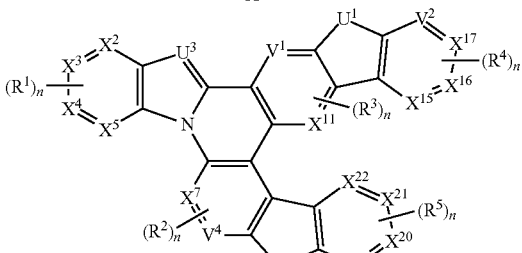
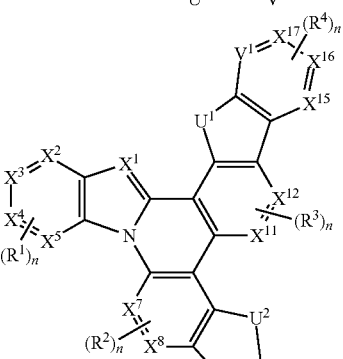
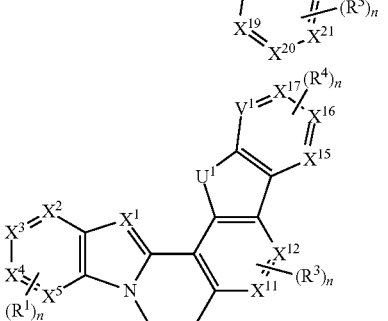
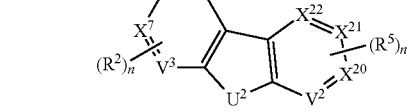
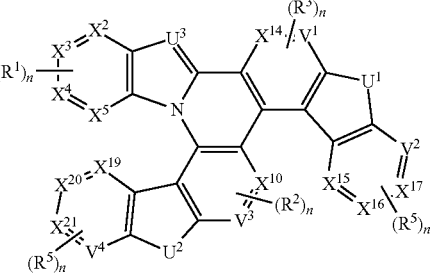

-continued
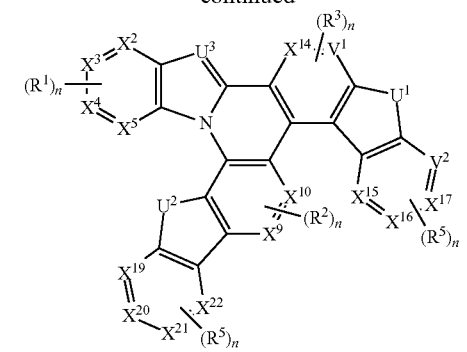
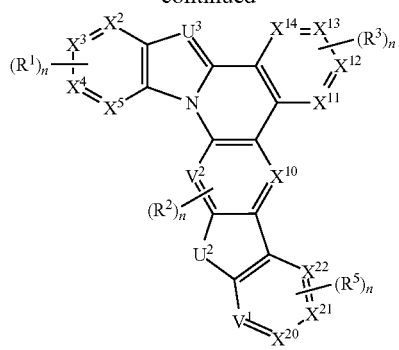
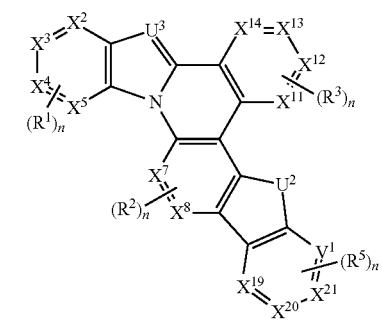
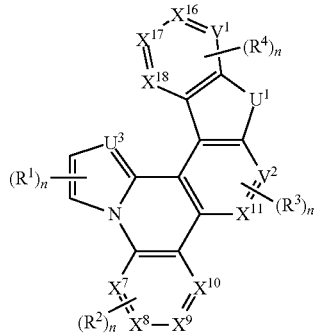
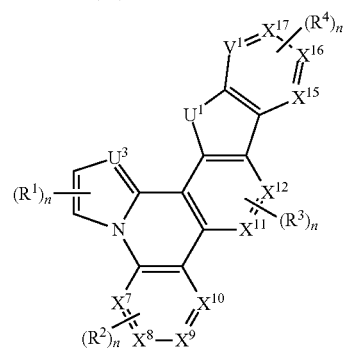
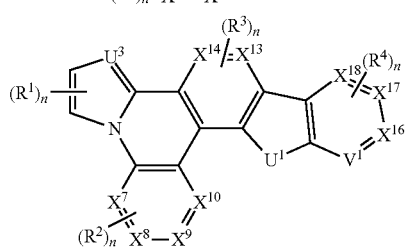

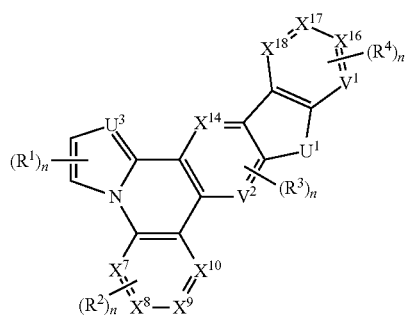
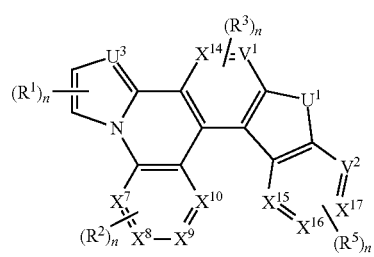
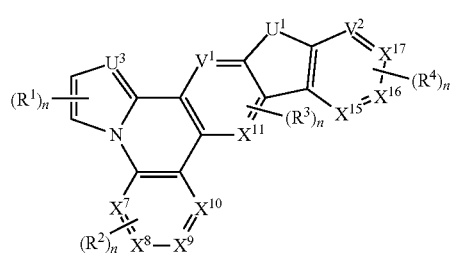
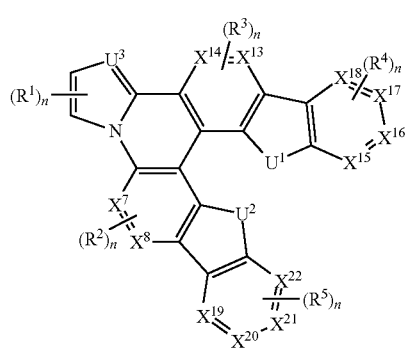
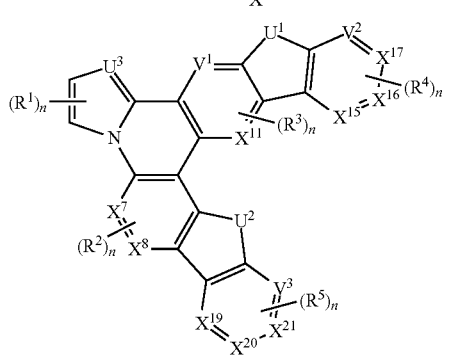
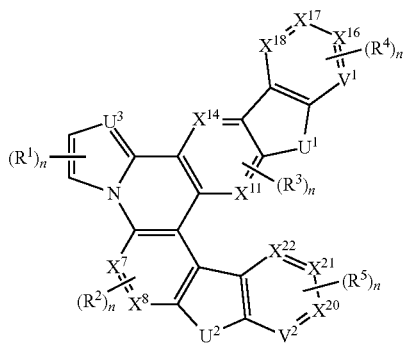
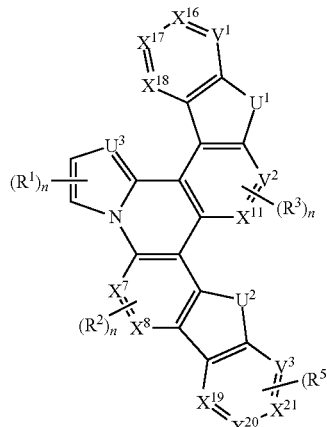
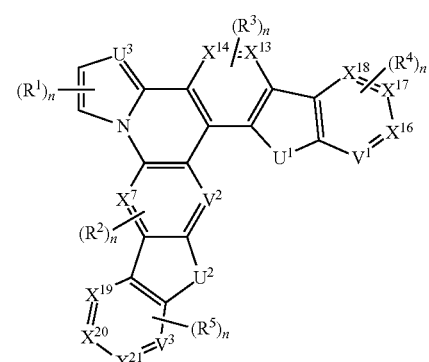
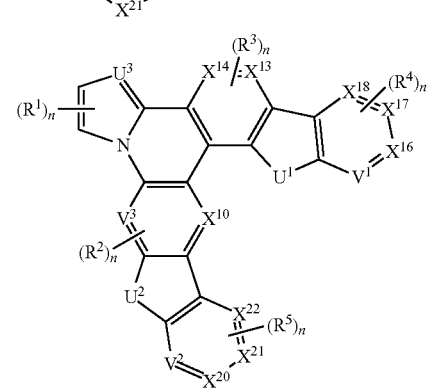

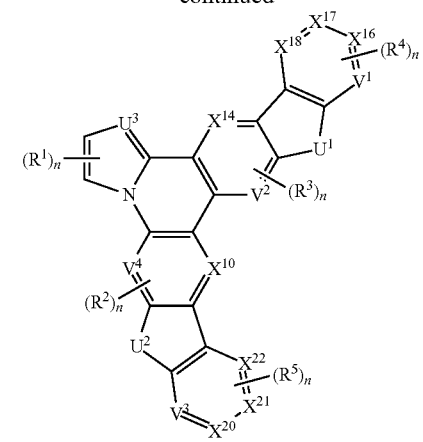
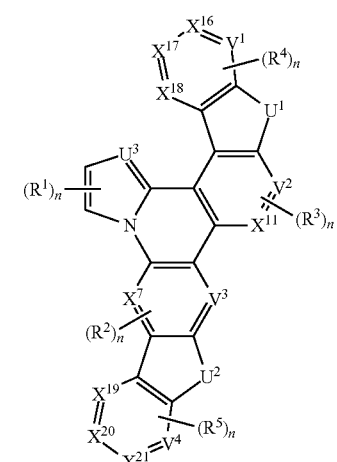
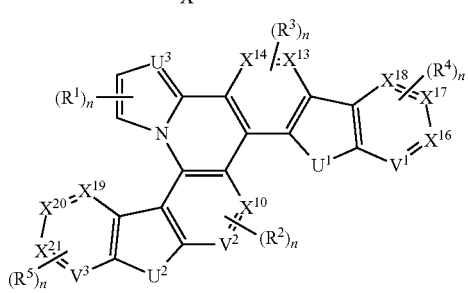
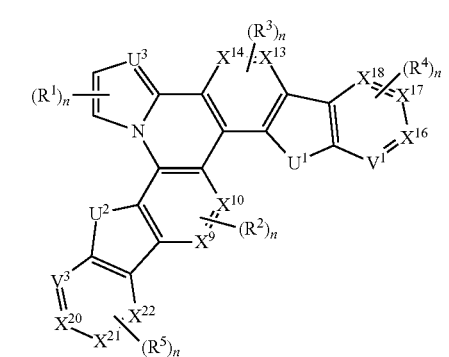
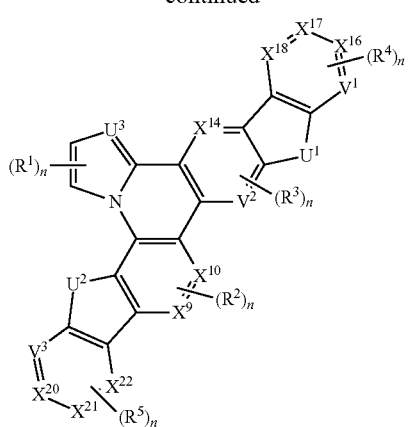
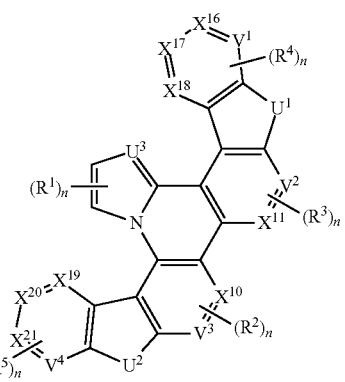
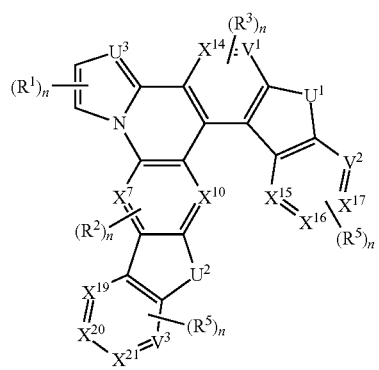
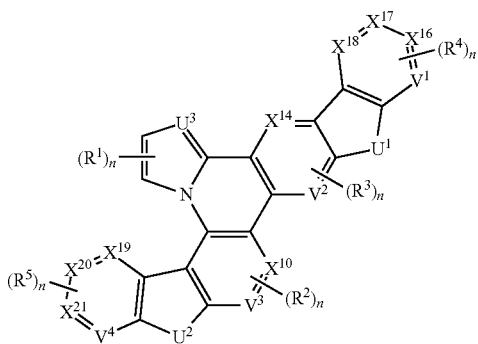

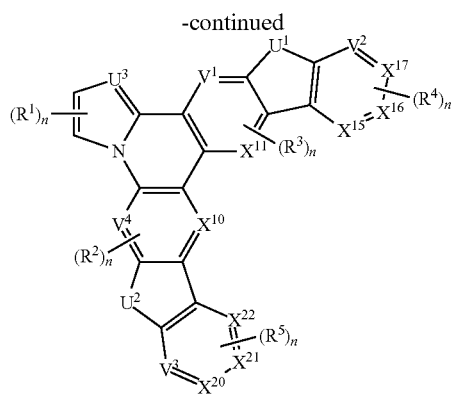
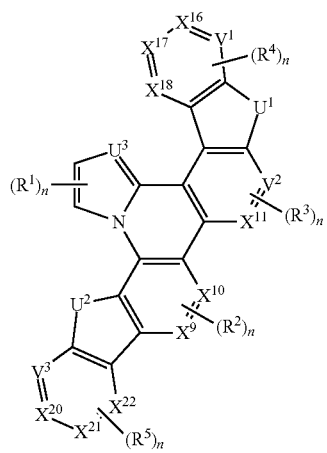
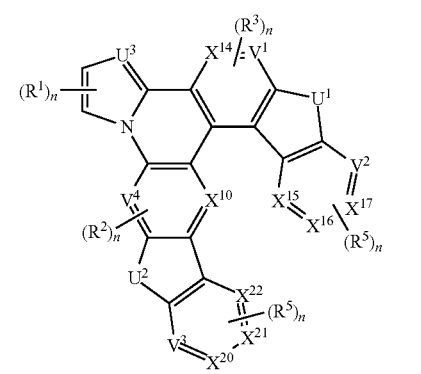
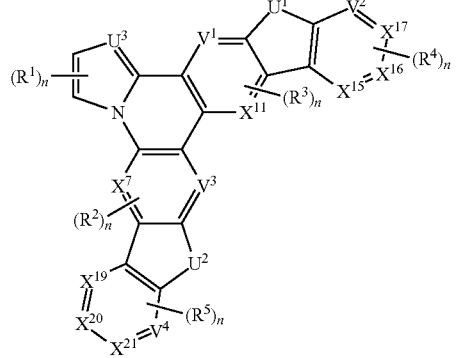
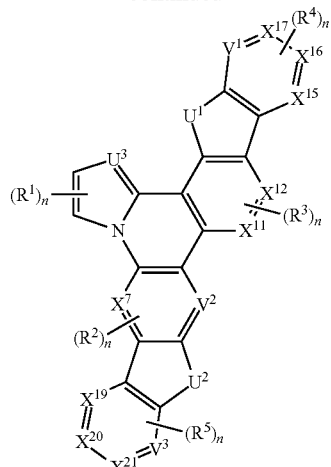
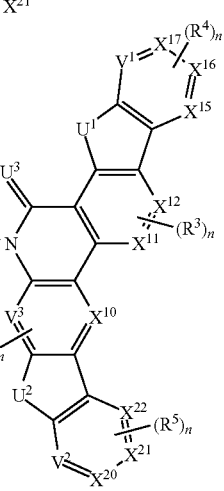
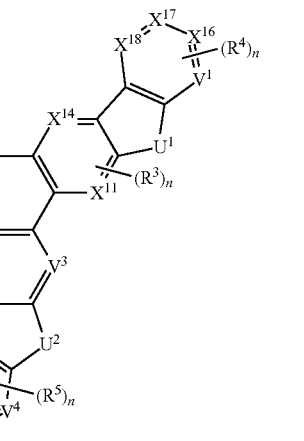

57
-continued
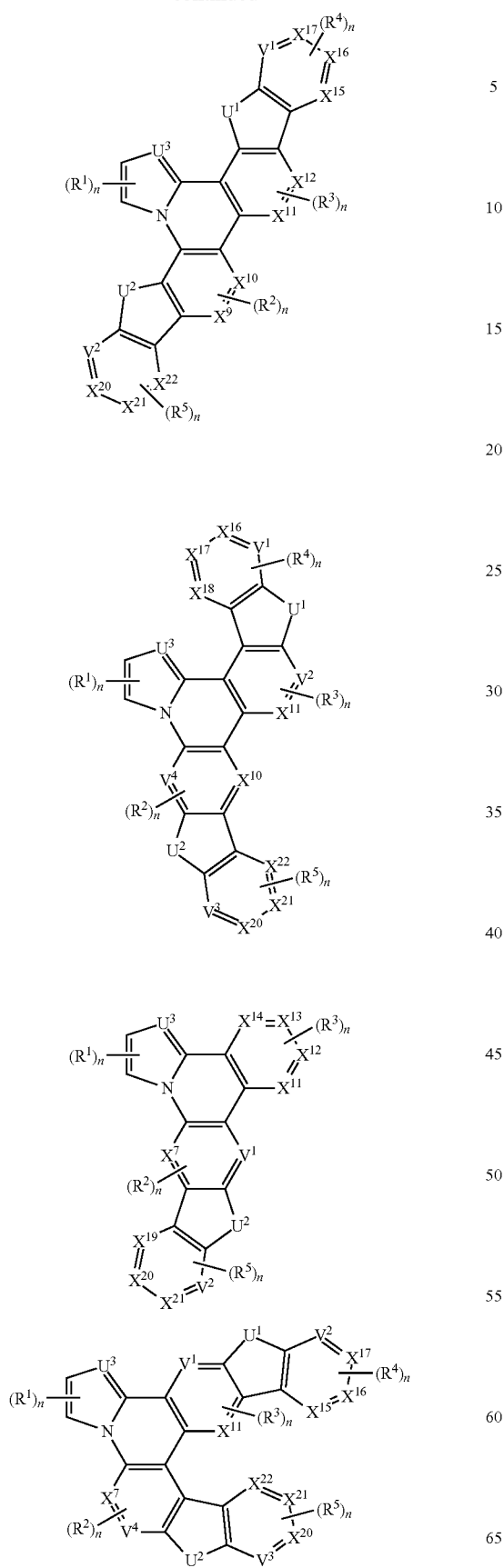
58
-continued
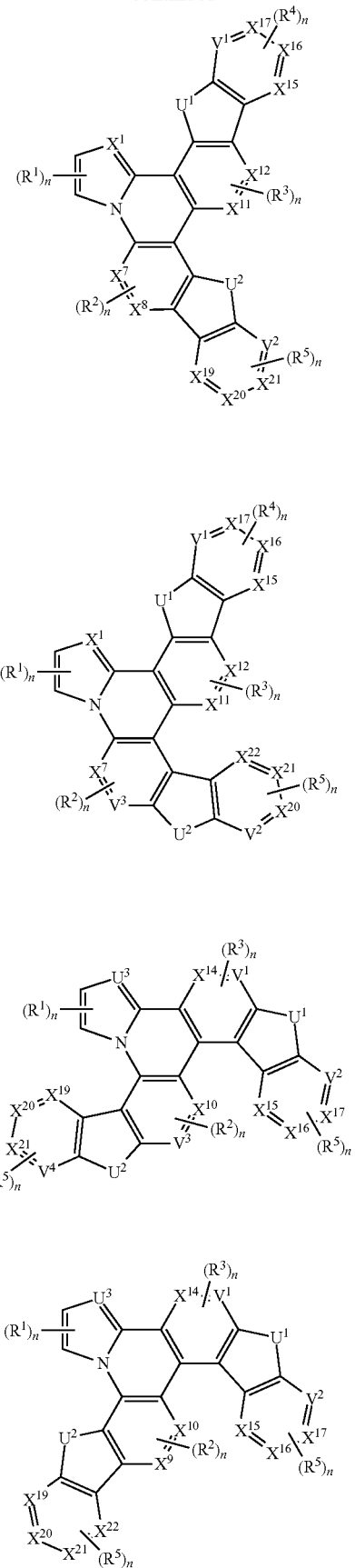

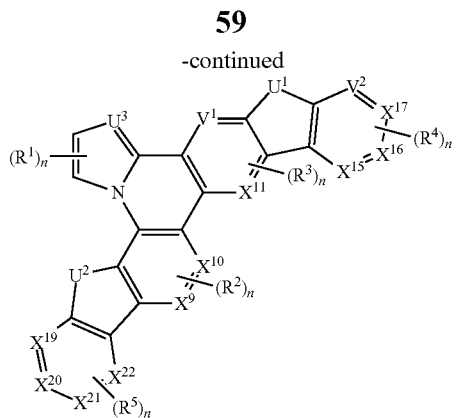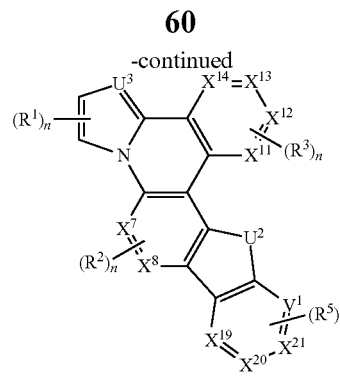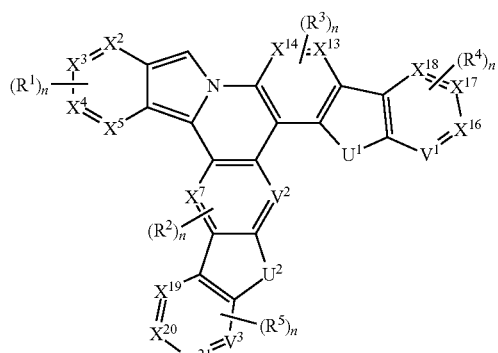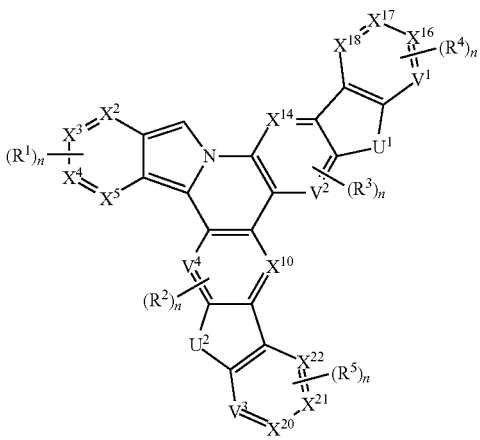

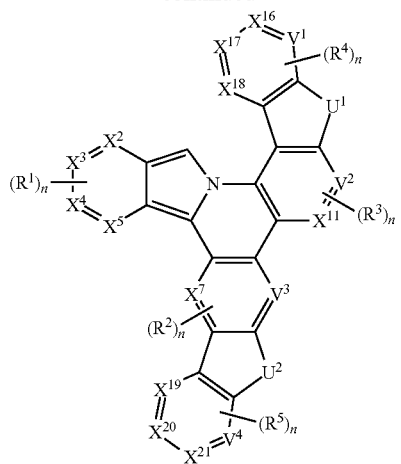
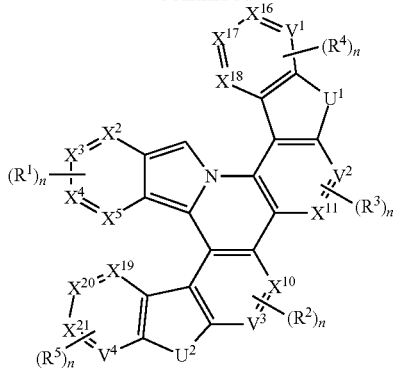
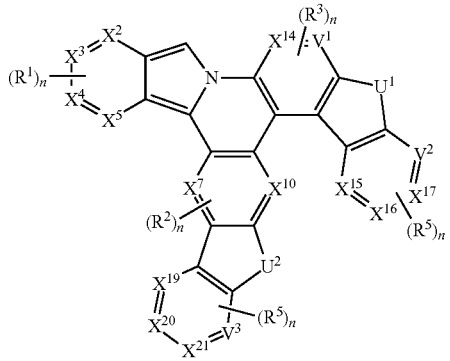
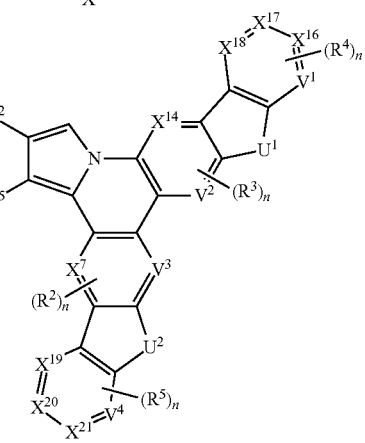
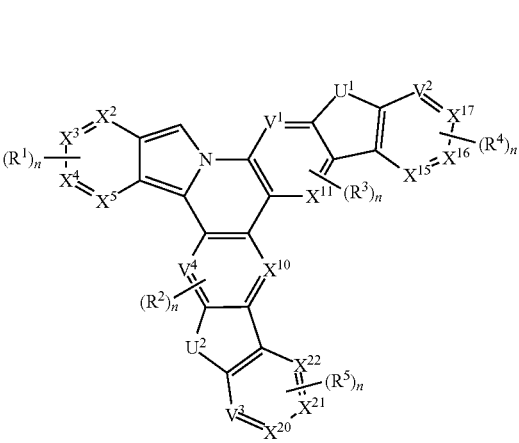

-continued
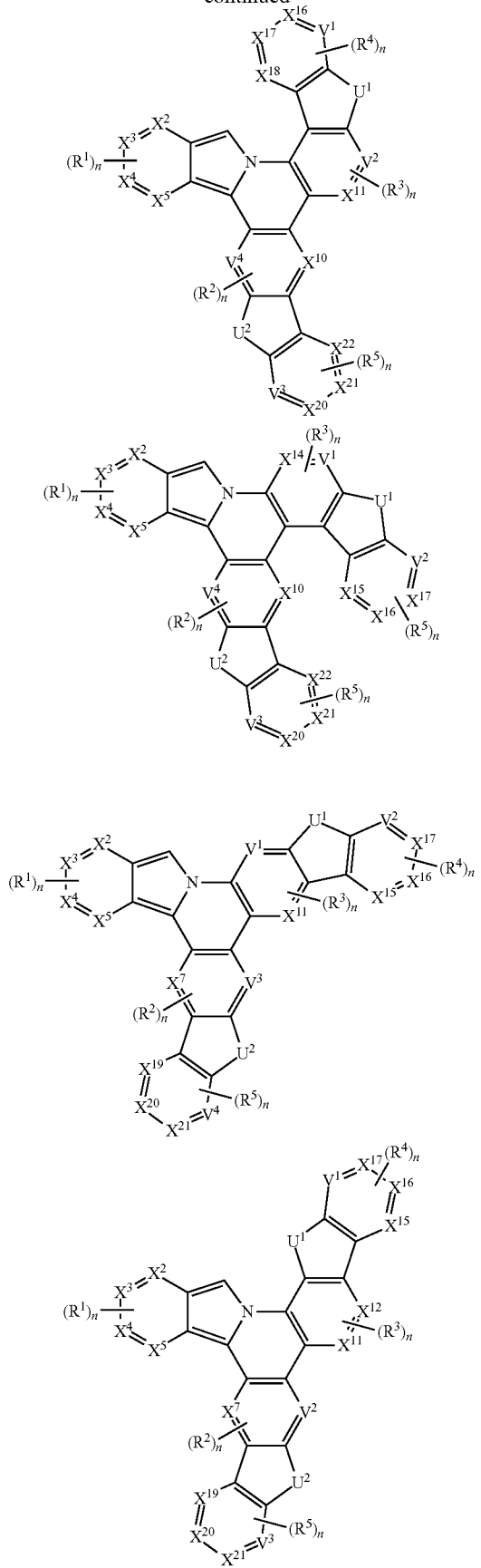
-continued
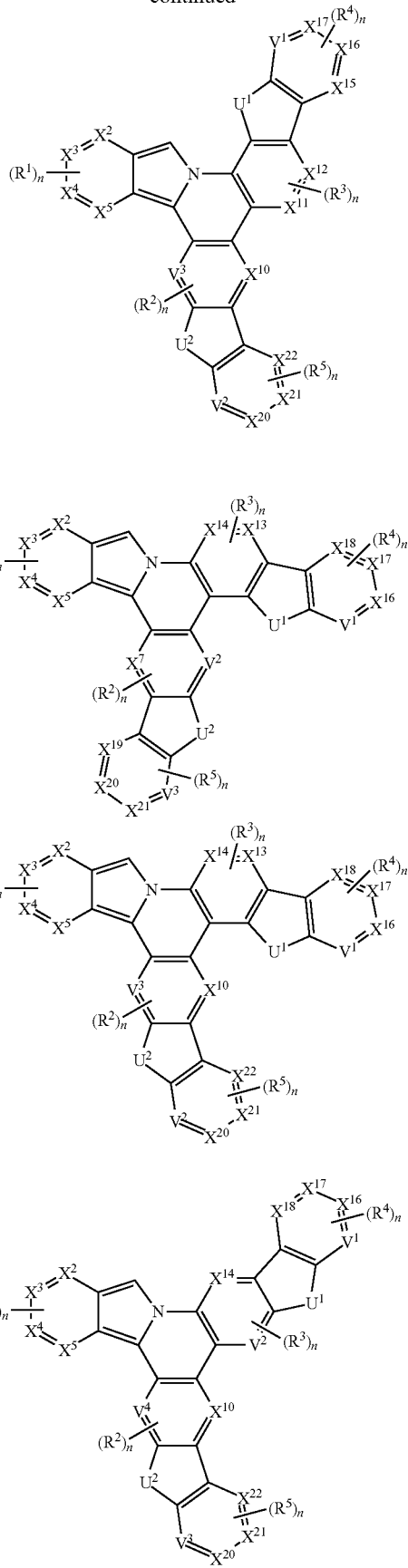

-continued
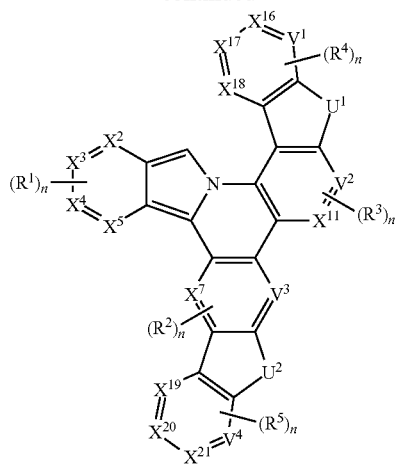
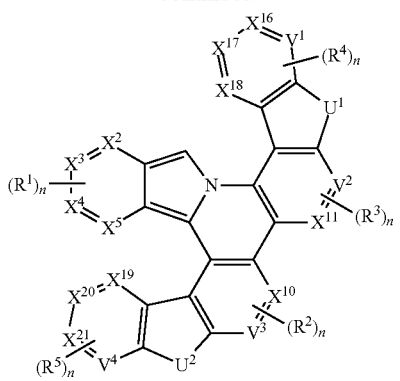
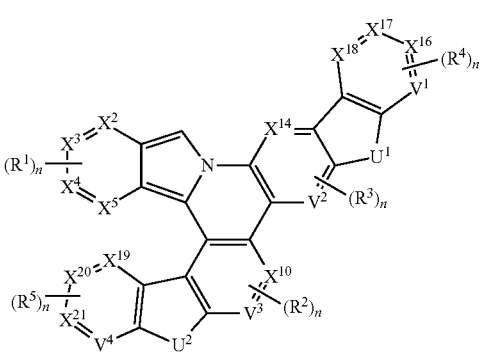
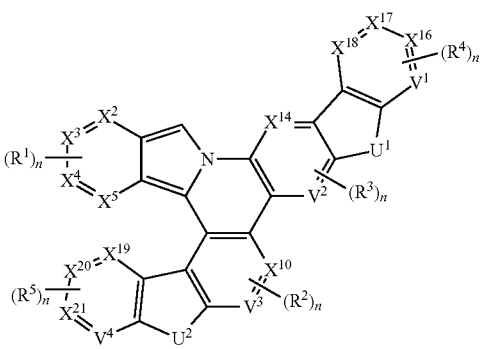
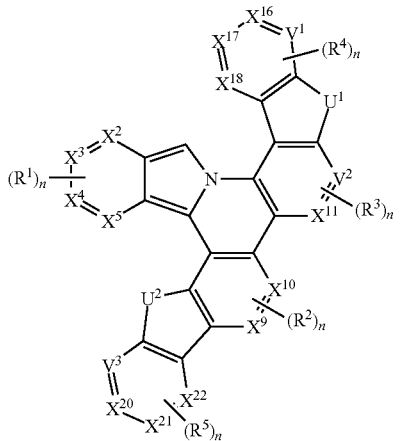

-continued
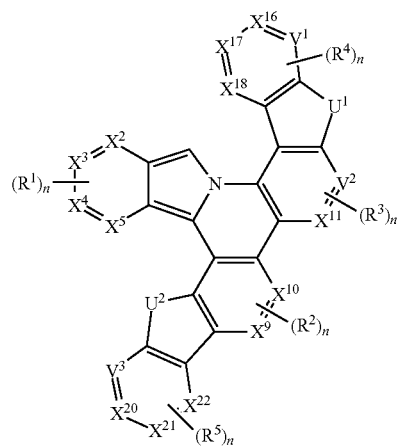
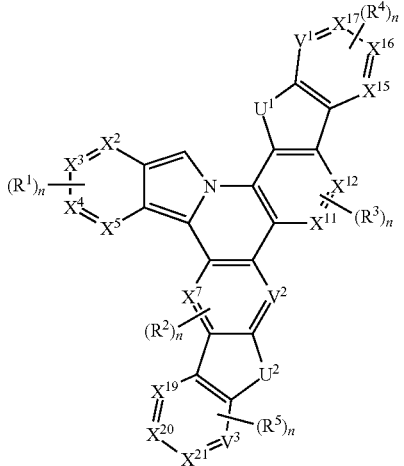
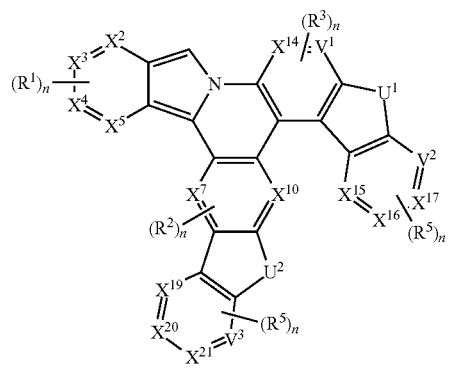
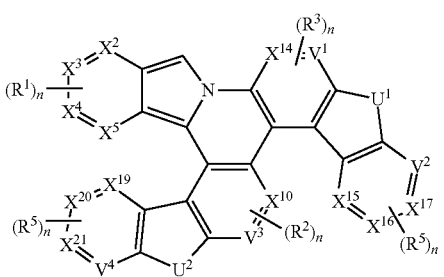
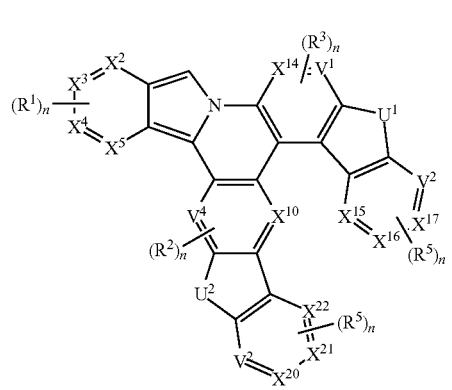
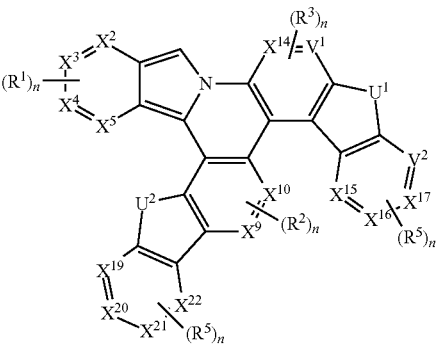
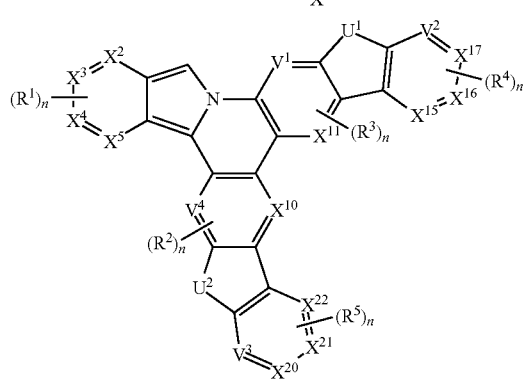
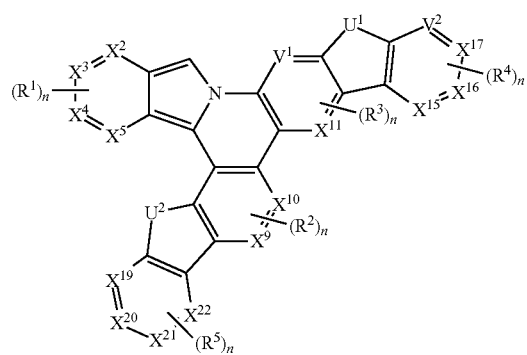

-continued
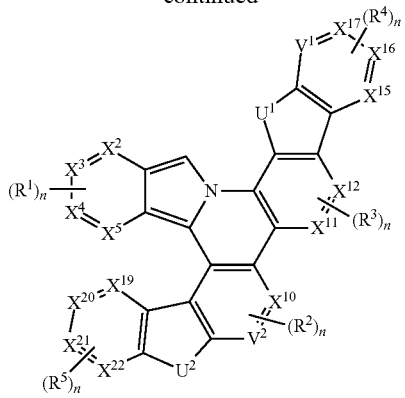
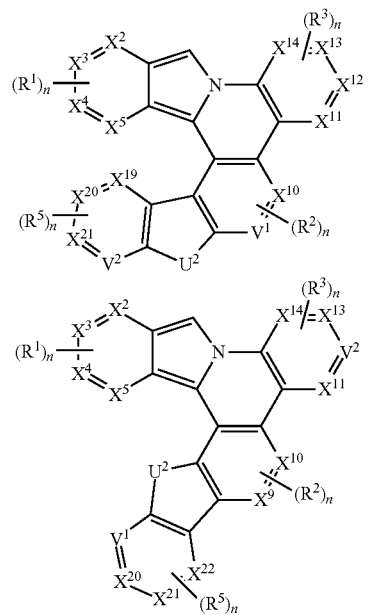
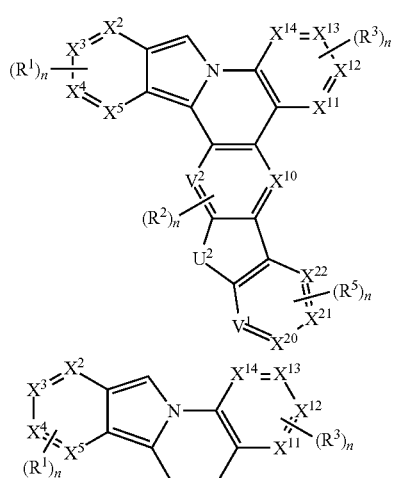
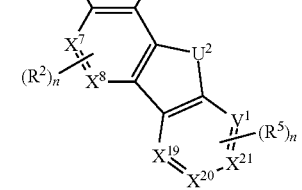
-continued
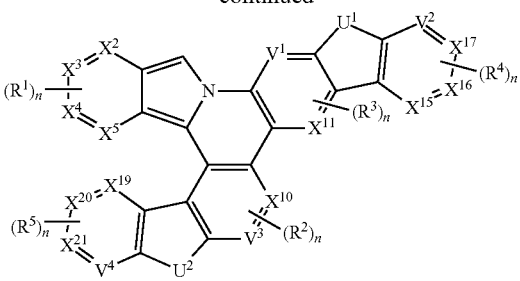
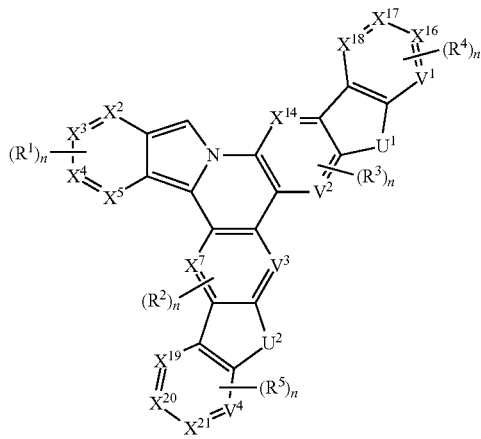
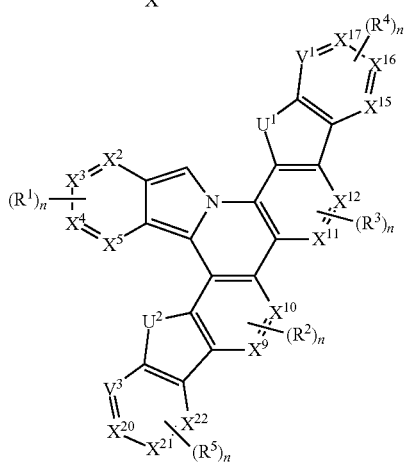
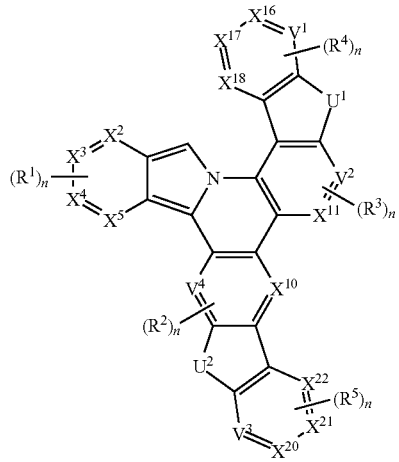

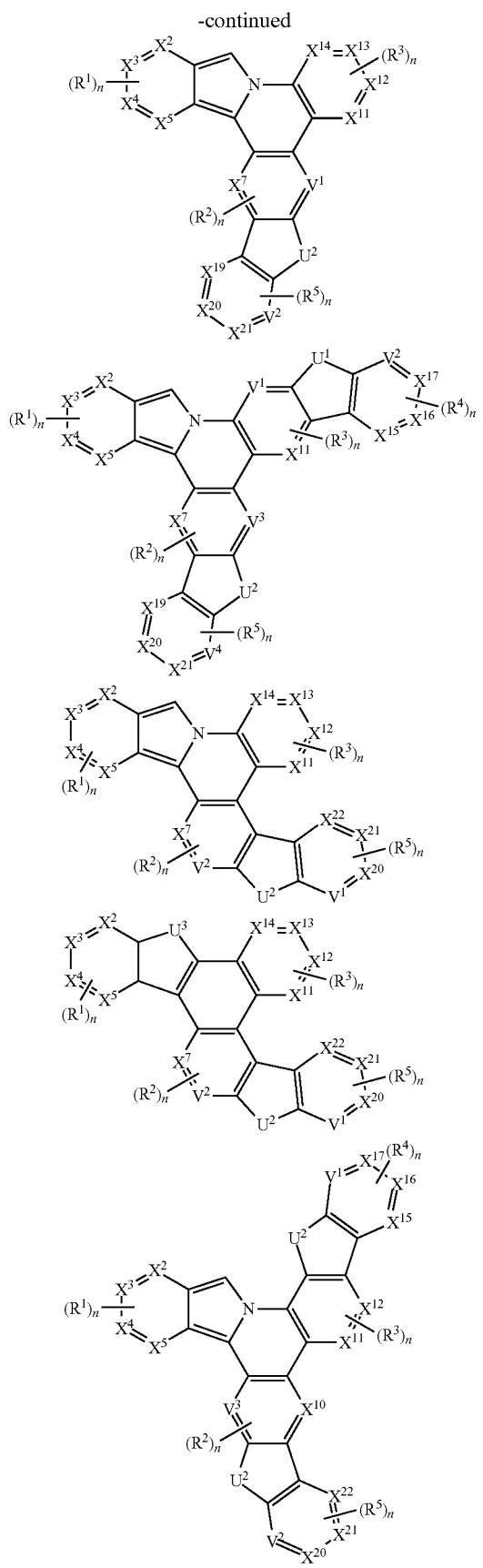

In these implementations of General Formulas I-IV, $R^1$, $R^2$, $R^3$, $R^4$, and $R^5$ each independently represents hydrogen, cyanide, halogen, hydroxy, amino, nitro, thiol, or substituted or unsubstituted $C_1$-$C_4$ alkyl, alkoxy, or aryl, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, and $X^{22}$ each independently represents substituted or unsubstituted C, N, Si, O, or S, valency permitting, $V^1$, $V^2$, $V^3$, and $V^4$ each independently represents substituted or unsubstituted C or N, valency permitting, $U^1$ and $U^2$ each independently represents O, S, CRR', SiRR', or NAr*, where R and R' each independently represents hydrogen, cyanide, halogen, hydroxy, amino, nitro, thiol, or optionally substituted $C_1$-$C_4$ alkyl, alkoxy, or aryl, and Ar* represents a substituted phenyl, pyridyl, naphthyl, pyrimidyl, pyridazinyl, pyrazinyl, pyrazolyl, imidazolyl, oxazolyl, or thiazolyl ring, and Ar* is optionally covalently bonded to $V^1$, $V^2$, $V^3$, or $V^4$ to form one or more 5-membered or 6-membered rings, $U^3$ and $U^4$ each independently represents CR, SiR, or N, where R represents optionally substituted $C_1$-$C_4$ alkyl, alkoxy, aryl or heteroaryl, and each n is independently an integer as permitted by valence.

Compounds of General Formulas I-IV are shown below.

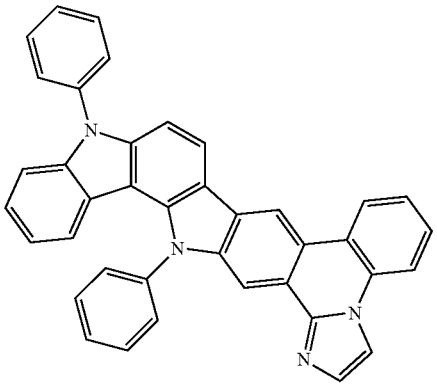

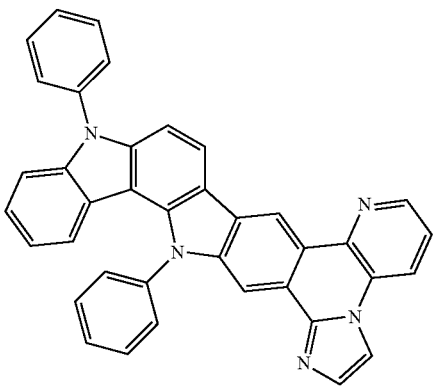

73
-continued
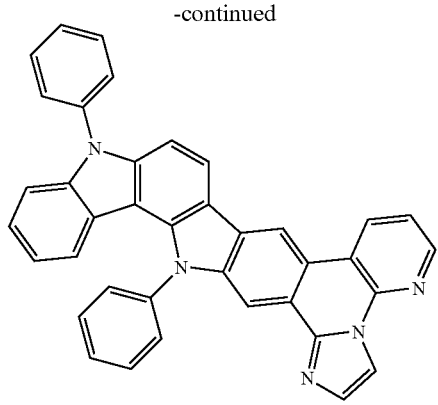
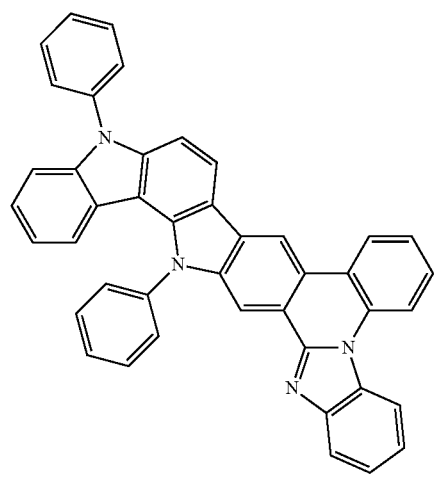
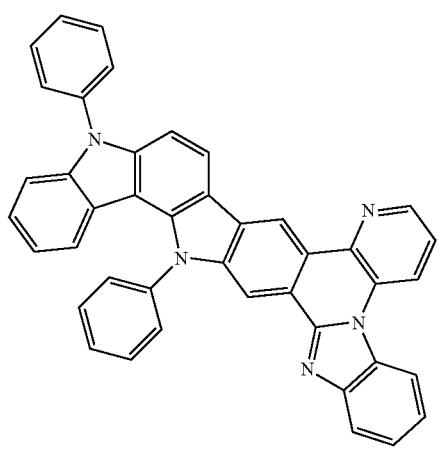
74
-continued
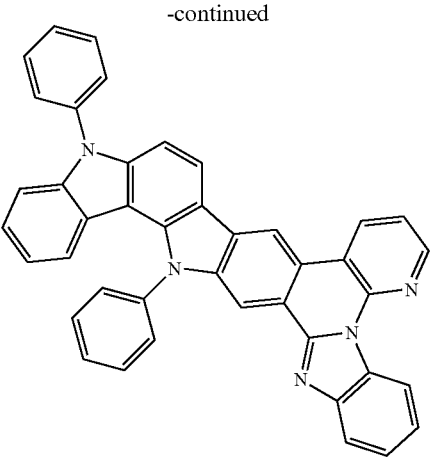
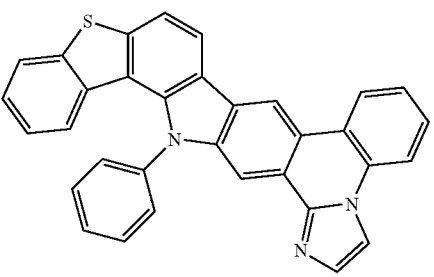
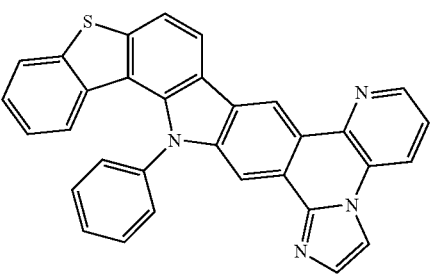
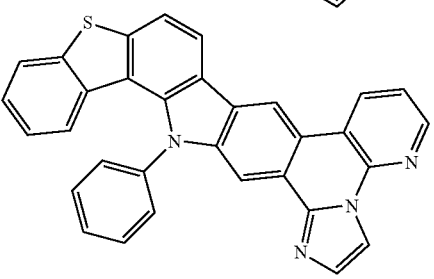
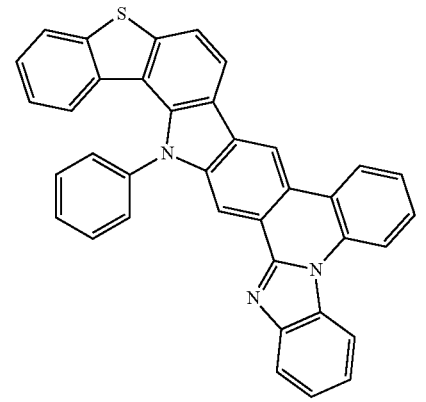

75
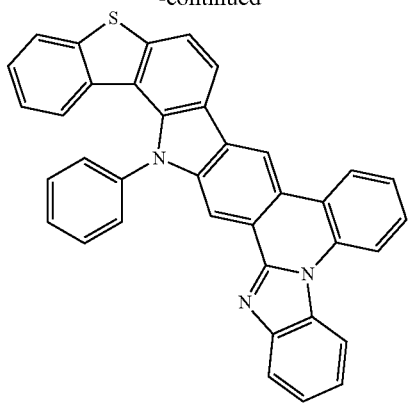
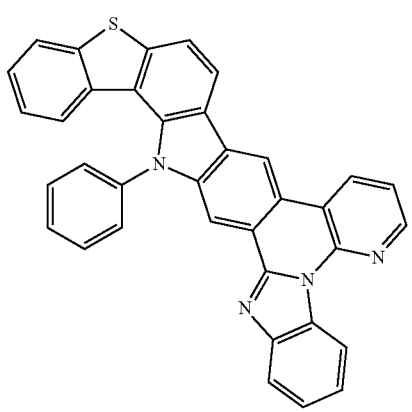
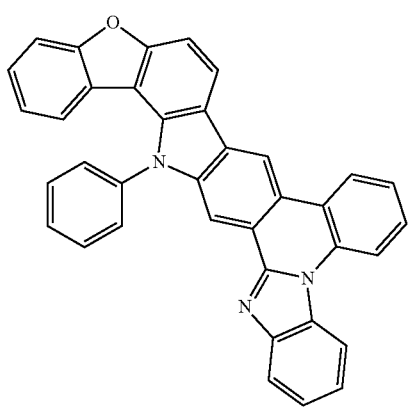
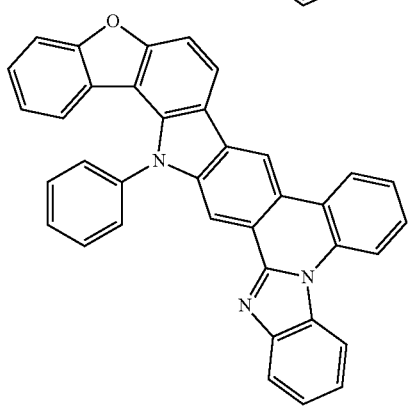
76
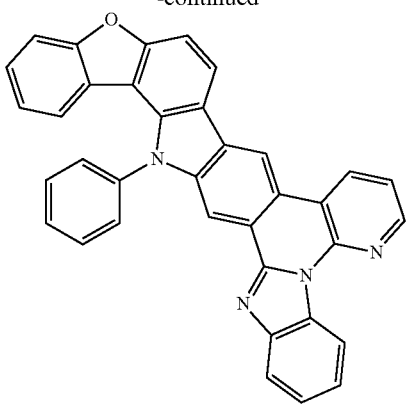
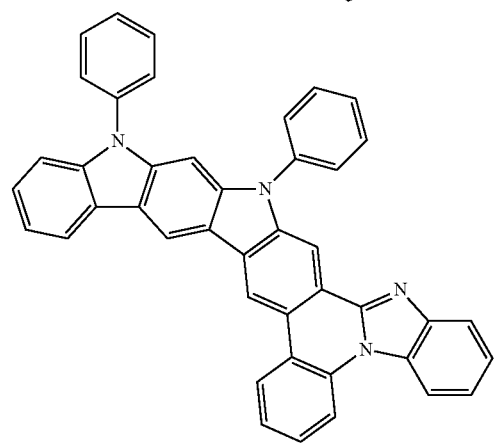
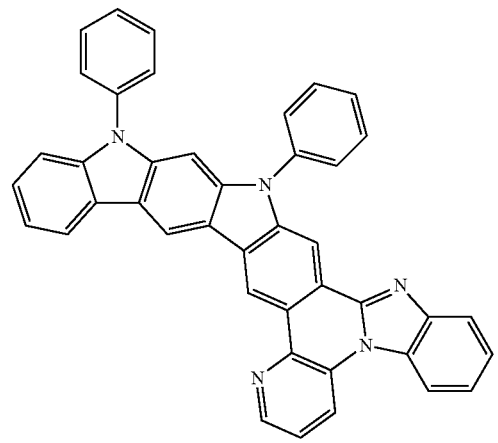
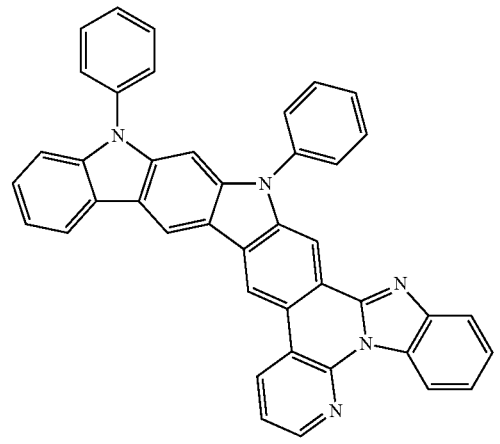

77
-continued
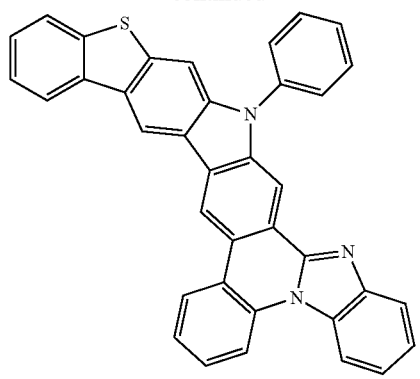
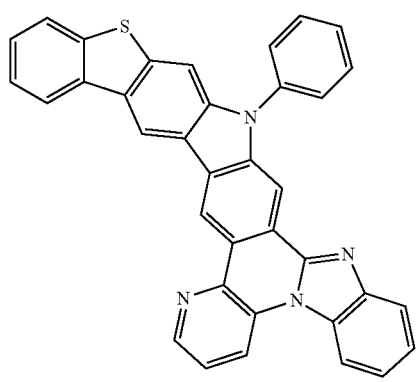
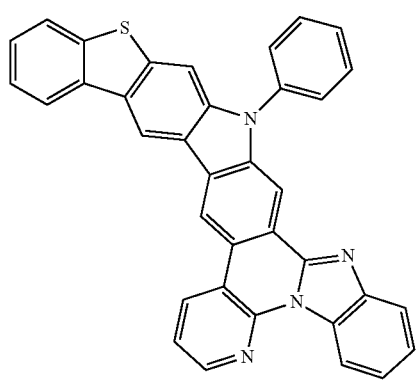
78
-continued
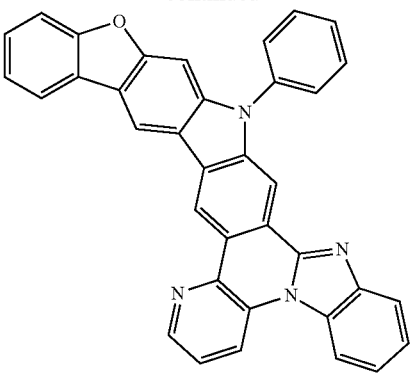
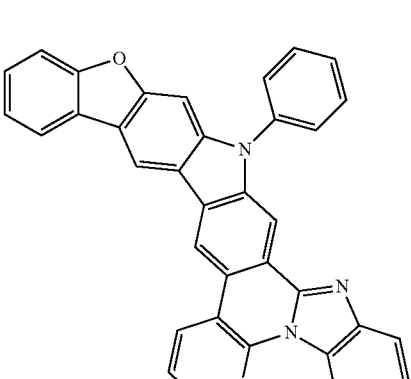
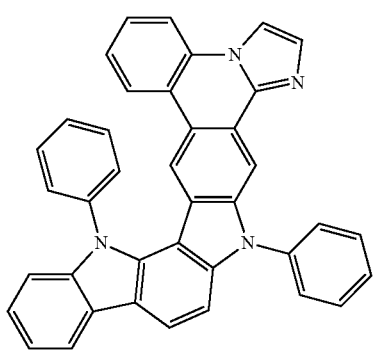
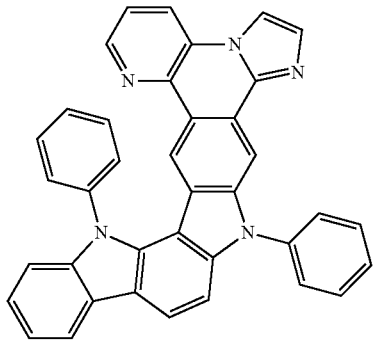

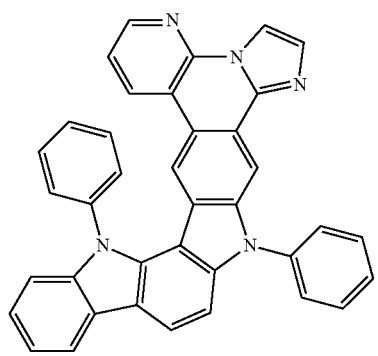
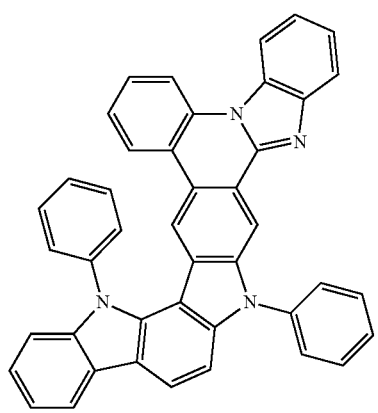
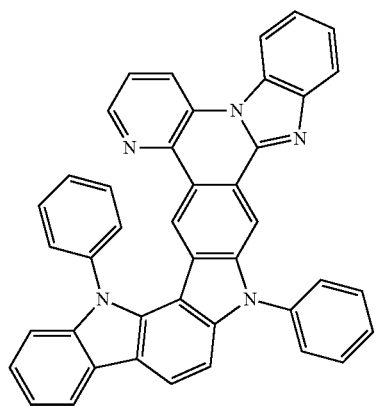
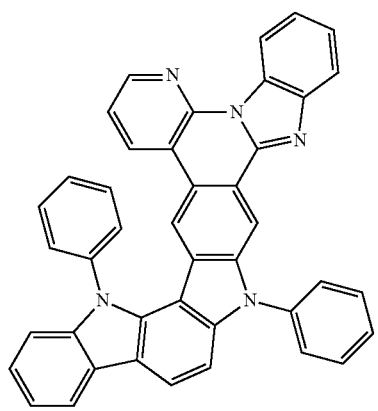
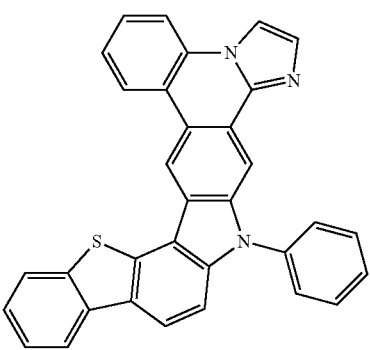
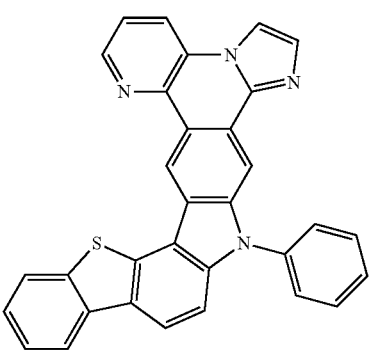
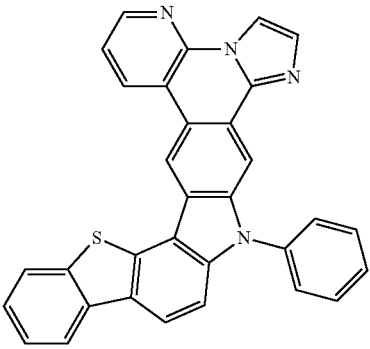
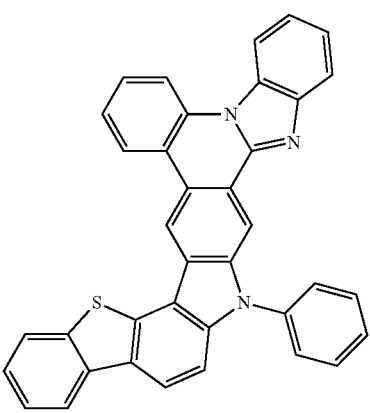

81
-continued
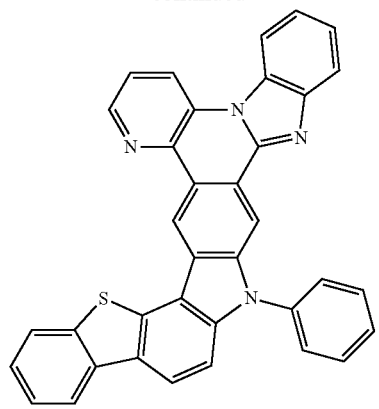
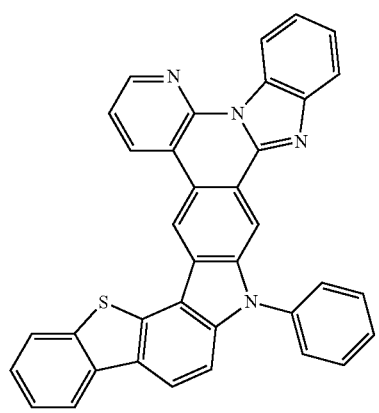
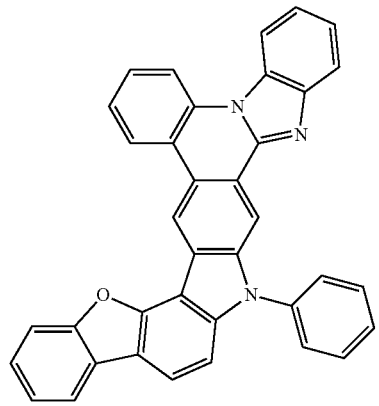
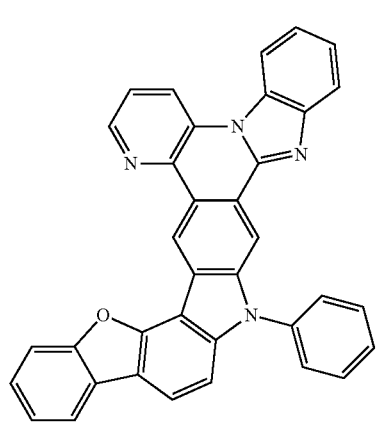
82
-continued
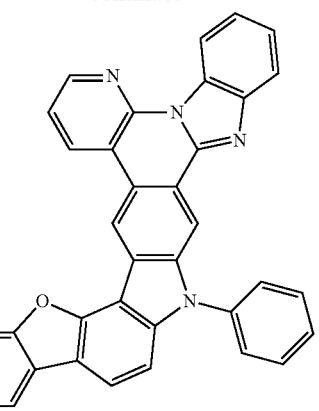
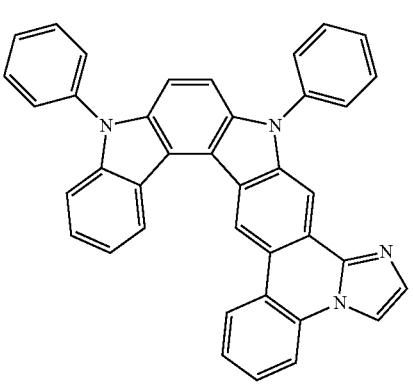
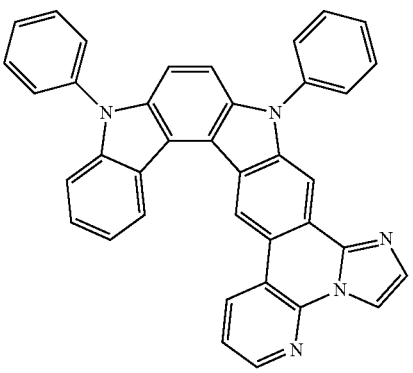
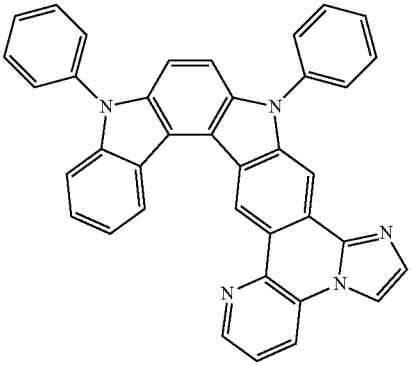

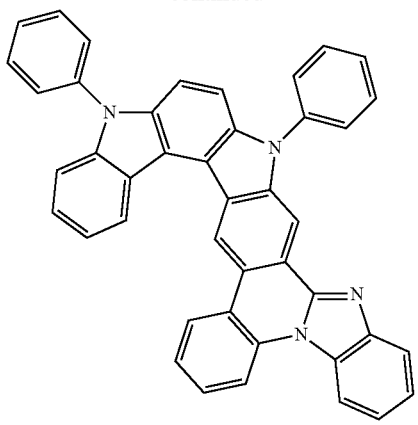
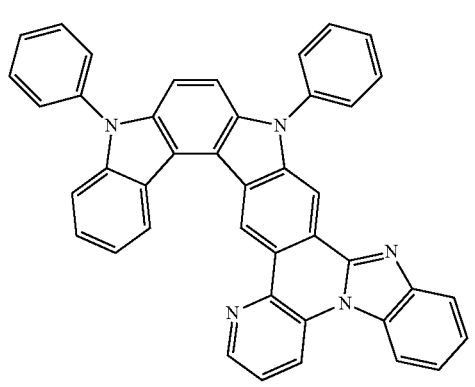
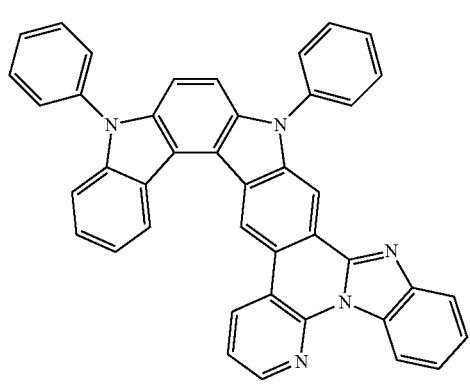
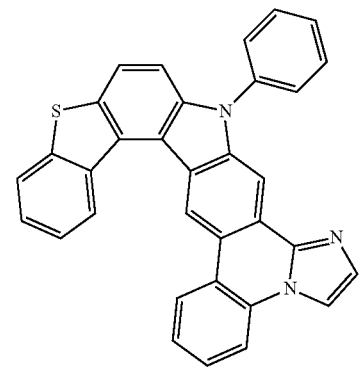
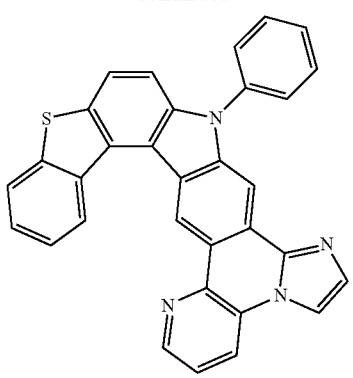
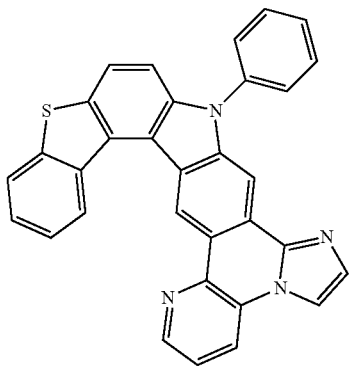
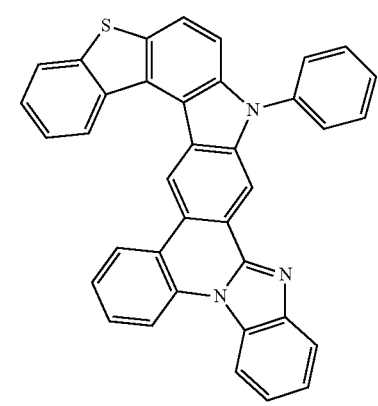
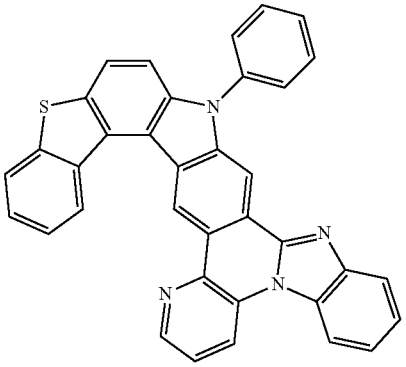

-continued
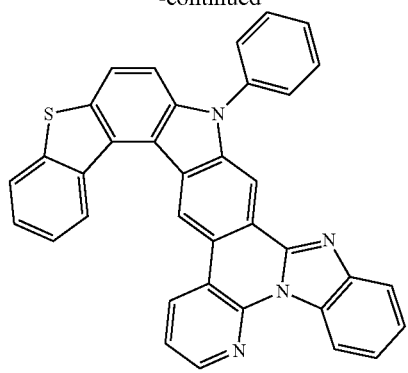
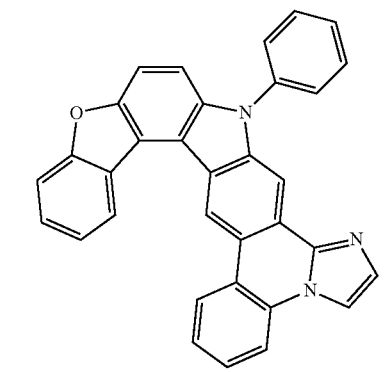
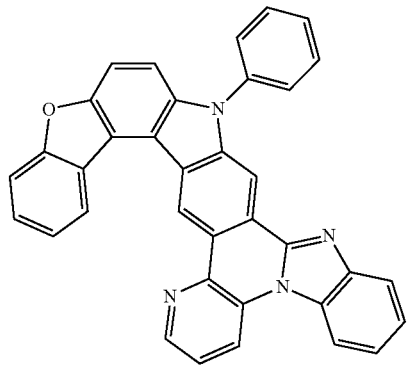
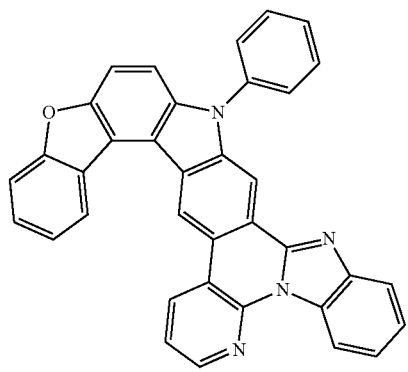
-continued
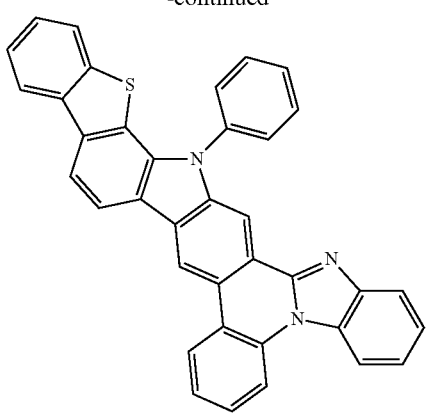
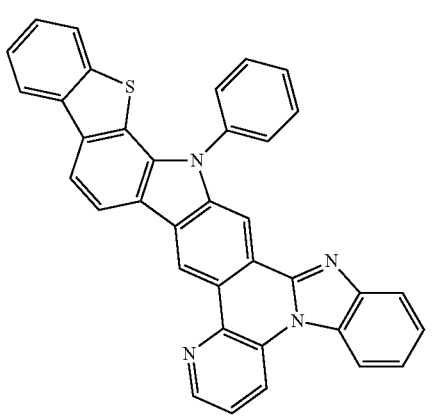
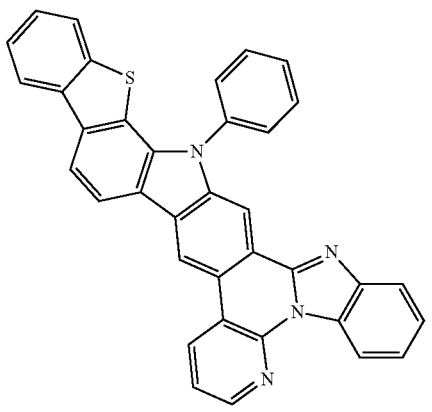
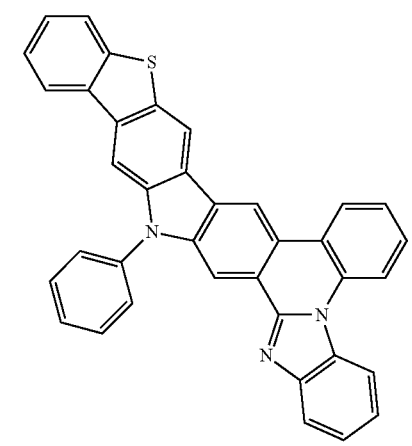

87
-continued
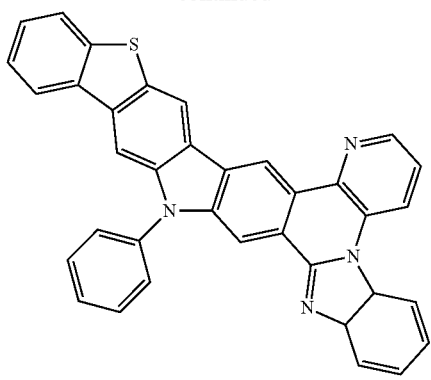
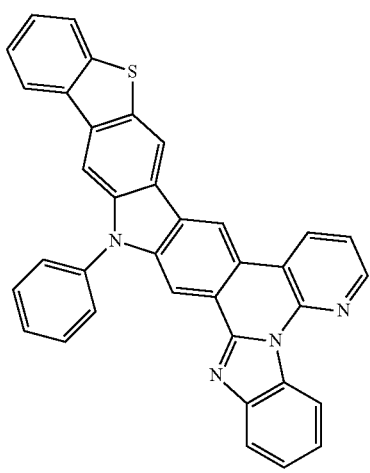
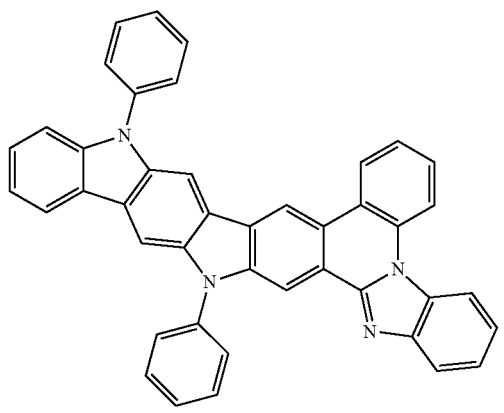
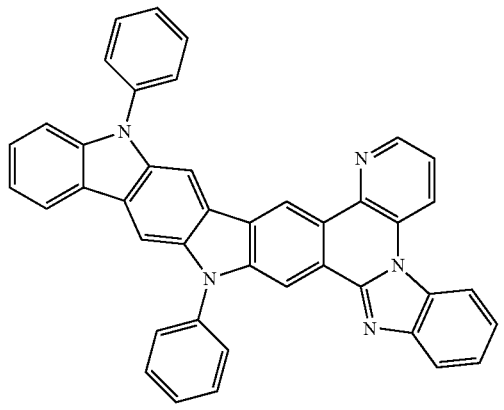
88
-continued
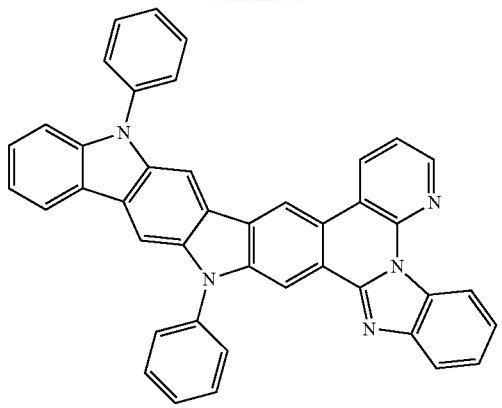
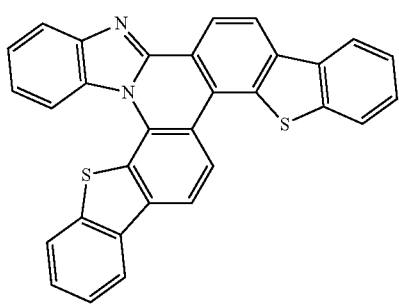
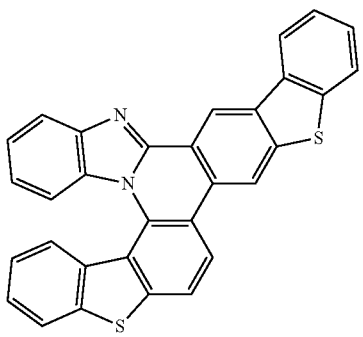
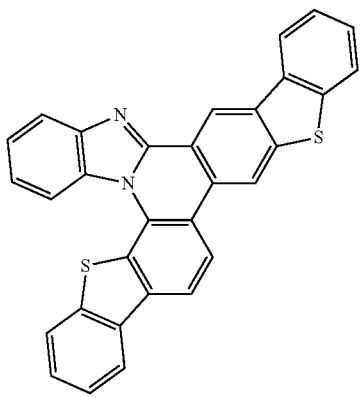

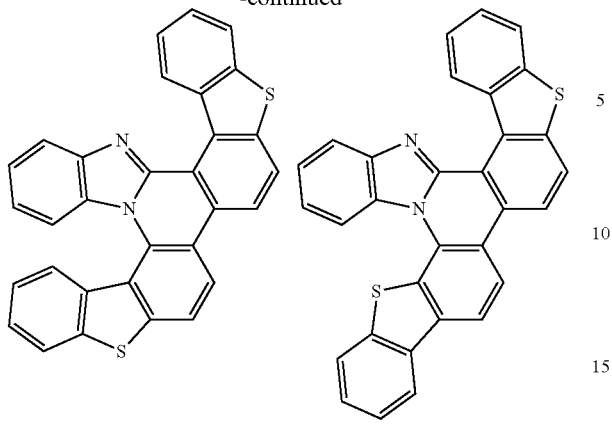
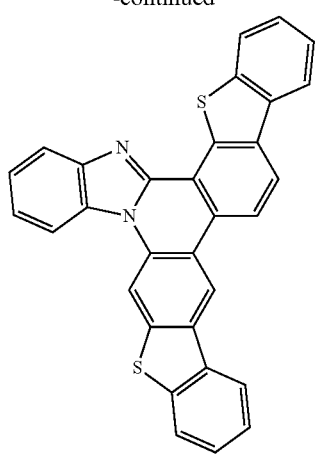
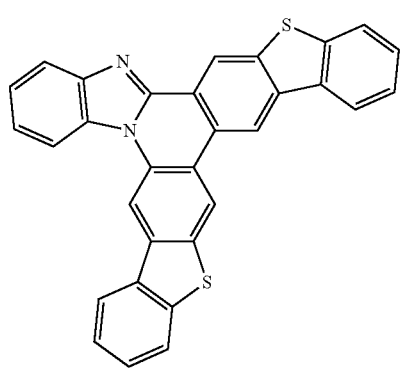
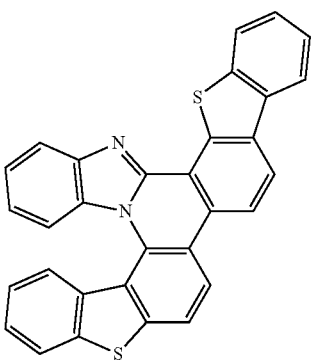

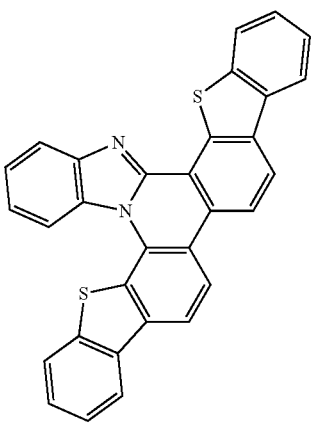
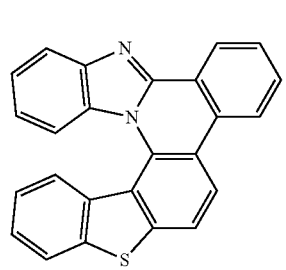
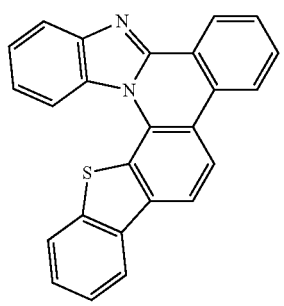

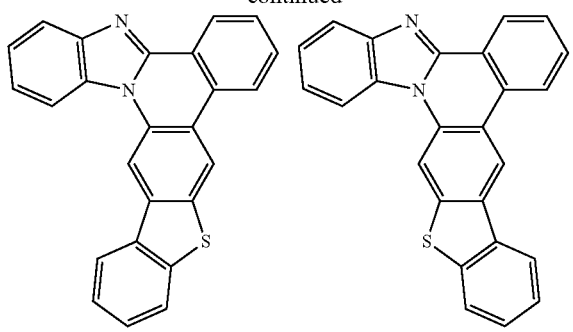
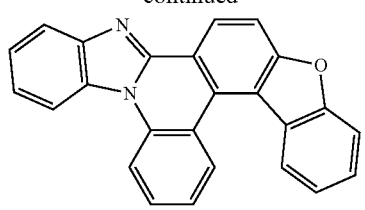
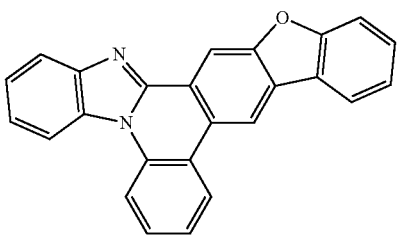
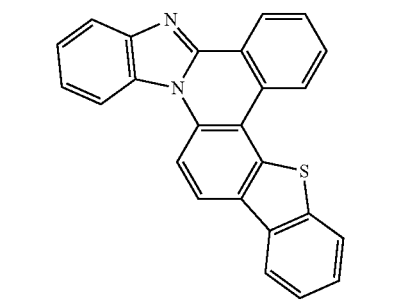
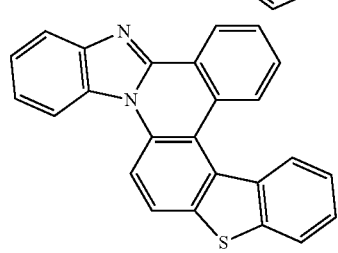
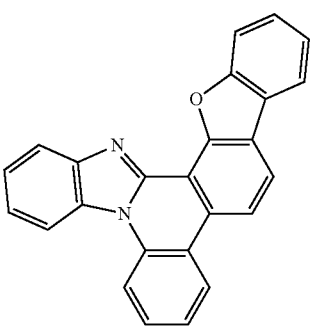
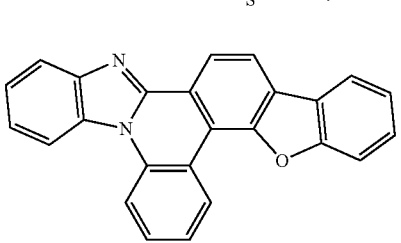
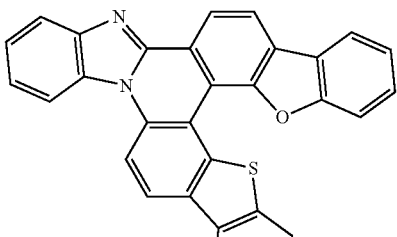
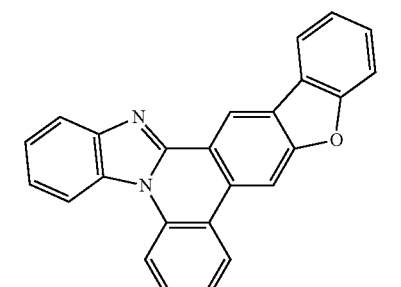
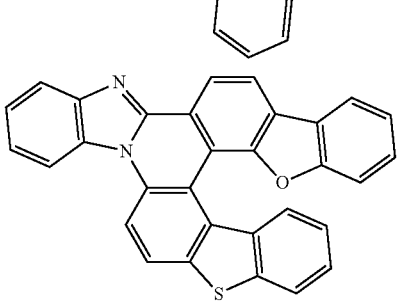
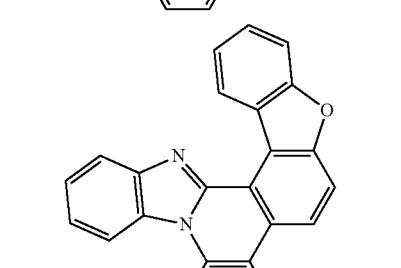
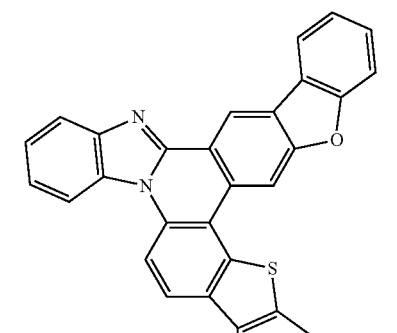

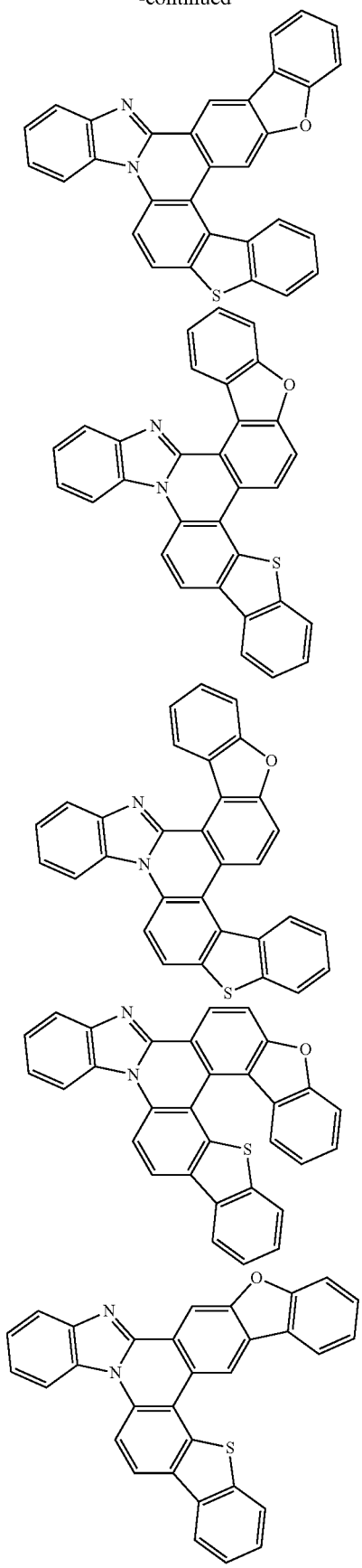
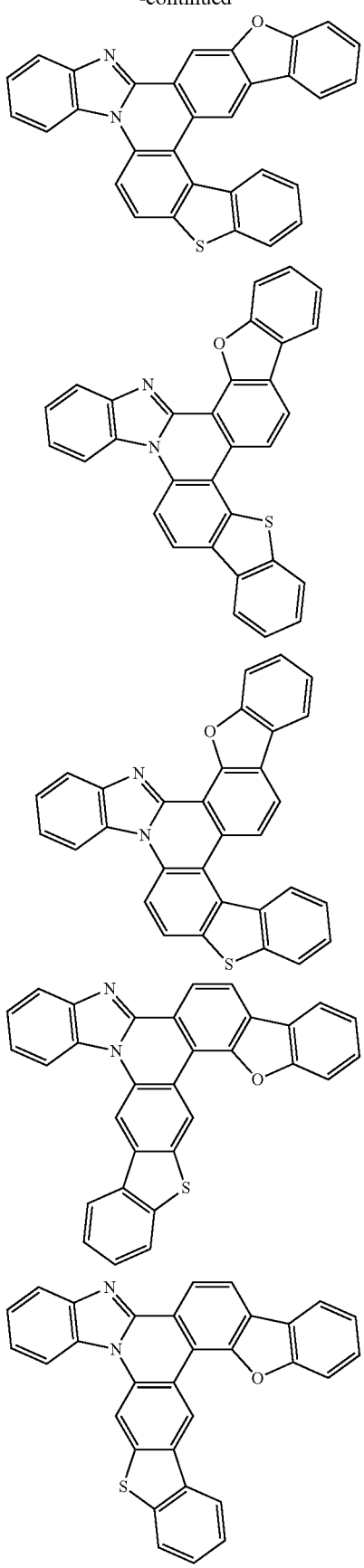

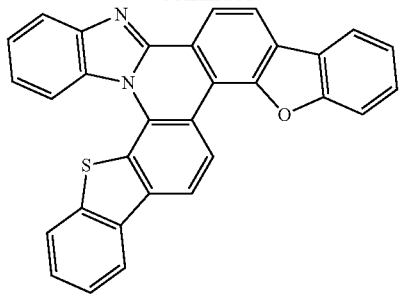
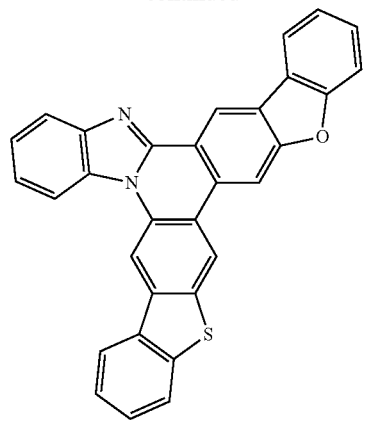
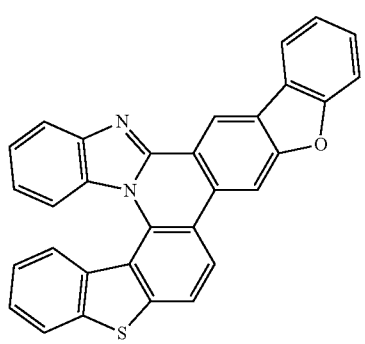
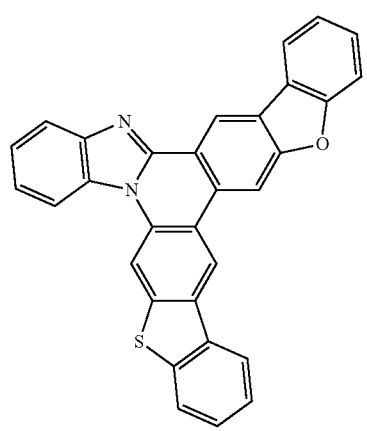
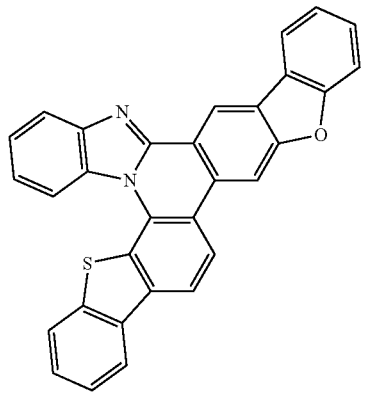
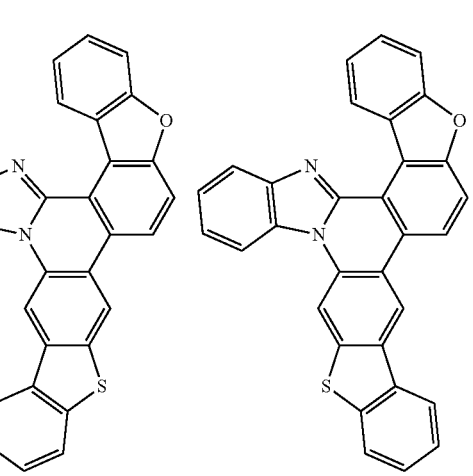
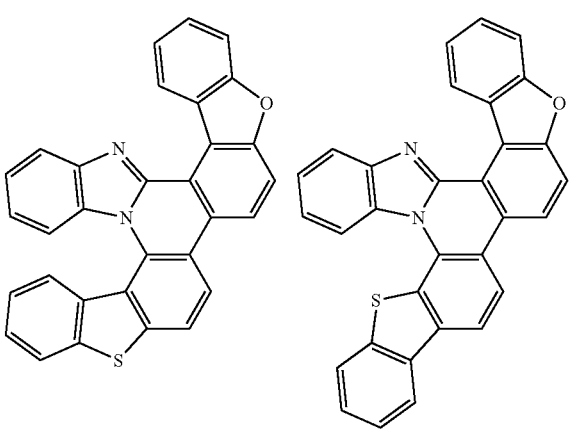
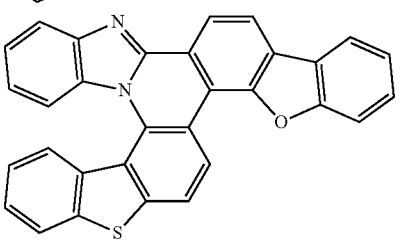

97
-continued
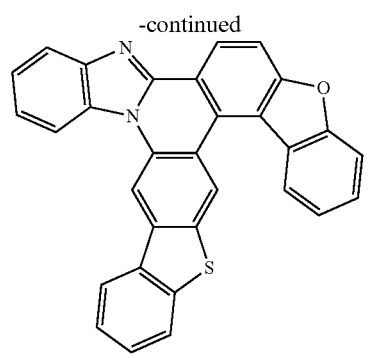
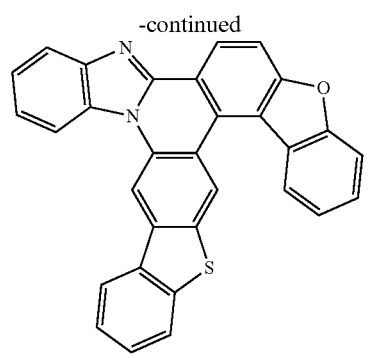
98
-continued
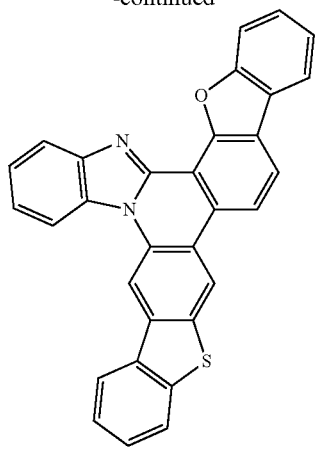
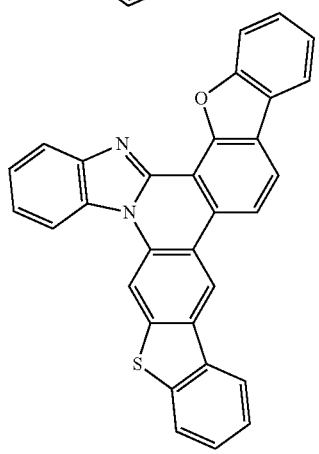
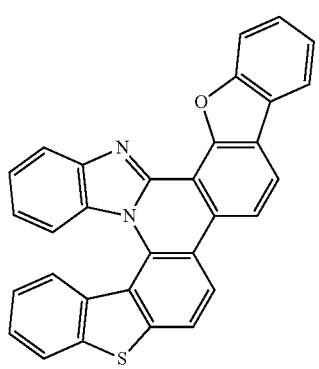
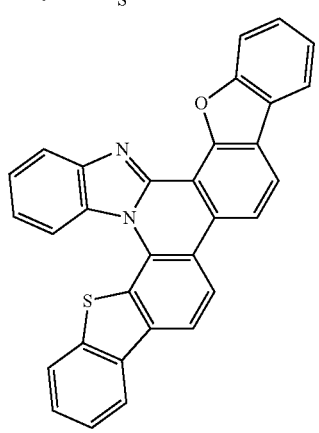

99
-continued
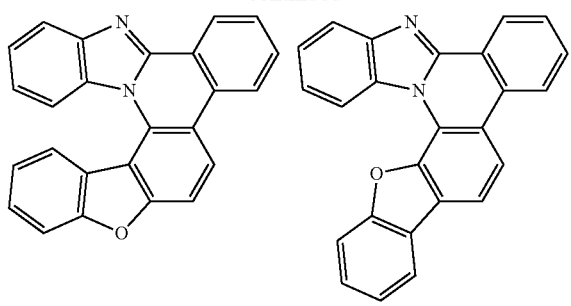
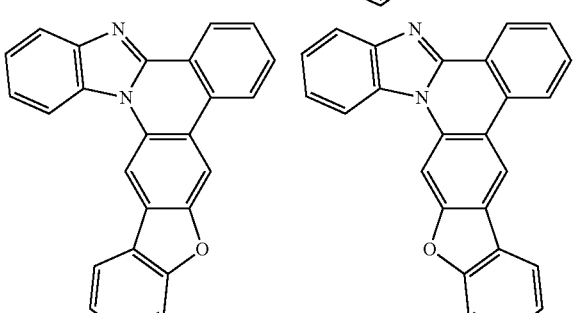
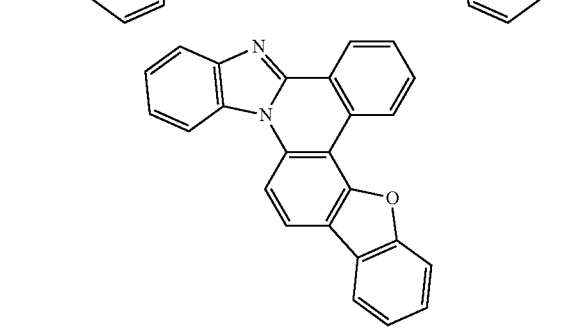
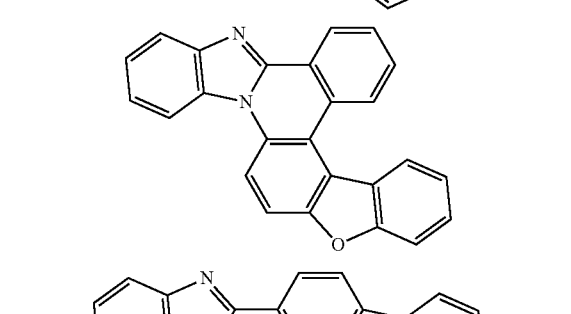
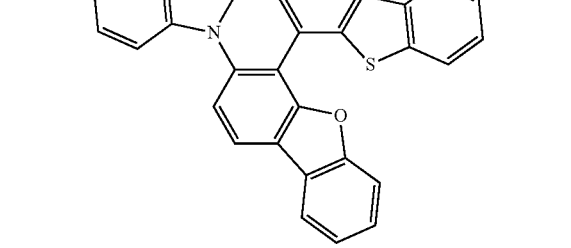
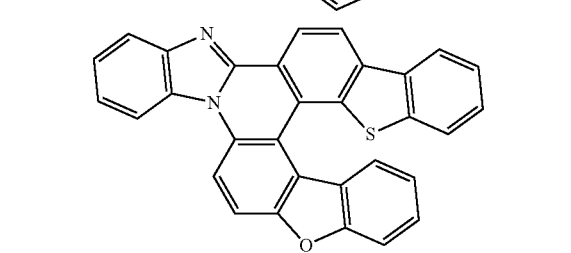
100
-continued
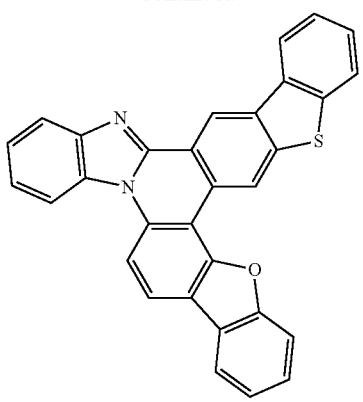
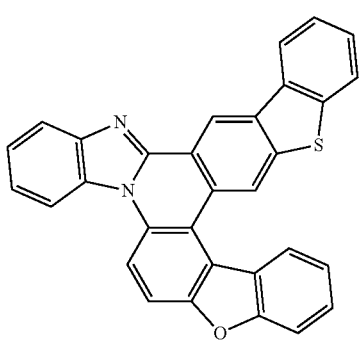
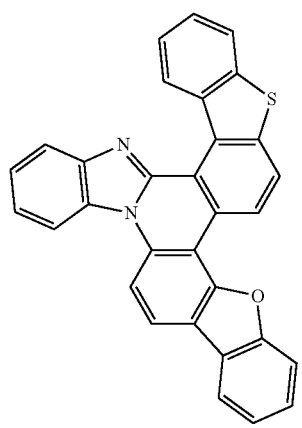
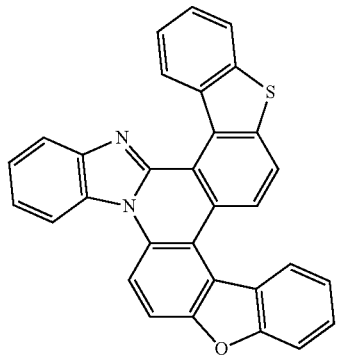

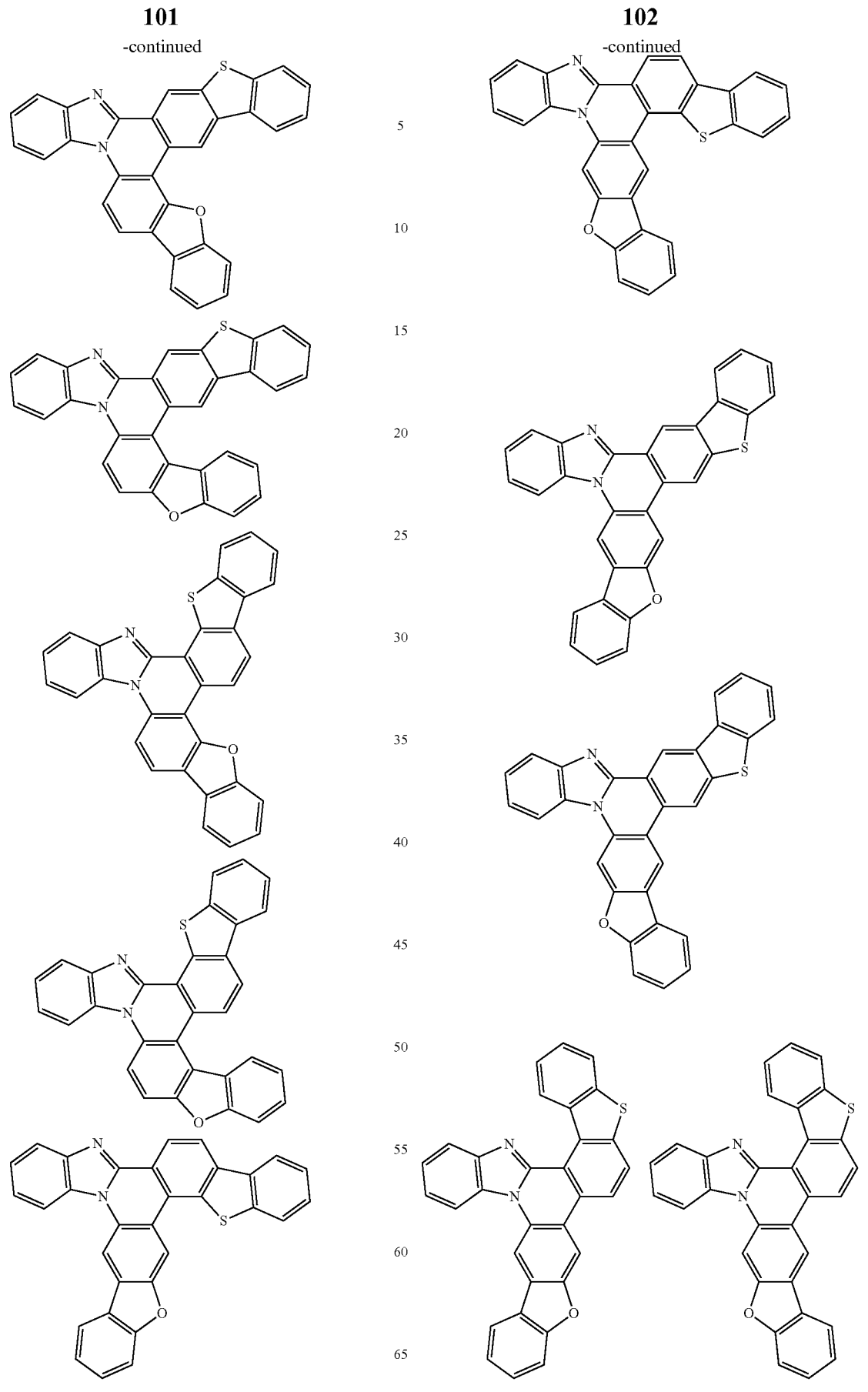

101
-continued

102
-continued

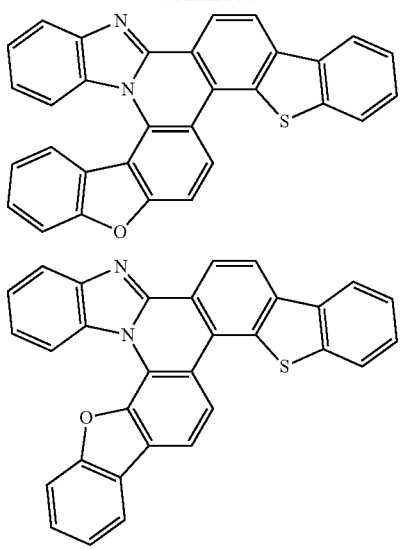
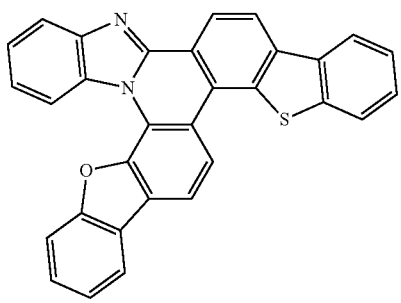
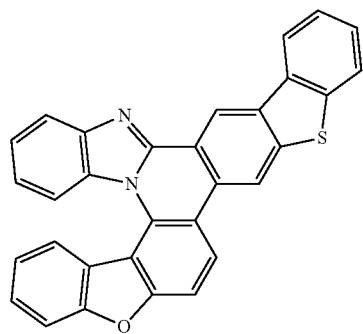
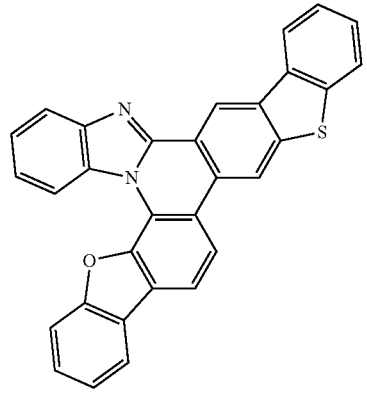
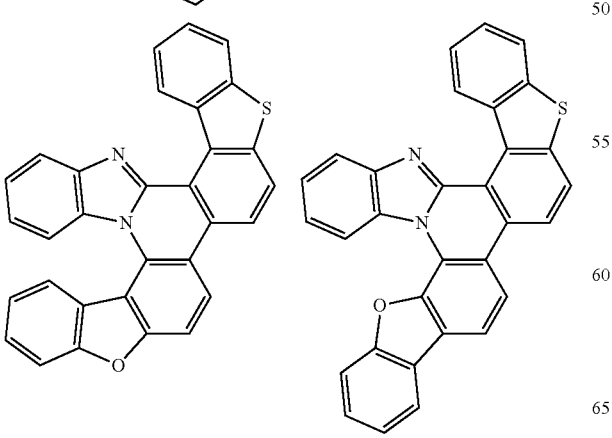
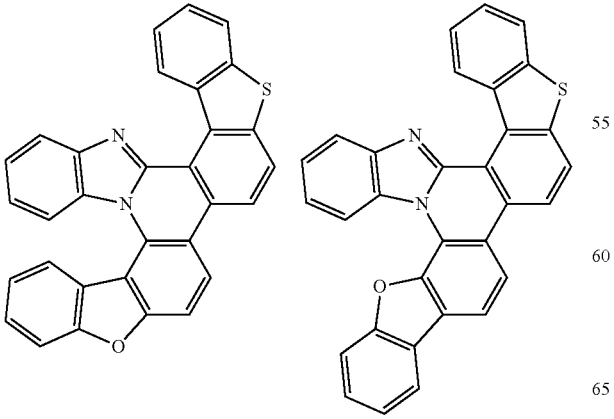
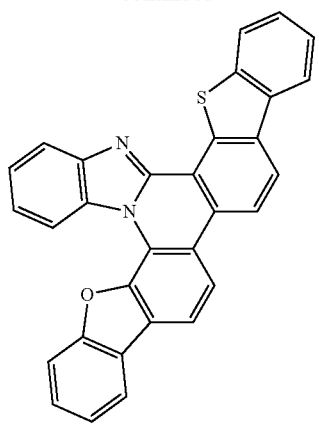
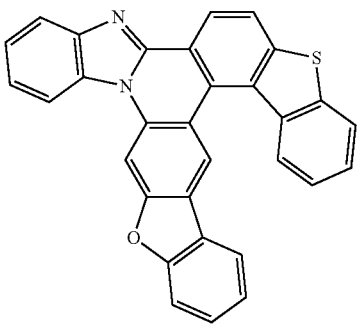
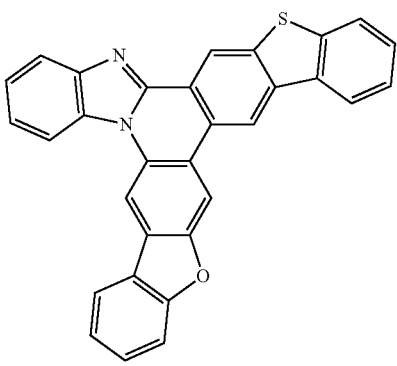
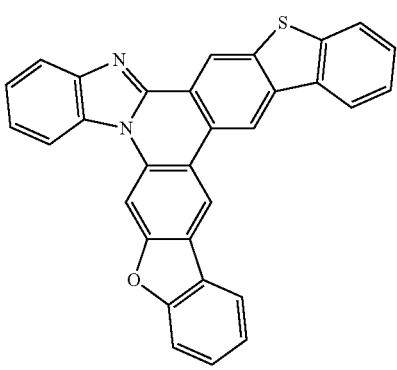

105
-continued
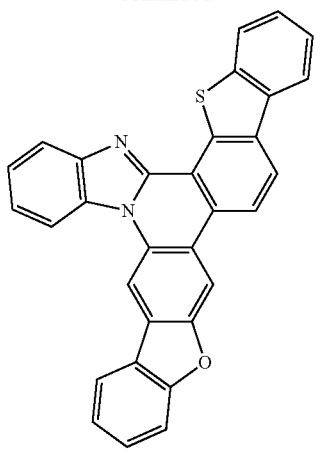
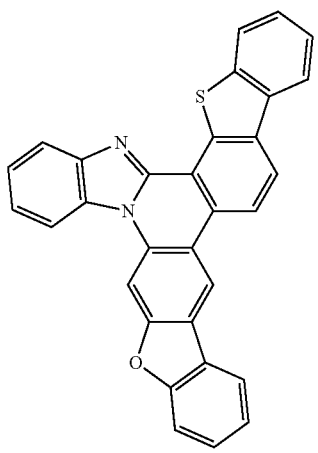
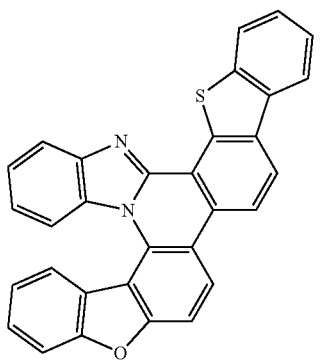
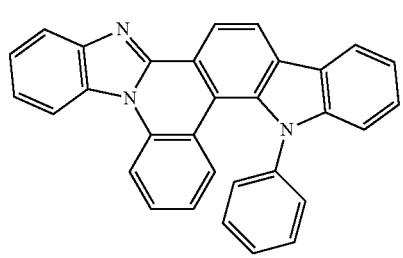
106
-continued
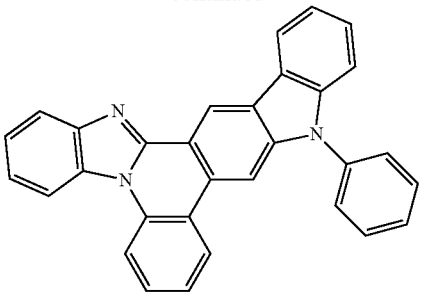
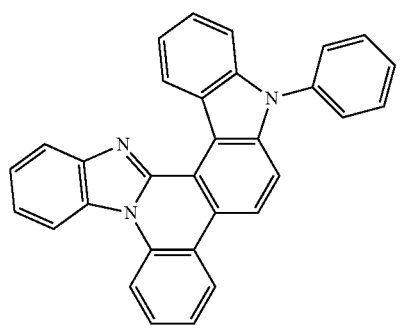
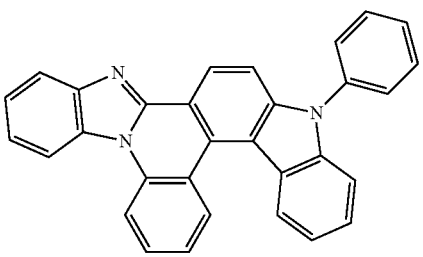
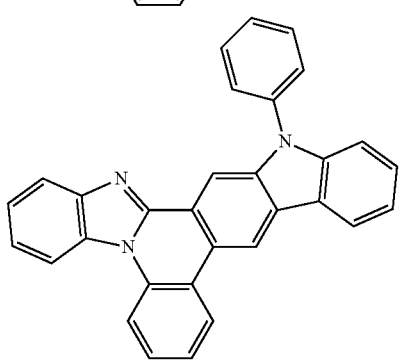
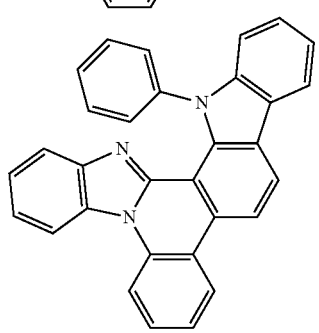

107
-continued
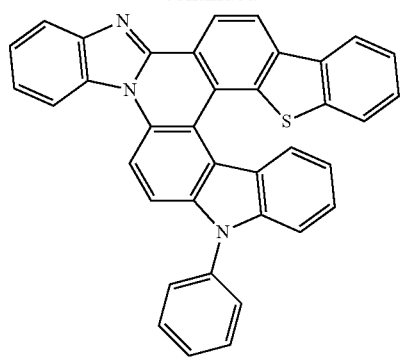 [SMILES: c1ccc(-n2c3ccccc3c3c4c5c(ccc6c7ccccc7sc65)c5nc6ccccc6n5c4ccc32)cc1]
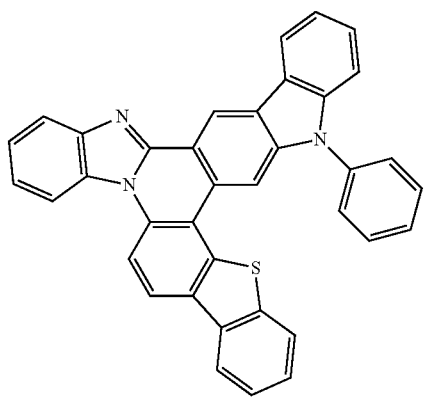
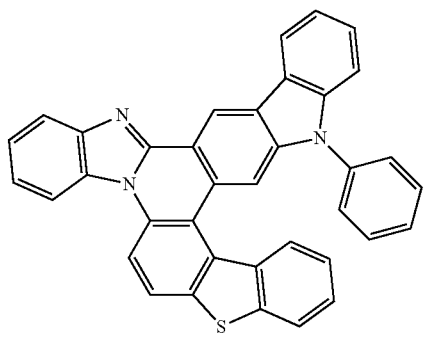
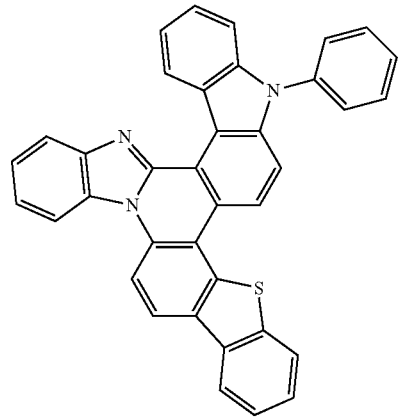
108
-continued
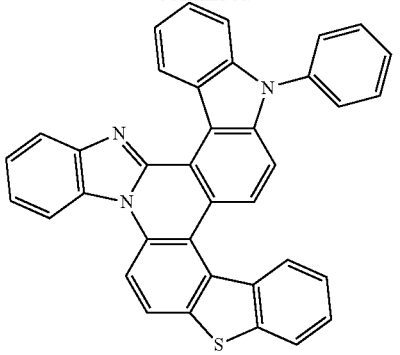
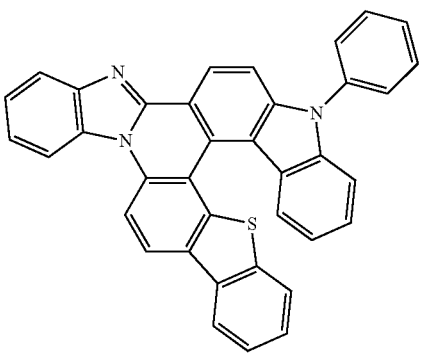
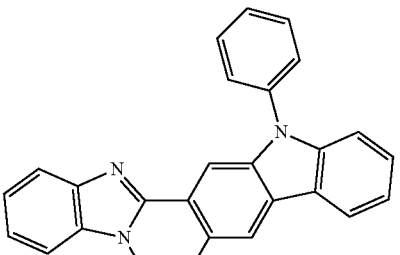
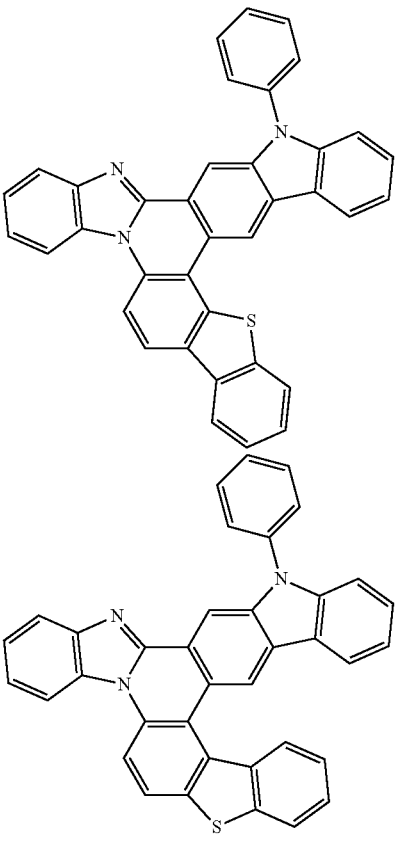

-continued
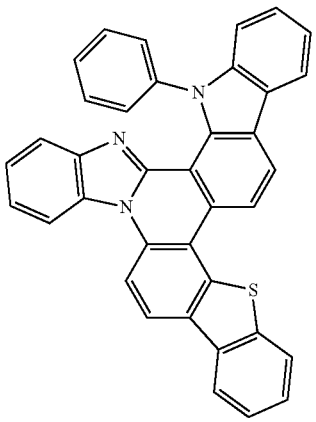
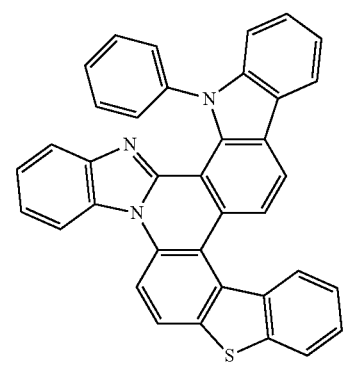
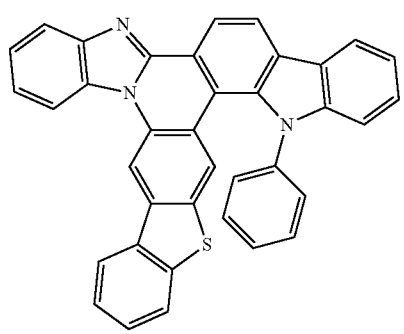
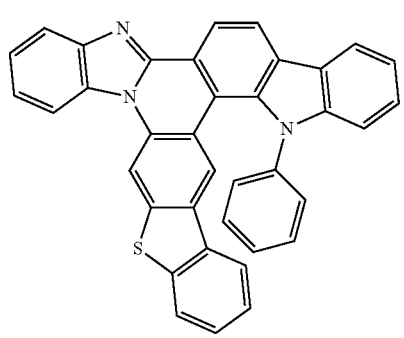
-continued
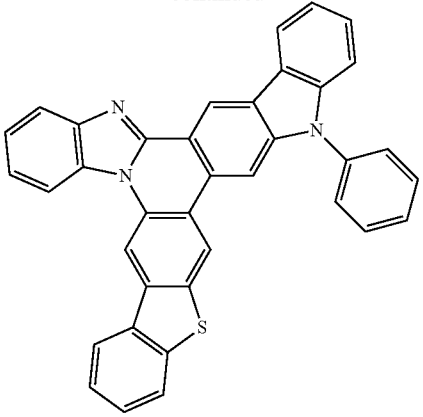
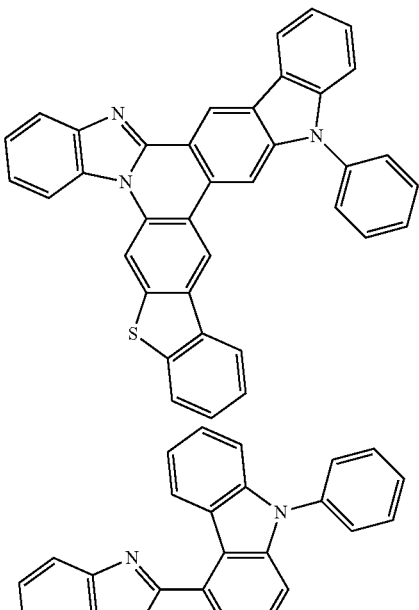
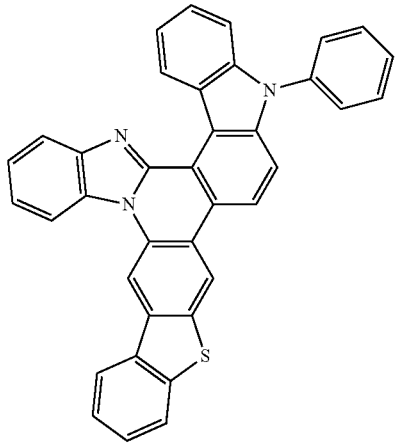
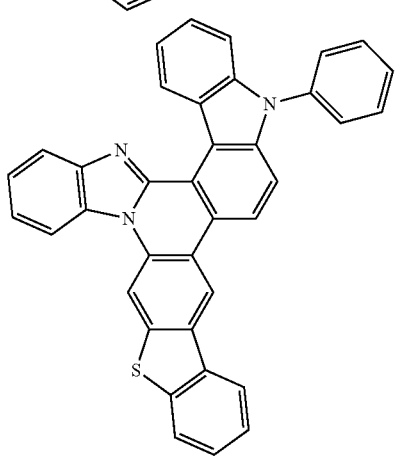

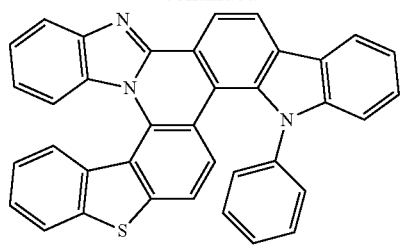
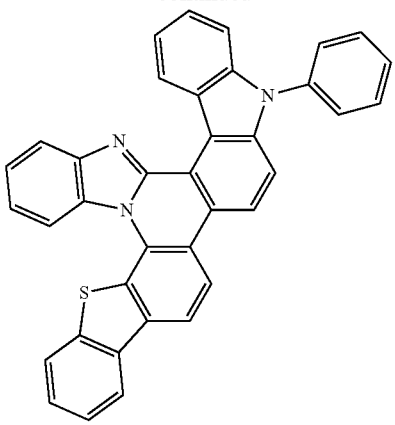
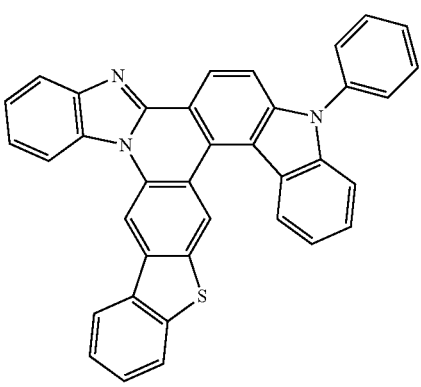
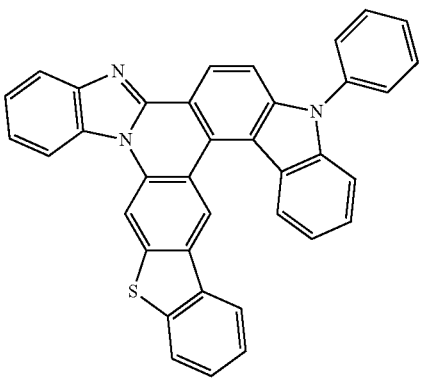
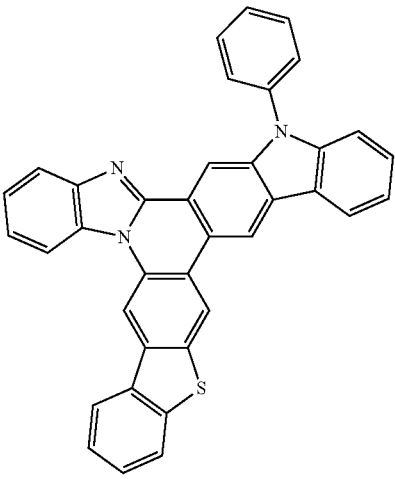

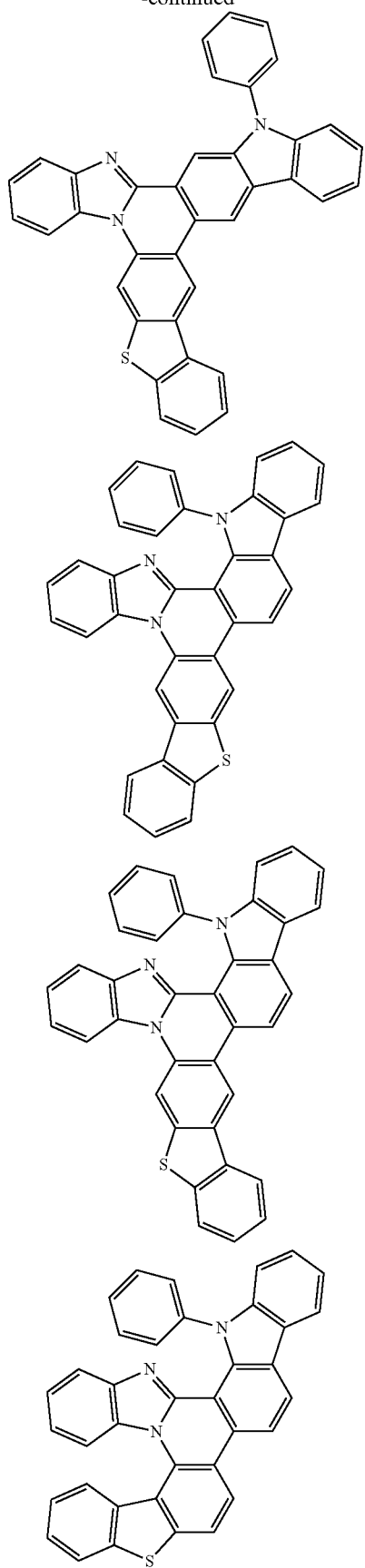
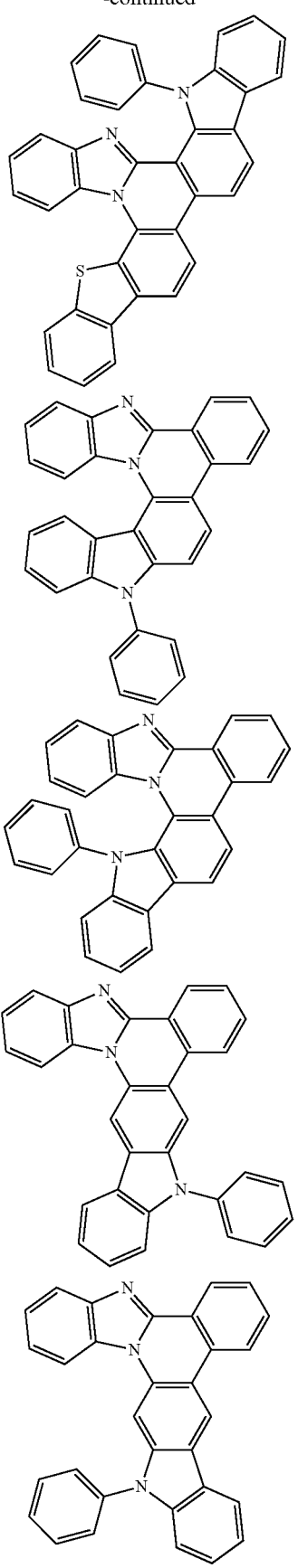

115
-continued
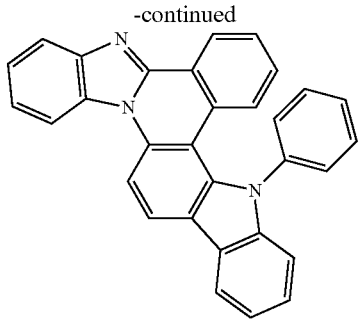
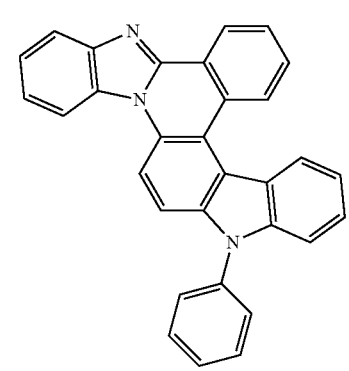
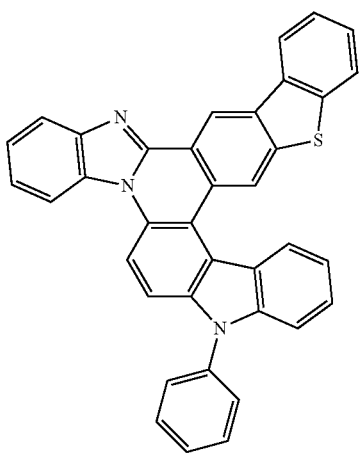
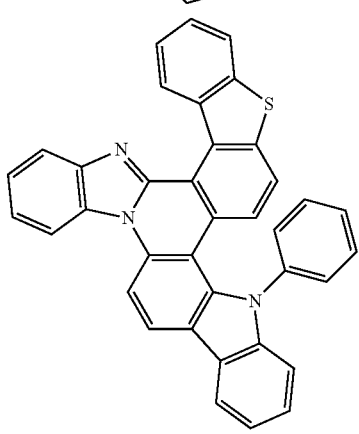
116
-continued
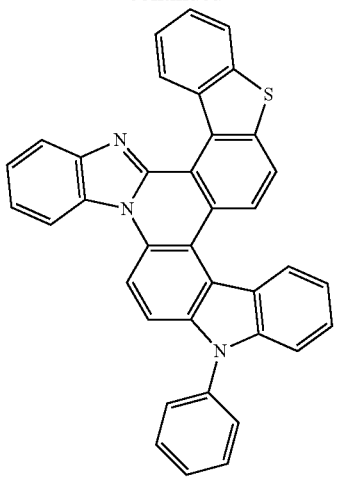
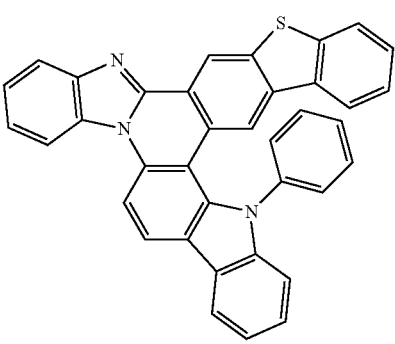
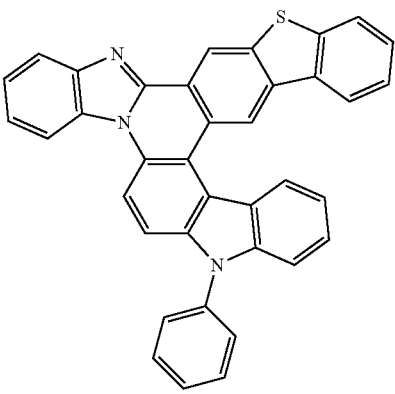
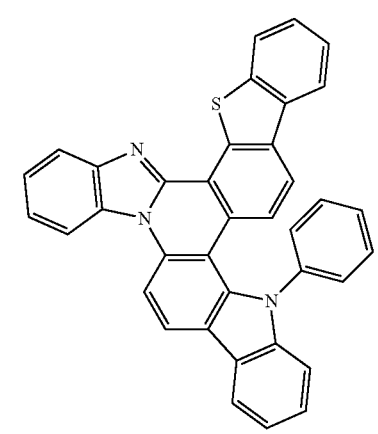

117
-continued
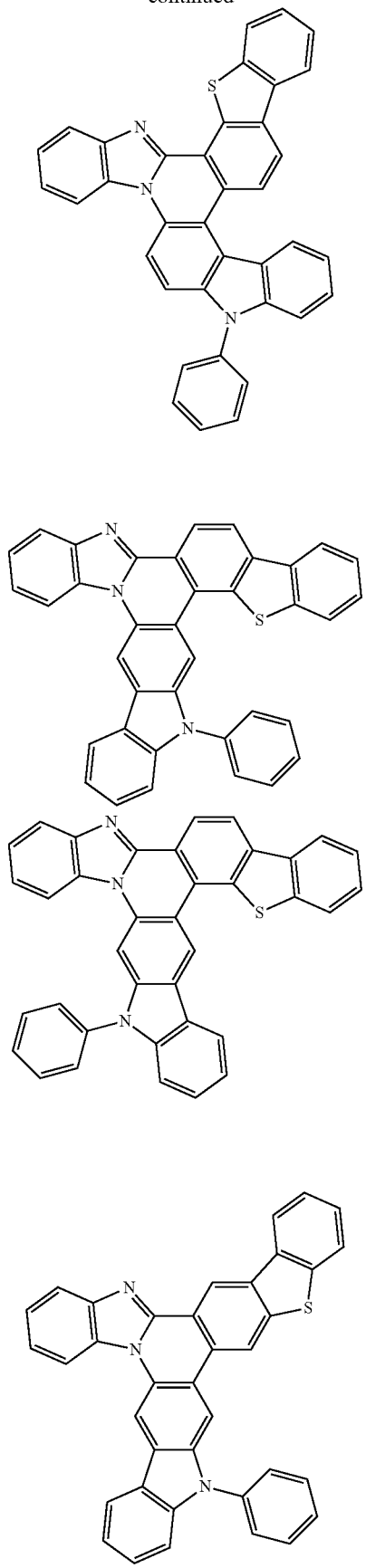
118
-continued
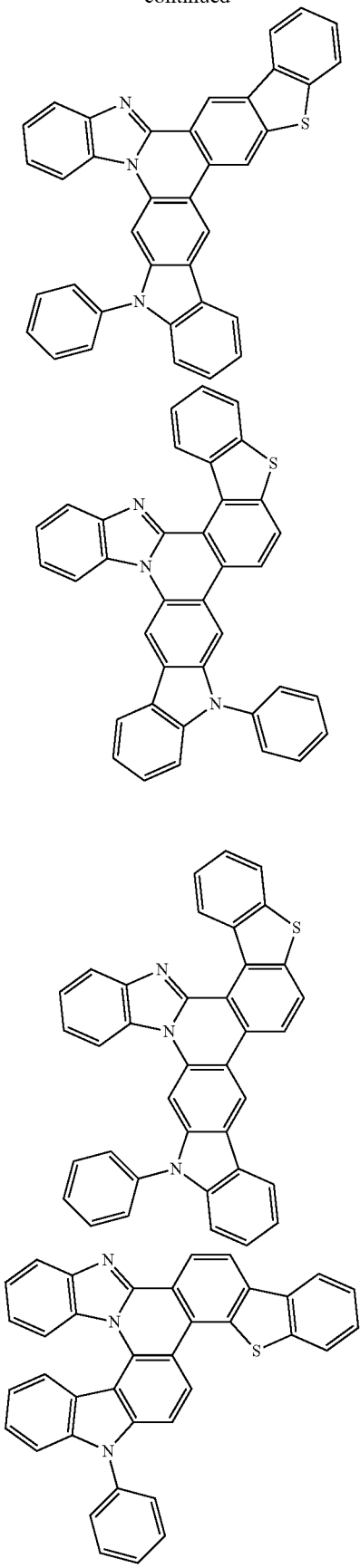

119
-continued
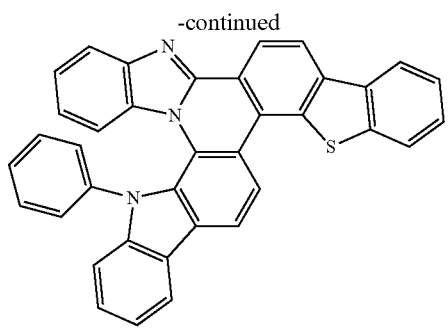
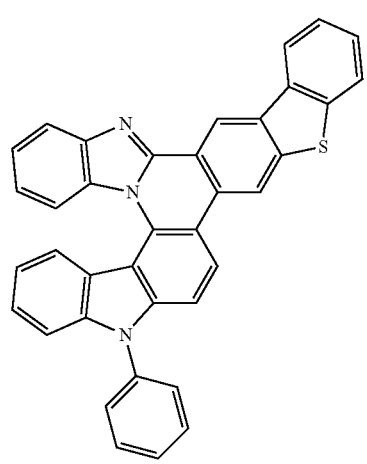
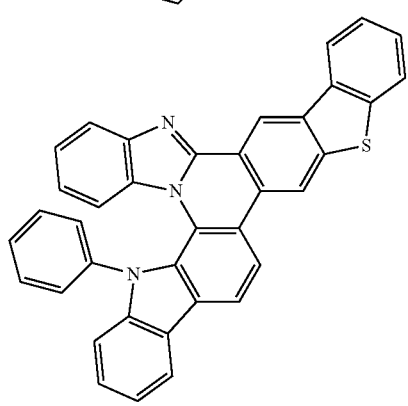
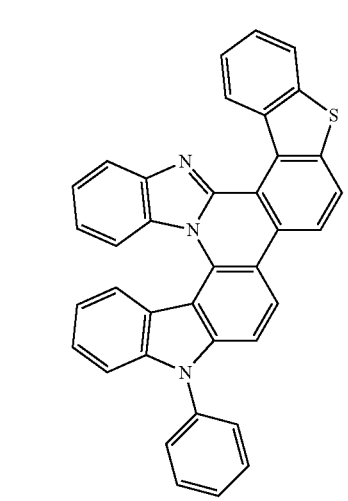
120
-continued
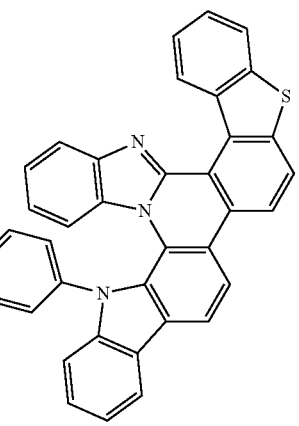
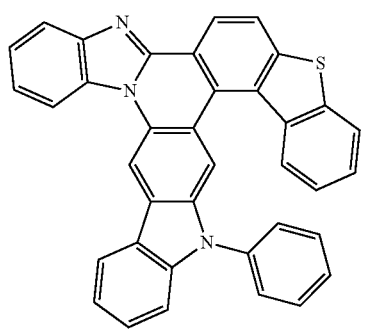
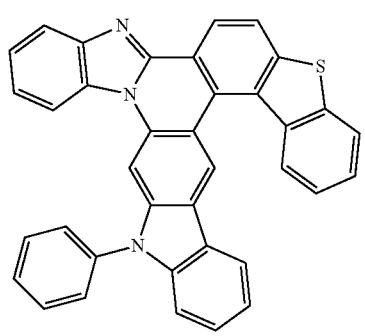
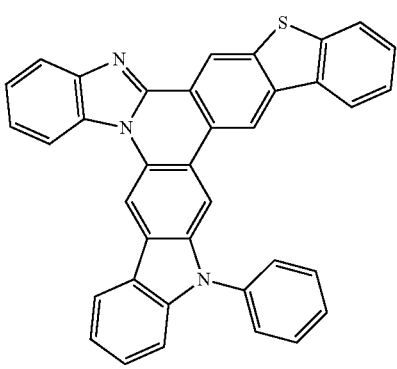

121
-continued
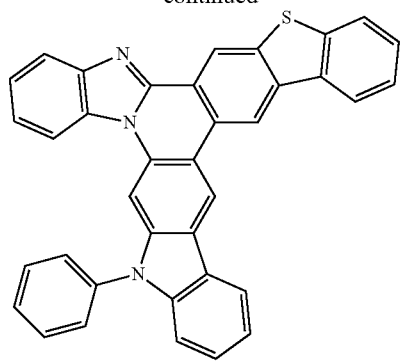
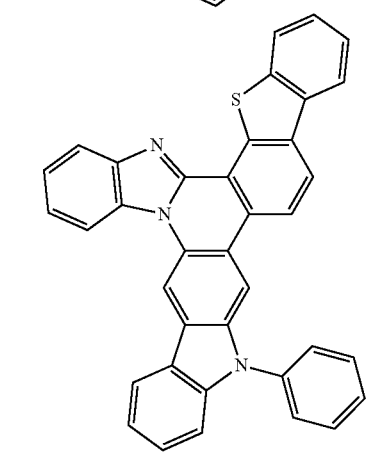
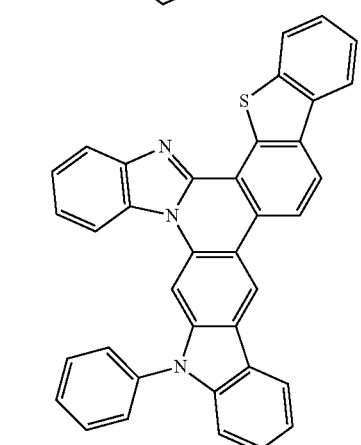
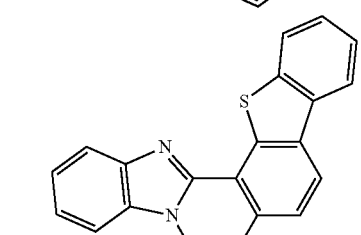
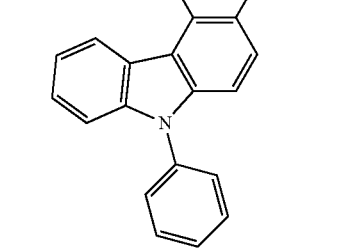
122
-continued
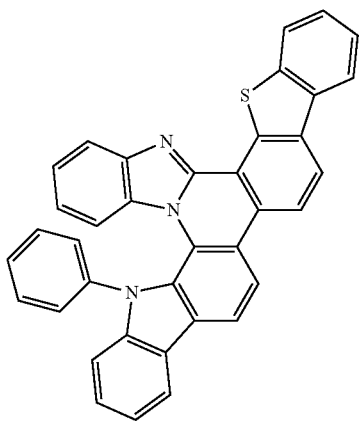 [SMILES: c1ccc(-n2c3ccccc3c3ccc4c5ccc6c7ccccc7sc6c5c5nc6ccccc6n5c4c32)cc1]
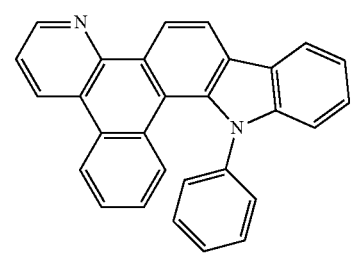
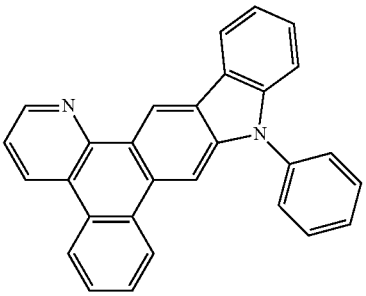
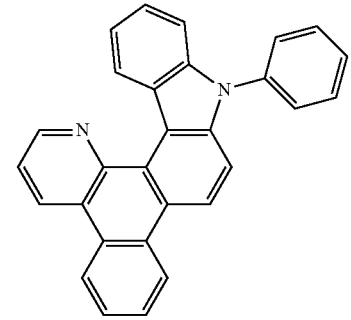
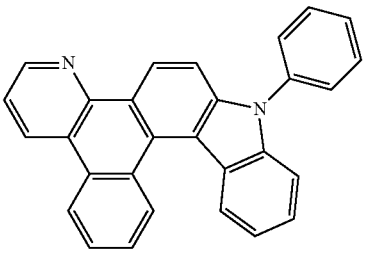

123
-continued
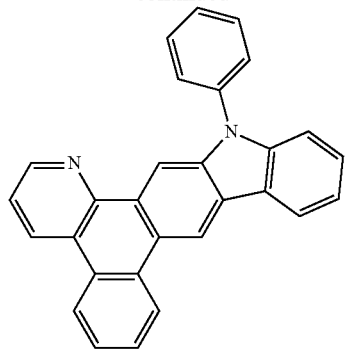
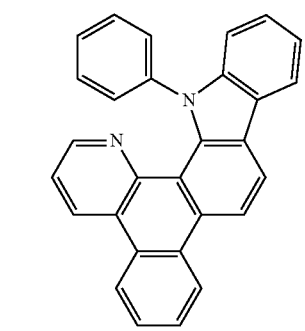
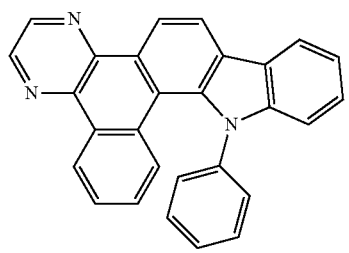
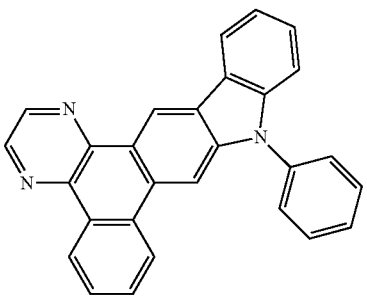
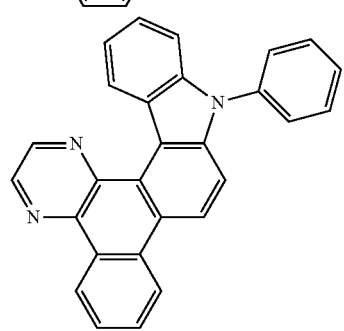
124
-continued
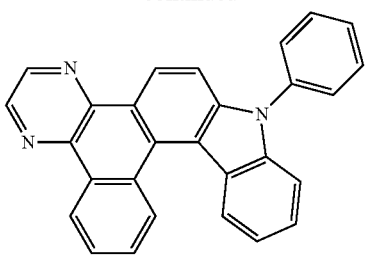
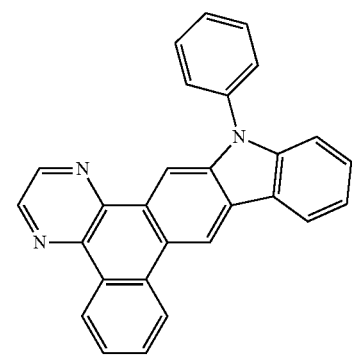
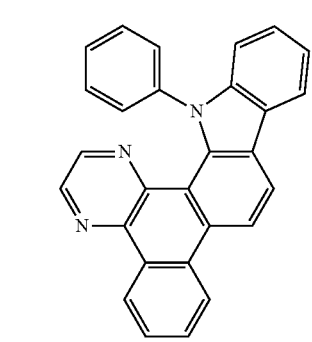
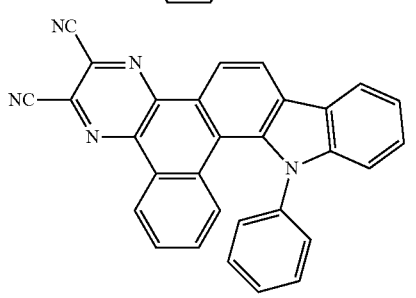
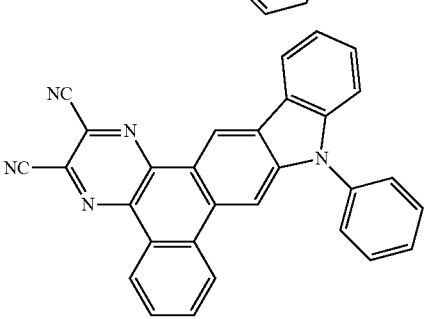

125
-continued
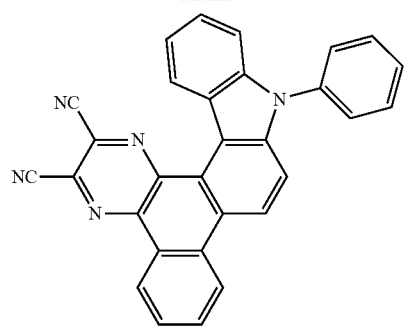
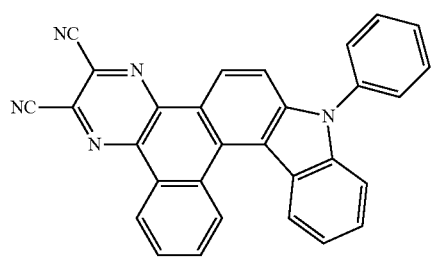
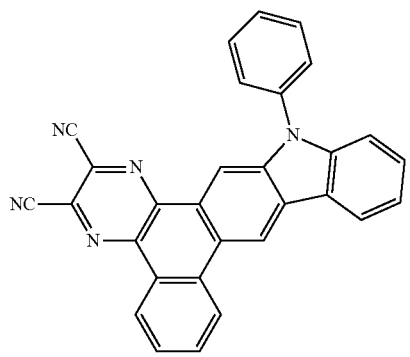
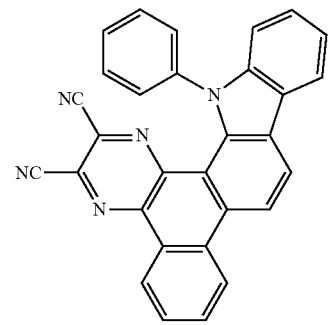
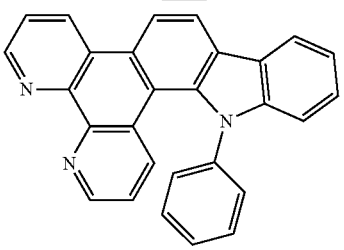
126
-continued
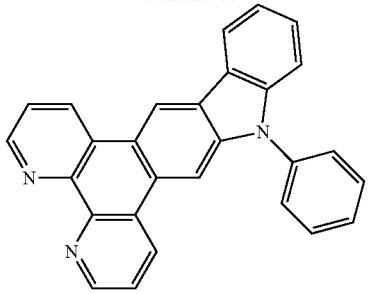
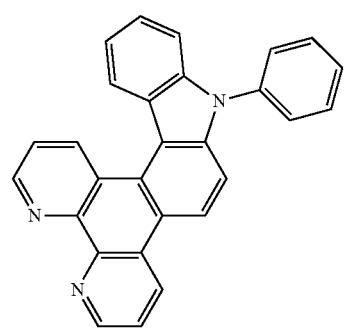
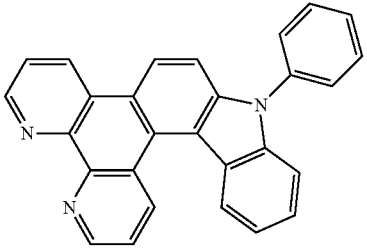
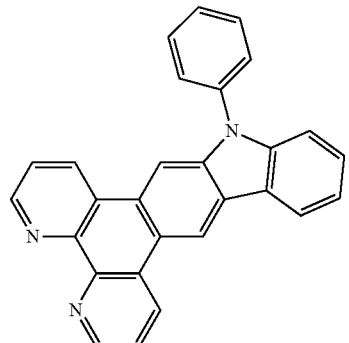
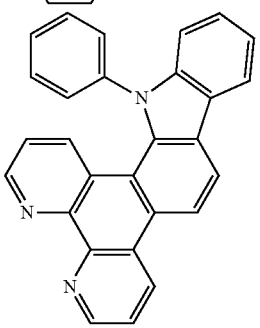

| 127 -continued | 128 -continued |
|---|---|
| 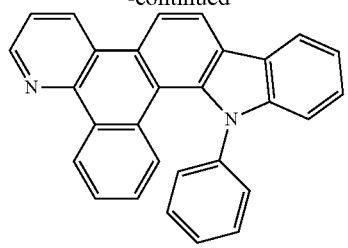 | 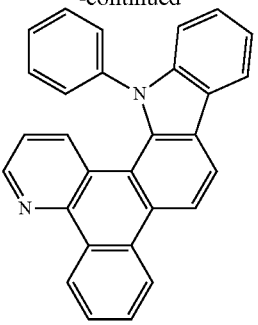 |
| 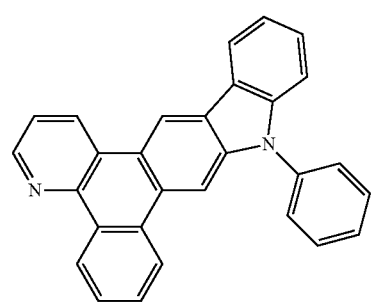 | 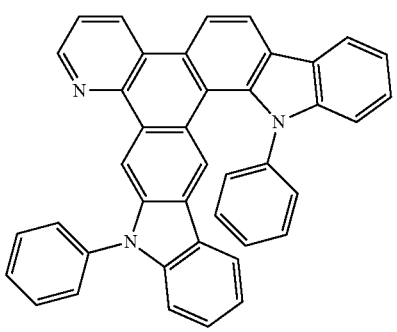 |
| 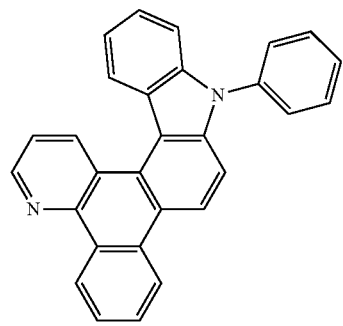 | 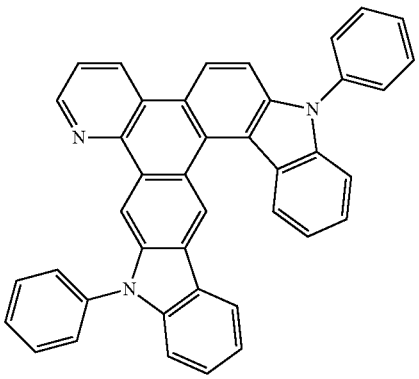 |
| 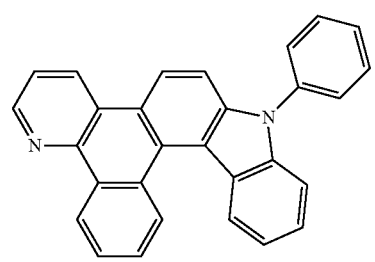 | 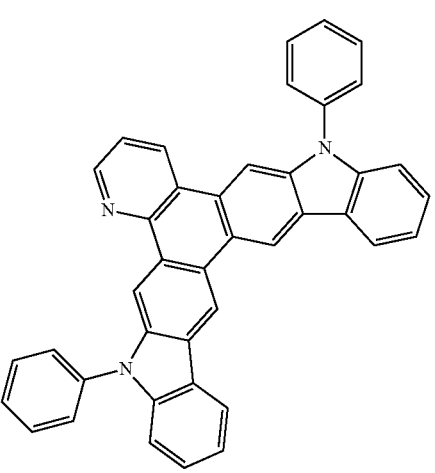 |

129
-continued
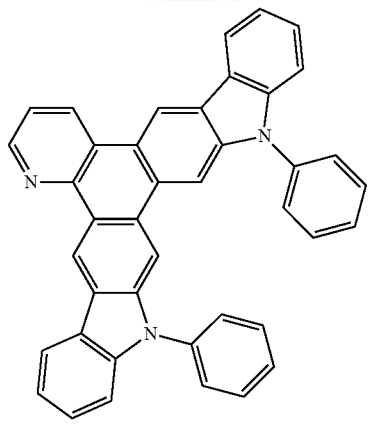
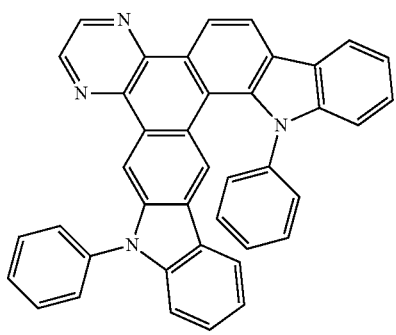
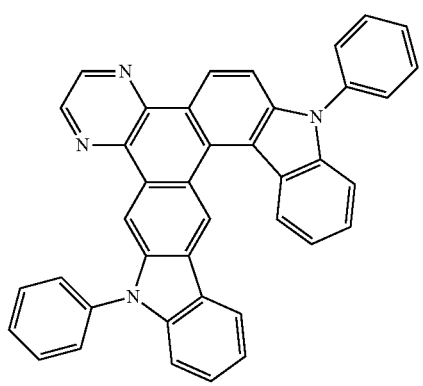
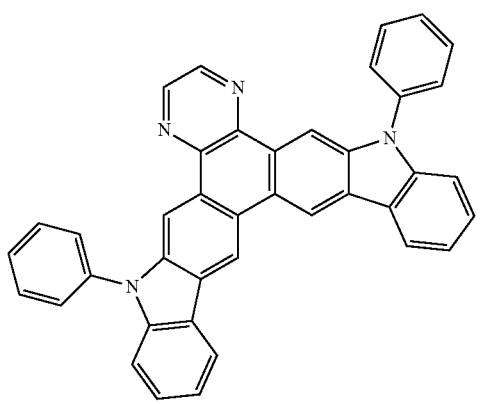
130
-continued
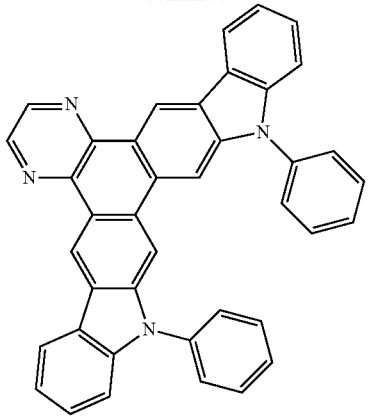
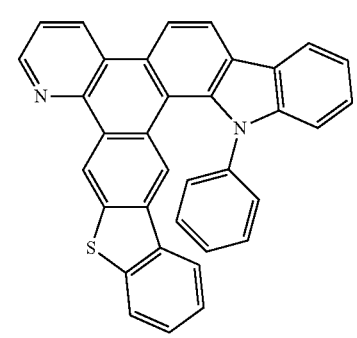
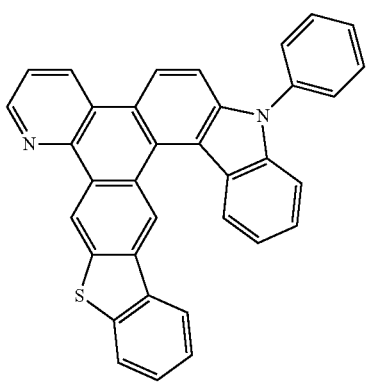
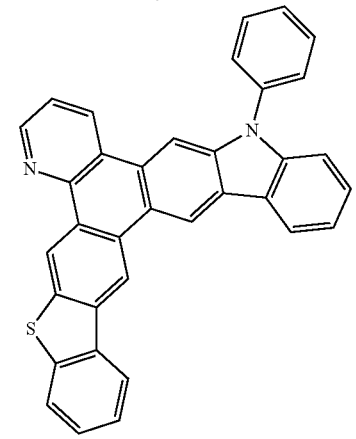

US 11,450,816 B2
131
-continued
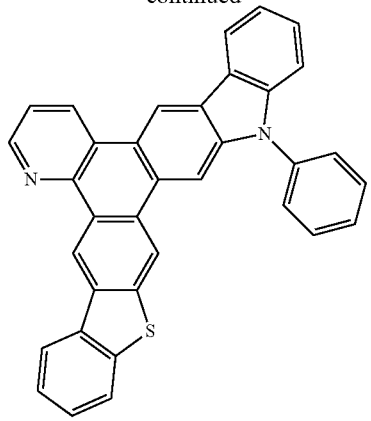
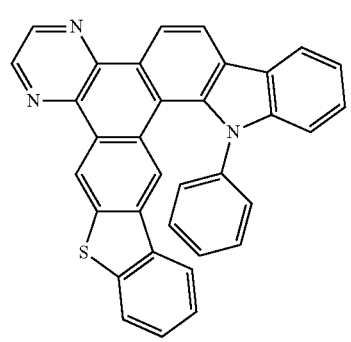
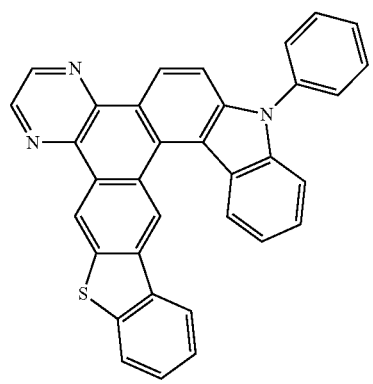
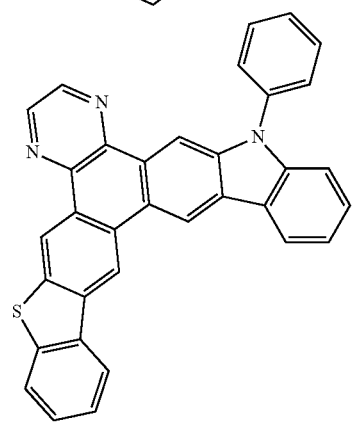
132
-continued
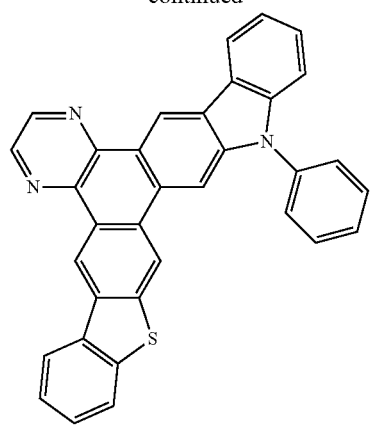
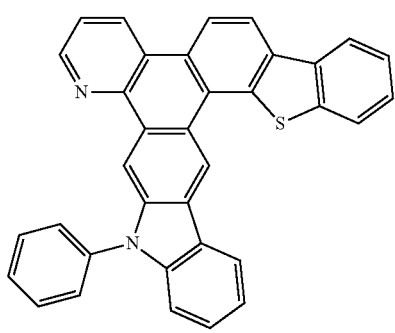
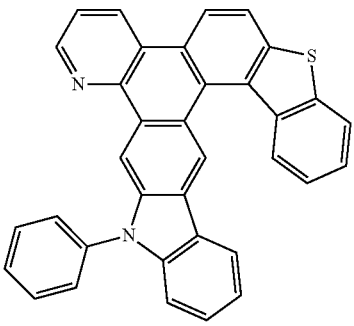
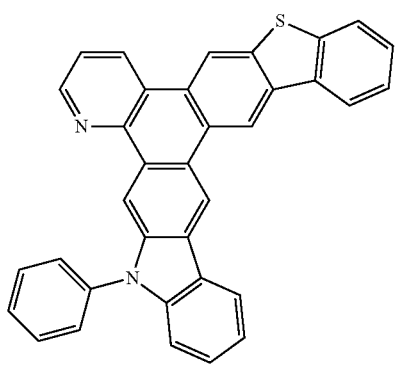

133
-continued
134
-continued
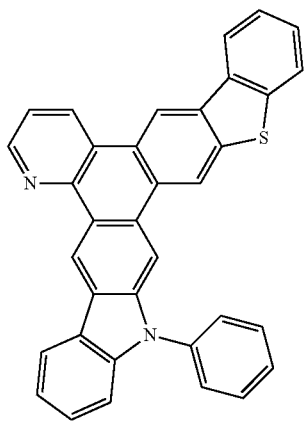
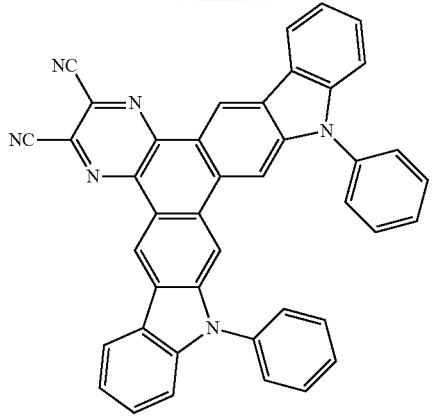
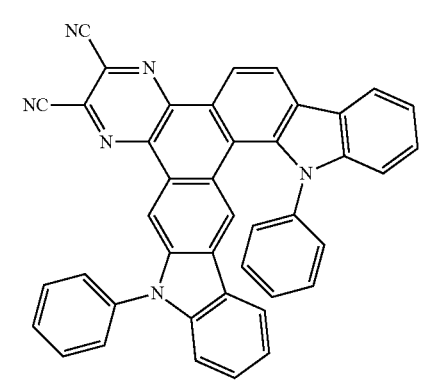
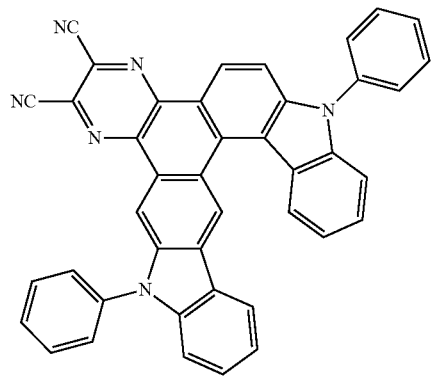
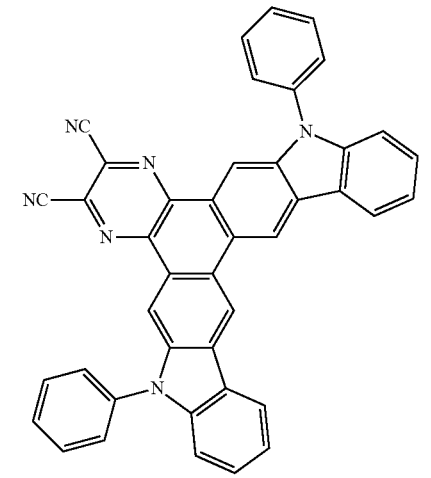

-continued
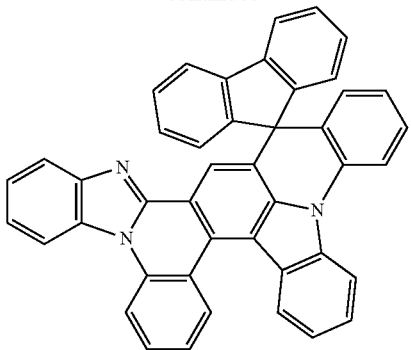
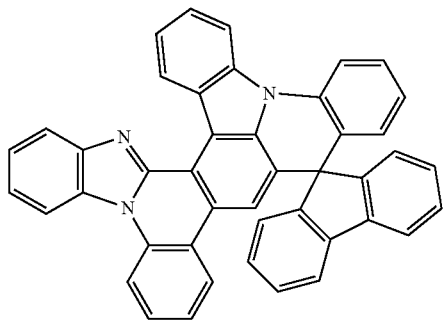
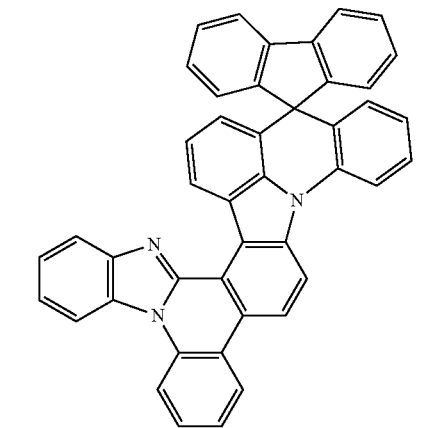
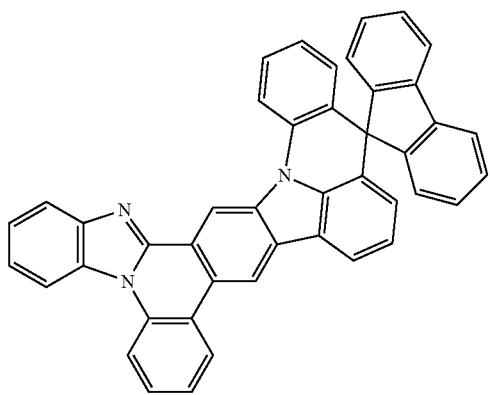
-continued
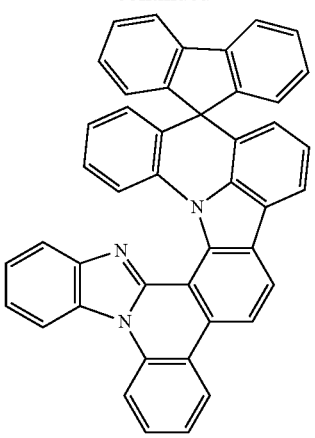
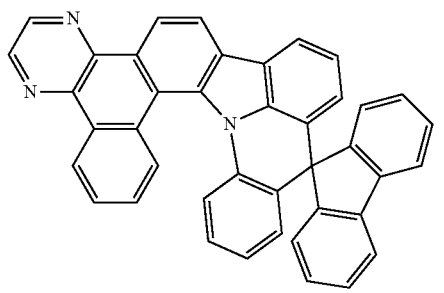
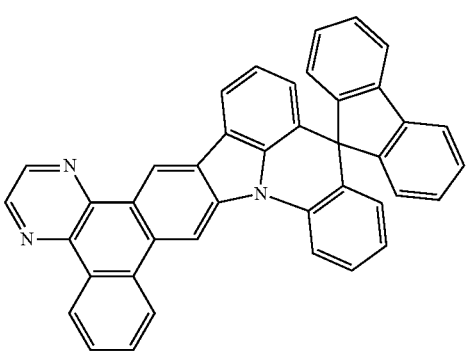
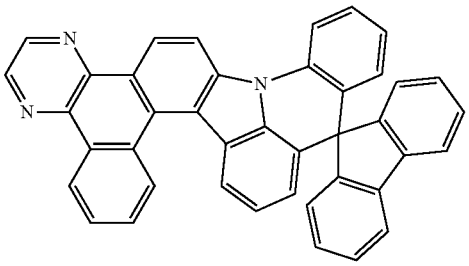
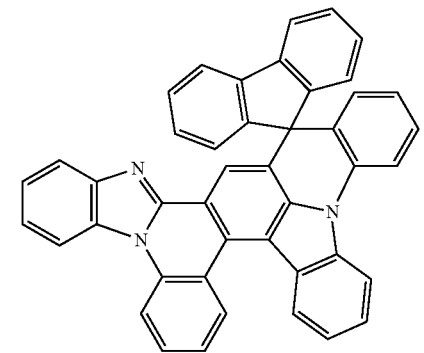

137
-continued
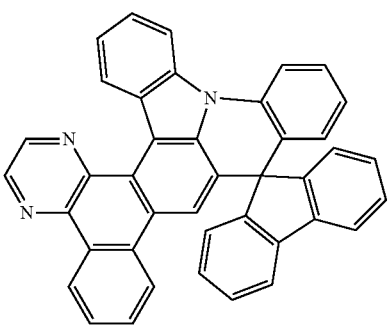
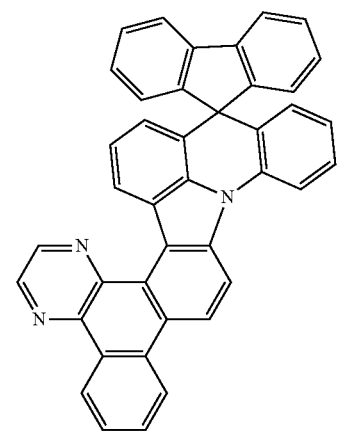
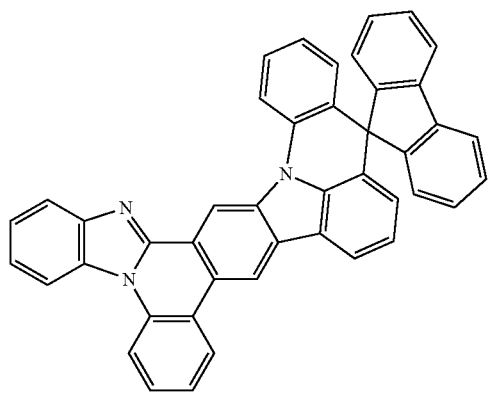
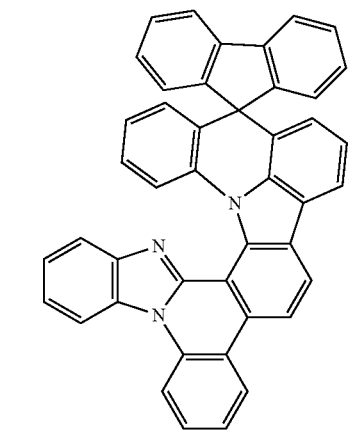
138
-continued
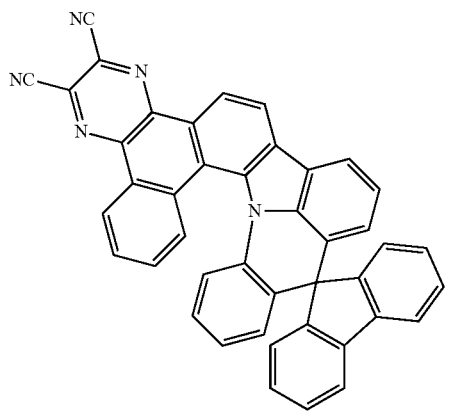
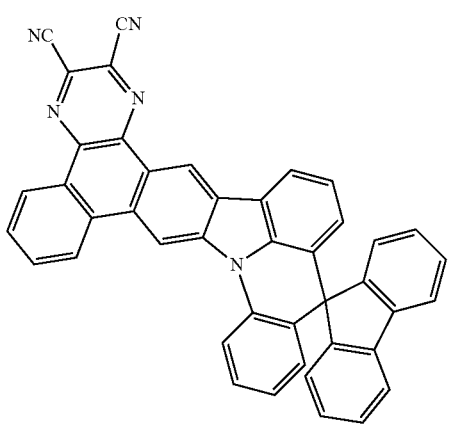
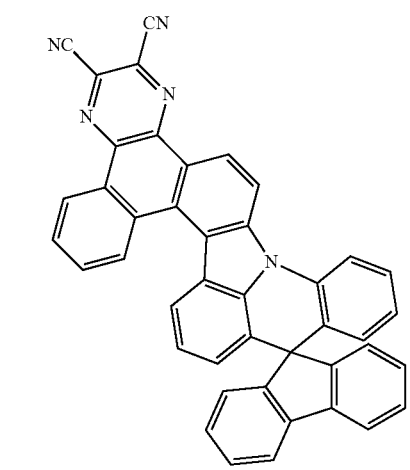
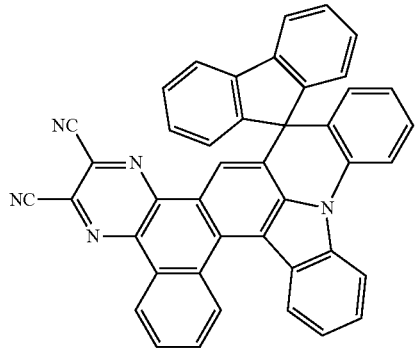

139
-continued
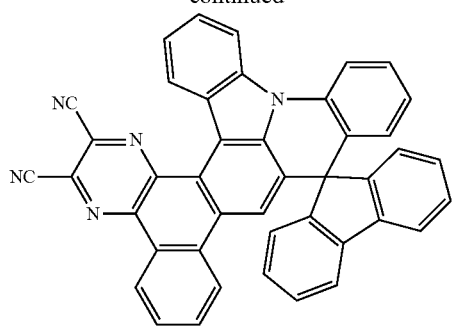
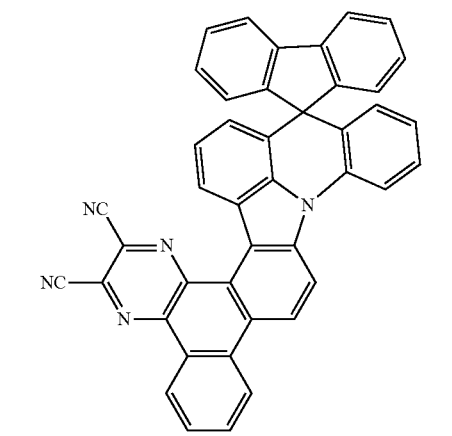
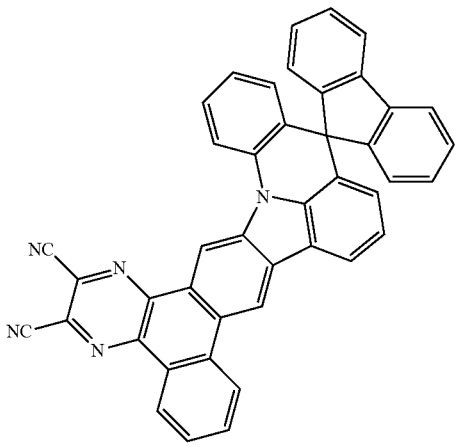
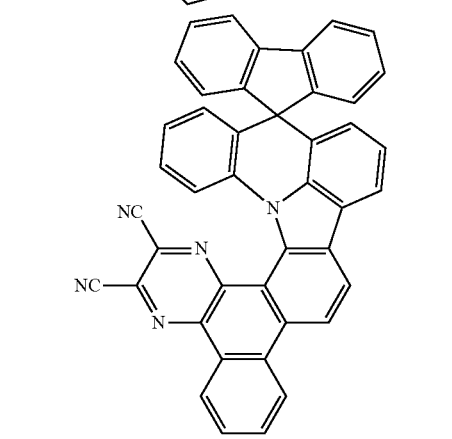
140
-continued
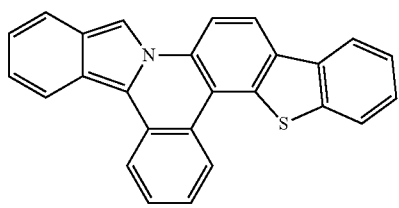
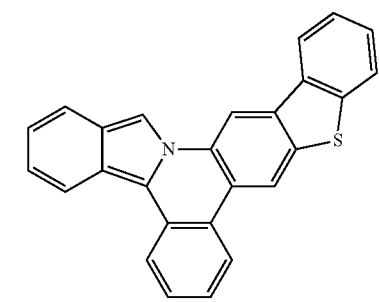
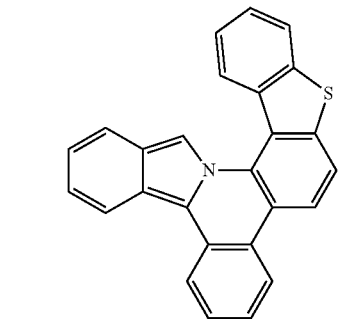
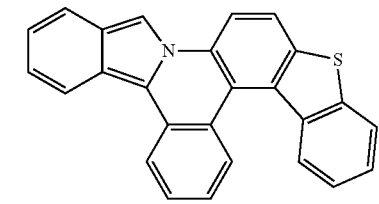
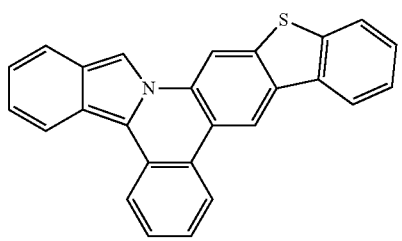
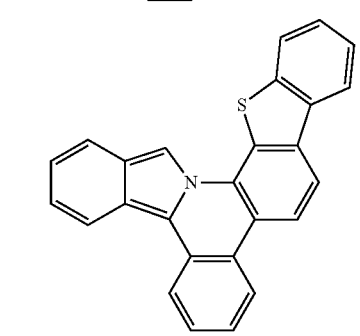

141
-continued
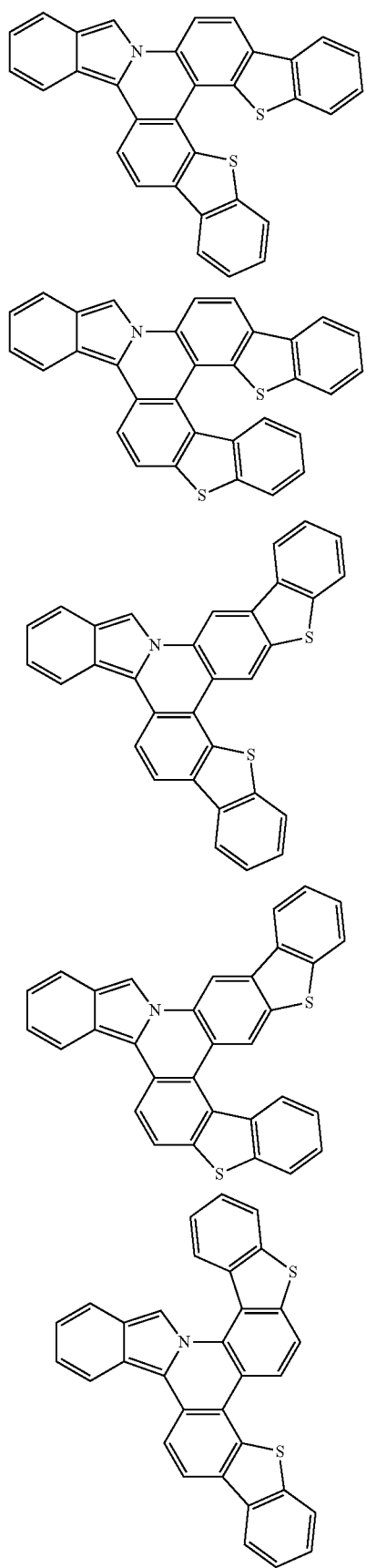
142
-continued
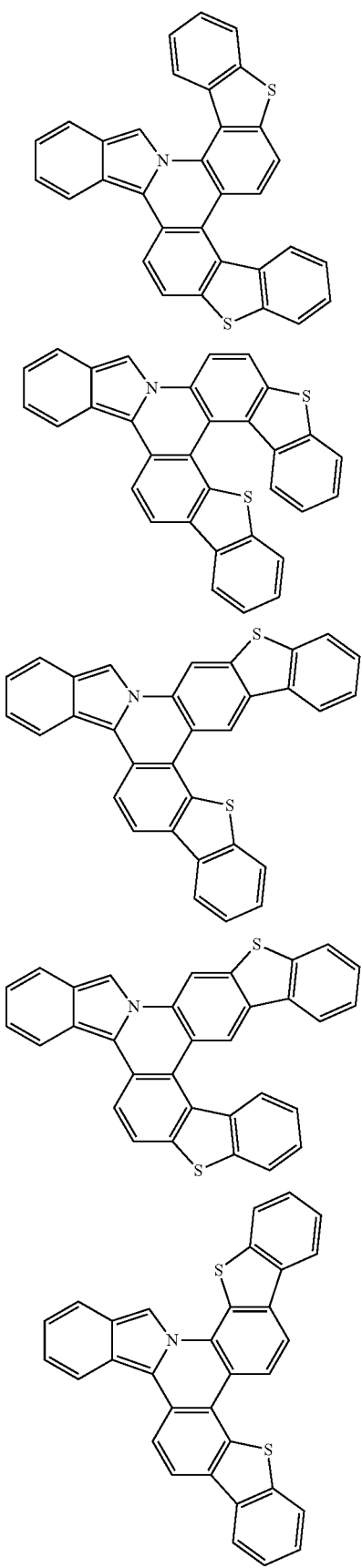

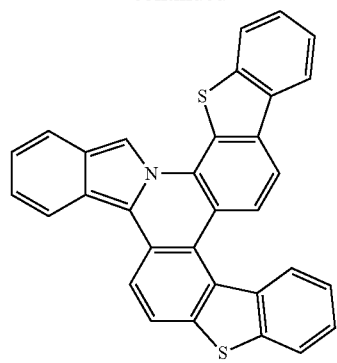
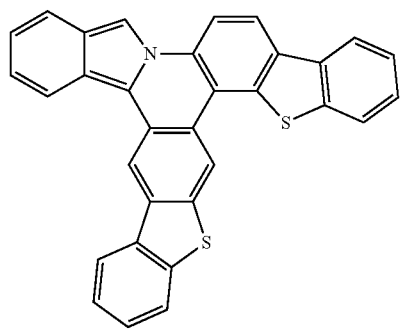
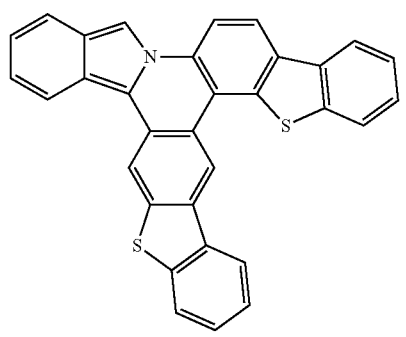
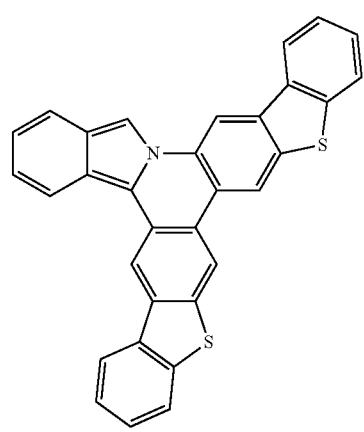
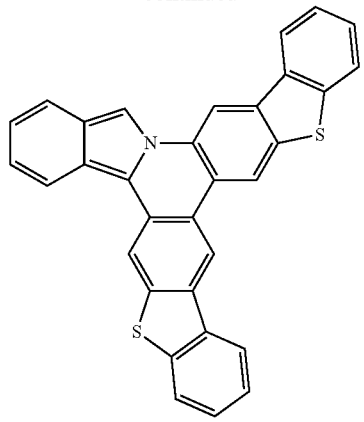
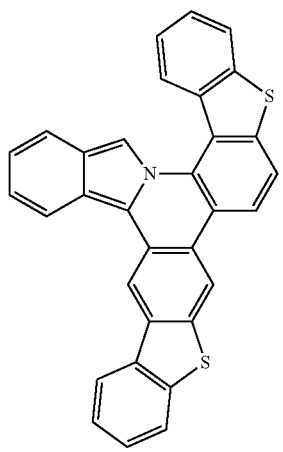
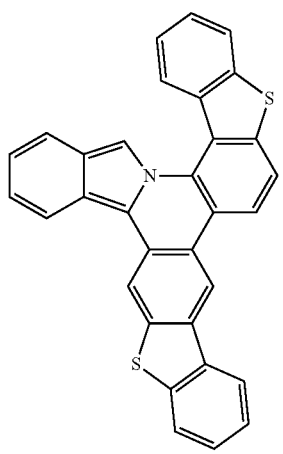
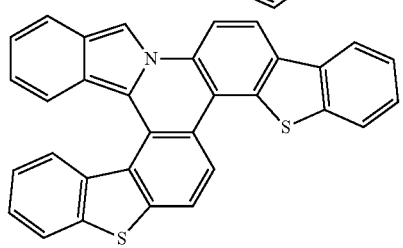

145
-continued
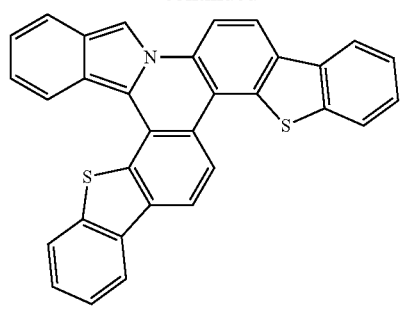
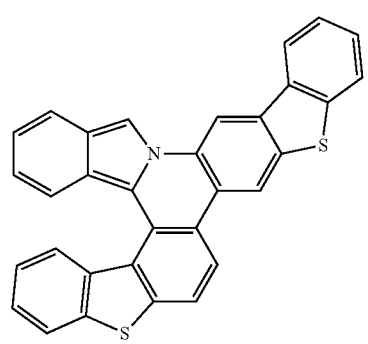
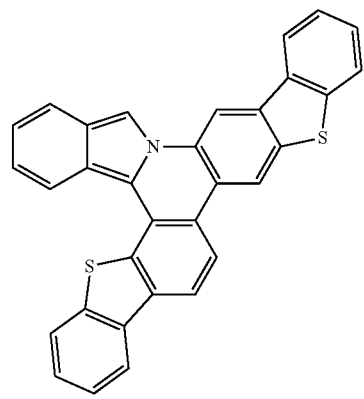
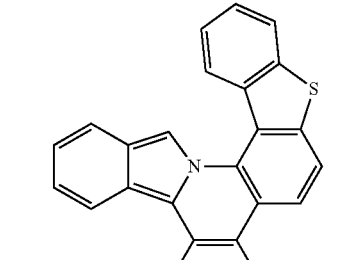
146
-continued
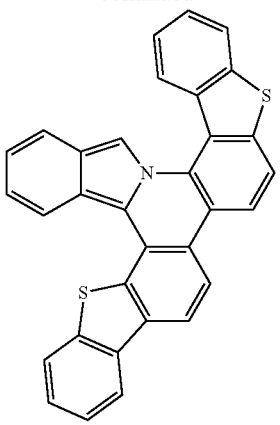
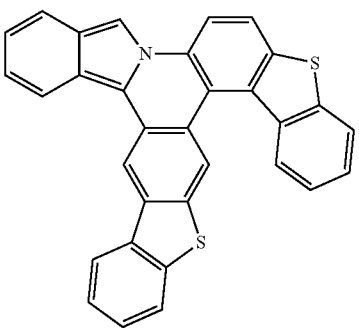
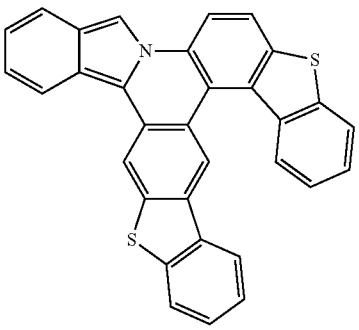
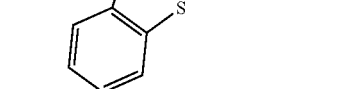

147
-continued
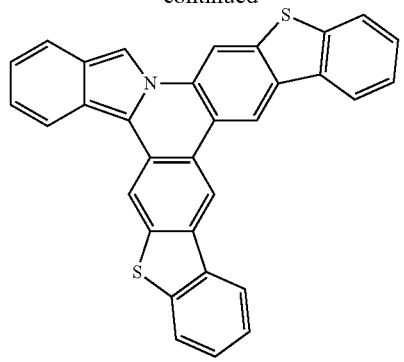
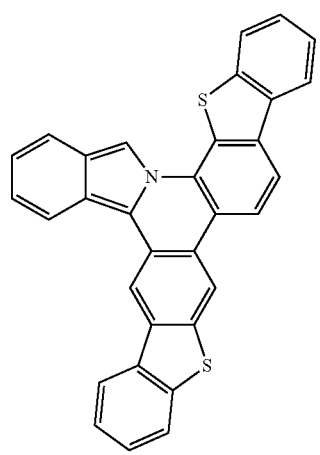
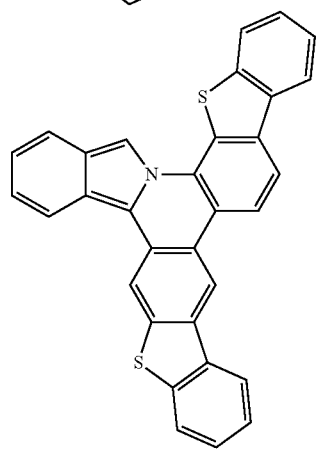
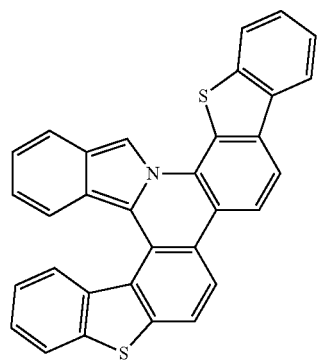
148
-continued
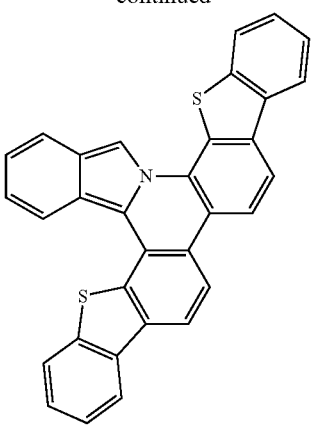
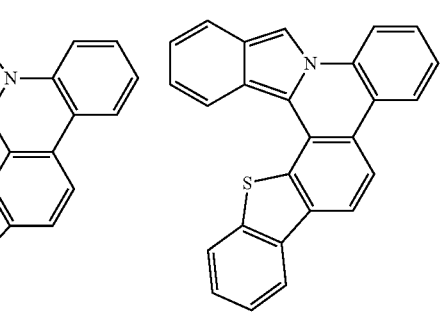
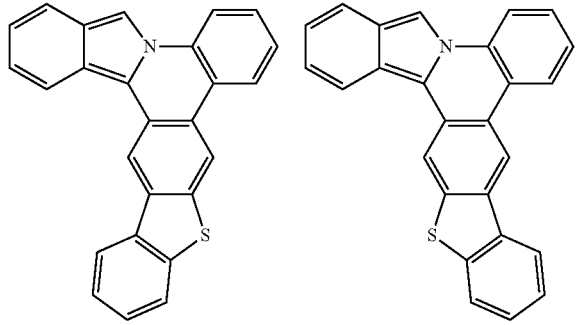
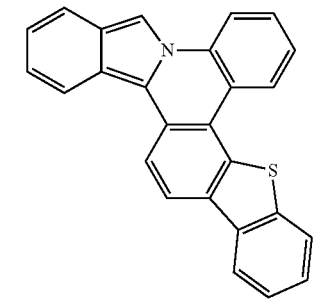
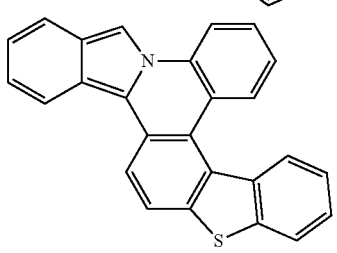

149
-continued
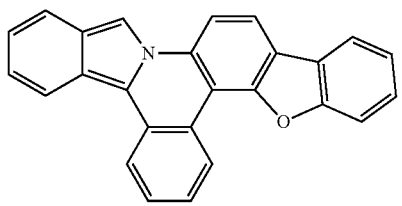
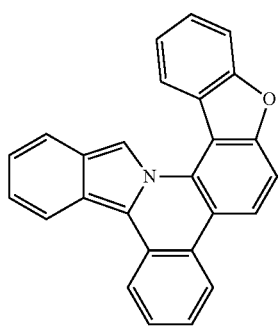
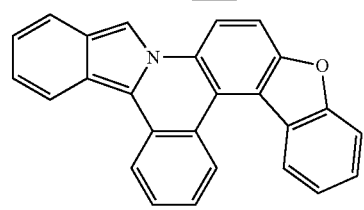
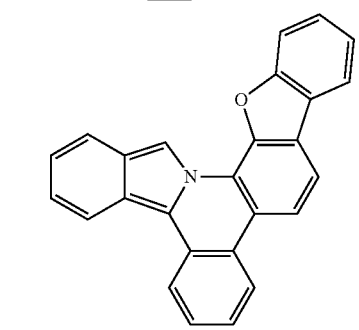
150
-continued
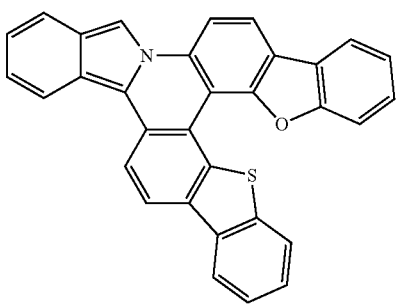
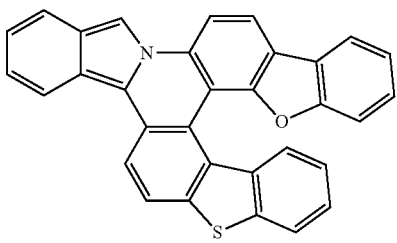
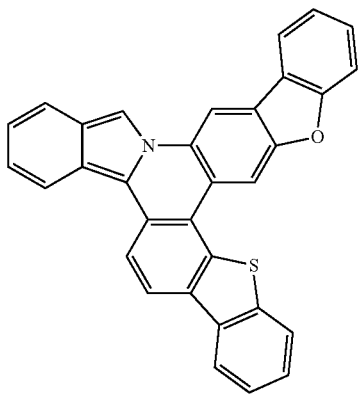
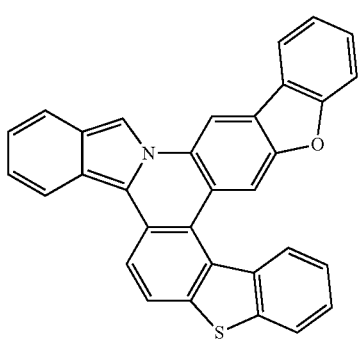
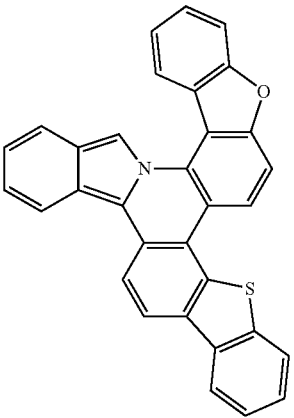

151
-continued
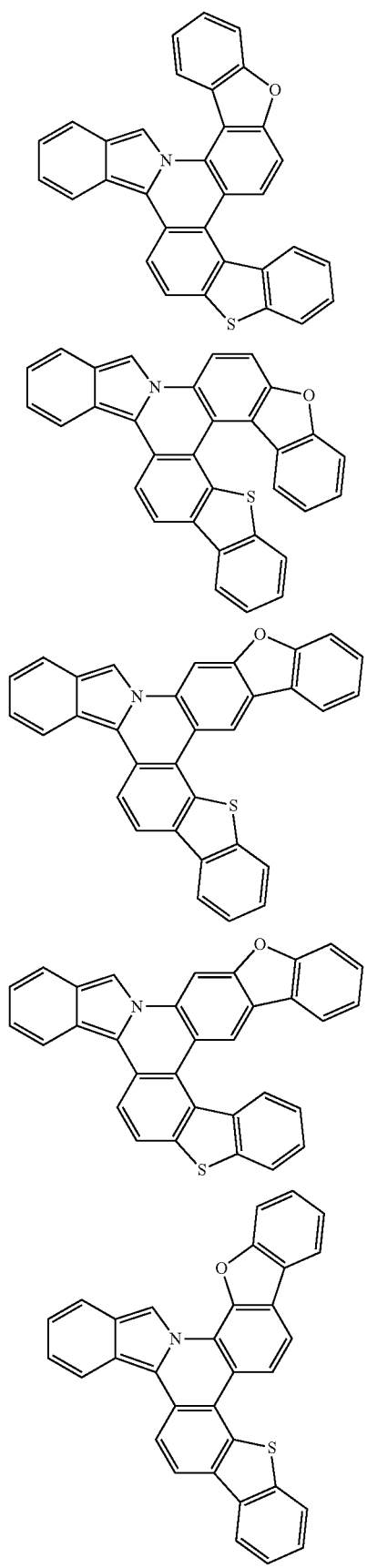
152
-continued
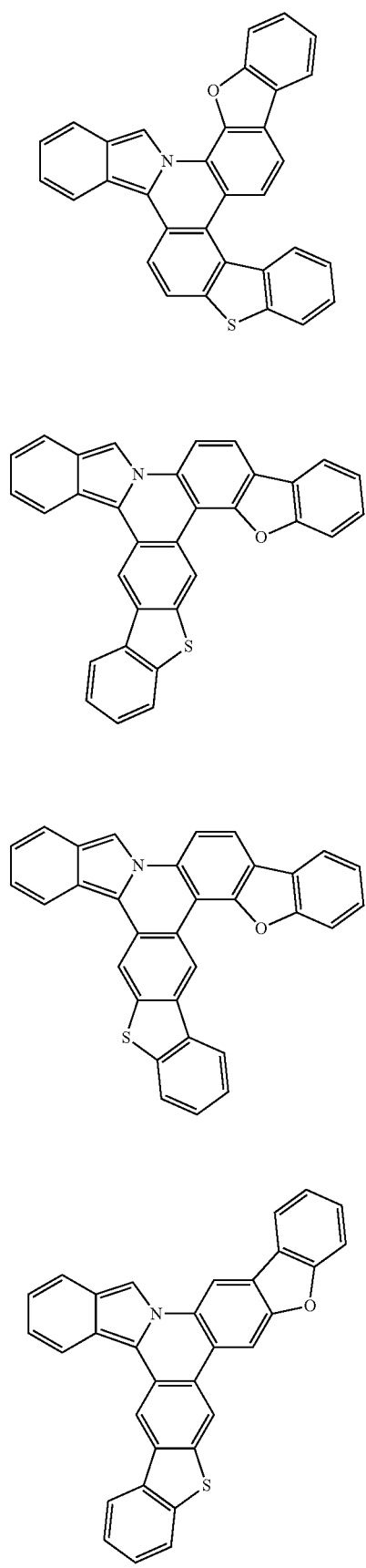

153
-continued
154
-continued
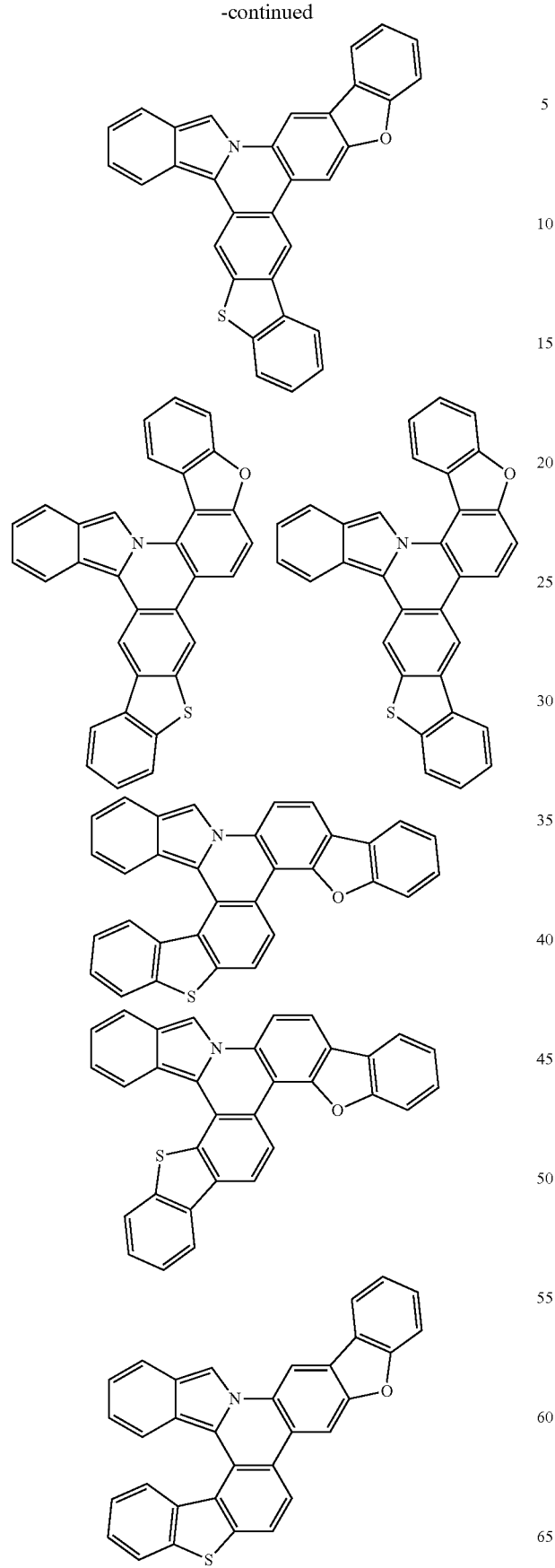
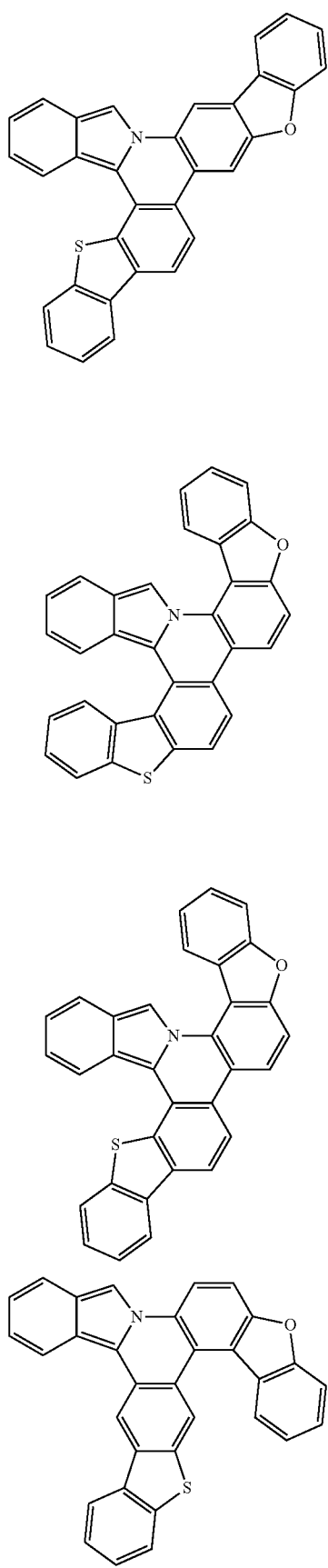

155
-continued
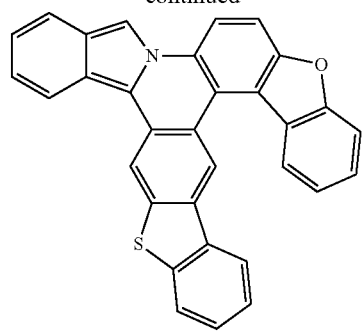
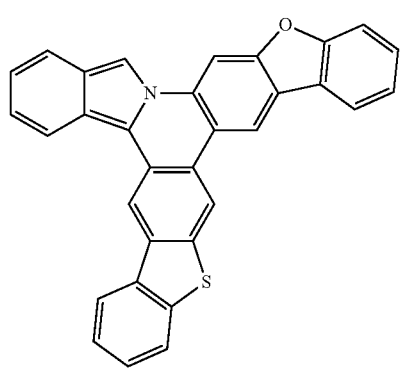
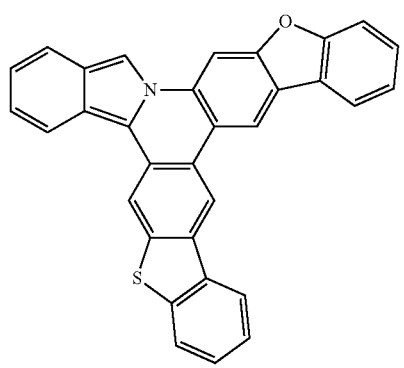
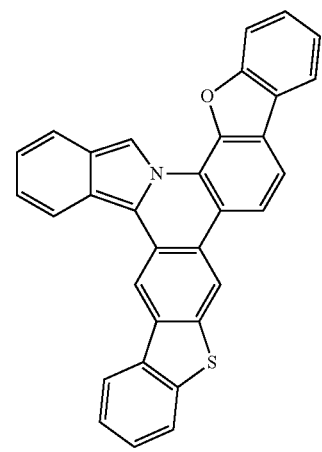
156
-continued
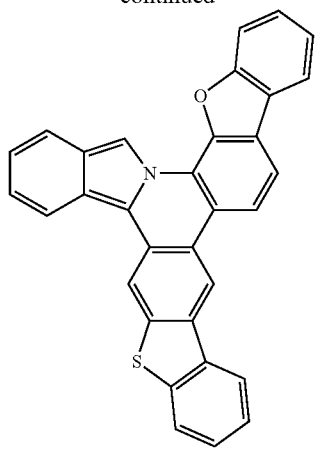
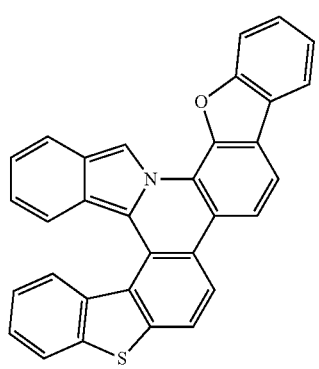
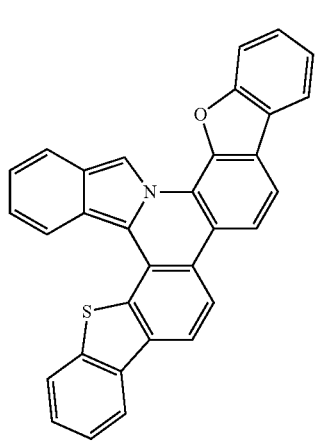
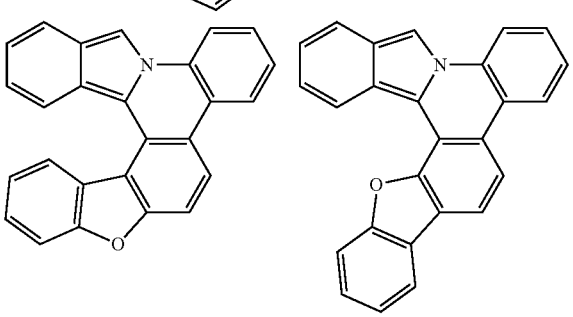

157
-continued
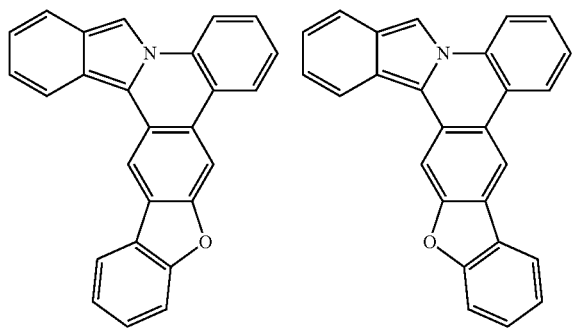
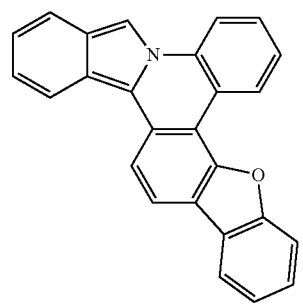
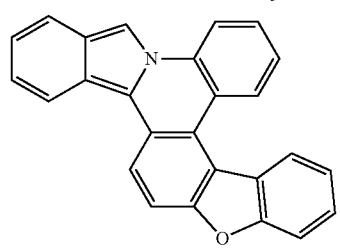
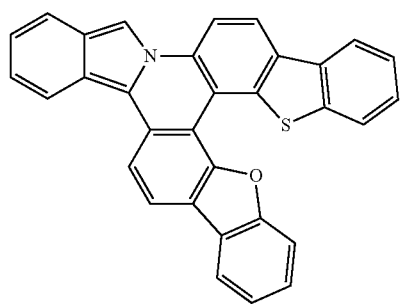 [SMILES: c1ccc2c(c1)cn1c3ccc4c5ccccc5sc4c3c3c(ccc4c5ccccc5oc43)c21]
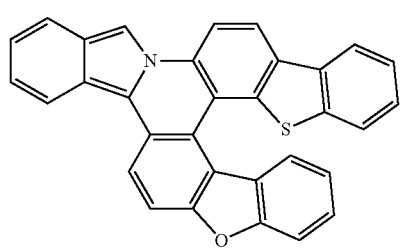
158
-continued
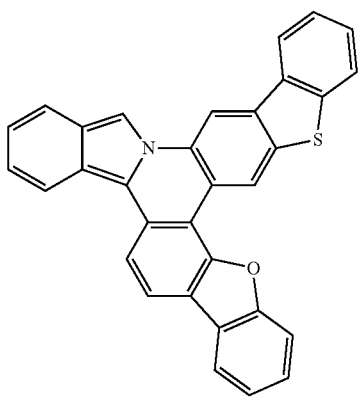
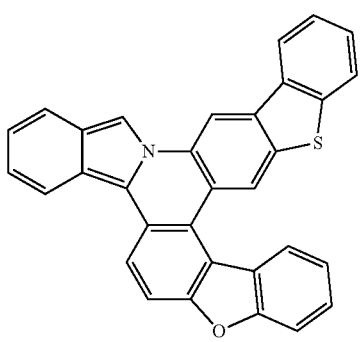
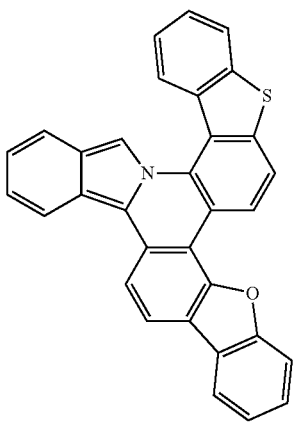
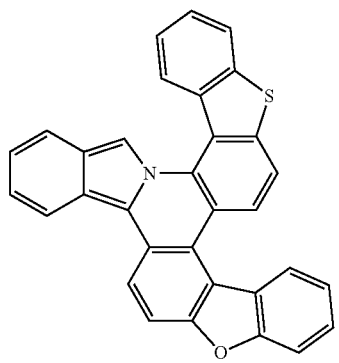

159
-continued
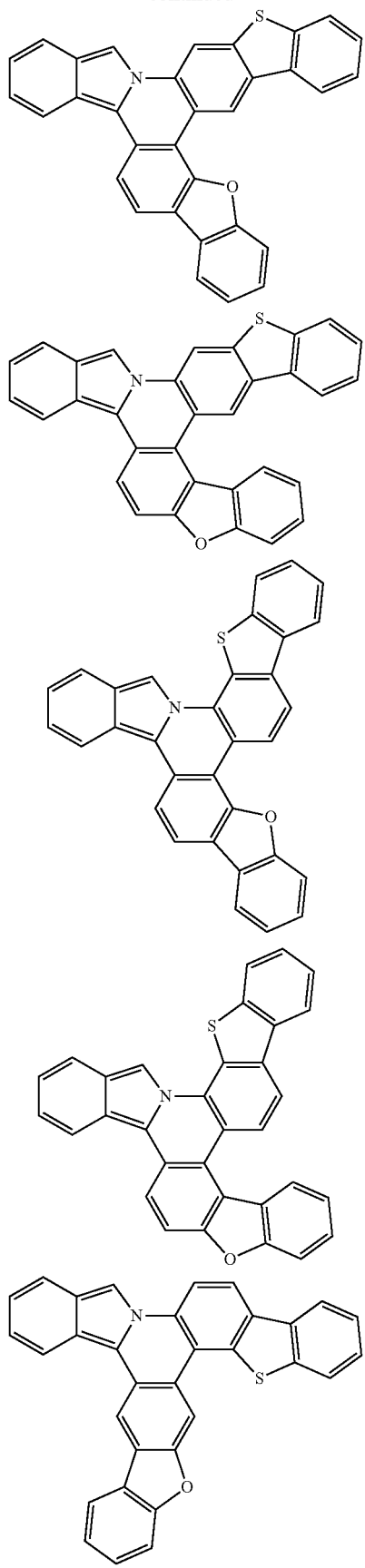
160
-continued
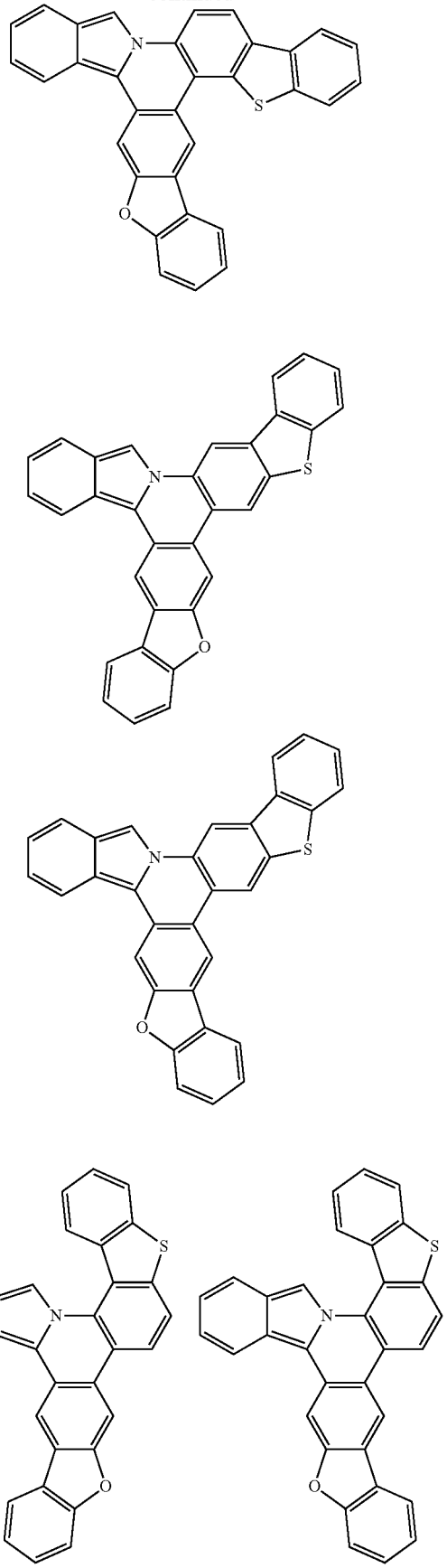

161
-continued
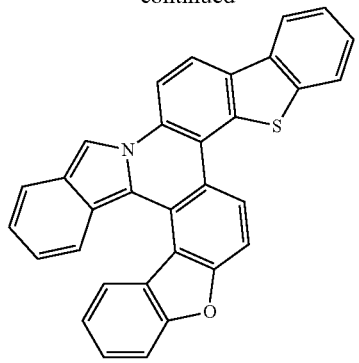
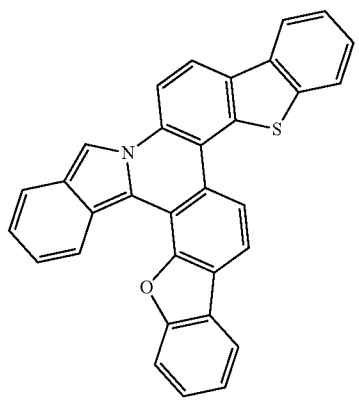
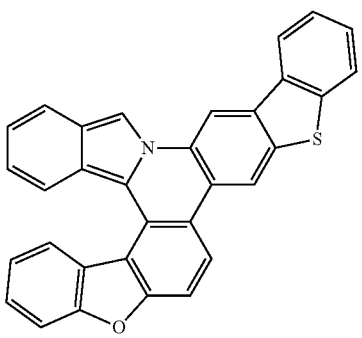
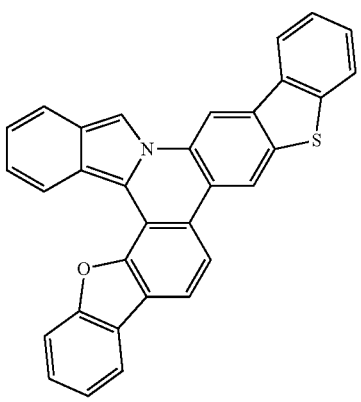
162
-continued
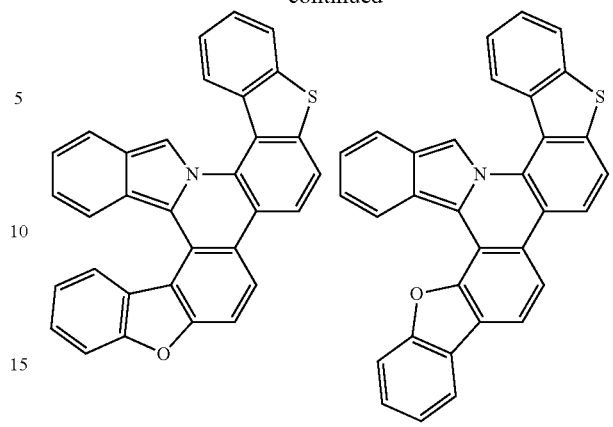
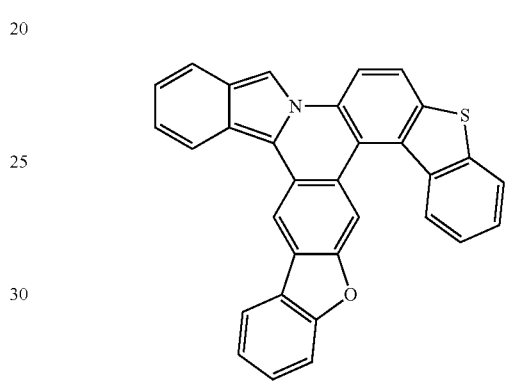
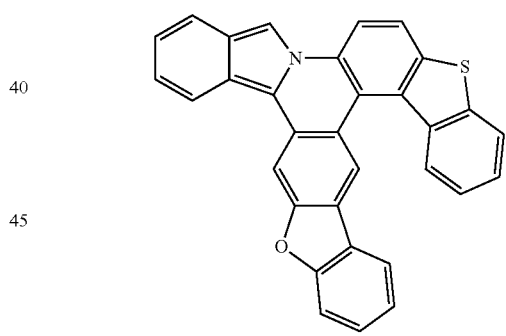
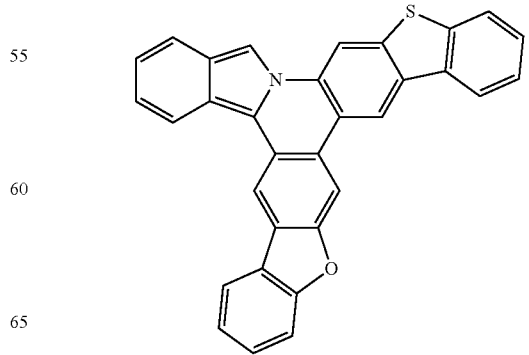

163
-continued
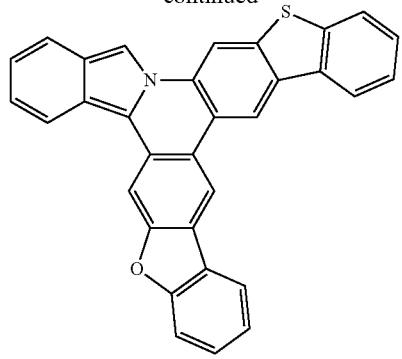
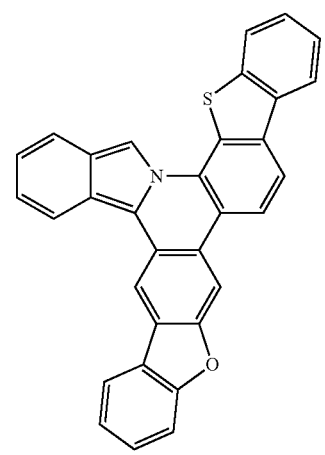
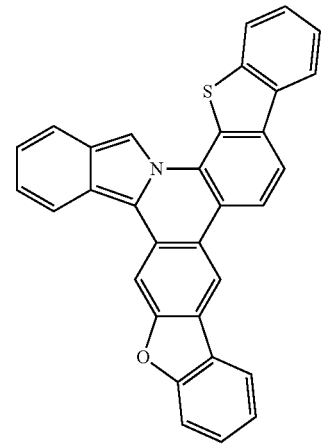
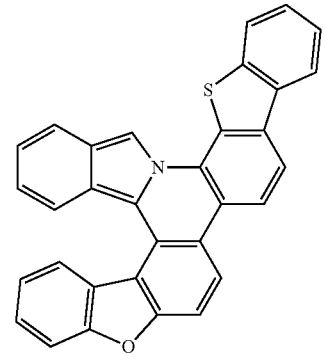
164
-continued
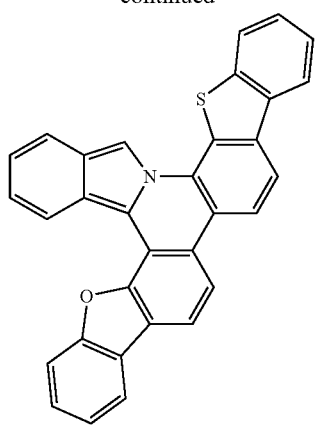
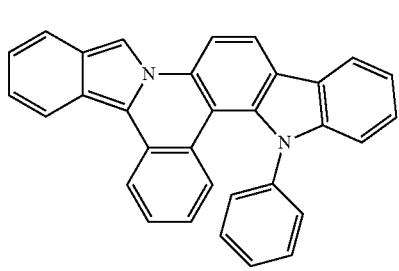
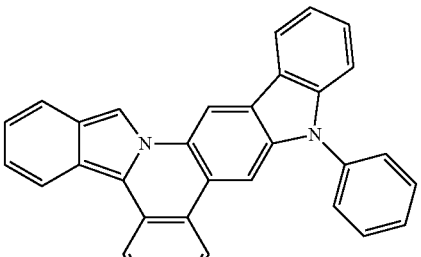
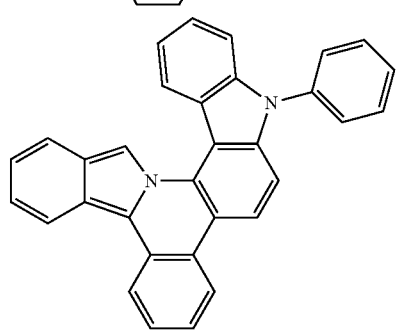
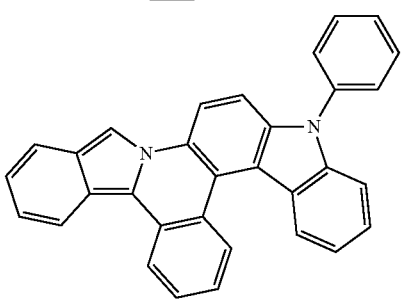

-continued
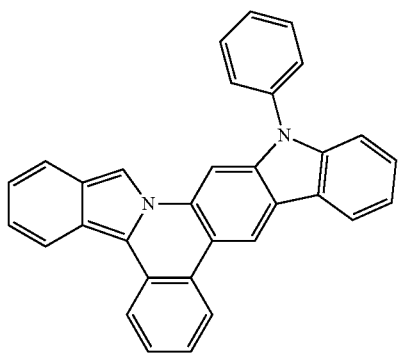
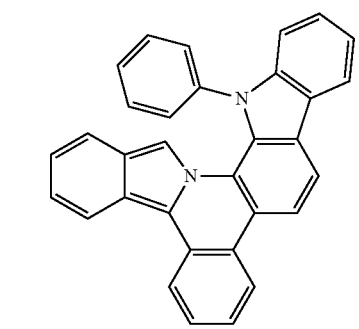
-continued
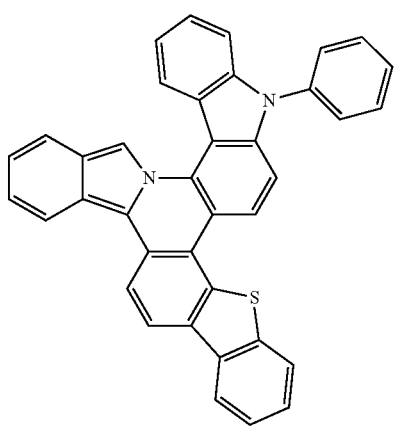
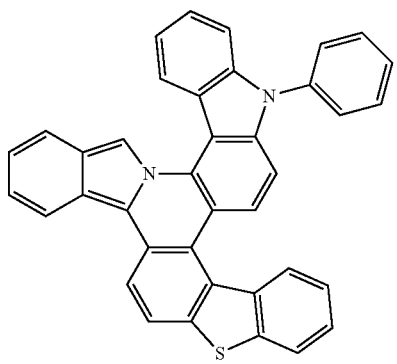
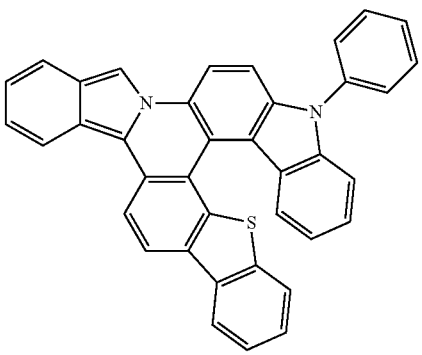

167
-continued
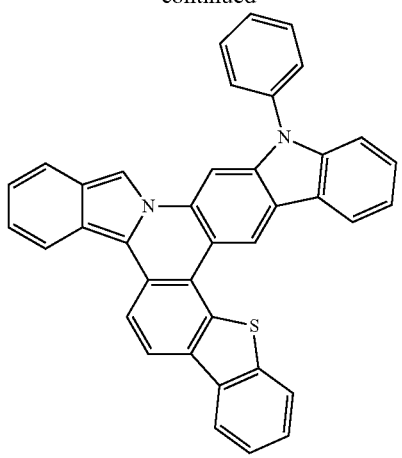
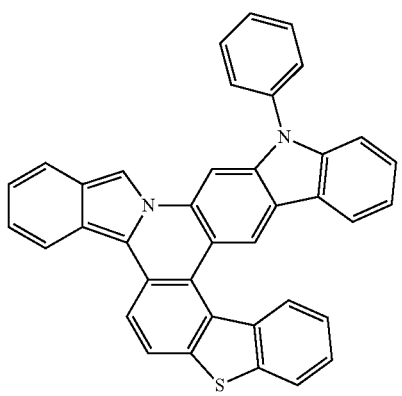
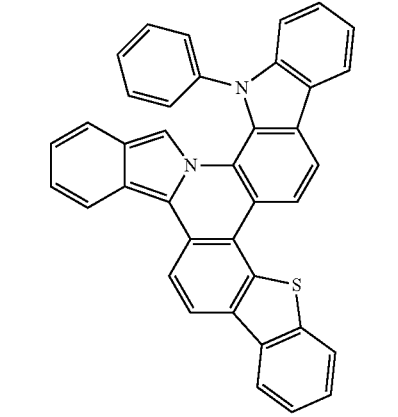
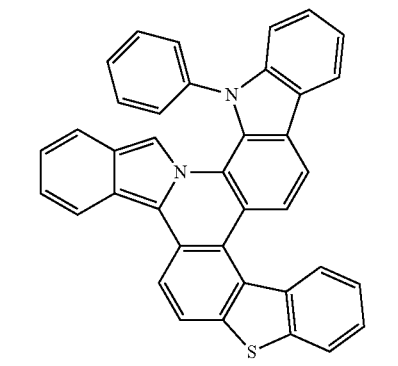
168
-continued
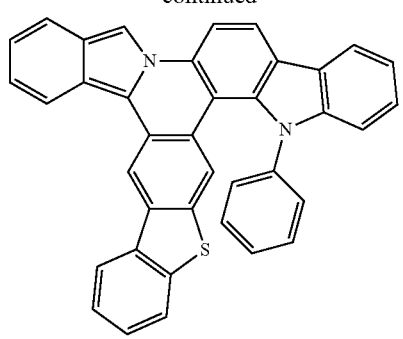
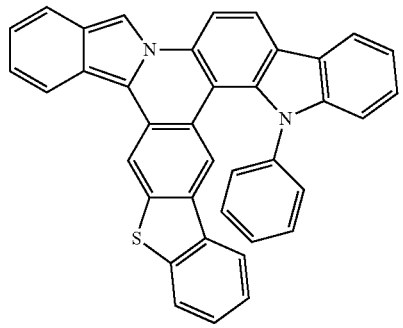
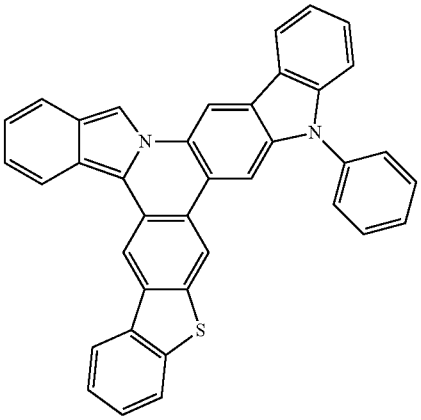
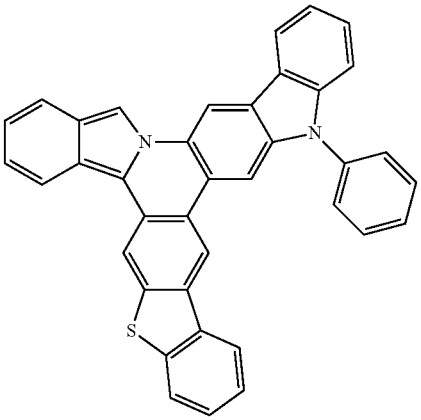

169
-continued
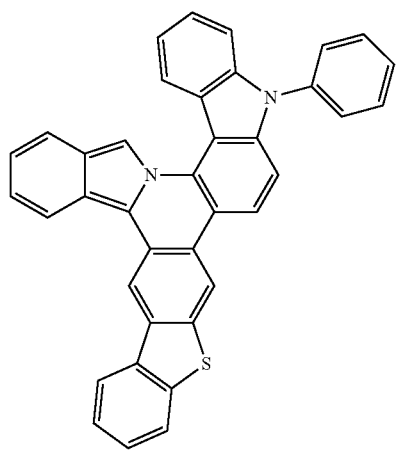
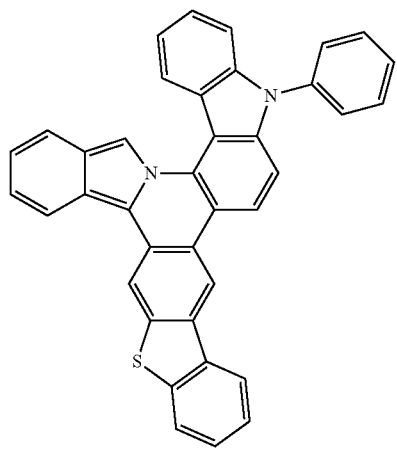
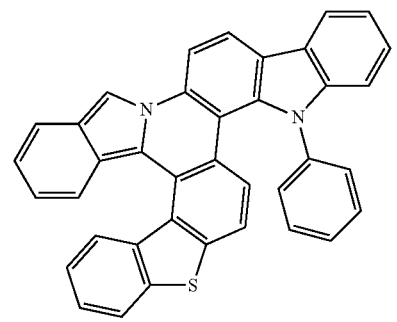
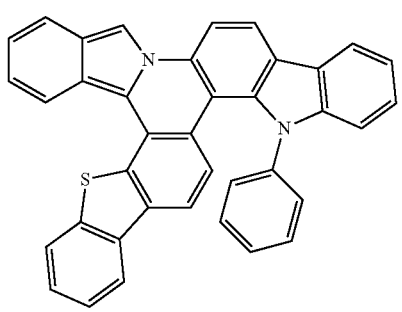
170
-continued
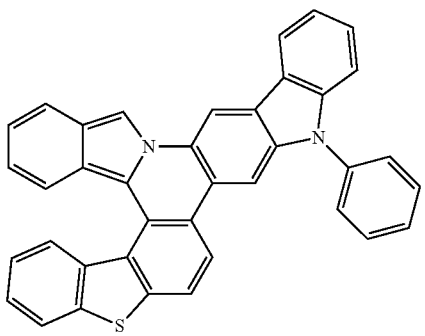
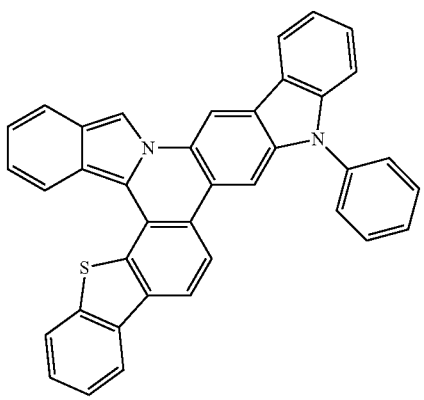
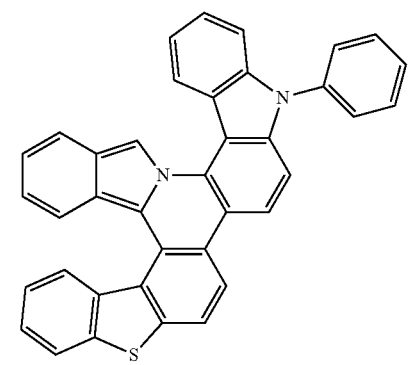
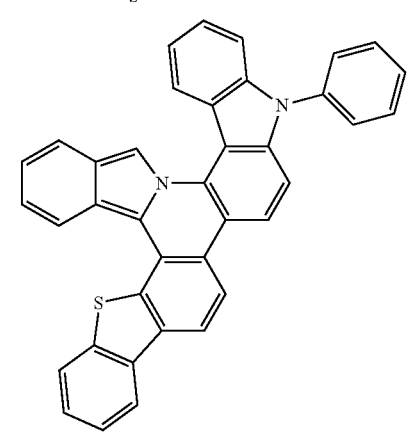

171
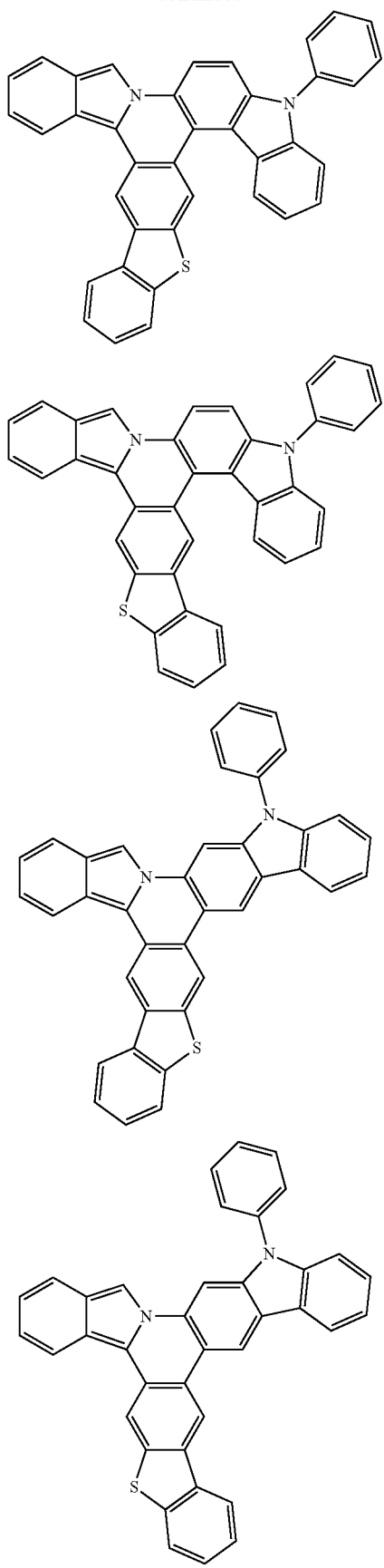
172
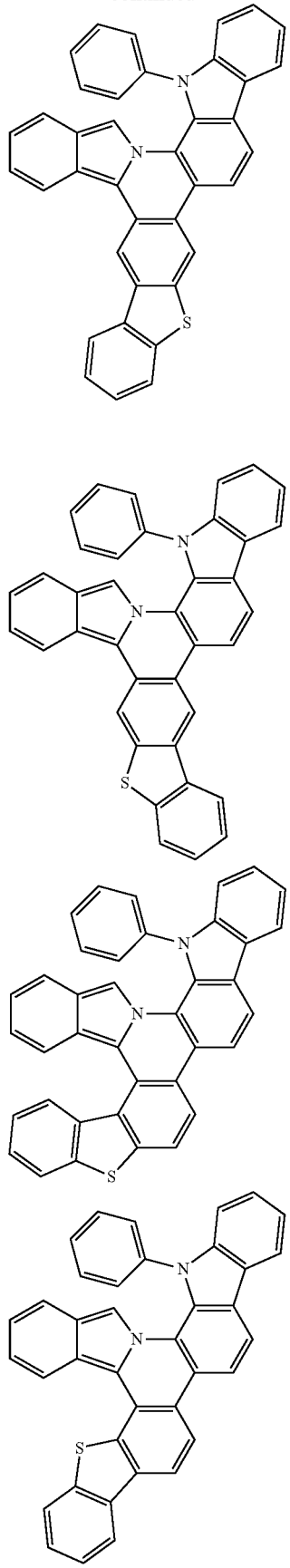

173
-continued
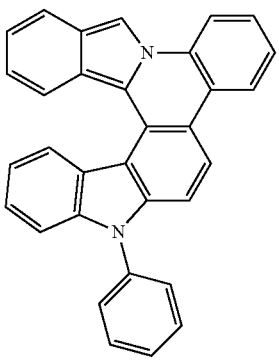
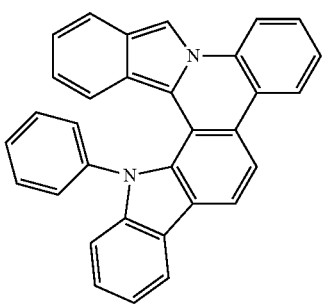
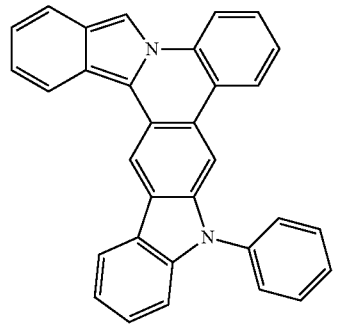
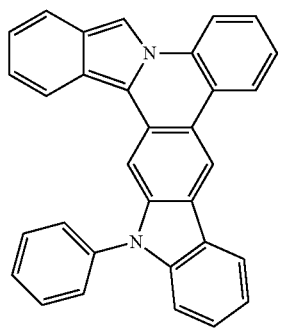
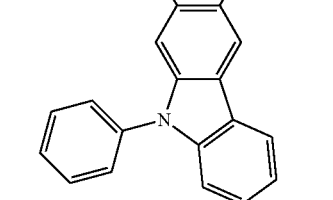
174
-continued
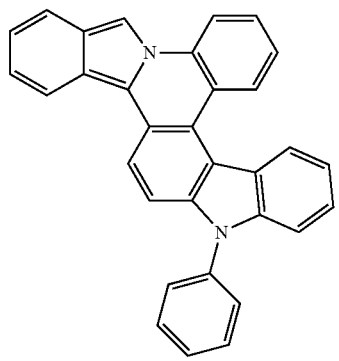
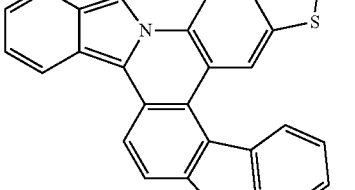
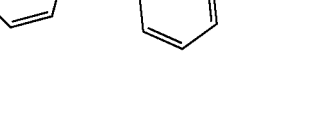

175
-continued
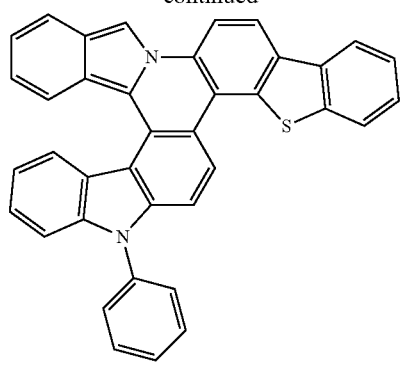
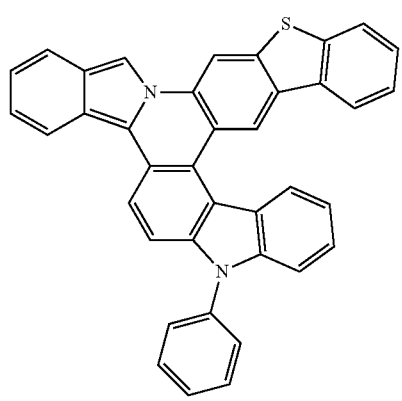
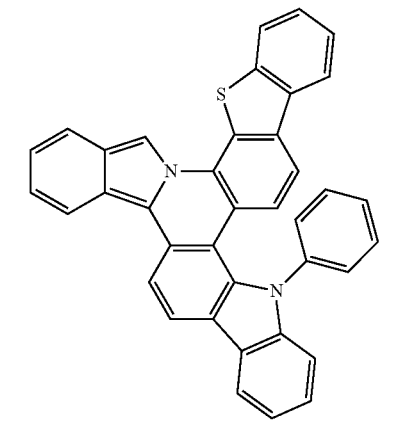
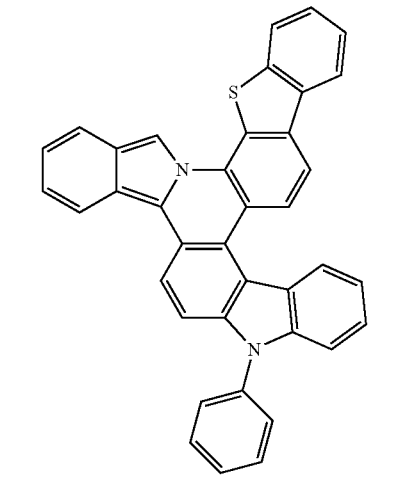
176
-continued
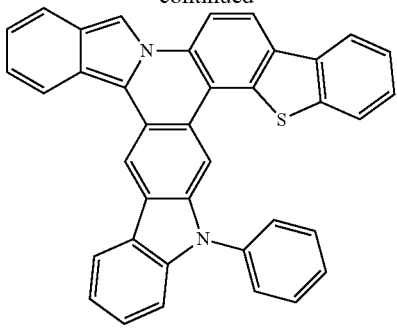
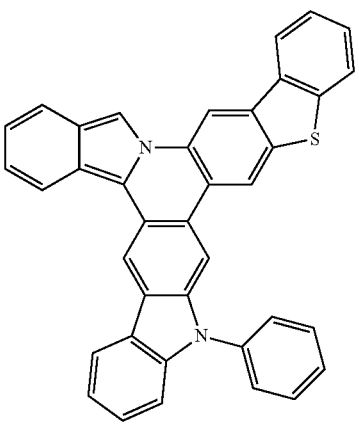
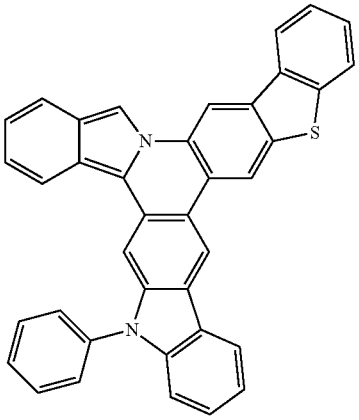
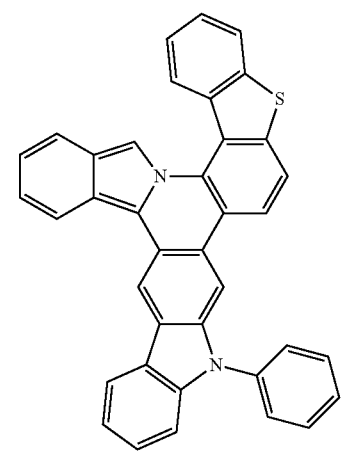

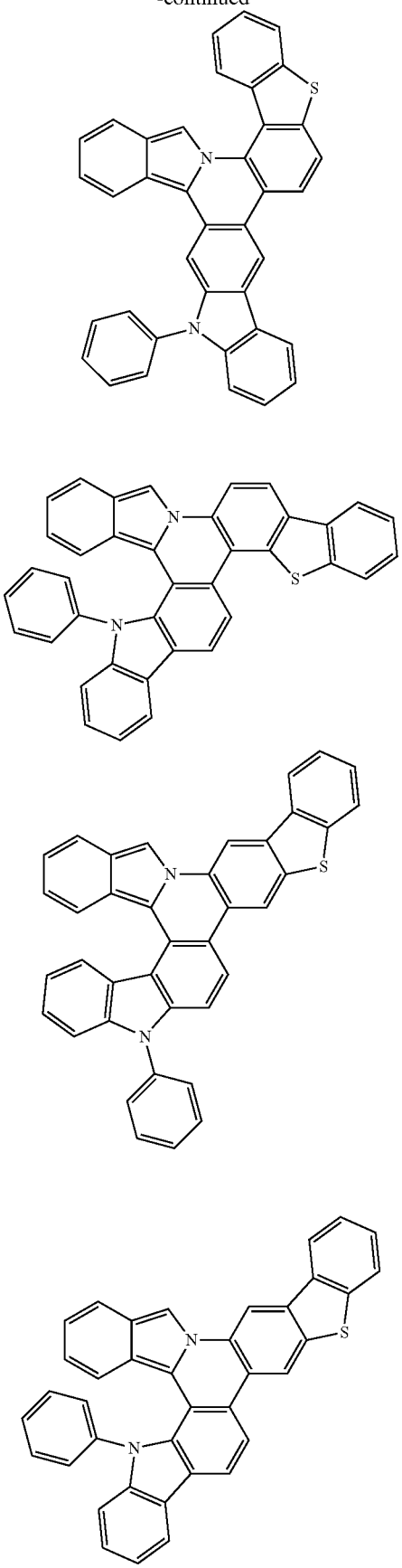
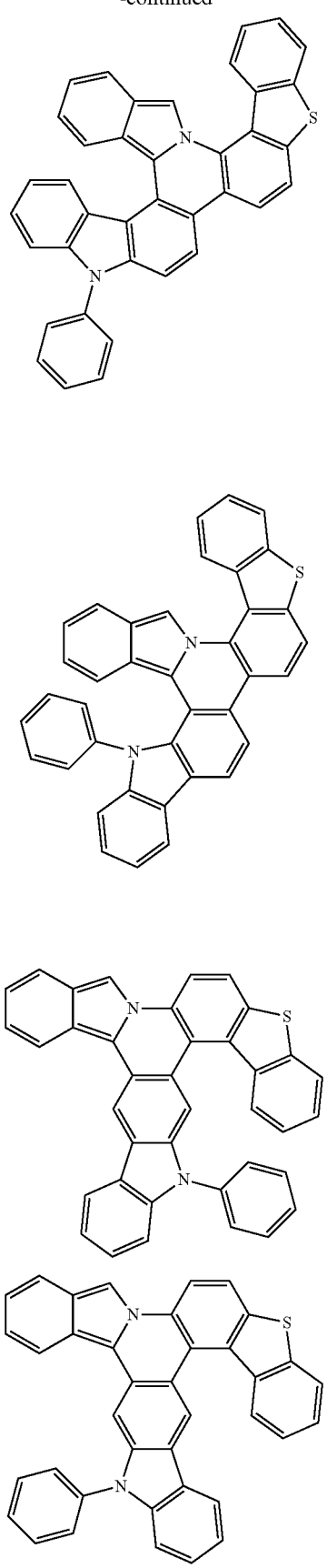

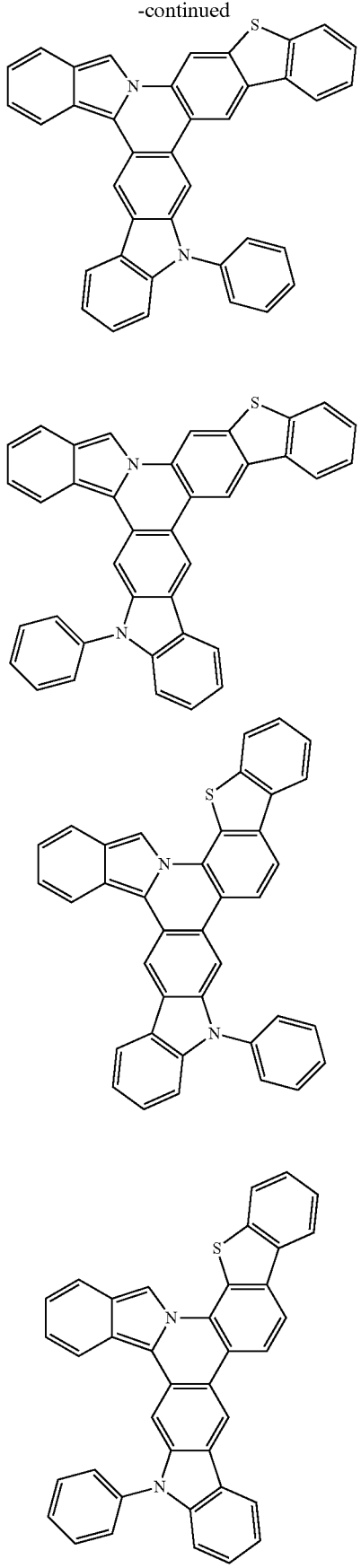
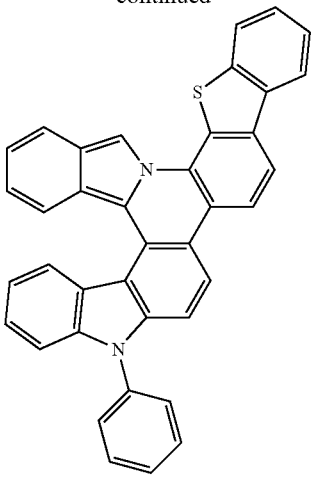
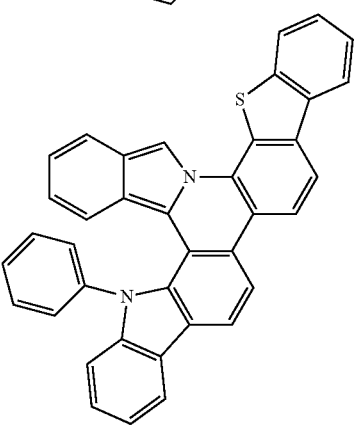

As referred to herein, a linking atom or group connects two atoms such as, for example, an N atom and a C atom. A linking atom or group is in one aspect disclosed as $L^1$, $L^2$, $L^3$, etc. herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties. The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", "$A^4$" and "$A^5$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$—$OA^2$ or —$OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula—$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula—($A^1$O(O)C-$A^2$-C(O)O)$_a$— or—($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula—($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" or "halo" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3, 4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "cyanide" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A'S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "R¹," "R²," "R³," "Rⁿ," where n is an integer, as used herein can, independently, possess one or more of the groups listed above. For example, if R¹ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

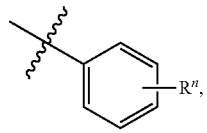

which is understood to be equivalent to a formula:

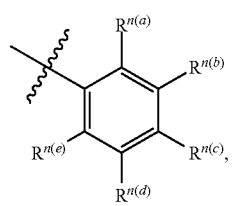

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. In a case where there is a single $R^n$ (e.g., only $R^{n(a)}$), $R^n$ is referred to as a "single substituent." In a case where there are two or more $R^n$ (e.g., at least $R^{n(a)}$ and $R^{n(b)}$) $R^n$ is referred to as a "multiple substituents."

Several references to R, $R^1$, $R^2$, $R^3$, $R^4$, $R^5$, $R^6$, etc. are made in chemical structures and moieties disclosed and described herein. Any description of R, $R^1$, $R^2$, $R^3$, $R^4$, $R^5$, $R^6$, etc. in the specification is applicable to any structure or moiety reciting R, $R^1$, $R^2$, $R^3$, $R^4$, $R^5$, $R^6$, etc. respectively.

The compounds disclosed herein are suited for use in a wide variety of devices, including, for example, organic light emitting diodes (OLEDs) for full color displays and lighting applications.

Also disclosed herein are compositions including one or more compounds disclosed herein. The present disclosure provides light emitting device that include one or more compositions described herein. The present disclosure also provides a photovoltaic device comprising one or more complexes or compositions described herein. Further, the present disclosure also provides a luminescent display device comprising one or more compounds described herein.

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Some of these synthetic examples have been performed. Others are based on an understanding of related synthetic procedures and are predictive in nature. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

Example 1

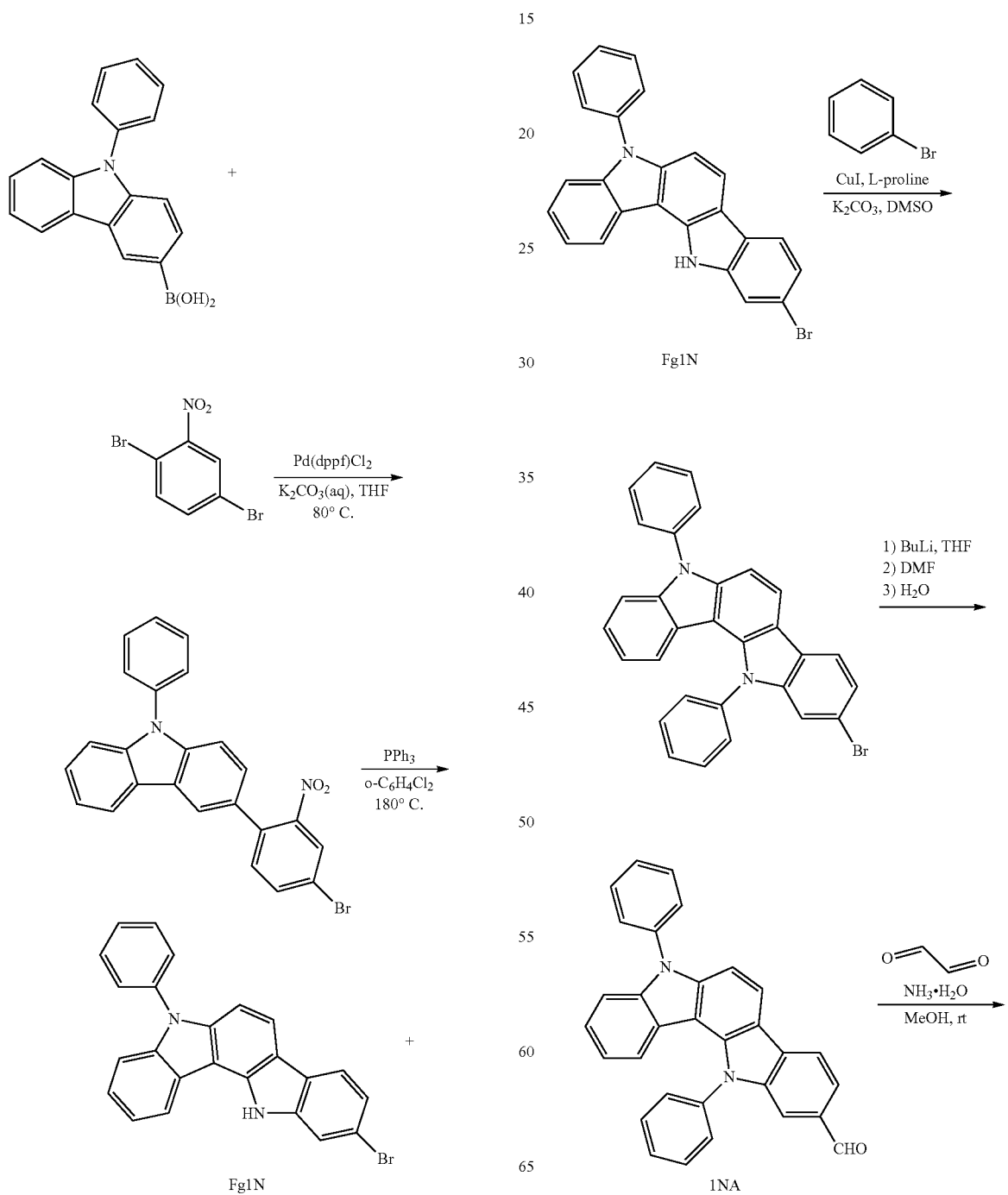

-continued

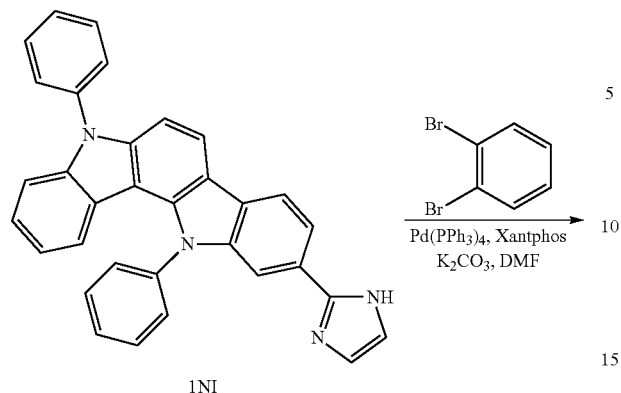

1NI

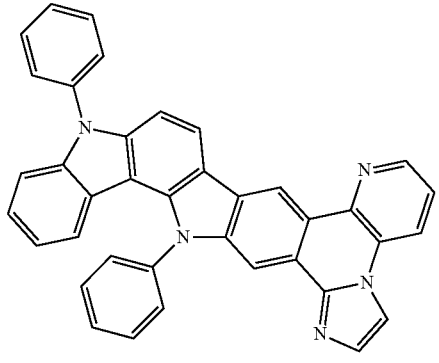

DFE-1N-2

To a flame-dried flask were added Pd(PPh₃)₄ (10 mol %), Xantphos (10 mol %), Cs₂CO₃ (3 eq) and 2-chloro-3-iodopyridine (1.2 eq). Then, 1NI (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1N-2 in 53% yield.

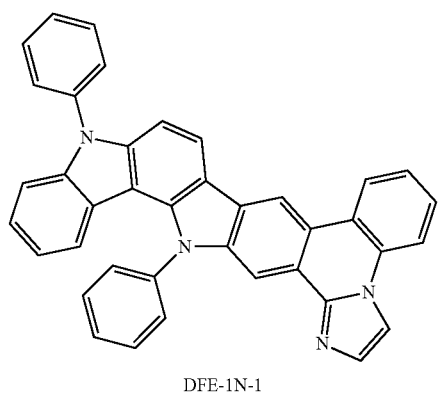 [SMILES: c1ccc(-n2c3ccccc3c3c2ccc2c4cc5c6ccccc6n6ccnc6c5cc4n(-c4ccccc4)c23)cc1]

DFE-1N-1

To a flame-dried flask were added Pd(PPh₃)₄ (10 mol %), Xantphos (10 mol %), Cs₂CO₃ (3 eq) and 1,2-dibromobenzene (1.2 eq). Then, 1NI (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1N-1 in 61% yield.

Example 2

Example 3

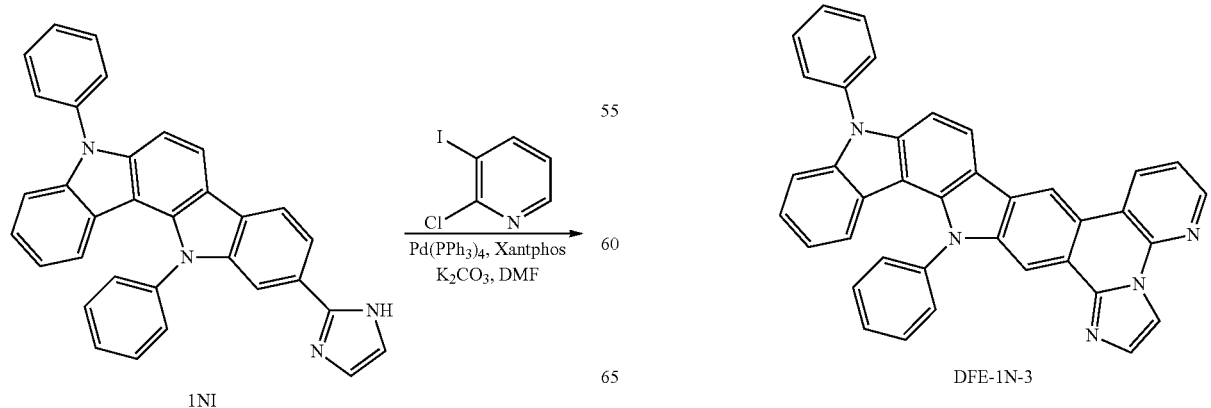

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 1NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1N-3 in 22% yield.

Example 4

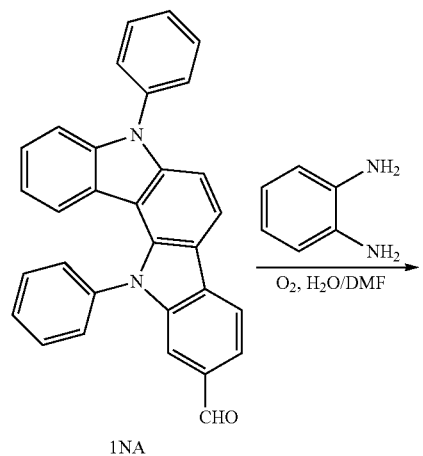

1NA

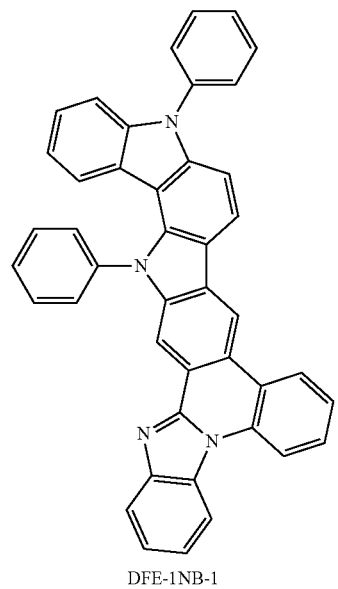

DFE-1NB-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 1NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1NB-1 in 55% yield.

Example 5

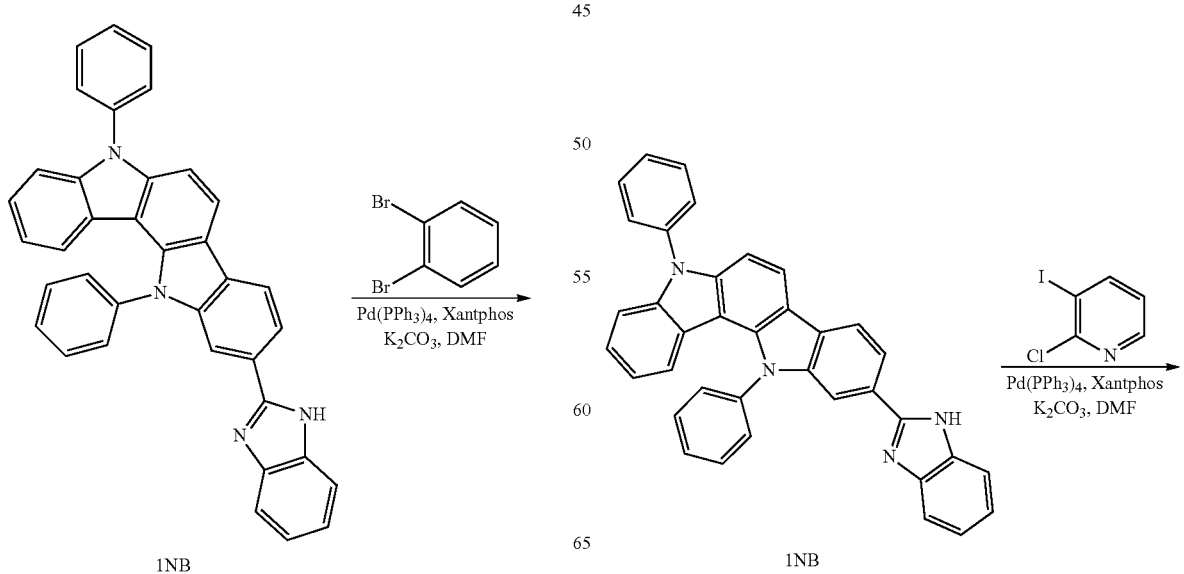

1NB

193
-continued

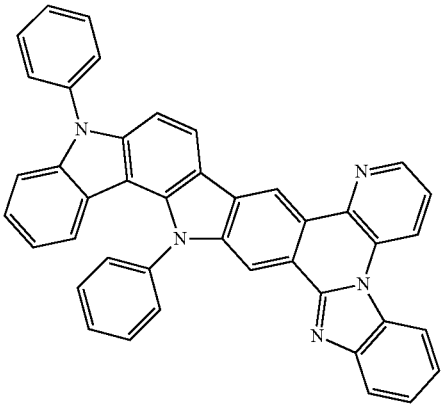

DFE-1NB-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 1NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1NB-2 in 42% yield.

Example 6

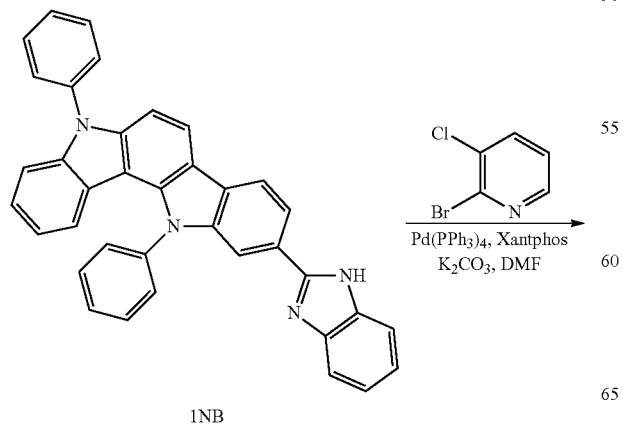

1NB

194
-continued

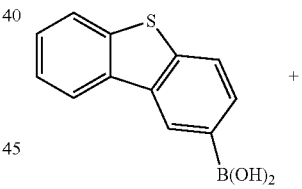

DFE-1NB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 1NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1NB-3 in 35% yield.

Example 7

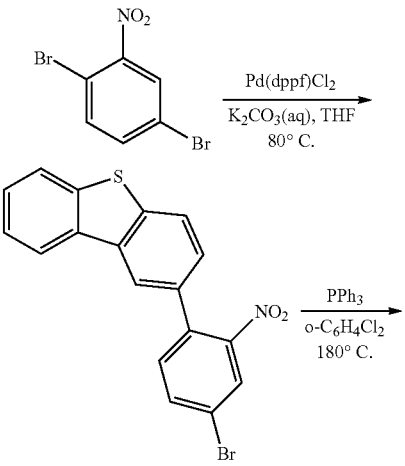

-continued

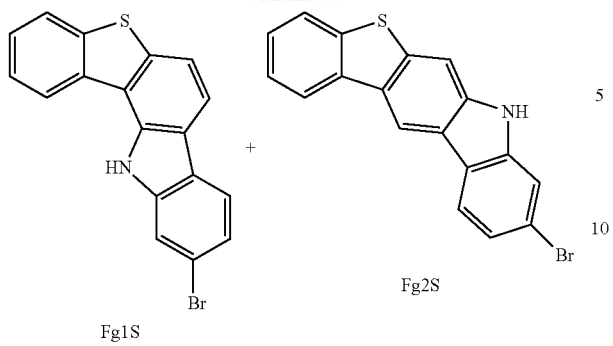

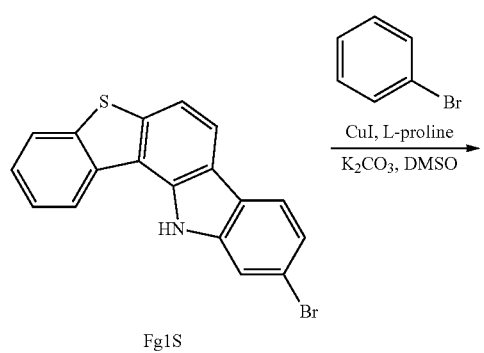

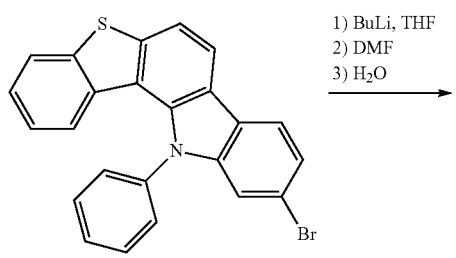

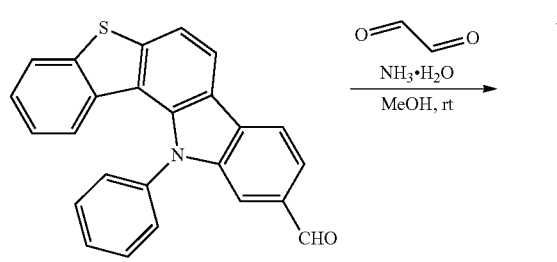

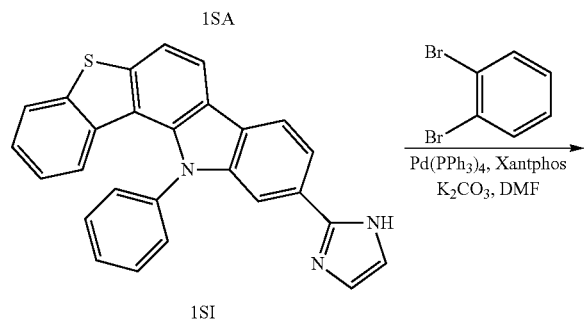

-continued

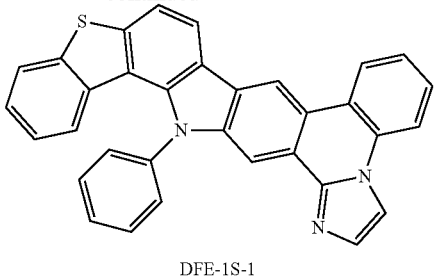

DFE-1S-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 1SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1S-1 in 64% yield.

Example 8

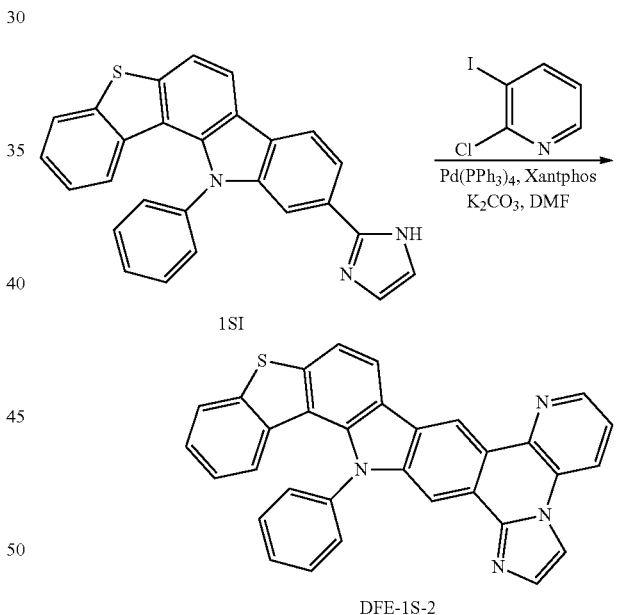

DFE-1S-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 1St (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1S-2 in 67% yield.

Example 9

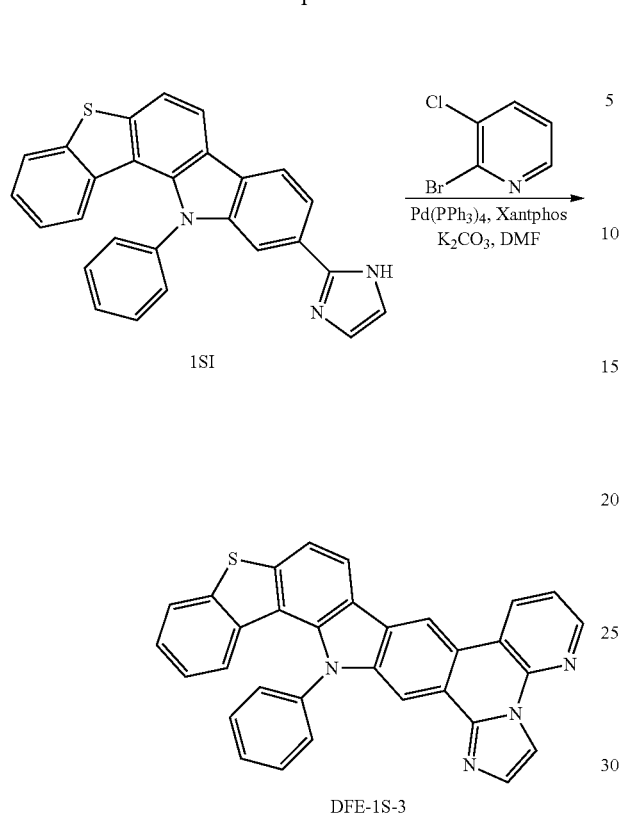

To a flame-dried flask were added Pd(PPh₃)₄ (10 mol %), Xantphos (10 mol %), Cs₂CO₃ (3 eq) and 2-bromo-3-chloropyridine (1.2 eq). Then, 1St (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1S-3 in 22% yield.

Example 10

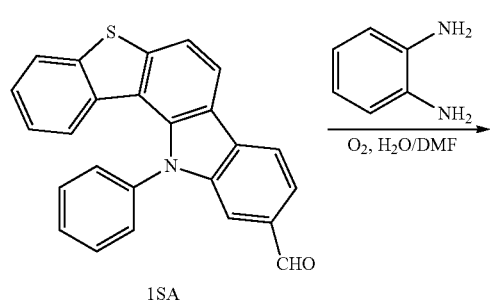

-continued

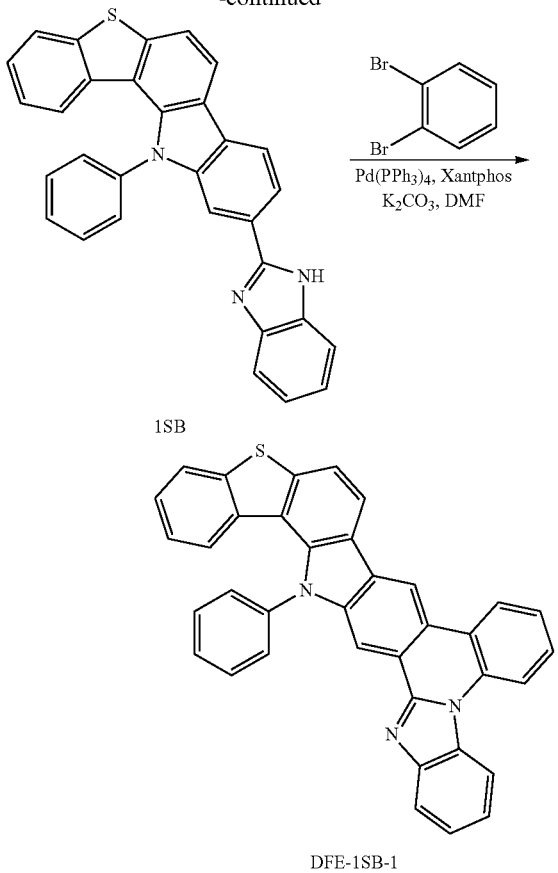

To a flame-dried flask were added Pd(PPh₃)₄ (10 mol %), Xantphos (10 mol %), Cs₂CO₃ (3 eq) and 1,2-dibromobenzene (1.2 eq). Then, 1SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1SB-1 in 66% yield.

Example 11

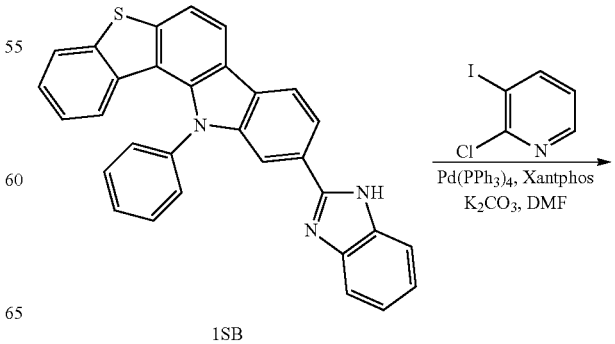

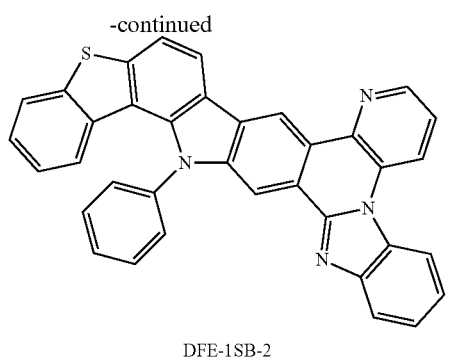

DFE-1SB-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 1SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1SB-2 in 45% yield.

Example 12

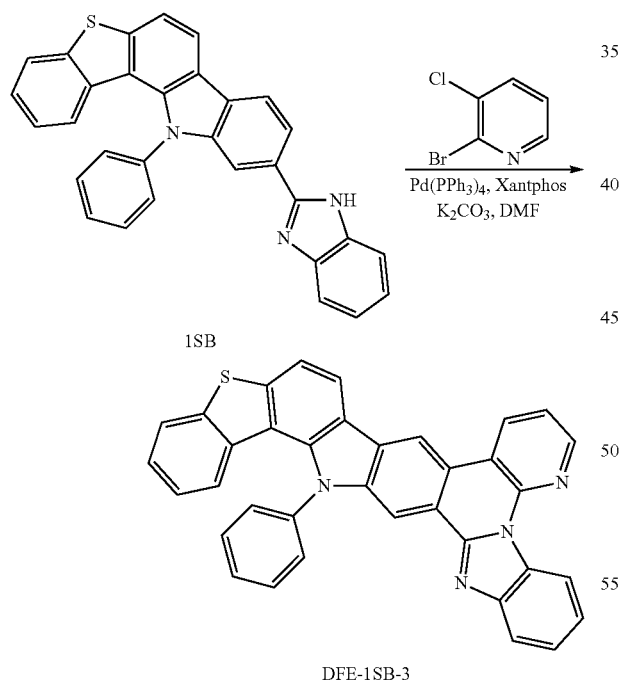

DFE-1SB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 1SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1SB-3 in 39% yield.

Example 13

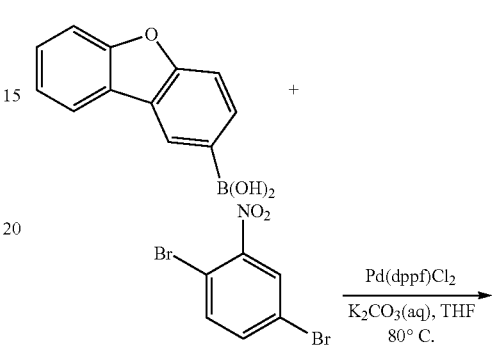

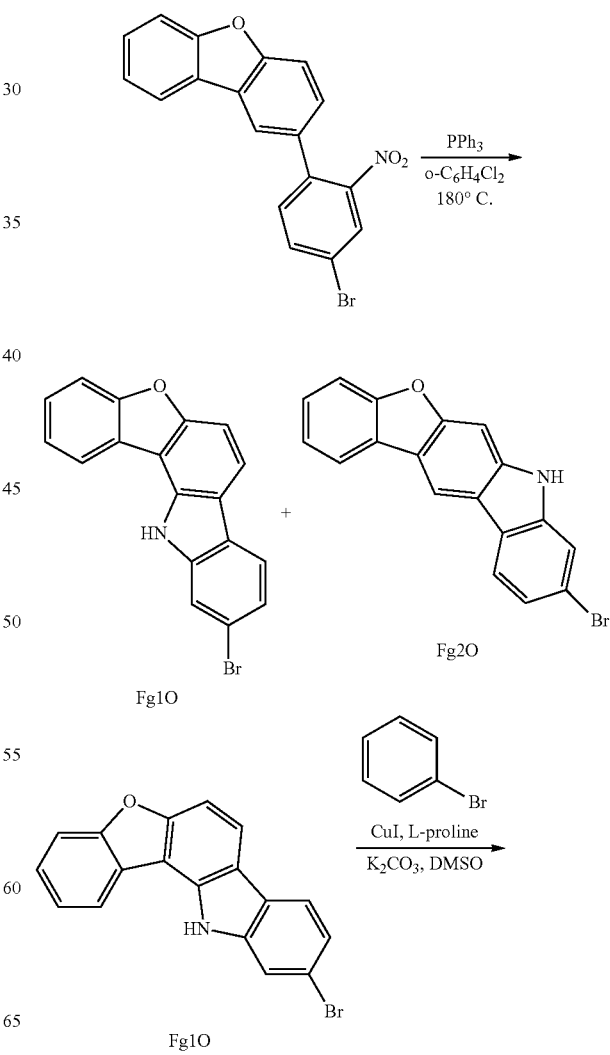

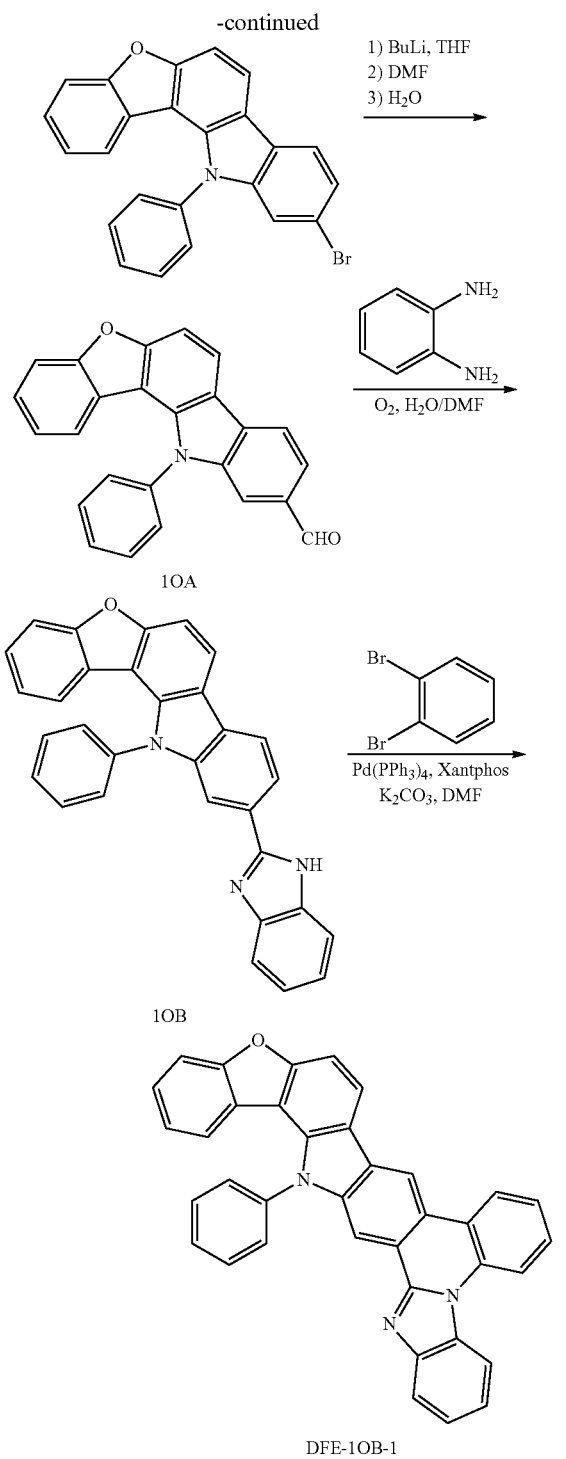

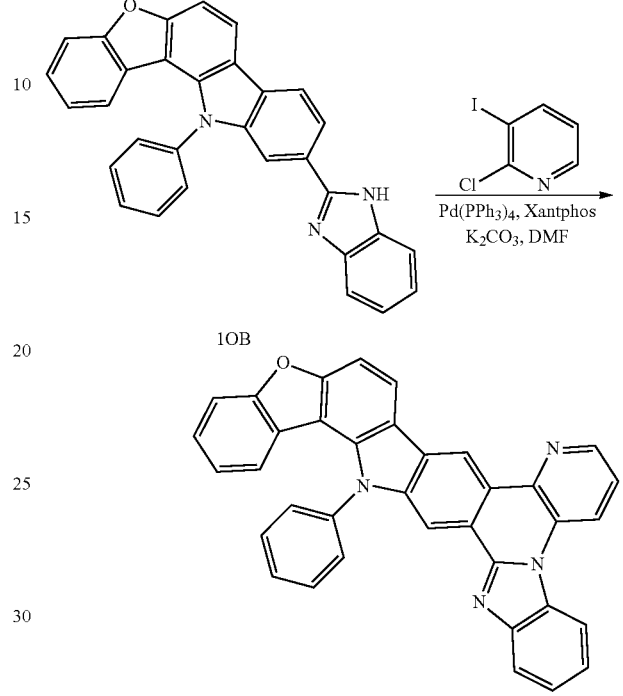

To a flame-dried flask were added Pd(PPh₃)₄ (10 mol %), Xantphos (10 mol %), Cs₂CO₃ (3 eq) and 1,2-dibromobenzene (1.2 eq). Then, 1OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1OB-1 in 61% yield.

Example 14

To a flame-dried flask were added Pd(PPh₃)₄ (10 mol %), Xantphos (10 mol %), Cs₂CO₃ (3 eq) and 2-chloro-3-iodopyridine (1.2 eq). Then, 1OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1OB-2 in 41% yield.

Example 15

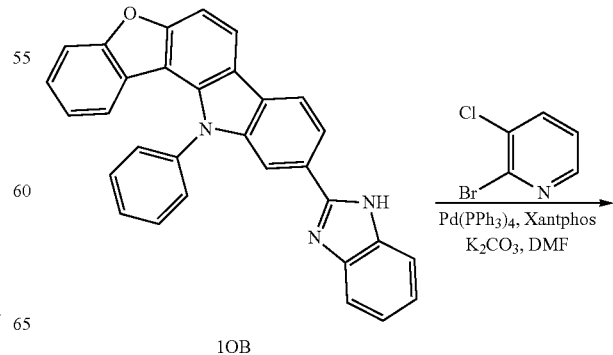

-continued

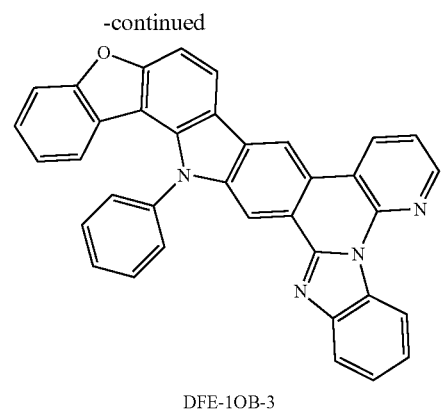

DFE-1OB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 1OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1OB-3 in 36% yield.

Example 16

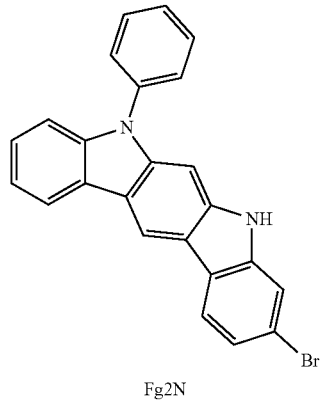

Fg2N

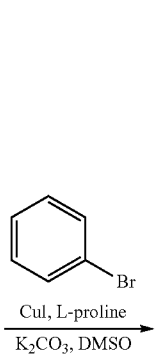

1) BuLi, THF
2) DMF
3) H$_2$O

-continued

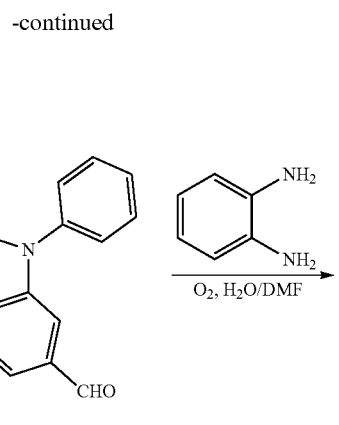

2NA

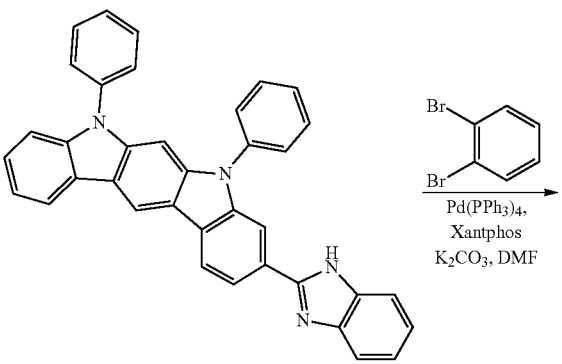

2NB

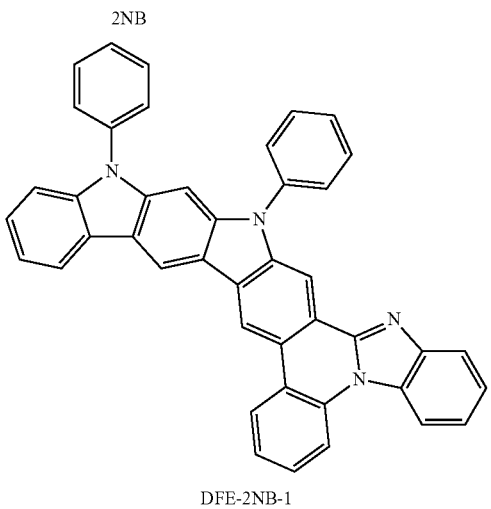

DFE-2NB-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 2NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-2NB-1 in 55% yield.

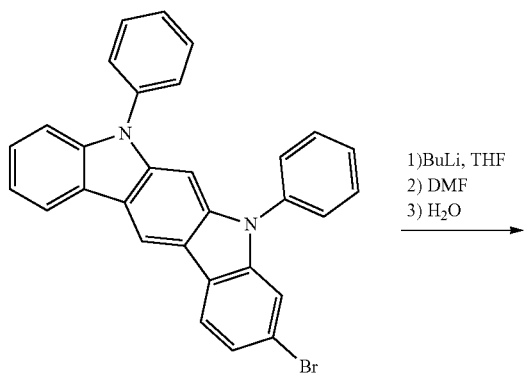

Example 17

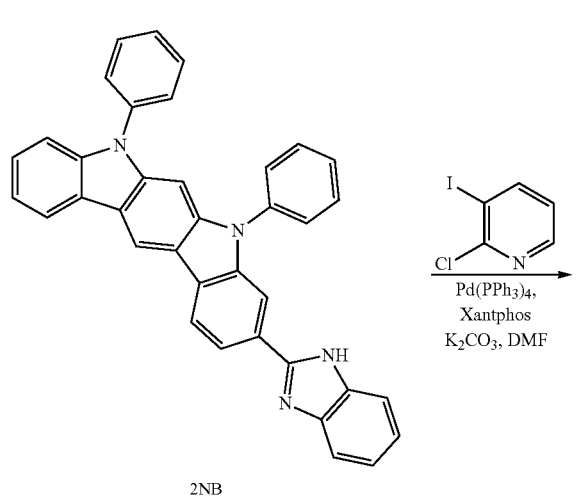

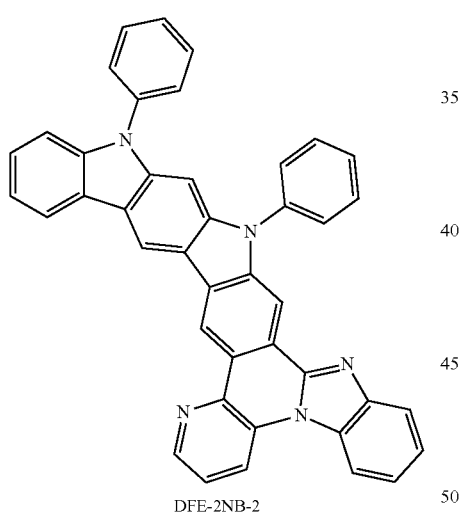

To a flame-dried flask were added Pd(PPh₃)₄ (10 mol %), Xantphos (10 mol %), Cs₂CO₃ (3 eq) and 2-chloro-3-iodopyridine (1.2 eq). Then, 2NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2NB-2 in 37% yield.

Example 18

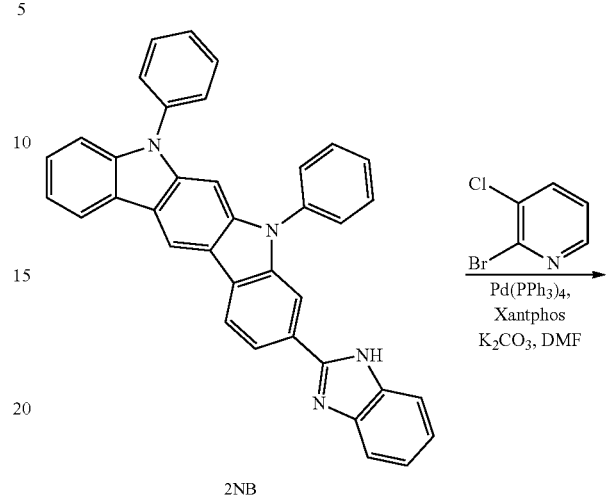

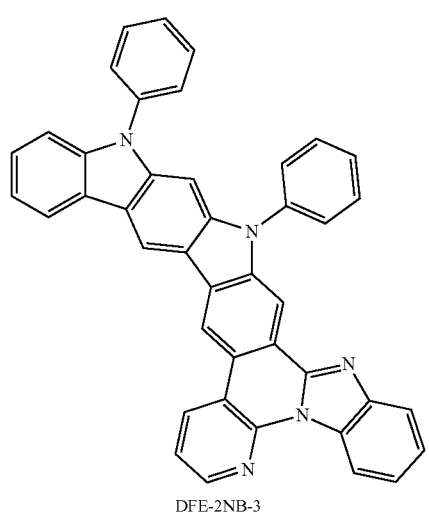

To a flame-dried flask were added Pd(PPh₃)₄ (10 mol %), Xantphos (10 mol %), Cs₂CO₃ (3 eq) and 2-bromo-3-chloropyridine (1.2 eq). Then, 2NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2NB-3 in 33% yield.

Example 19

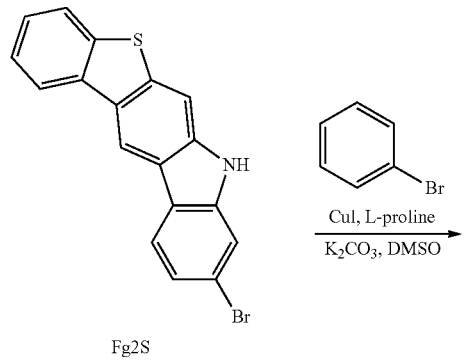

Fg2S

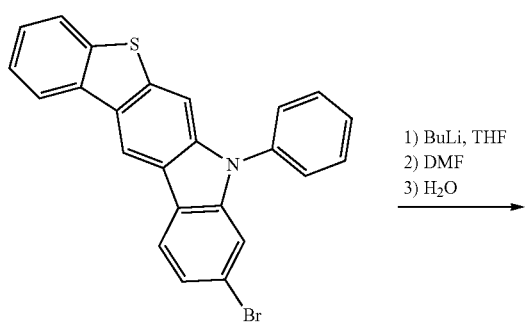

2SA

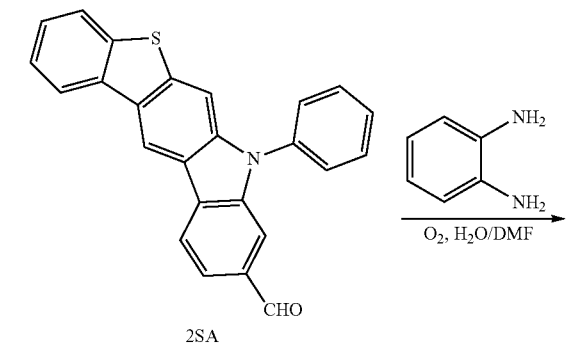

2SB

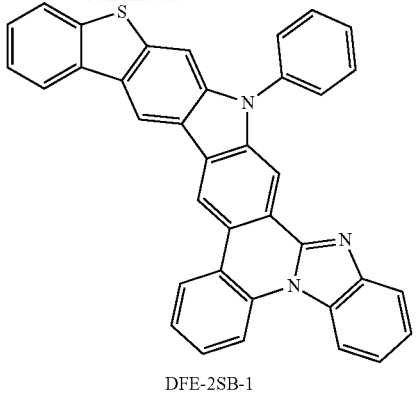 [SMILES: c1ccc(-n2c3cc4oc5ccccc5c4cc3c3cc4c5ccccc5n5c6ccccc6nc5c4cc32)cc1]

DFE-2SB-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 2SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-2SB-1 in 73% yield.

Example 20

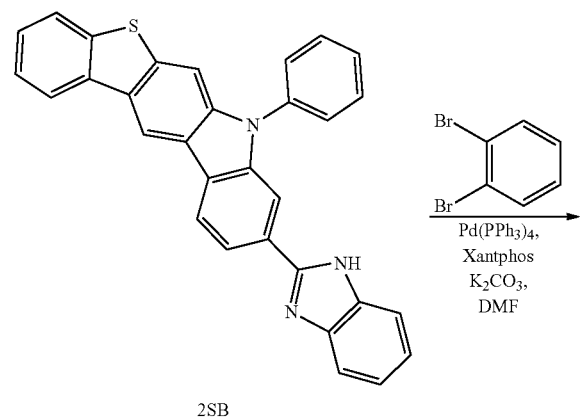

2SB

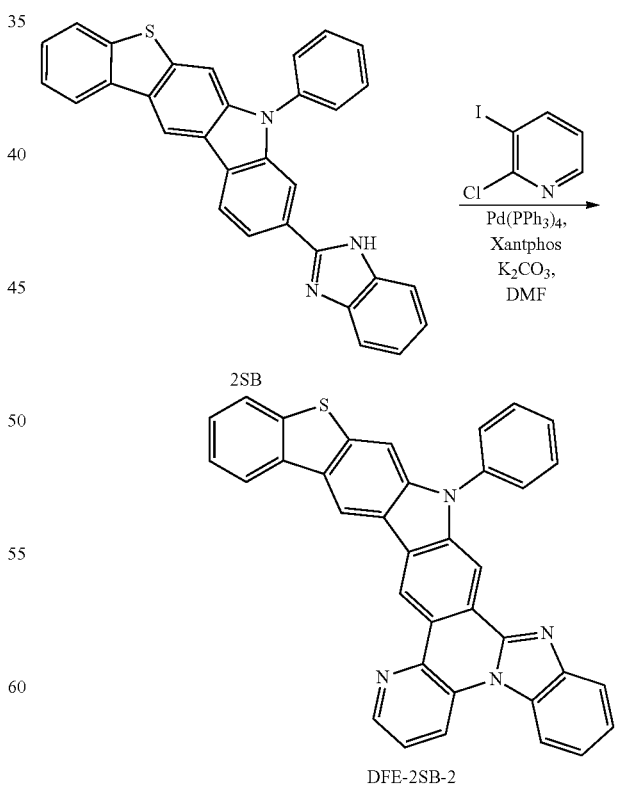

DFE-2SB-2

To a flame-dried flask were added Pd(PPh$_3$)$_4$ (10 mol %), Xantphos (10 mol %), Cs$_2$CO$_3$ (3 eq) and 2-chloro-3- iodopyridine (1.2 eq). Then, 2SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2SB-2 in 42% yield.

Example 21

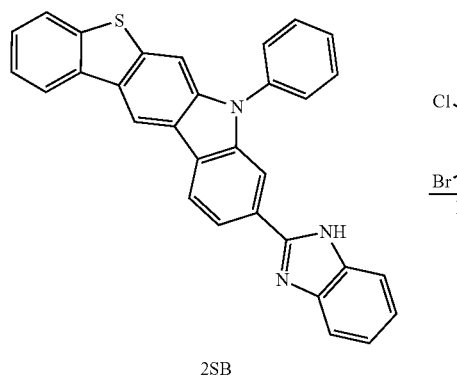
2SB

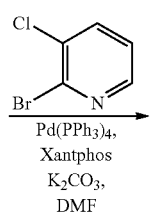

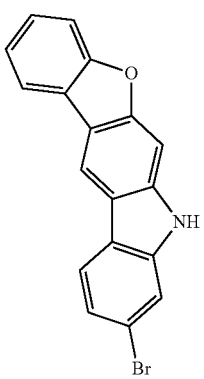
DFE-2SB-3

To a flame-dried flask were added Pd(PPh₃)₄ (10 mol %), Xantphos (10 mol %), Cs₂CO₃ (3 eq) and 2-bromo-3-chloropyridine (1.2 eq). Then, 2SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2SB-3 in 38% yield.

Example 22

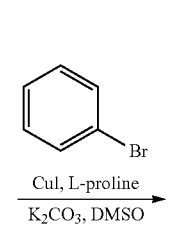
Fg2O

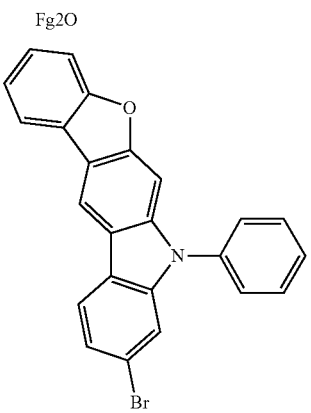

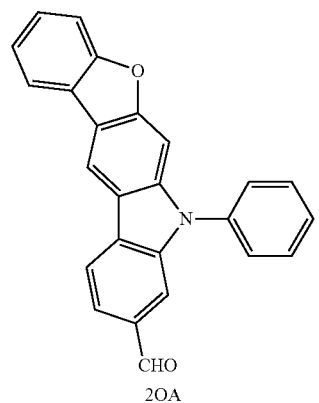
2OA

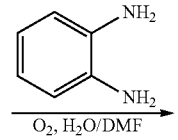

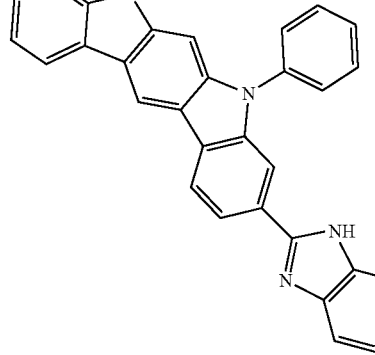
2OB

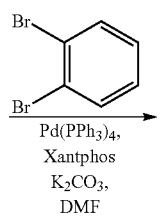

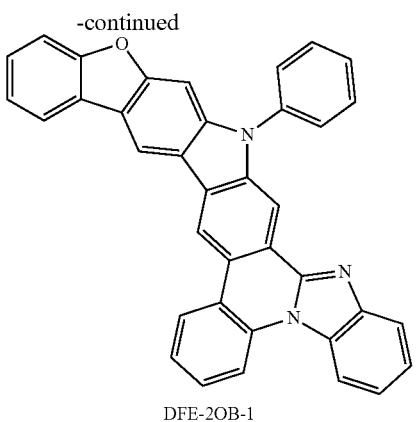

DFE-2OB-1

To a flame-dried flask were added Pd(PPh₃)₄ (10 mol %), Xantphos (10 mol %), Cs₂CO₃ (3 eq) and 1,2-dibromobenzene (1.2 eq). Then, 2OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2OB-1 in 68% yield.

Example 23

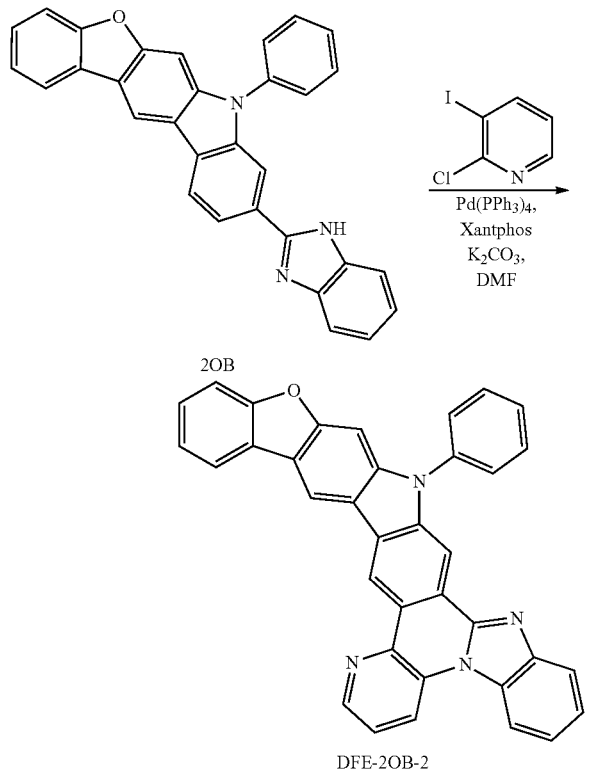

To a flame-dried flask were added Pd(PPh₃)₄ (10 mol %), Xantphos (10 mol %), Cs₂CO₃ (3 eq) and 2-chloro-3-iodopyridine (1.2 eq). Then, 2OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2OB-2 in 34% yield.

Example 24

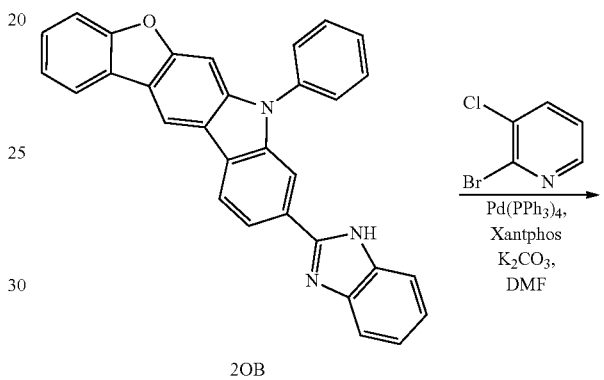

DFE-2OB-3

To a flame-dried flask were added Pd(PPh₃)₄ (10 mol %), Xantphos (10 mol %), Cs₂CO₃ (3 eq) and 2-bromo-3-chloropyridine (1.2 eq). Then, 2OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2OB-3 in 32% yield.

Example 25

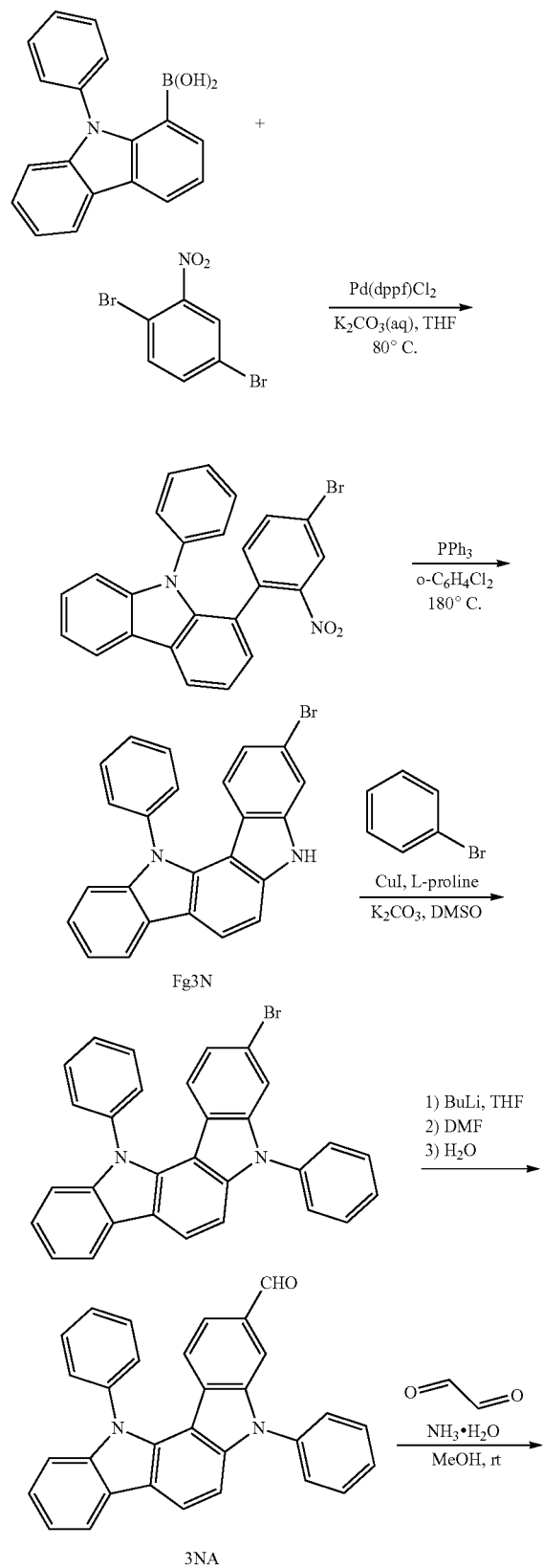

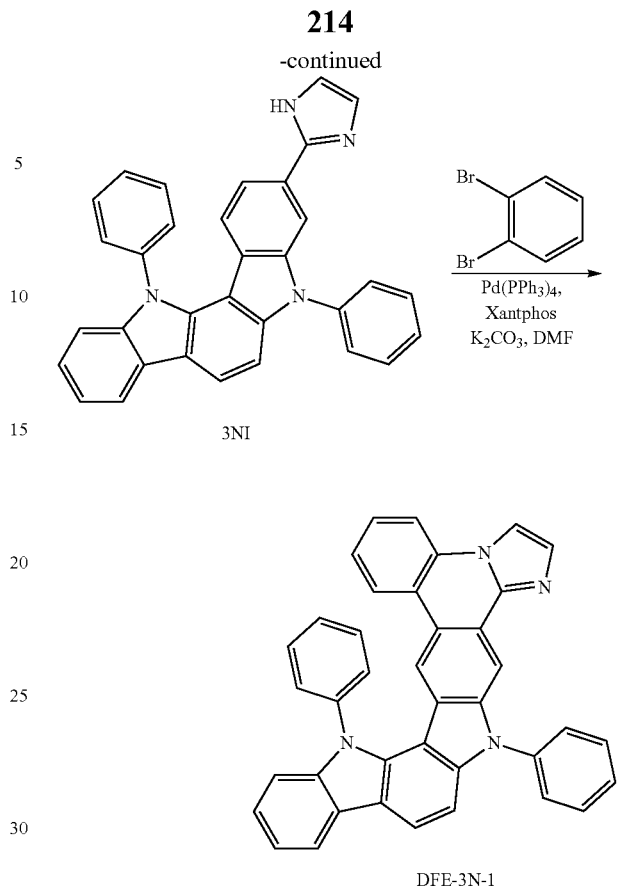

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 3NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3N-1 in 71% yield.

Example 26

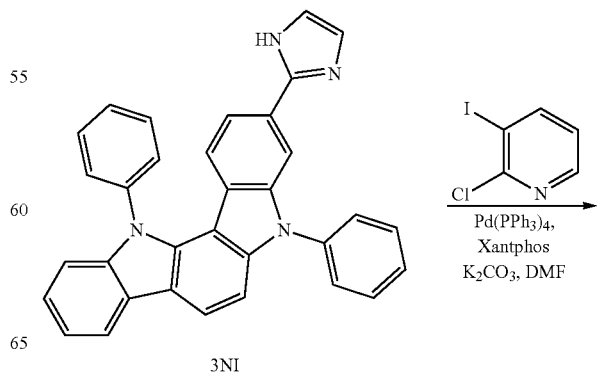

-continued

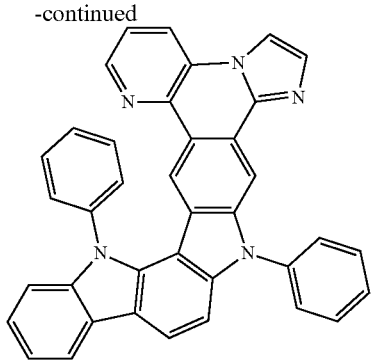

DFE-3N-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 3NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3N-2 in 30% yield.

Example 27

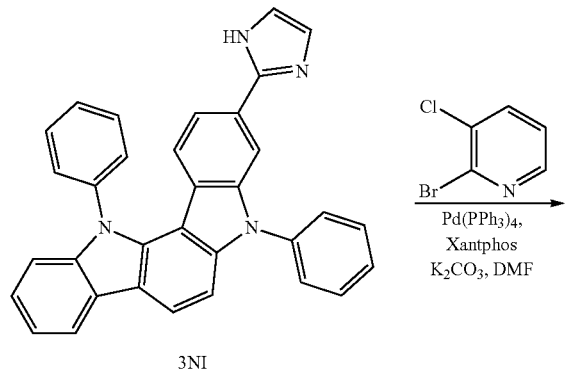

3NI

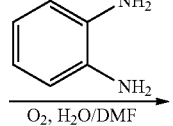

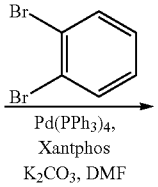

DFE-3N-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 3NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3N-3 in 24% yield.

Example 28

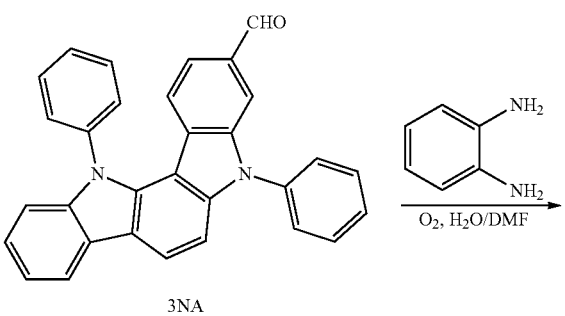

3NA

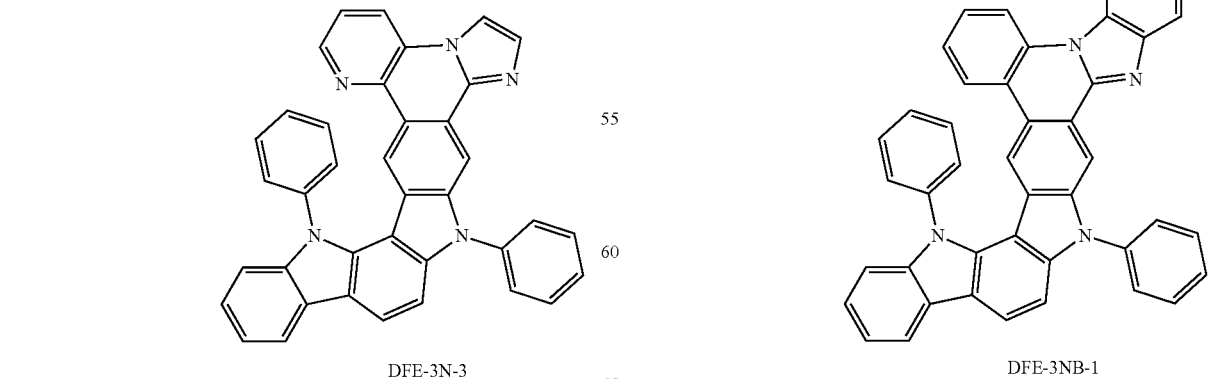

3NB

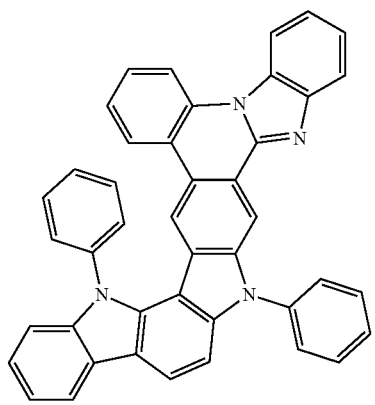

DFE-3NB-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 3NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3NB-1 in 66% yield.

Example 29

Example 30

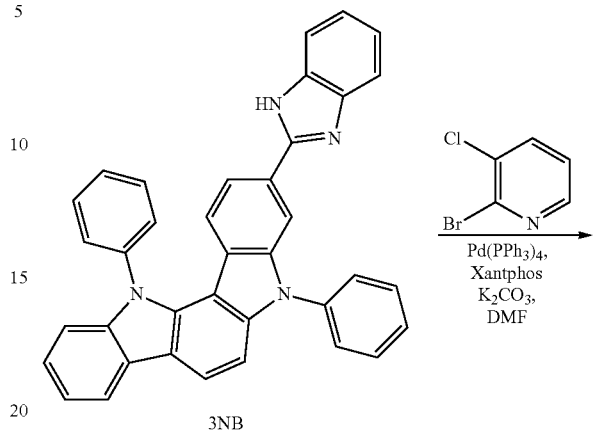

3NB

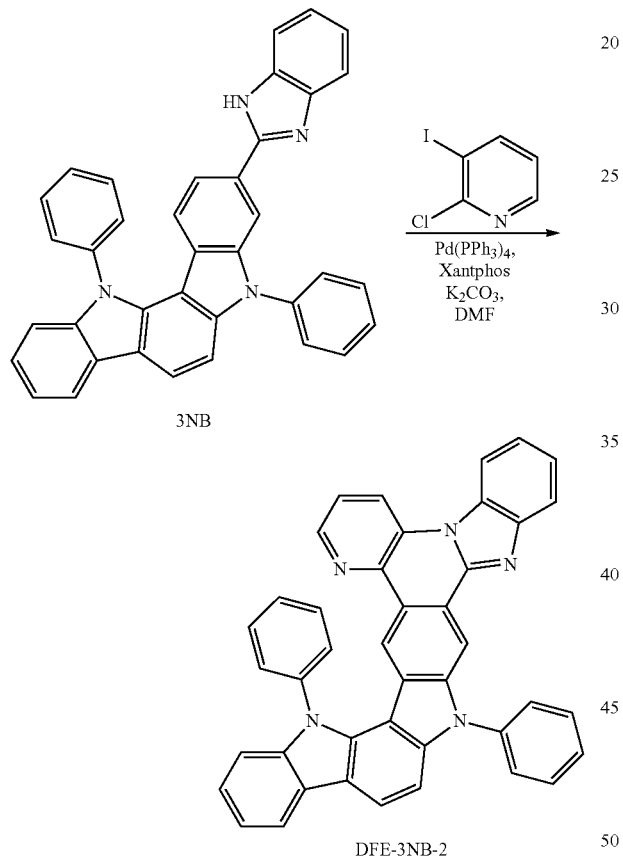

3NB

DFE-3NB-2

DFE-3NB-3

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 3NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3N-2 in 44% yield.

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 3NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3NB-3 in 21% yield.

Example 31

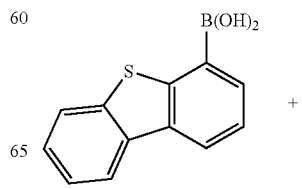

+

219

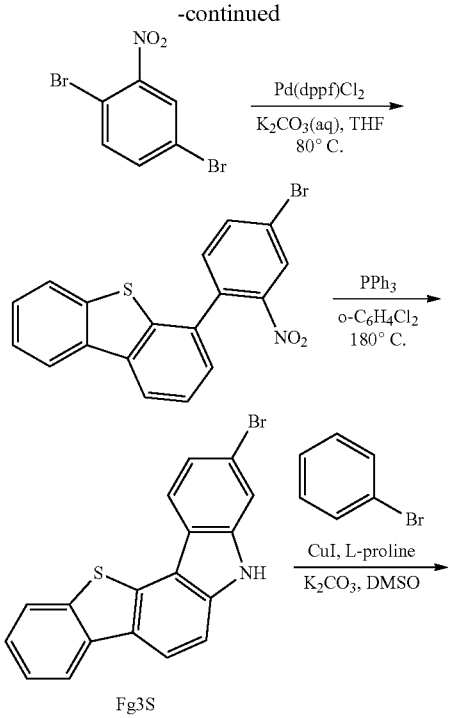

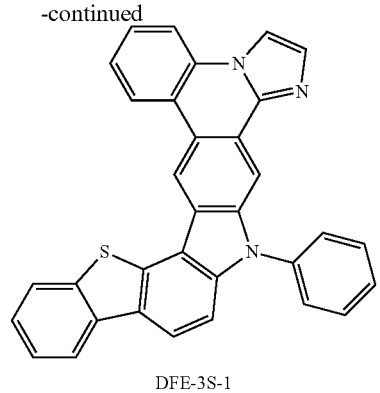

DFE-3S-1

To a flame-dried flask were added Pd(PPh₃)₄ (10 mol %), Xantphos (10 mol %), Cs₂CO₃ (3 eq) and 1,2-dibromobenzene (1.2 eq). Then, 3SI (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3S-1 in 75% yield.

Example 32

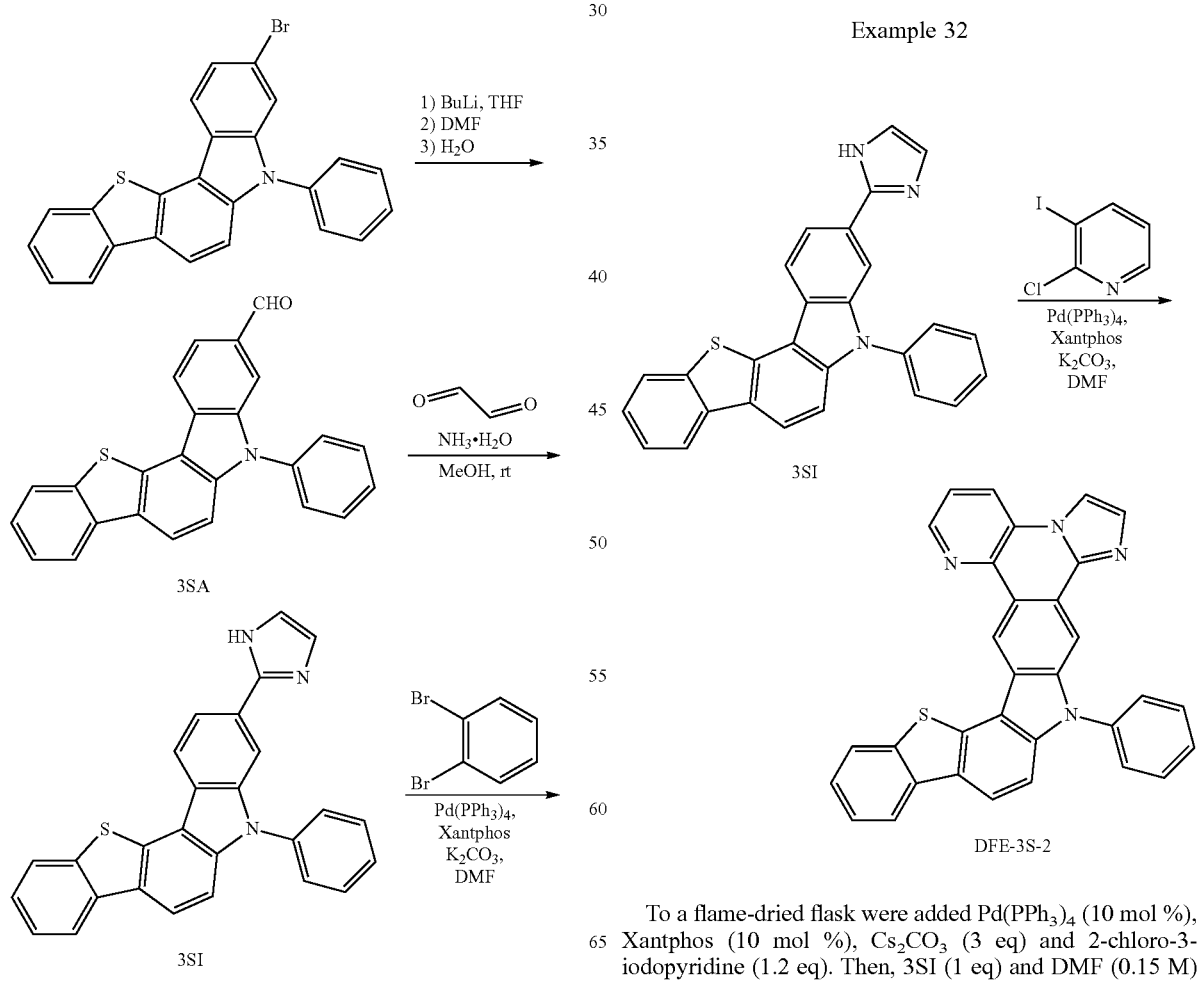

DFE-3S-2

To a flame-dried flask were added Pd(PPh₃)₄ (10 mol %), Xantphos (10 mol %), Cs₂CO₃ (3 eq) and 2-chloro-3-iodopyridine (1.2 eq). Then, 3SI (1 eq) and DMF (0.15 M) were added to the reaction mixture under an N₂ atmosphere.

The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3S-2 in 64% yield.

Example 33

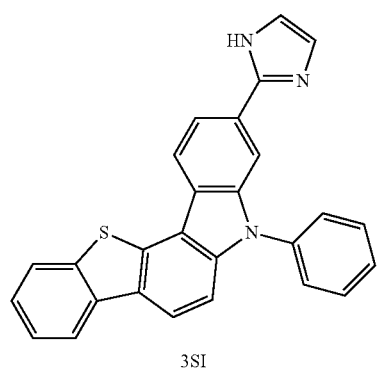
3SI

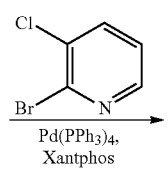
Pd(PPh$_3$)$_4$,
Xantphos
K$_2$CO$_3$,
DMF

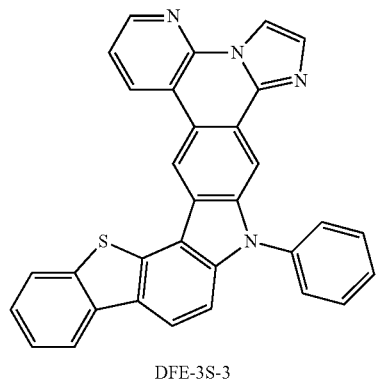
DFE-3S-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 3SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3S-3 in 29% yield.

Example 34

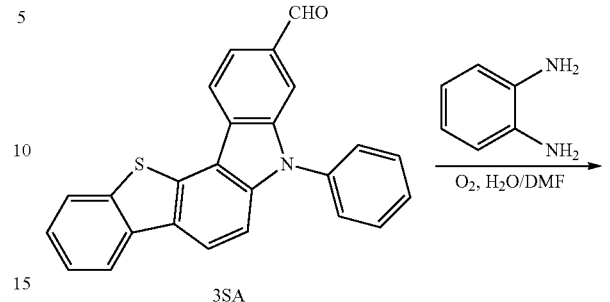
3SA

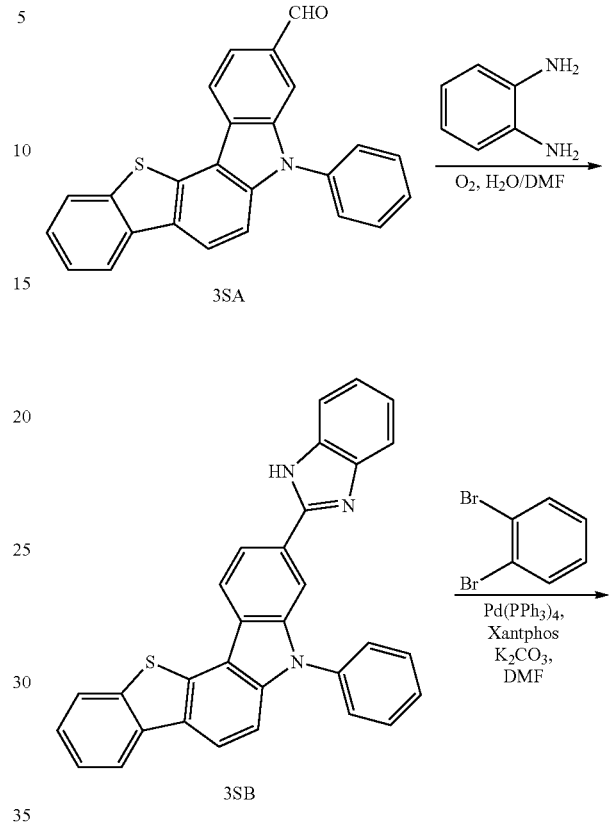
3SB

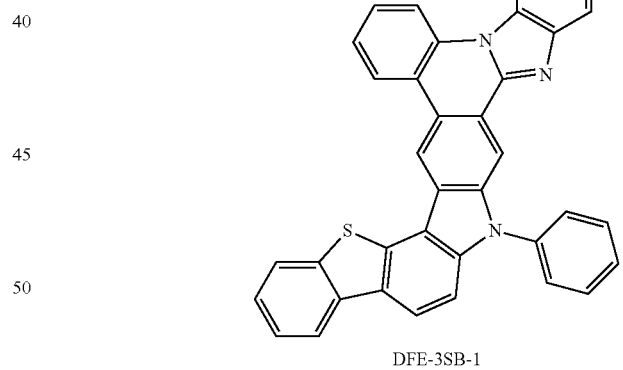
DFE-3SB-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 3SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3SB-1 in 72% yield.

Example 35

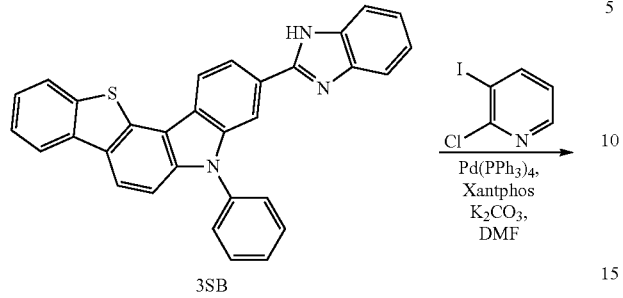

3SB

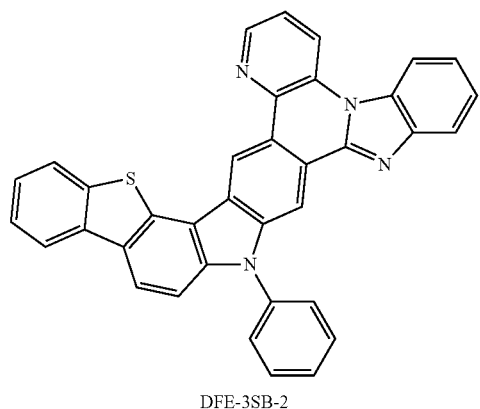

DFE-3SB-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 3SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3SB-2 in 59% yield.

Example 36

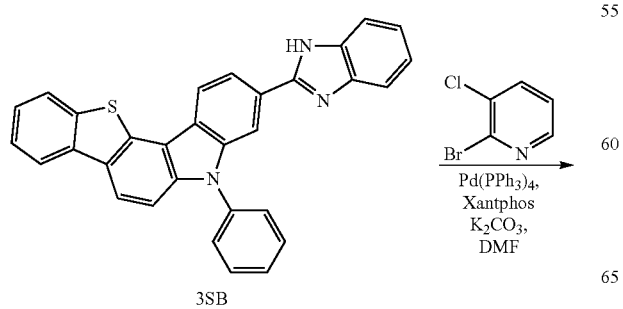

3SB

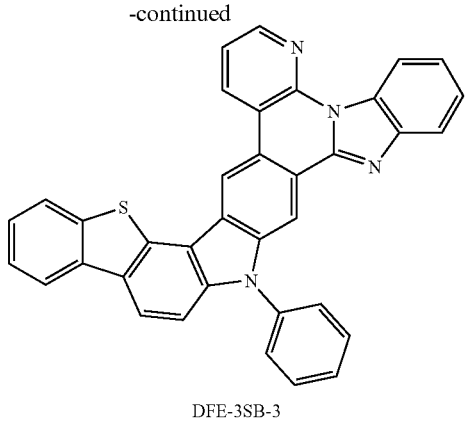

DFE-3SB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 3SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3SB-3 in 24% yield.

Example 37

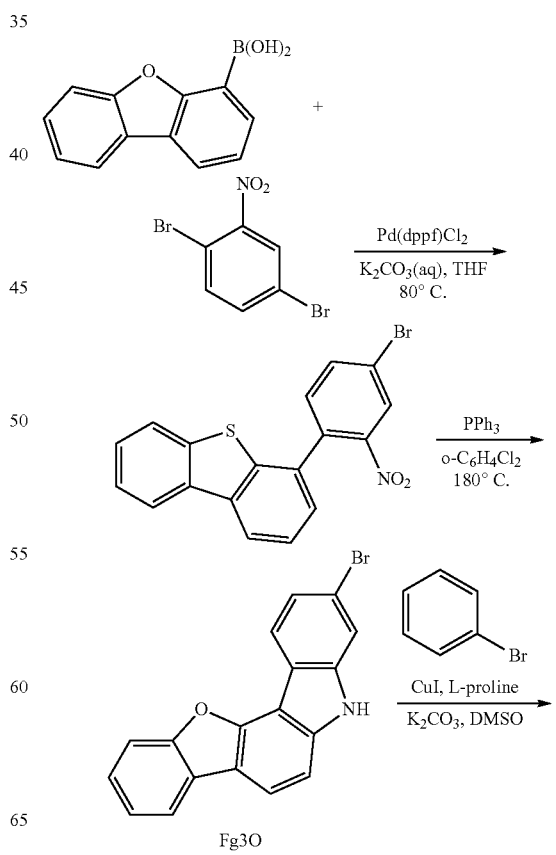

Fg3O

225
-continued

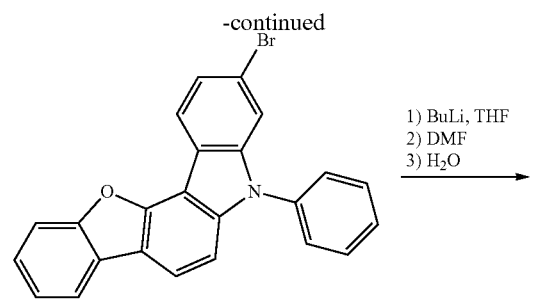

1) BuLi, THF
2) DMF
3) H₂O

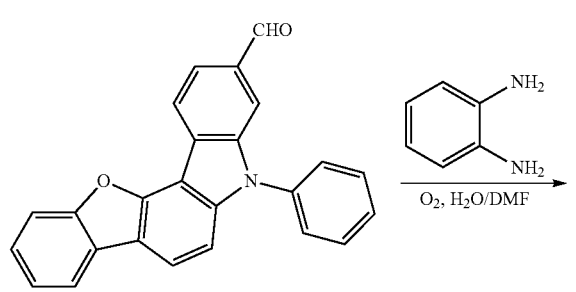

3OA

NH₂
NH₂

O₂, H₂O/DMF

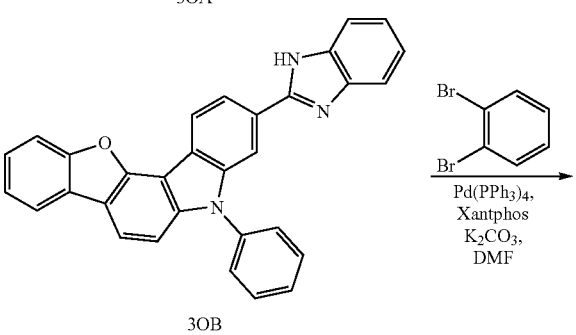

3OB

Br
Br

Pd(PPh₃)₄,
Xantphos
K₂CO₃,
DMF

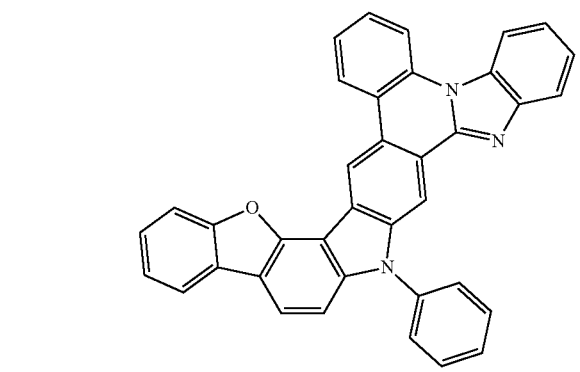

DFE-3OB-1

To a flame-dried flask were added Pd(PPh₃)₄ (10 mol %), Xantphos (10 mol %), Cs₂CO₃ (3 eq) and 1,2-dibromobenzene (1.2 eq). Then, 3OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3OB-1 in 68% yield.

226
Example 38

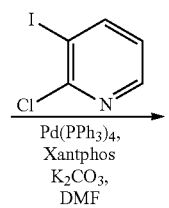

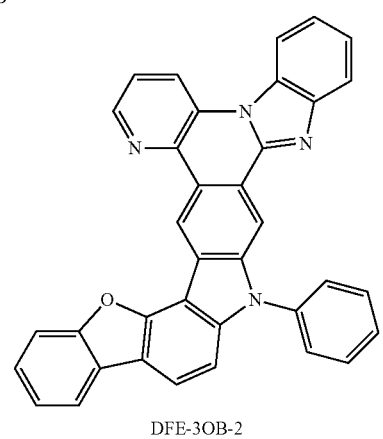

3OB

Pd(PPh₃)₄,
Xantphos
K₂CO₃,
DMF

DFE-3OB-2

To a flame-dried flask were added Pd(PPh₃)₄ (10 mol %), Xantphos (10 mol %), Cs₂CO₃ (3 eq) and 2-chloro-3-iodopyridine (1.2 eq). Then, 3OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3OB-2 in 62% yield.

Example 39

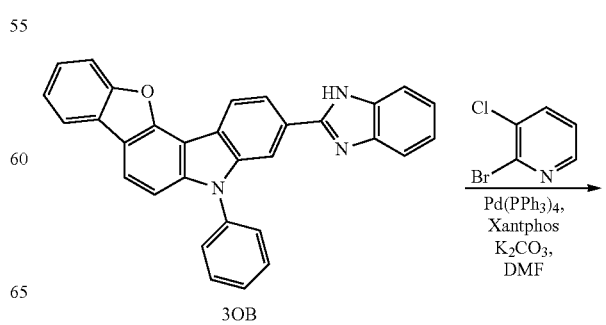

3OB

Cl
Br

Pd(PPh₃)₄,
Xantphos
K₂CO₃,
DMF

-continued

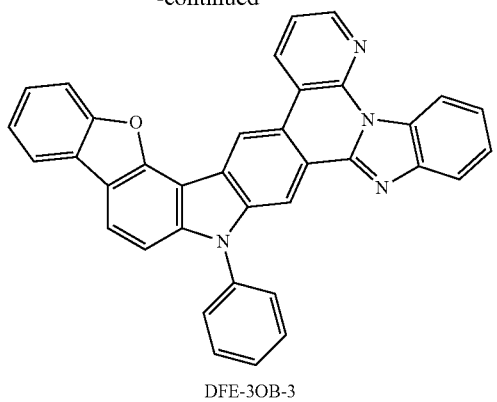

DFE-3OB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 3OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3OB-3 in 32% yield.

Example 40

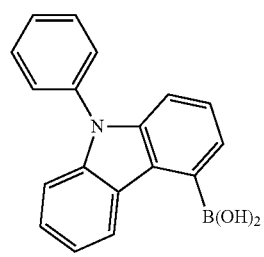

+

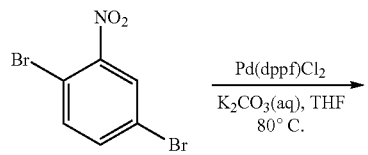

$\xrightarrow{\text{Pd(dppf)Cl}_2}{\text{K}_2\text{CO}_3\text{(aq), THF}\atop 80°\text{ C.}}$

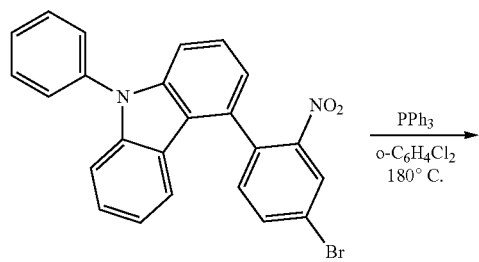

$\xrightarrow{\text{PPh}_3}{o\text{-C}_6\text{H}_4\text{Cl}_2\atop 180°\text{ C.}}$ -continued

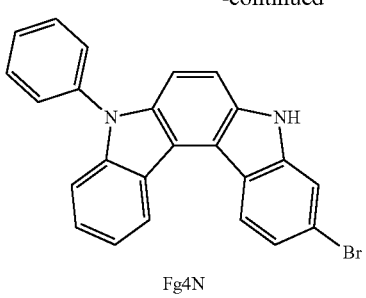 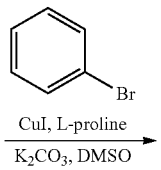

Fg4N $\xrightarrow[\text{K}_2\text{CO}_3\text{, DMSO}]{\text{CuI, L-proline}}$

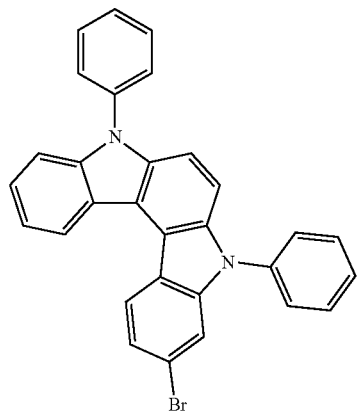

1) BuLi, THF
2) DMF
3) H$_2$O

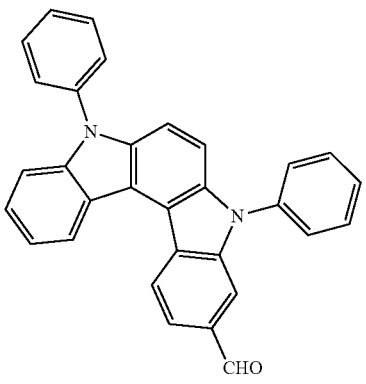 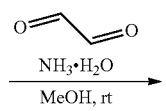

4NA $\xrightarrow[\text{MeOH, rt}]{\text{NH}_3\cdot\text{H}_2\text{O}}$

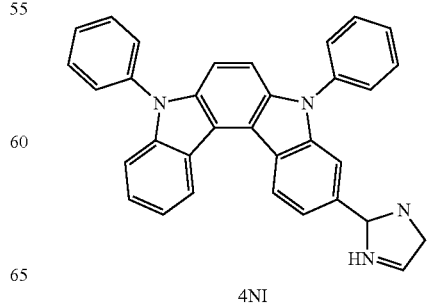 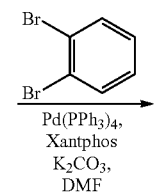

4NI $\xrightarrow[\substack{\text{Pd(PPh}_3)_4,\\ \text{Xantphos}\\ \text{K}_2\text{CO}_3,\\ \text{DMF}}]{}$

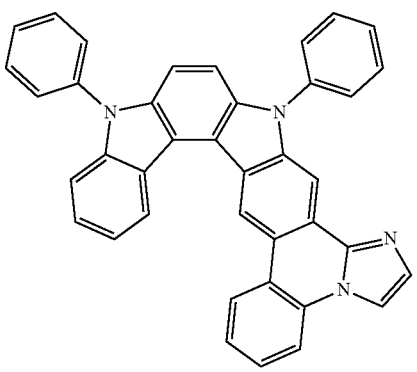

DFE-4N-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 4NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4N-1 in 61% yield.

Example 41

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 4NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4N-2 in 51% yield.

Example 42

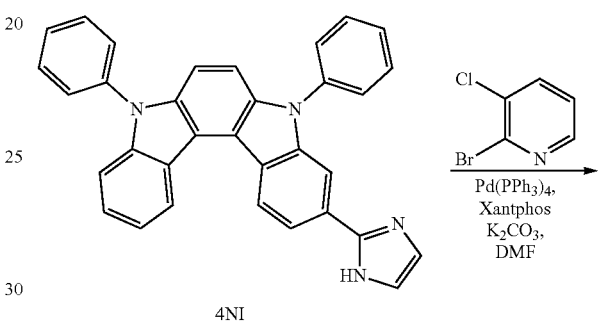

4NI

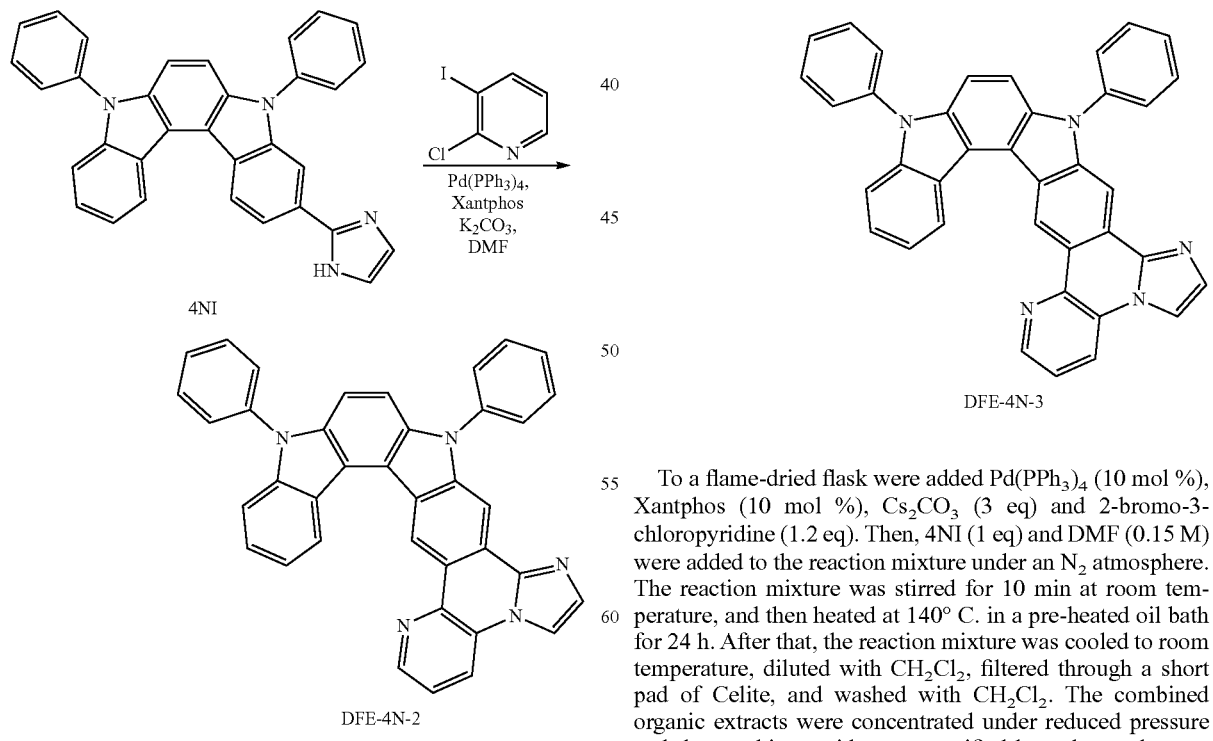

DFE-4N-2

DFE-4N-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 4NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4N-3 in 27% yield.

Example 43

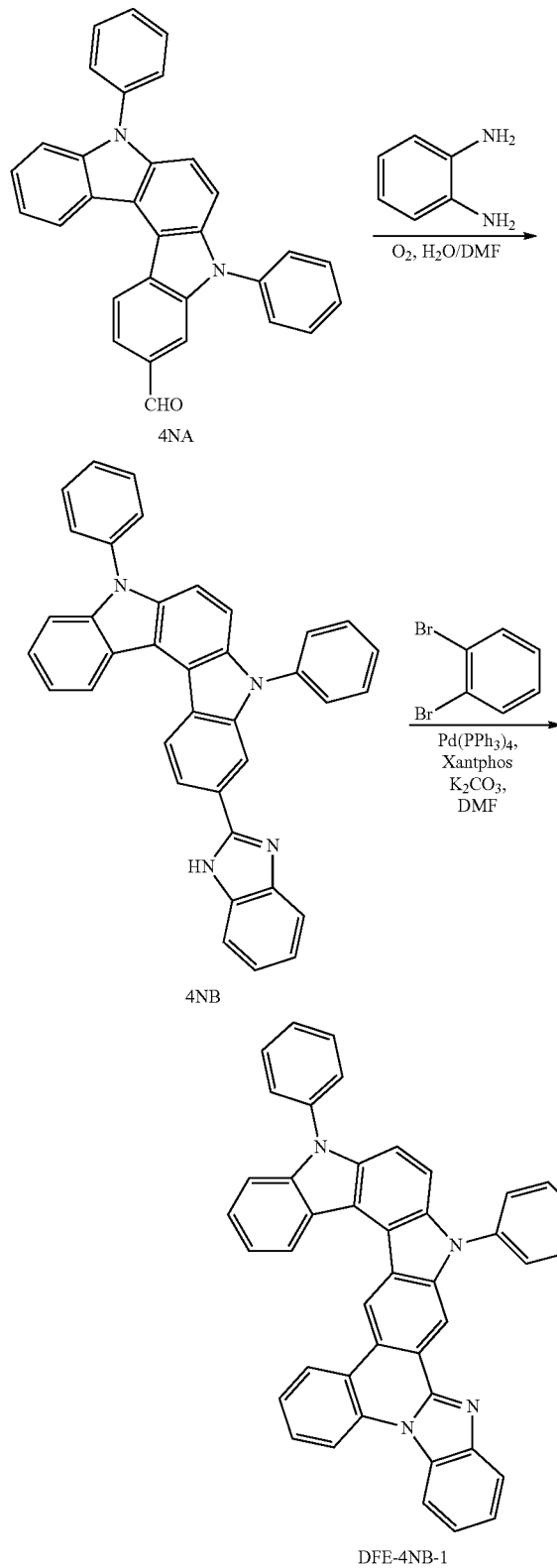

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 4NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4NB-1 in 57% yield.

Example 44

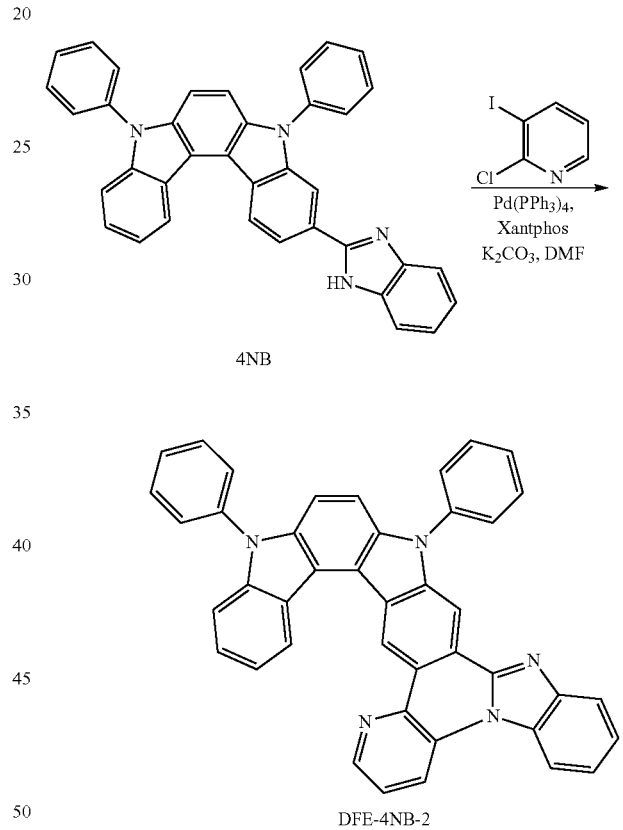

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 4NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4NB-2 in 43% yield.

Example 45

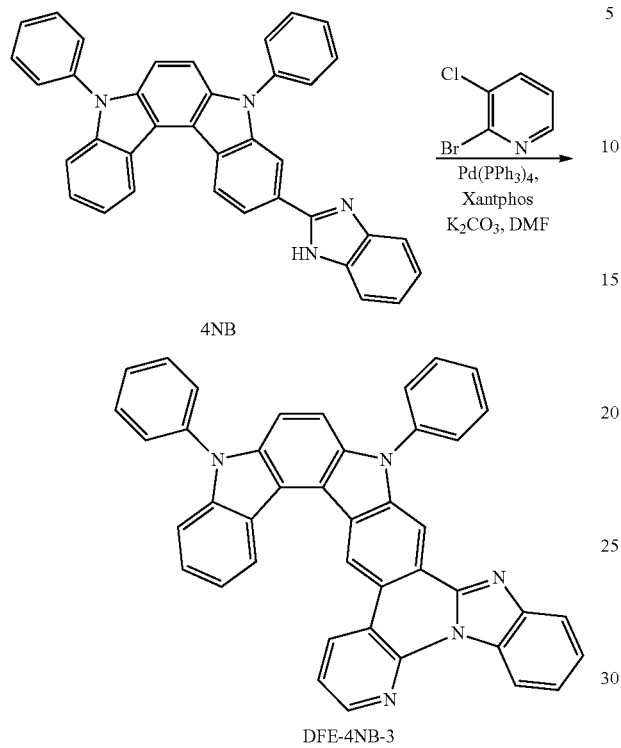

4NB

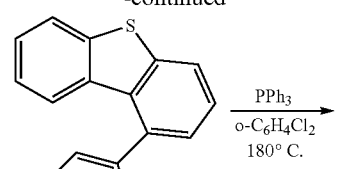

DFE-4NB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 4NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4NB-3 in 22% yield.

Example 46

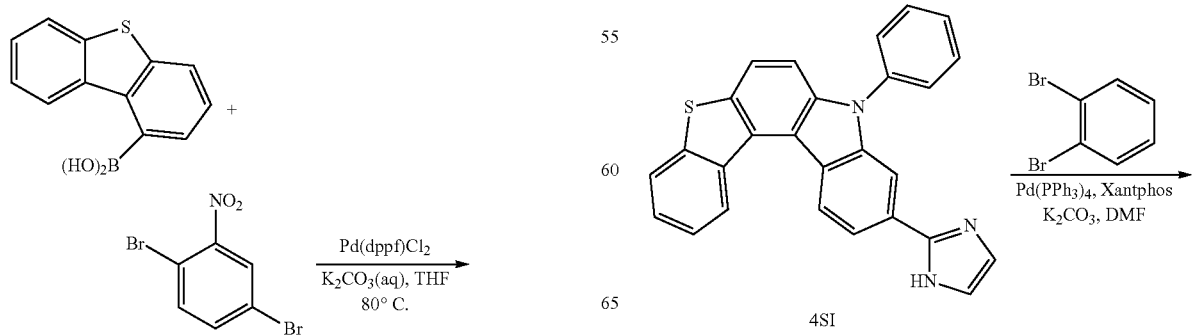

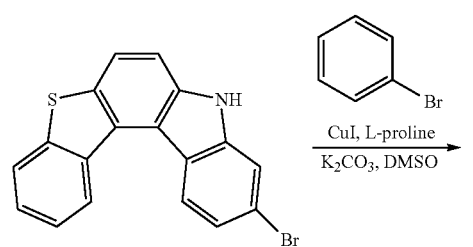

Fg4S

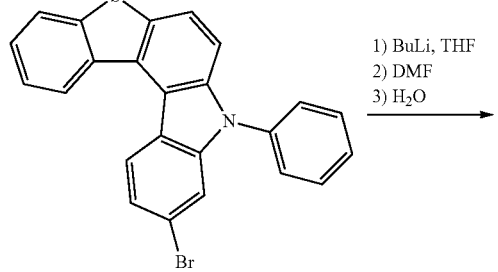

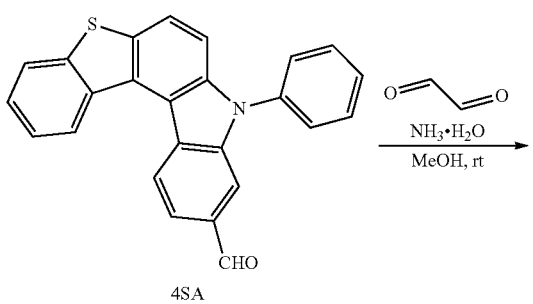

4SA

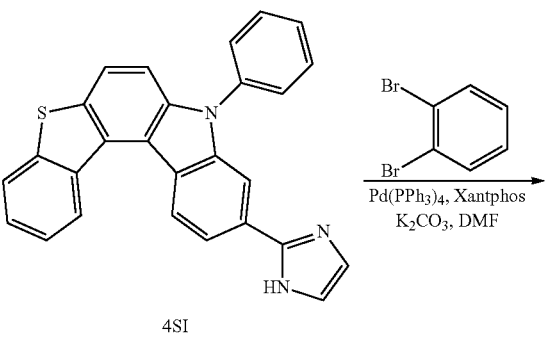

4SI

-continued

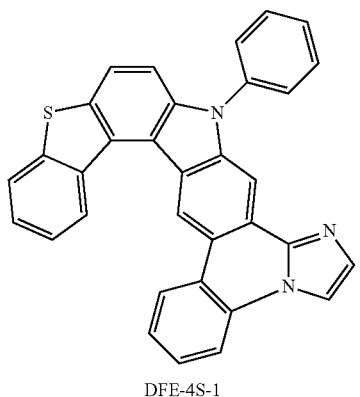

DFE-4S-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 4SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4S-1 in 57% yield.

Example 47

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 4SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4S-2 in 44% yield.

Example 48

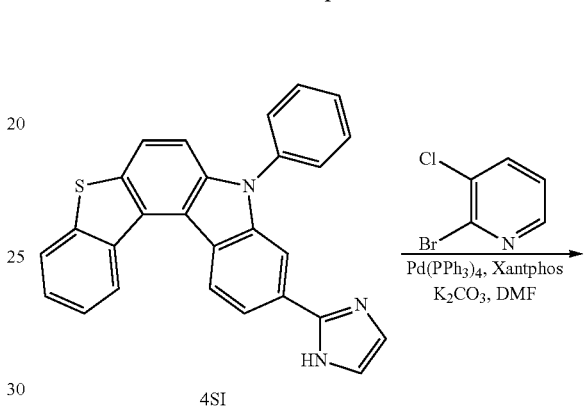

4SI

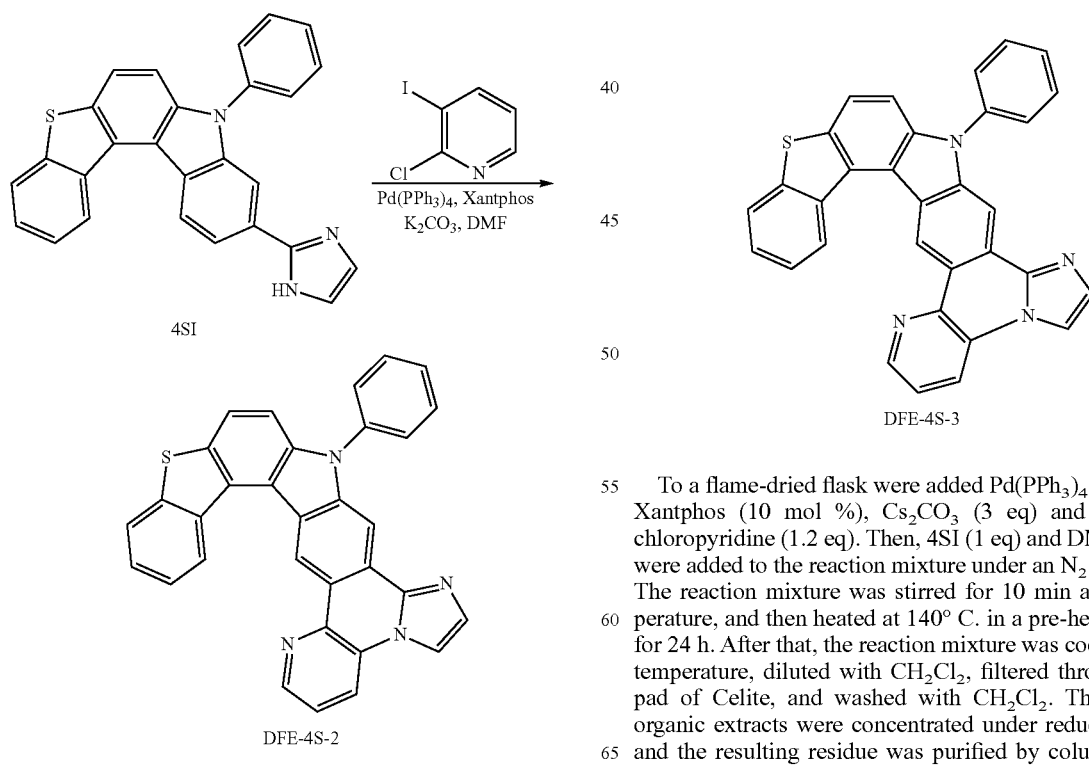

DFE-4S-2

DFE-4S-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 4SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4S-3 in 23% yield.

Example 49

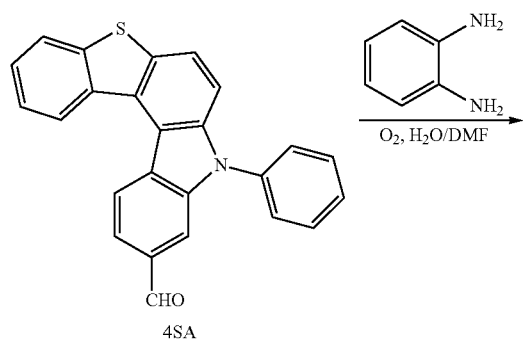

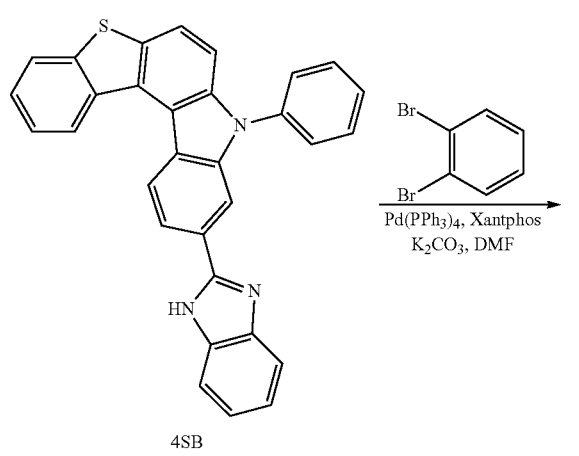

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 4SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4SB-1 in 51% yield.

Example 50

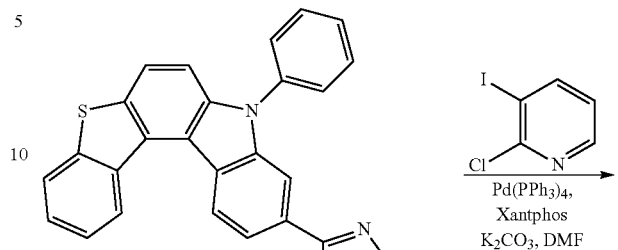

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 4SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4SB-2 in 39% yield.

Example 51

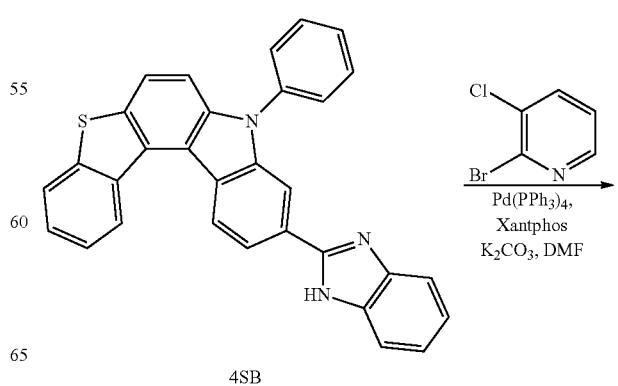

-continued

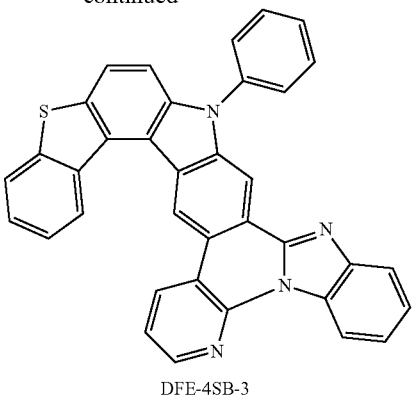

DFE-4SB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 4SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4SB-3 in 31% yield.

Example 52

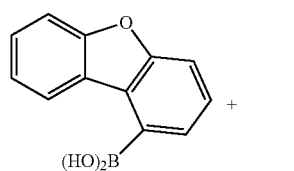

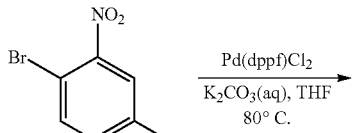

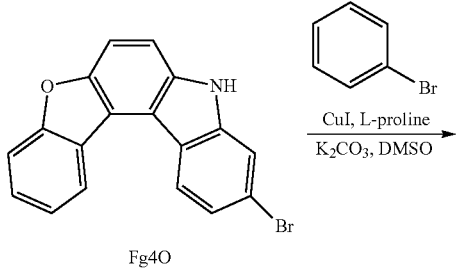

Fg4O

-continued

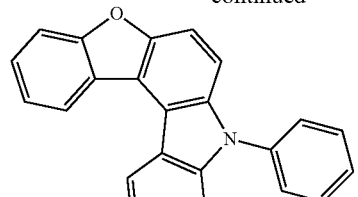

1) BuLi, THF
2) DMF
3) H$_2$O

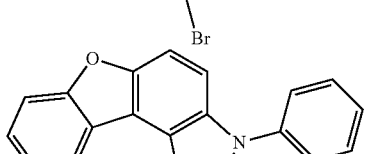

NH$_3$·H$_2$O
MeOH, rt

4OA

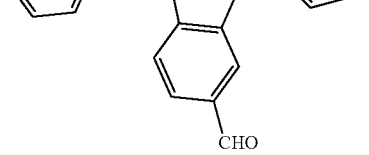

4OI

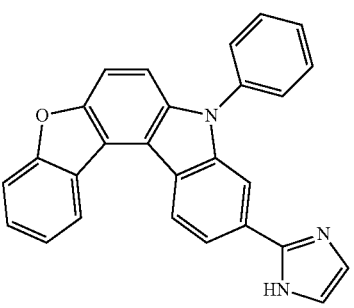

DFE-4O-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 4OI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4O-1 in 64% yield.

Example 53

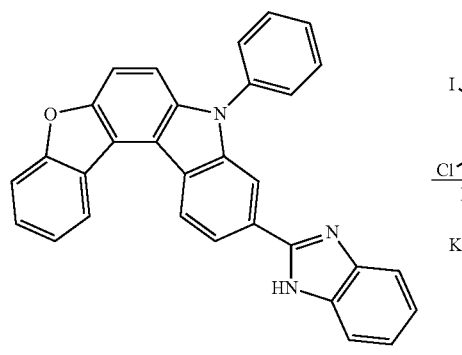

4OB

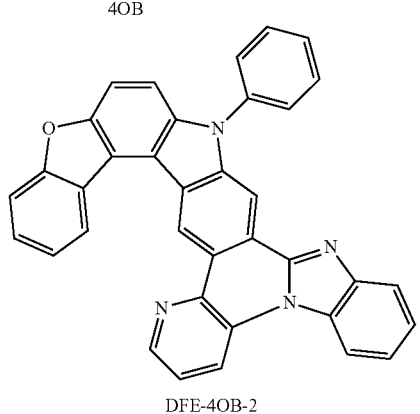

DFE-4OB-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 4OI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4O-2 in 37% yield.

Example 54

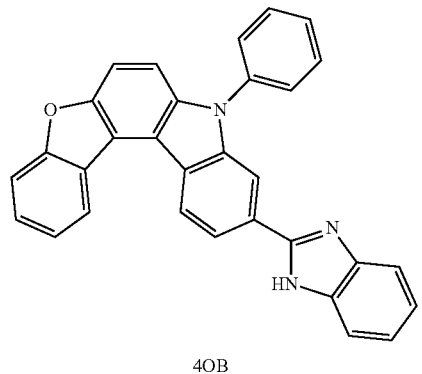

4OB

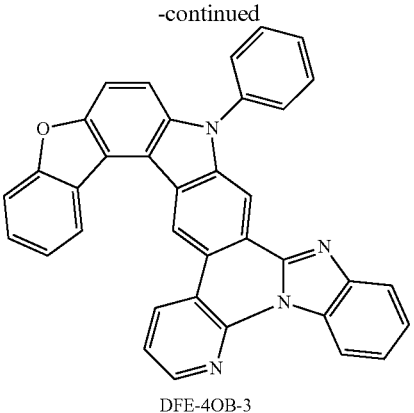

DFE-4OB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 4OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4OB-3 in 26% yield.

Example 55

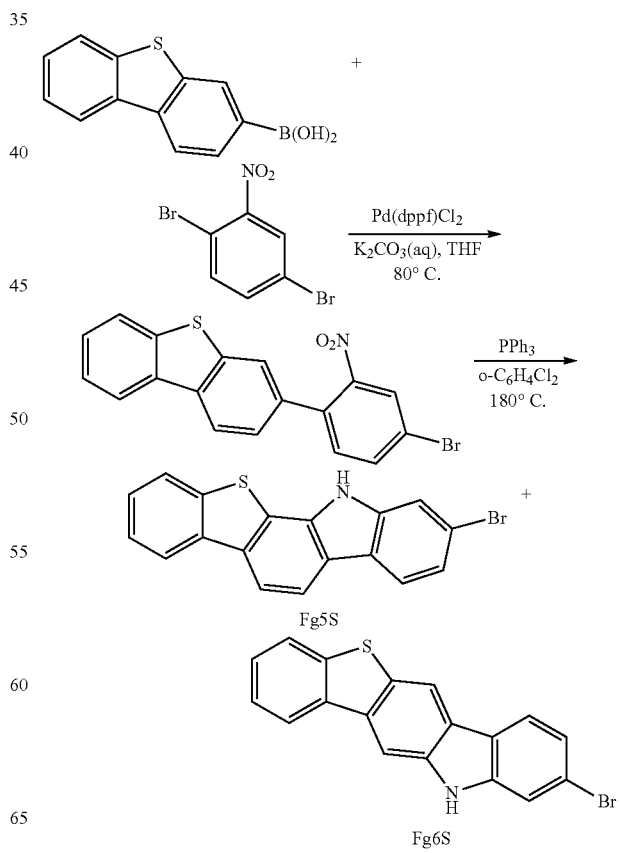

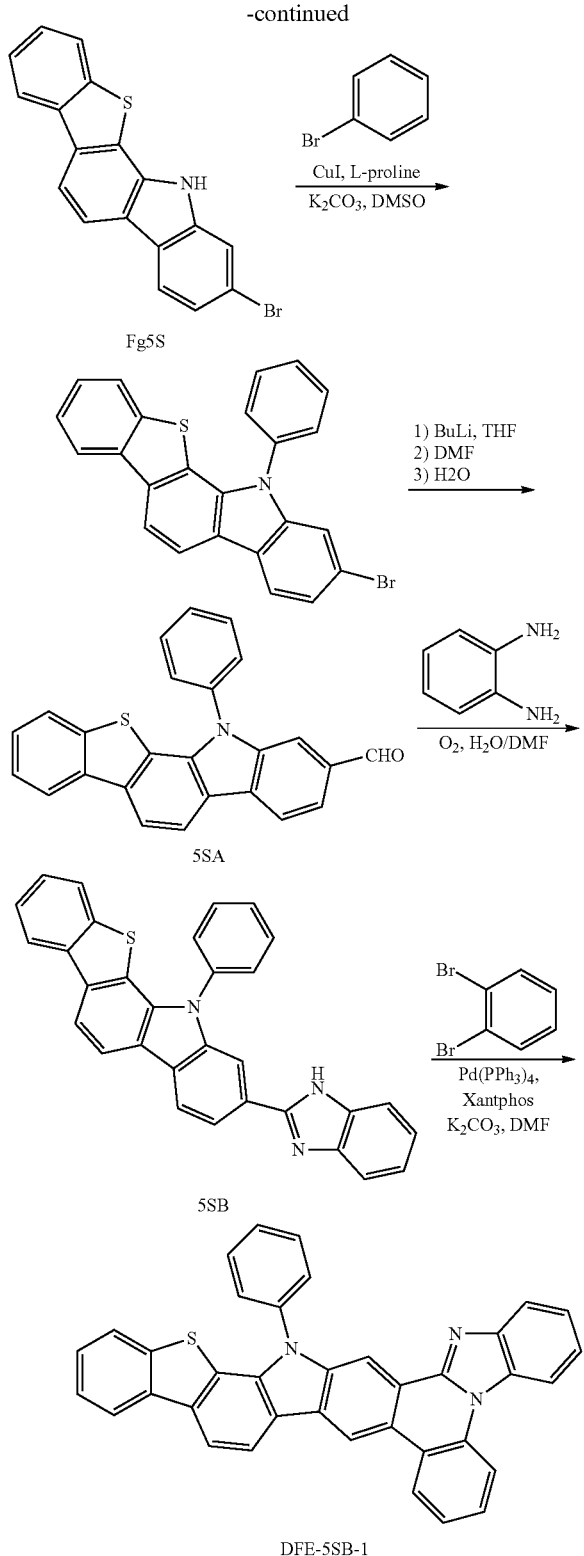

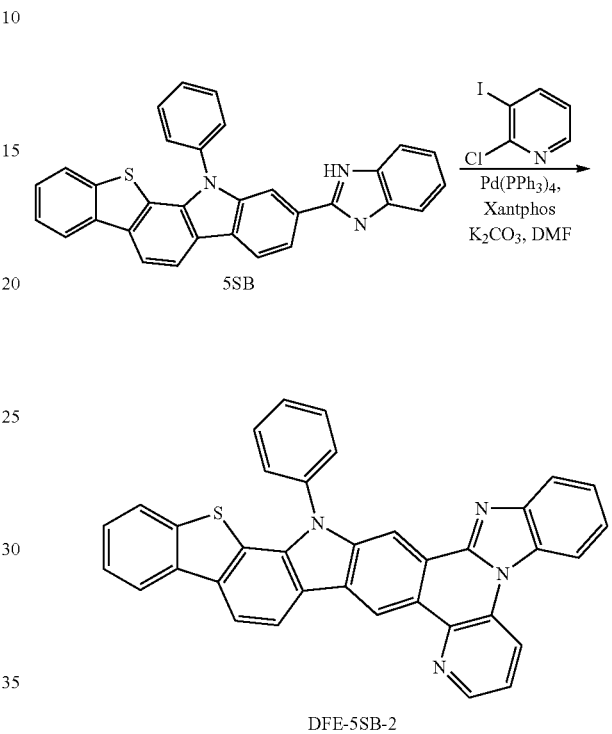

DFE-5SB-2

After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-5SB-1 in 56% yield.

Example 56

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 5SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-5SB-2 in 33% yield.

Example 57

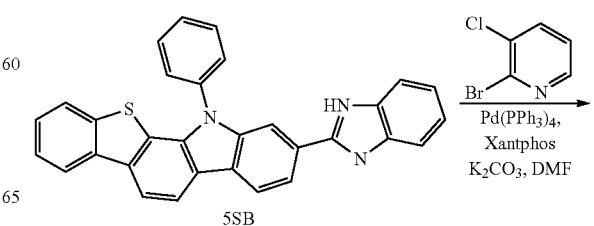

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 5SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h.

-continued

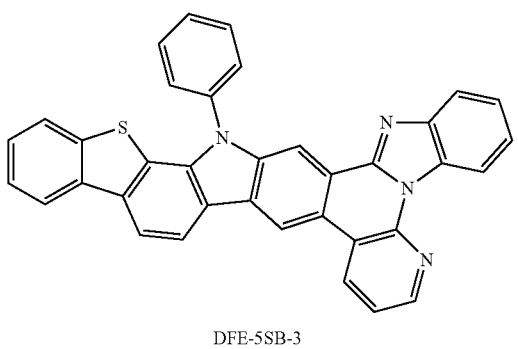

DFE-5SB-3

To a flame-dried flask were added Pd(PPh₃)₄ (10 mol %), Xantphos (10 mol %), Cs₂CO₃ (3 eq) and 2-bromo-3-chloropyridine (1.2 eq). Then, 5SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-5SB-3 in 35% yield.

Example 58

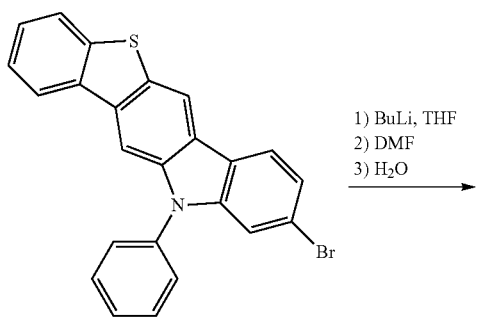

Fg6S

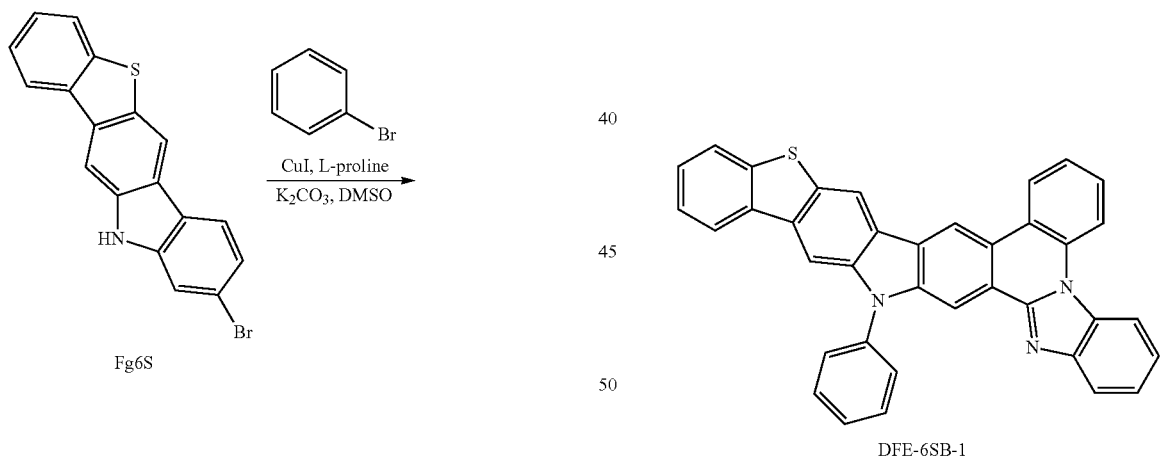

-continued

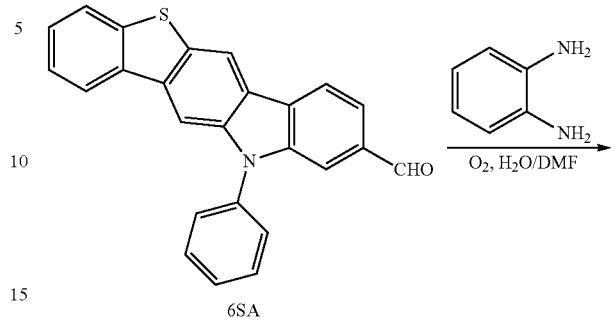

6SA

6SB

DFE-6SB-1

To a flame-dried flask were added Pd(PPh₃)₄ (10 mol %), Xantphos (10 mol %), Cs₂CO₃ (3 eq) and 1,2-dibromobenzene (1.2 eq). Then, 6SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-6SB-1 in 59% yield.

Example 59

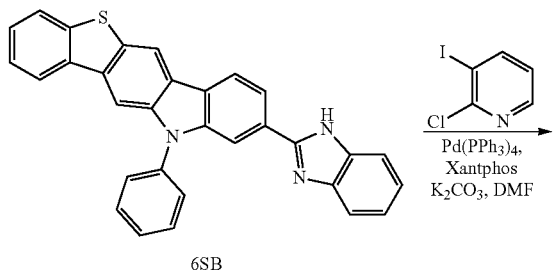
6SB

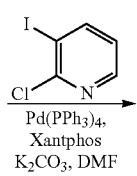
Pd(PPh$_3$)$_4$,
Xantphos
K$_2$CO$_3$, DMF

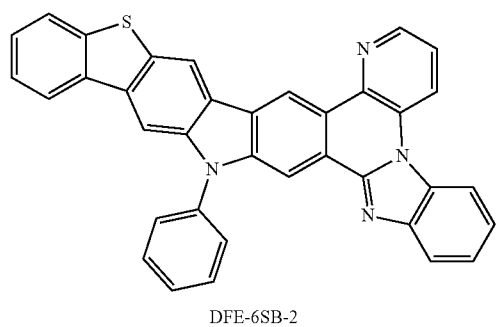
DFE-6SB-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 6SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-6SB-2 in 39% yield.

Example 60

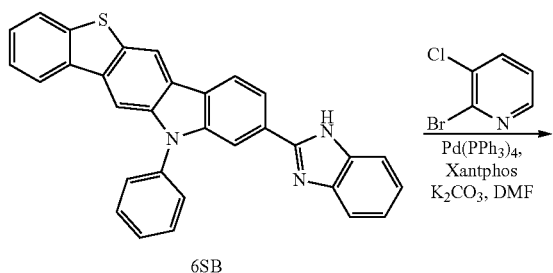
6SB

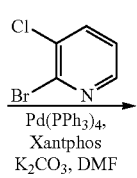
Pd(PPh$_3$)$_4$,
Xantphos
K$_2$CO$_3$, DMF

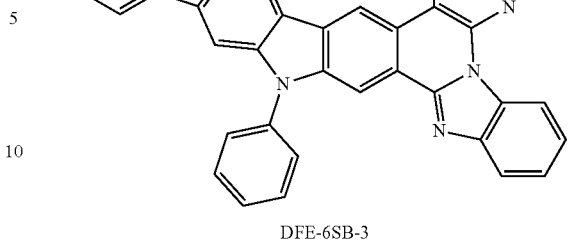
DFE-6SB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 6SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-6SB-3 in 28% yield.

Example 61

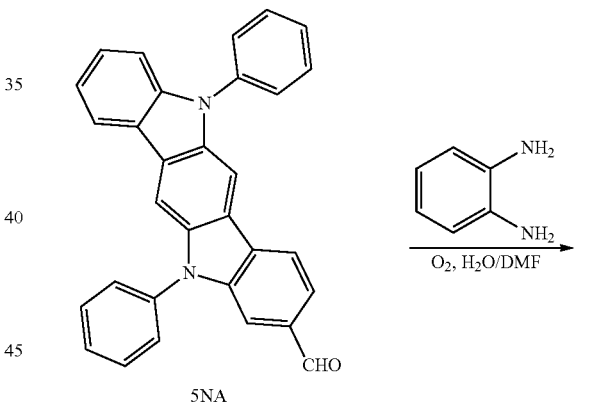
5NA

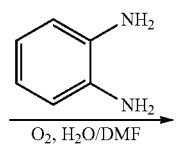
O$_2$, H$_2$O/DMF

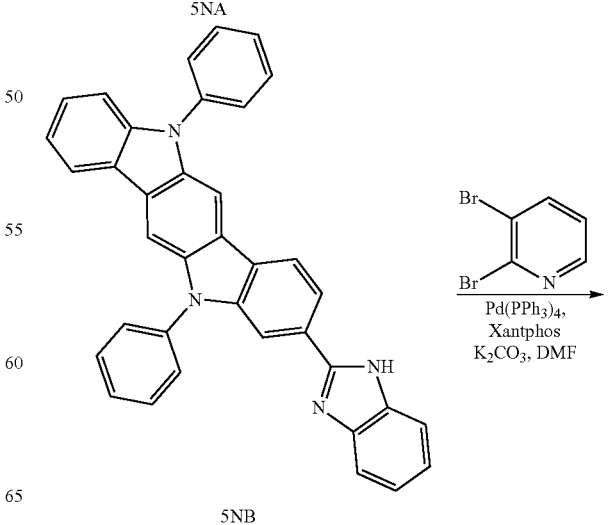
5NB

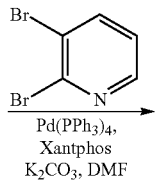
Pd(PPh$_3$)$_4$,
Xantphos
K$_2$CO$_3$, DMF

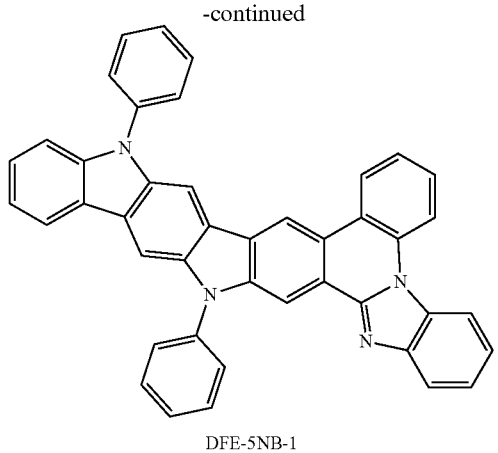

DFE-5NB-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 5NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-5NB-1 in 54% yield.

Example 62

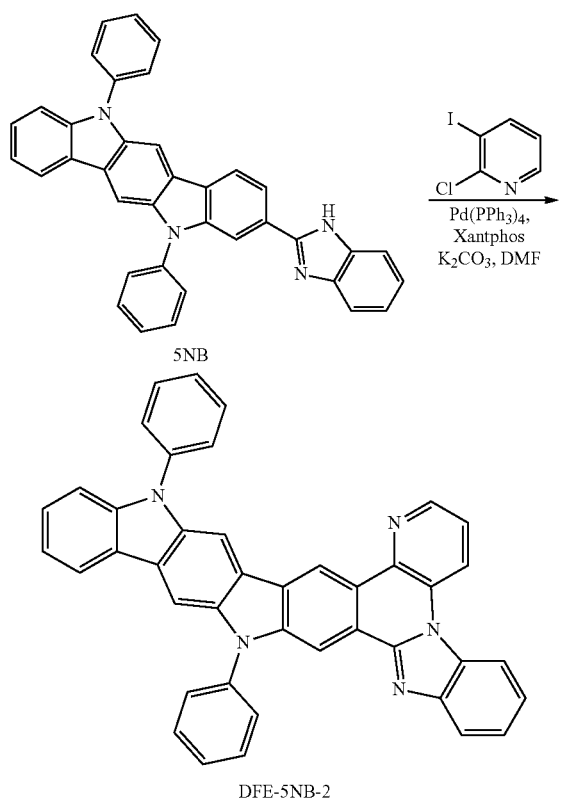

DFE-5NB-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 5NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-5NB-2 in 43% yield.

Example 63

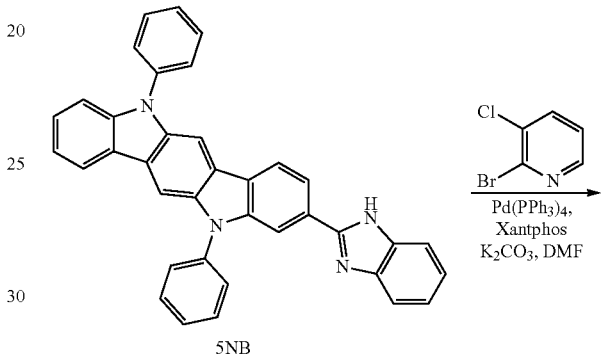

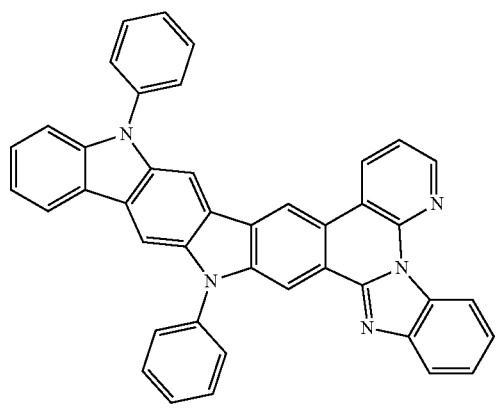

DFE-5NB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 5NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-5NB-3 in 25% yield.

Example 64

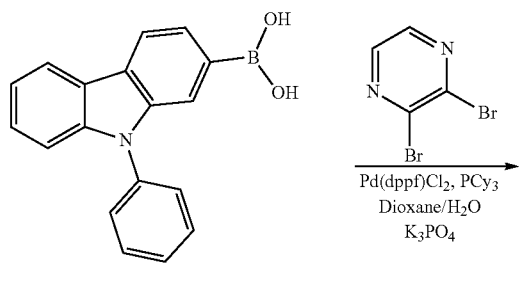

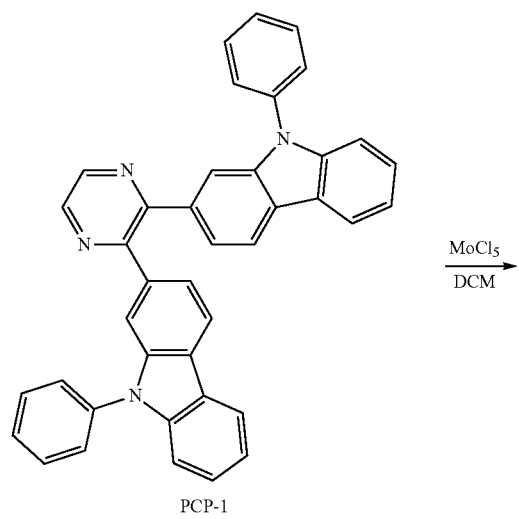

PCP-1

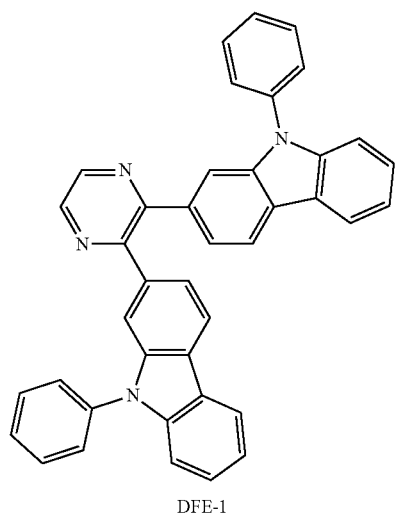

DFE-1

MoCl$_5$ (1.0 equiv) was added quickly to a solution of PCP-1 (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-1 in 45% yield.

Example 65

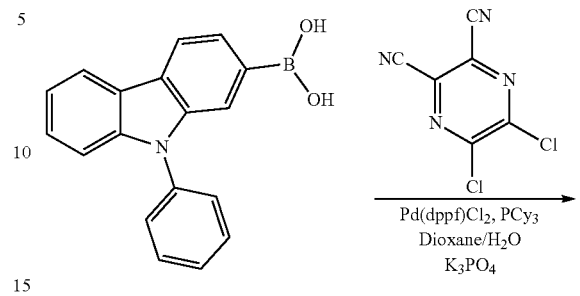

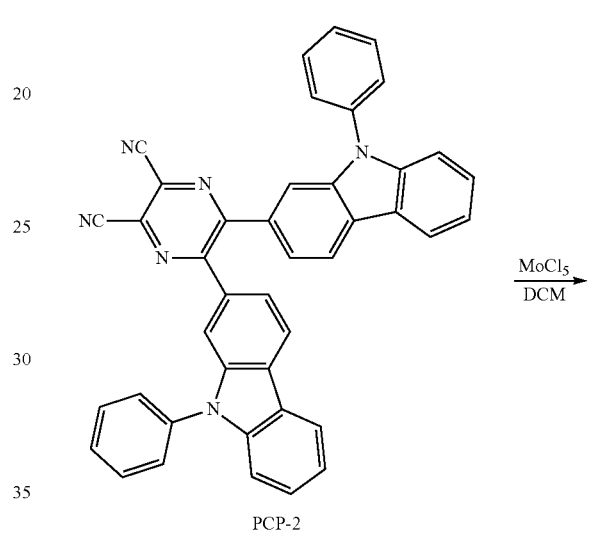

PCP-2

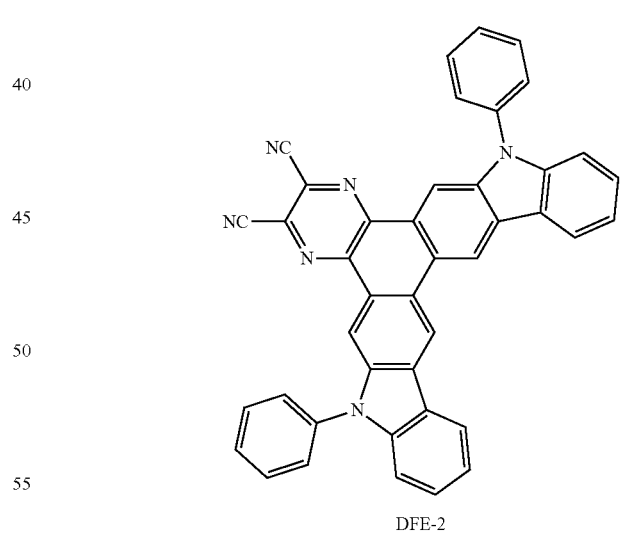

DFE-2

MoCl$_5$ (1.0 equiv) was added quickly to a solution of PCP-2 (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-2 in 41% yield.

Example 66

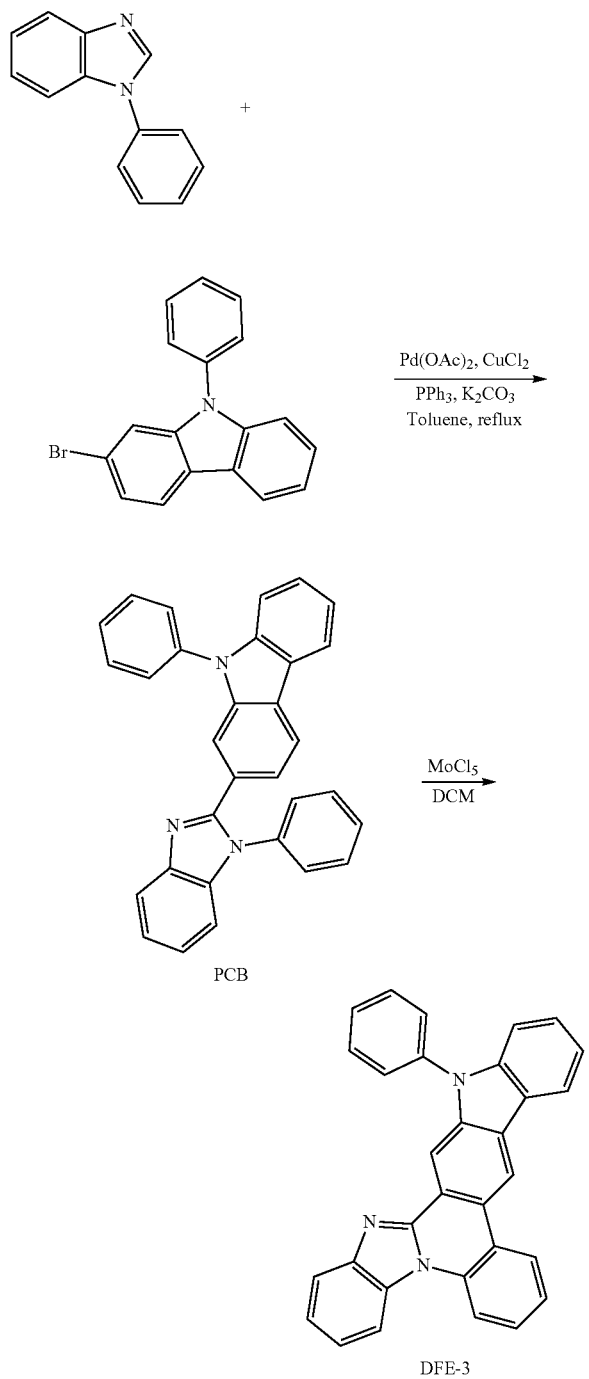

MoCl$_5$ (1.0 equiv) was added quickly to a solution of PCB (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-3 in 38% yield.

Example 67

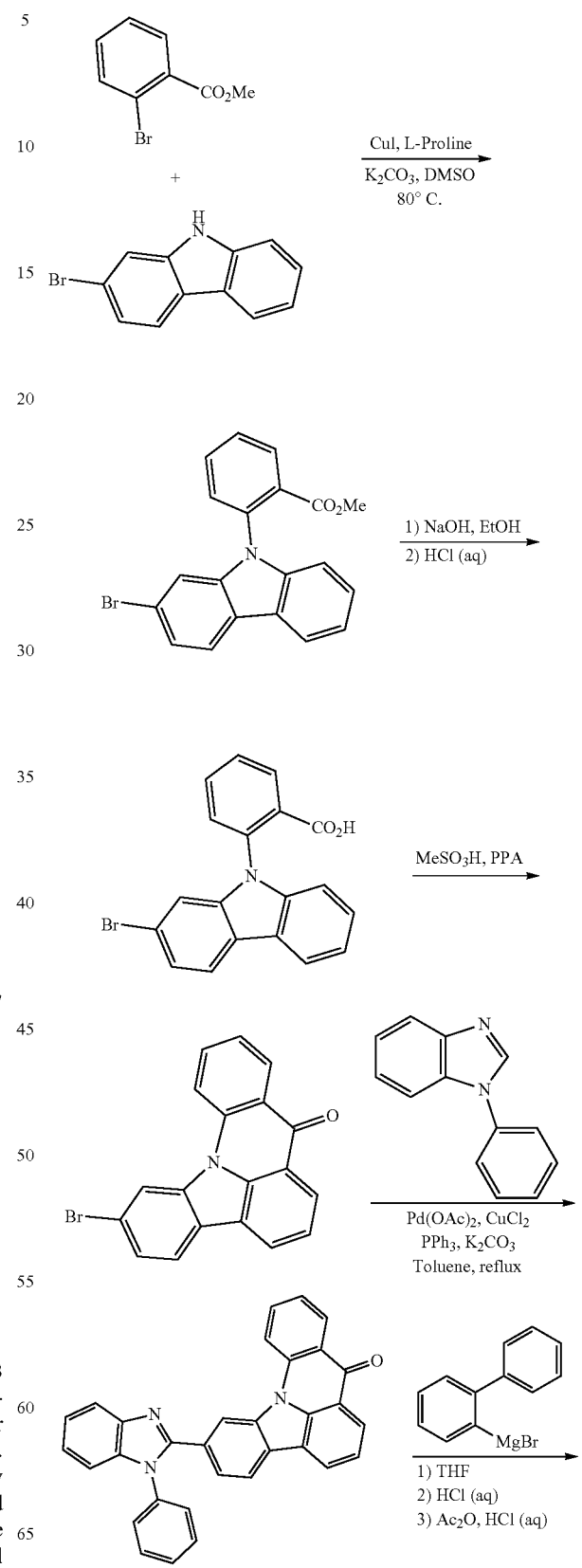

-continued

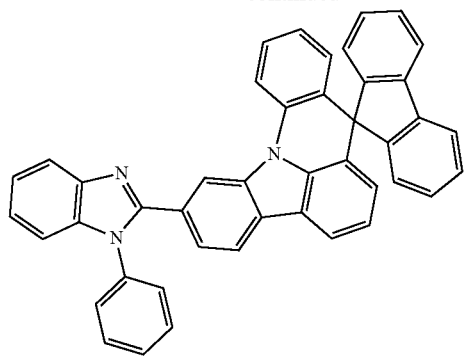

BCF

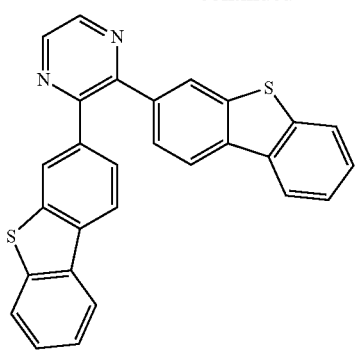

BTP-1

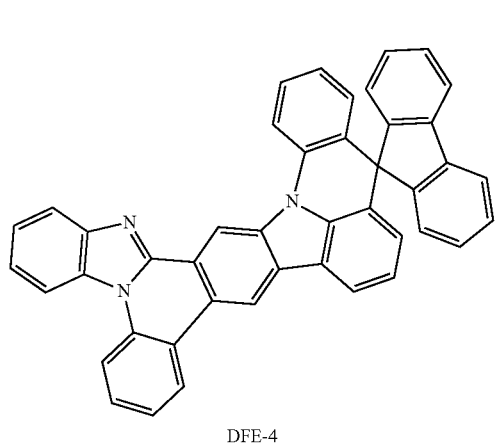 [SMILES: c1ccc2c(c1)-c1ccccc1C21c2ccccc2-n2c3cc4c(cc3c3cccc1c32)c1ccccc1n1c2ccccc2nc41 ; "DFE-4"]

DFE-4

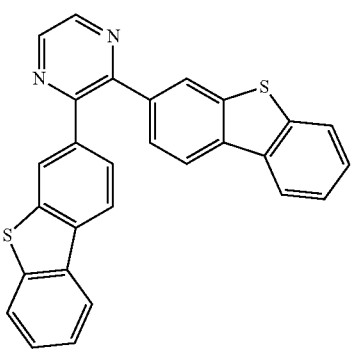

DFE-5

MoCl₅ (1.0 equiv) was added quickly to a solution of BCF (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-4 in 42% yield.

Example 68

MoCl₅ (1.0 equiv) was added quickly to a solution of BTP-1 (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-5 in 49% yield.

Example 69

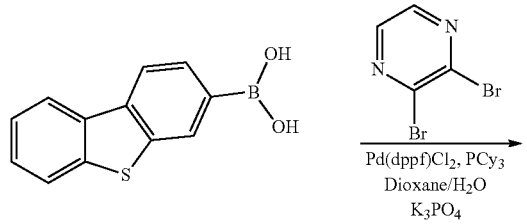

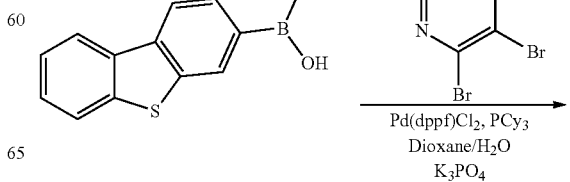

257
-continued

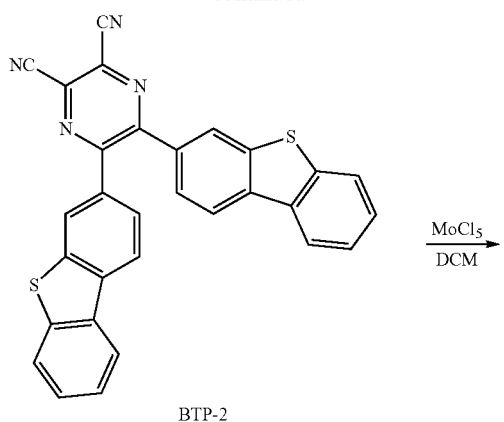

BTP-2

DFE-6

MoCl₅ (1.0 equiv) was added quickly to a solution of BTP-2 (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-6 in 38% yield.

Example 70

258
-continued

BFB

DFE-7

MoCl₅ (1.0 equiv) was added quickly to a solution of BFB (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-7 in 34% yield.

Example 71

259
-continued

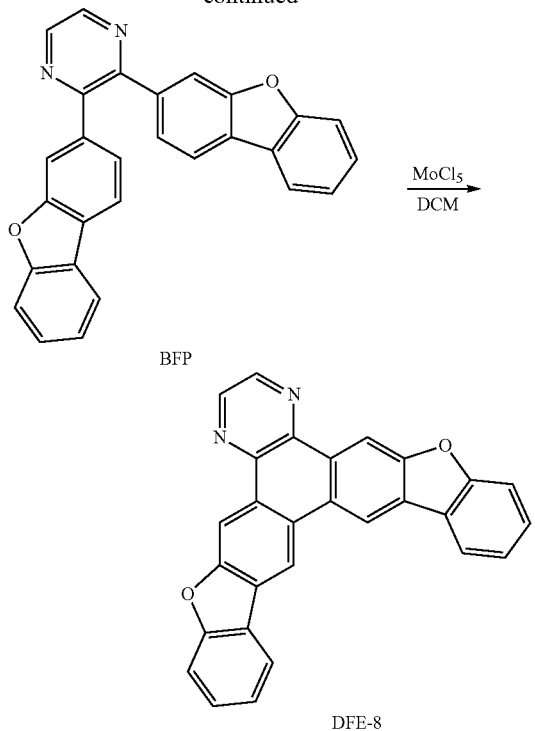

BFP

DFE-8

MoCl₅ (1.0 equiv) was added quickly to a solution of BFP (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-8 in 52% yield.

Example 72

260
-continued

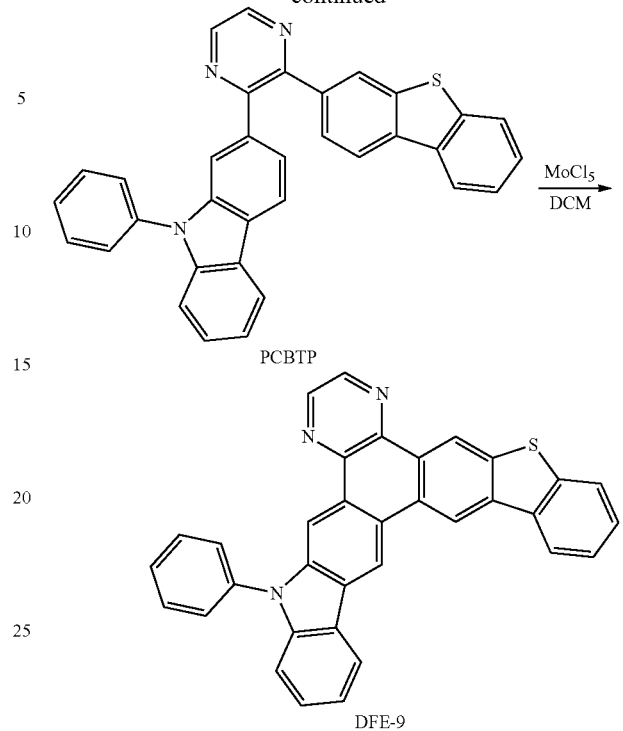

PCBTP

DFE-9

MoCl₅ (1.0 equiv) was added quickly to a solution of PCBTP (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-8 in 49% yield.

Example 73

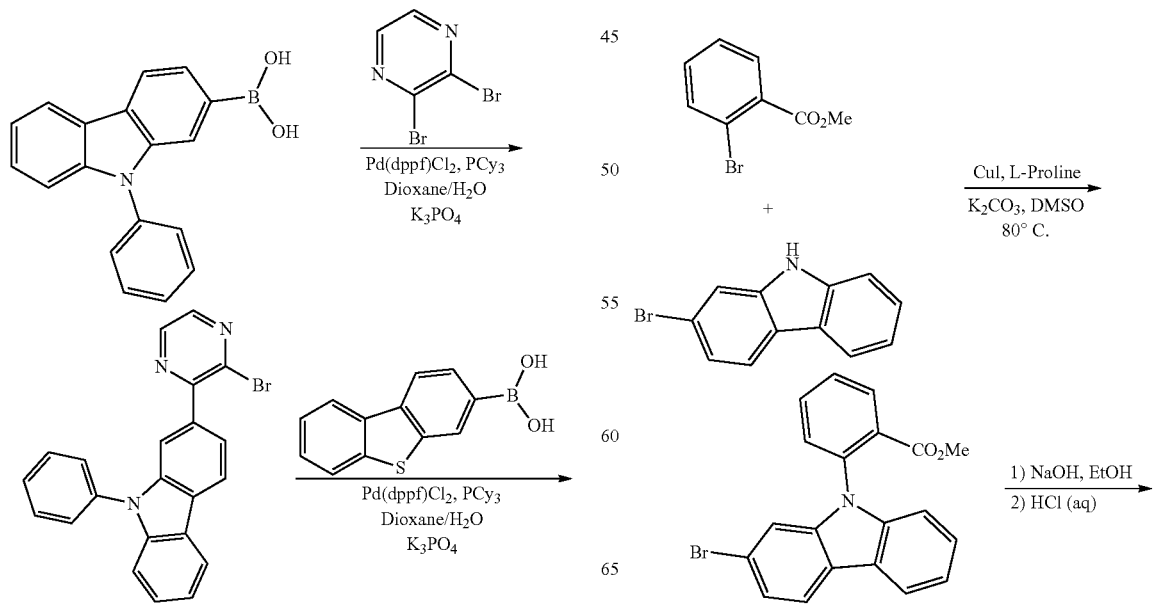

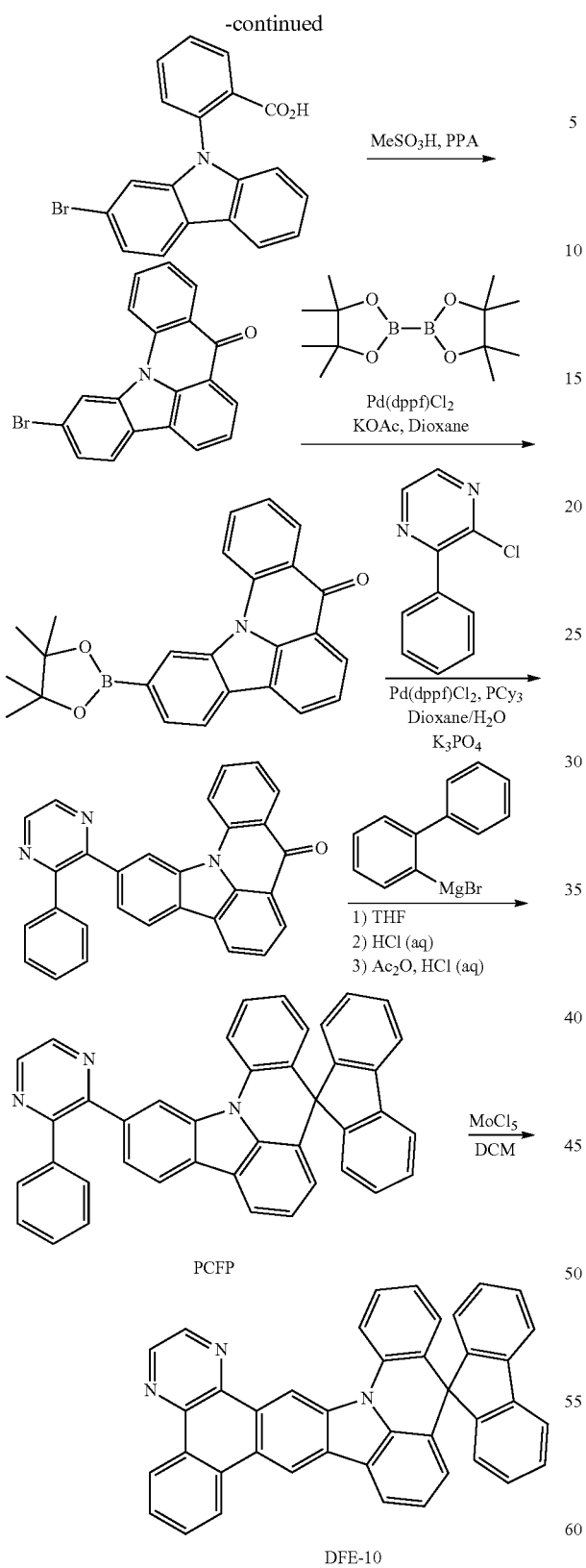

PCFP

DFE-10

MoCl₅ (1.0 equiv) was added quickly to a solution of PCFP (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-10 in 33% yield.

Only a few implementations are described and illustrated. Variations, enhancements and improvements of the described implementations and other implementations can be made based on what is described and illustrated in this document.

What is claimed is:

1. A compound represented by Formula A

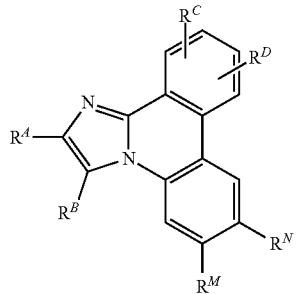

Formula A wherein $R^A$ and $R^B$ can be hydrogen or joined to form a phenyl group, $R^C$, $R^D$, $R^M$, and $R^N$ are hydrogen or combined form a group having Formula B with the proviso that at least one of the combination of $R^C$ and $R^D$ or the combination of $R^M$ and $R^N$ form a group having Formula B

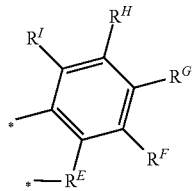

Formula B wherein $R^E$ is NPh, S or O; $R^{F-I}$ are independently hydrogen or two adjacent positions combine to form a group having Formula C with the proviso that at least one of the combination of $R^I$ and $R^H$, $R^H$ and $R^G$, $R^G$ and $R^F$ have Formula C

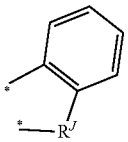

Formula C and $R^J$ is NPh, S or O.

2. A compound according to claim 1 and represented by one of the following structures:
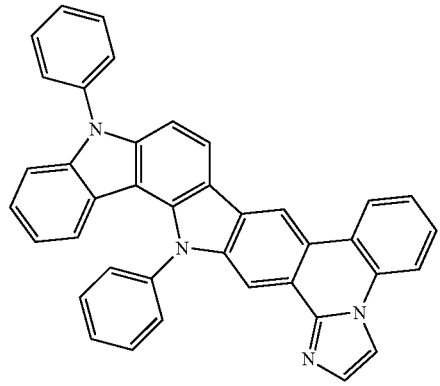
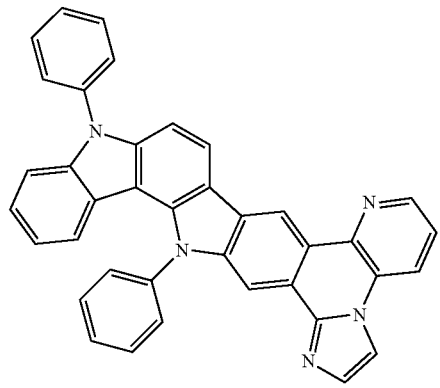
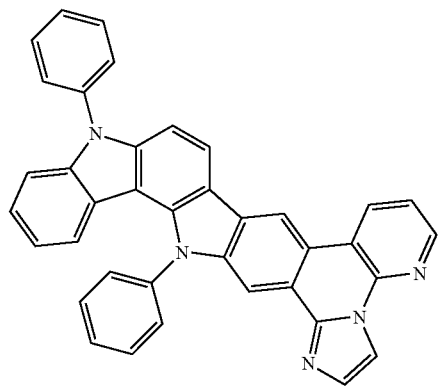
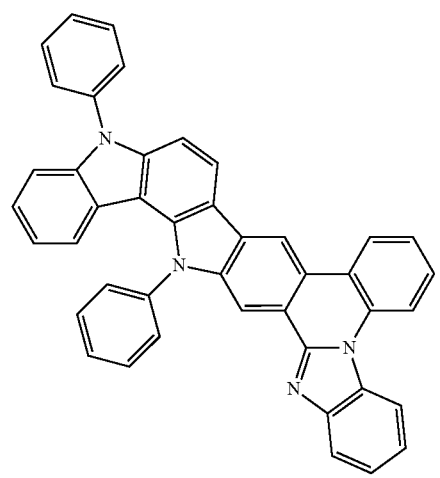
-continued
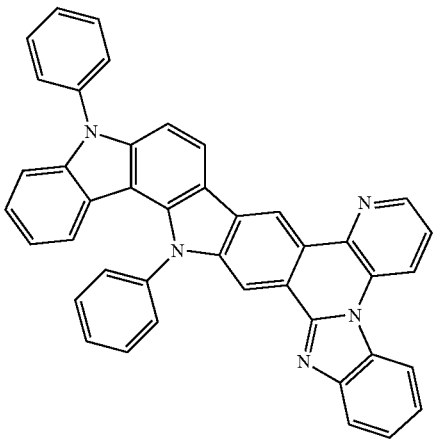
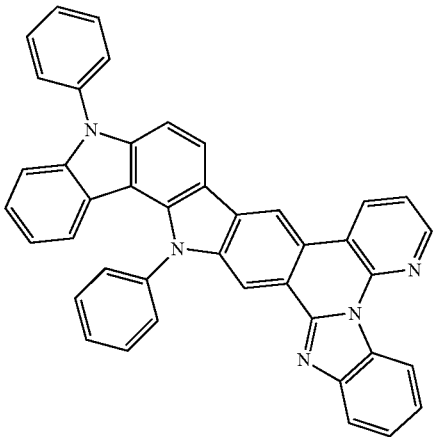
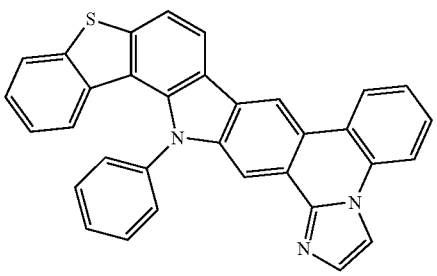
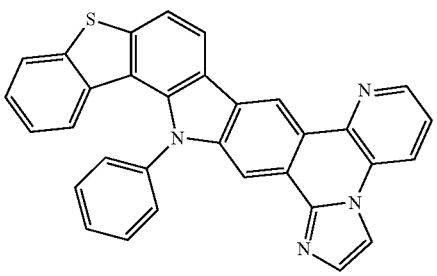
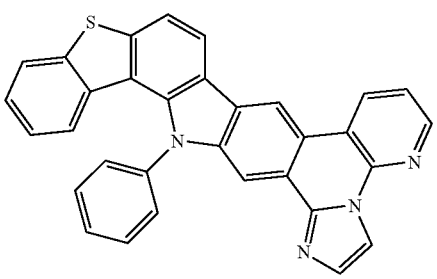

265
-continued
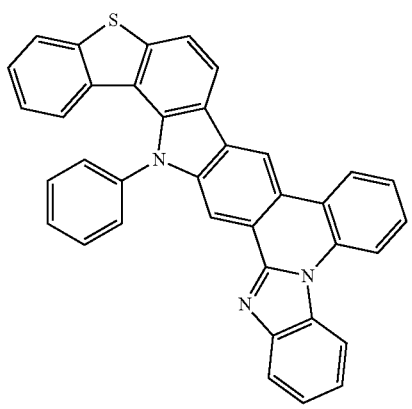
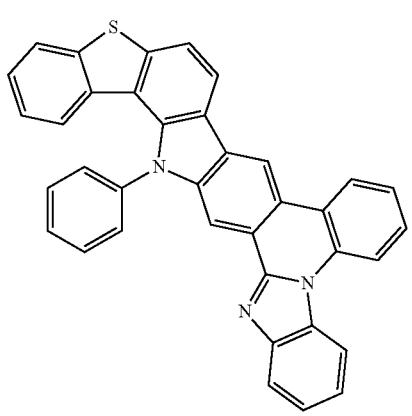
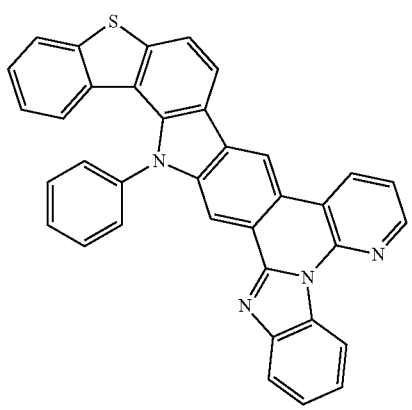
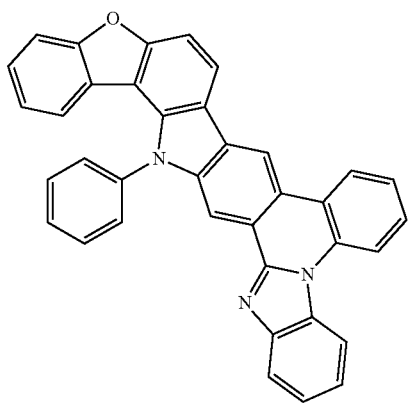
266
-continued
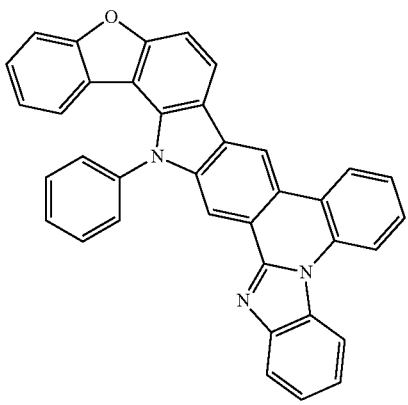
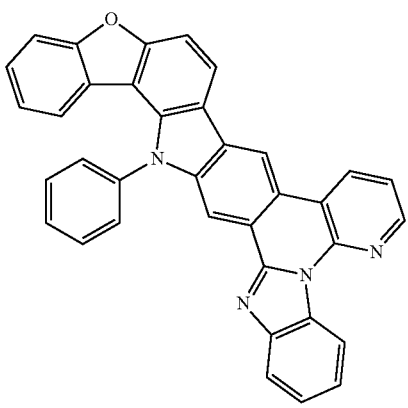
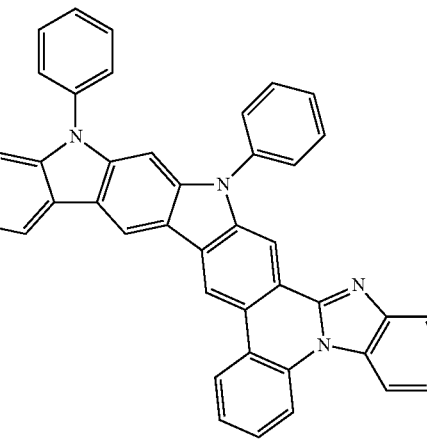
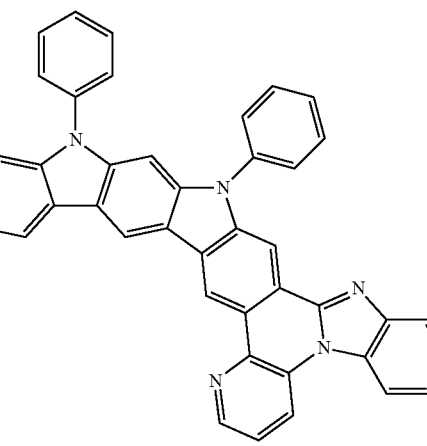

267
-continued
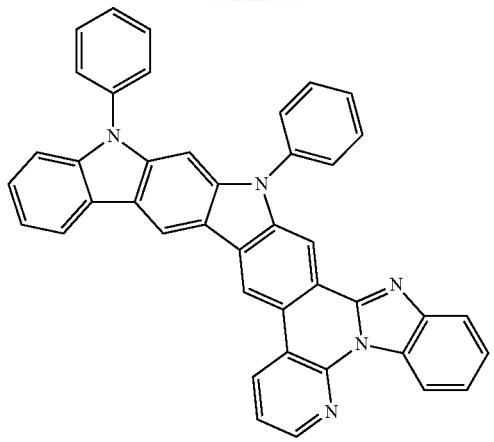
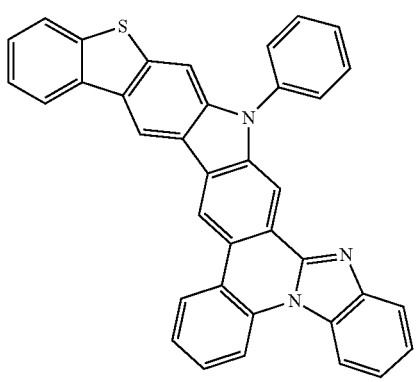
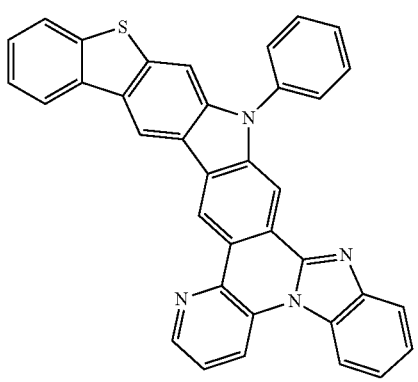
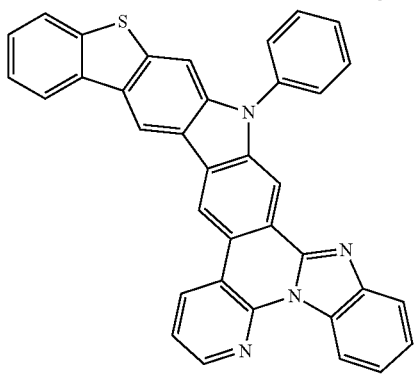
268
-continued
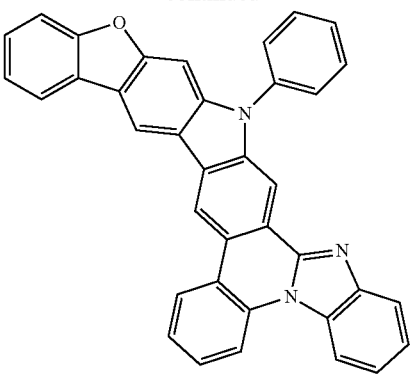
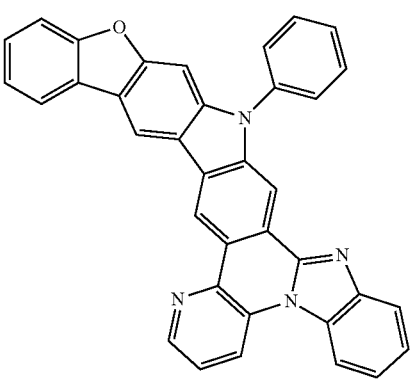
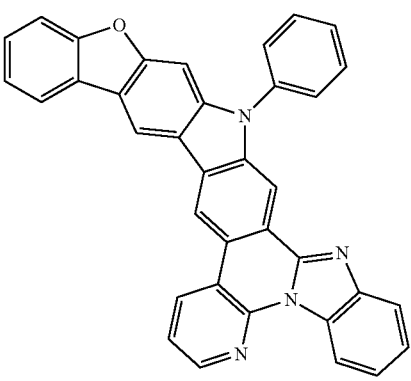
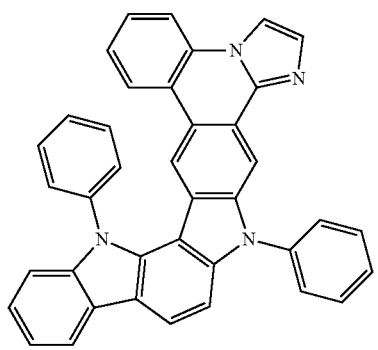

269
-continued
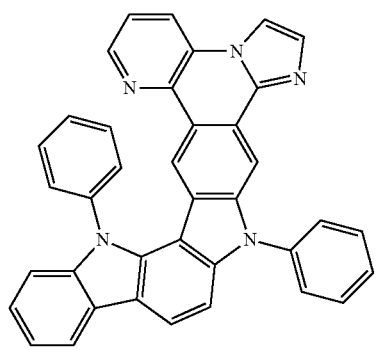
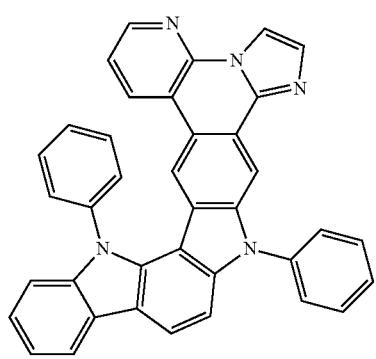
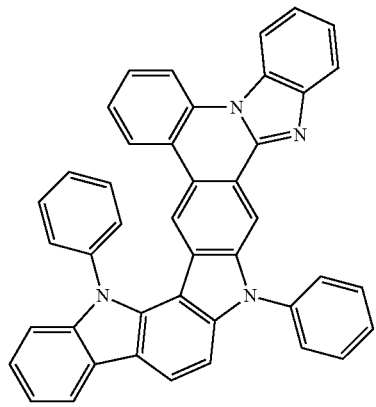
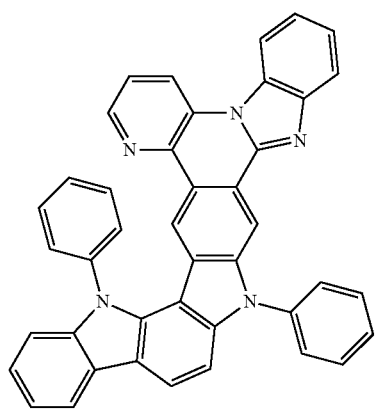
270
-continued
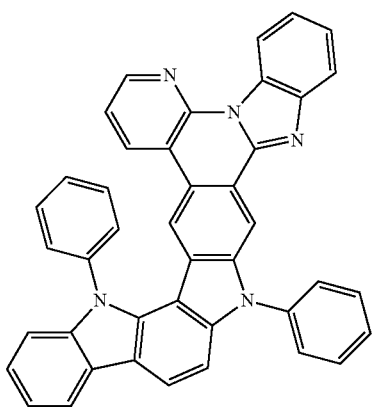
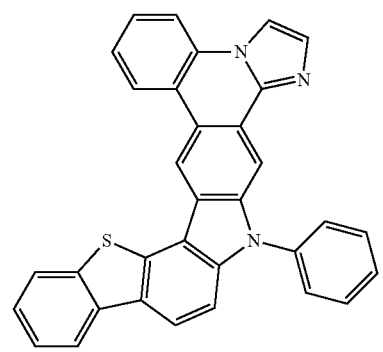
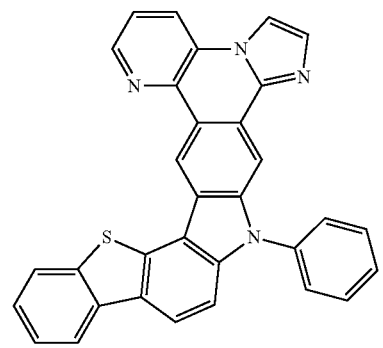
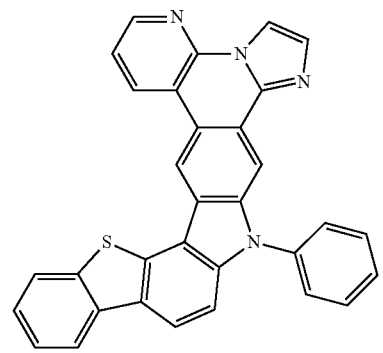

271
-continued
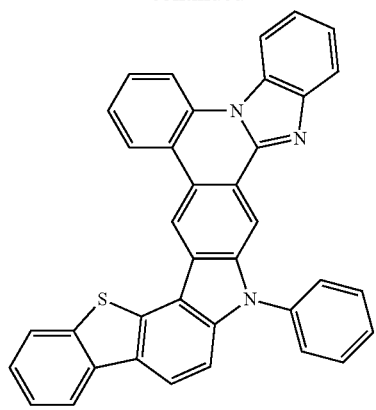
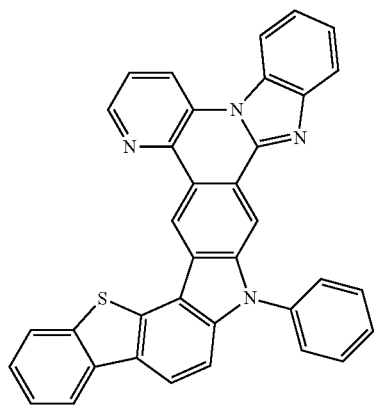
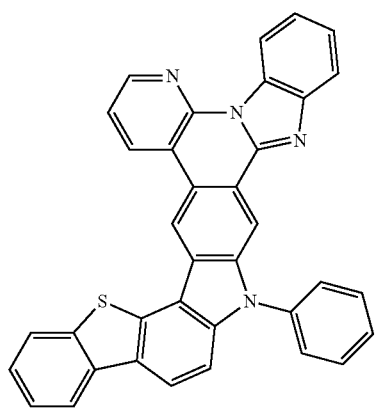
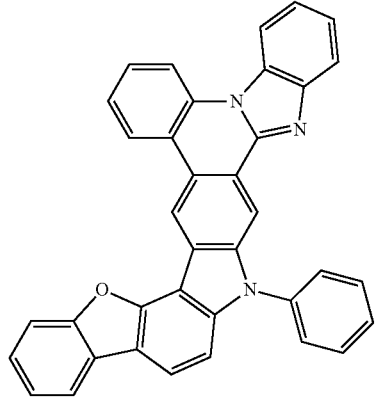
272
-continued
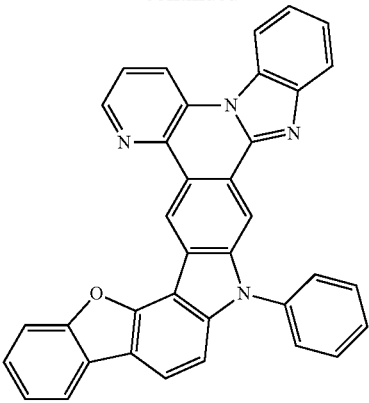
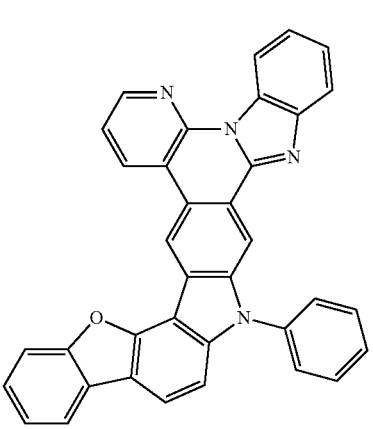
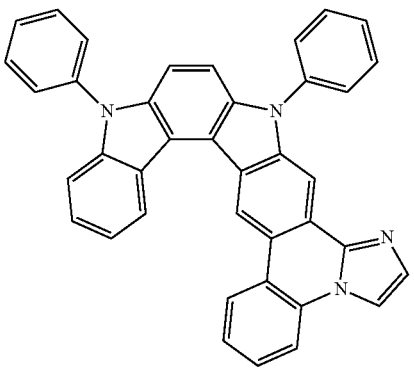
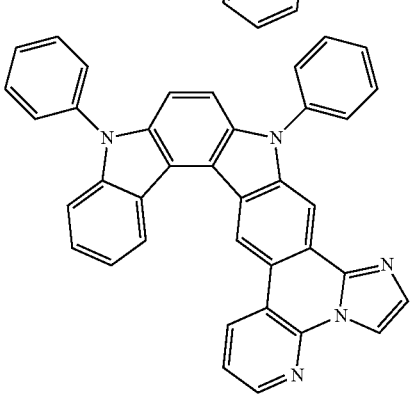

273
-continued
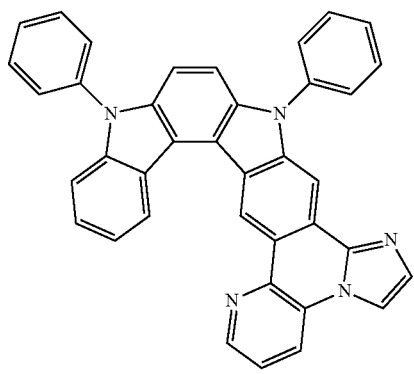
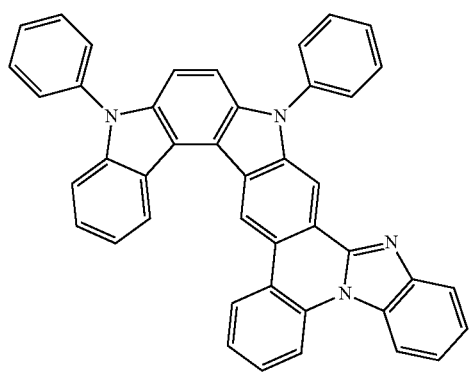
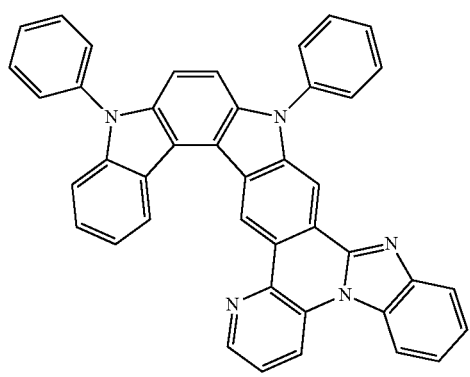
274
-continued
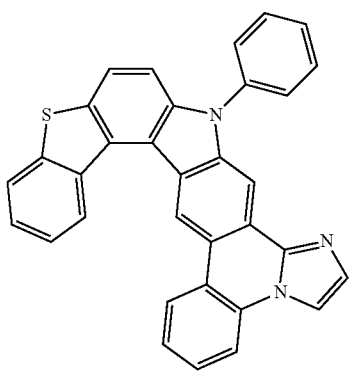
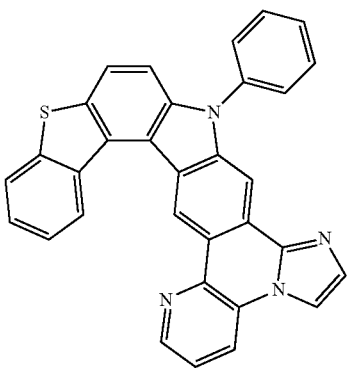
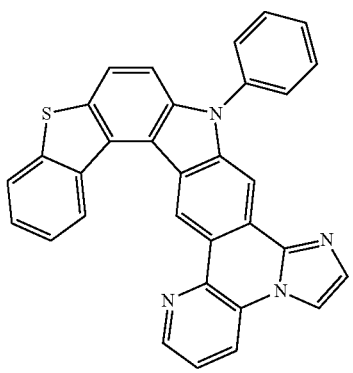
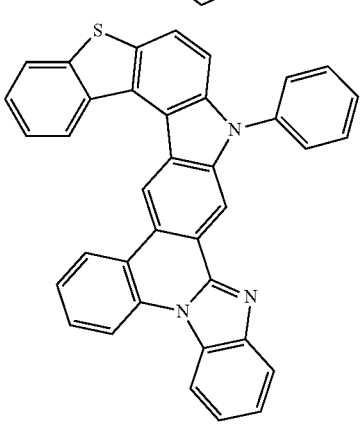

275
-continued
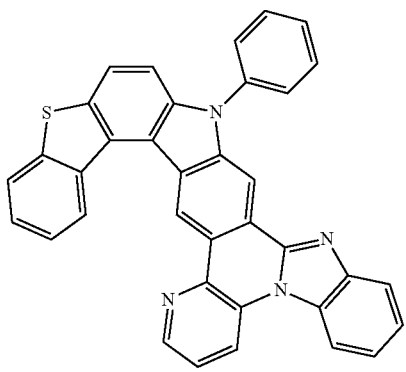
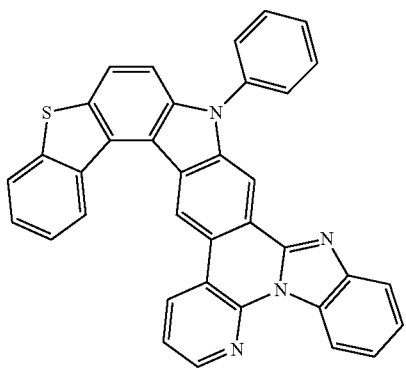
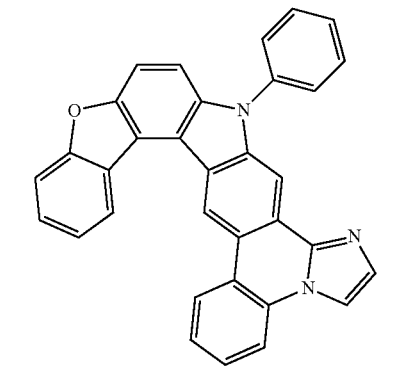
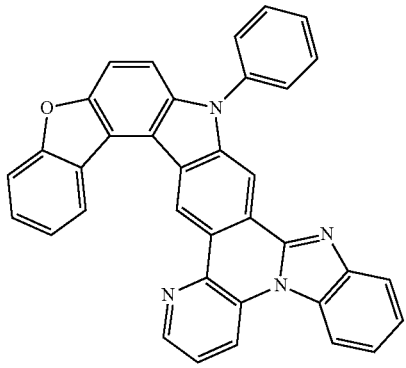
276
-continued
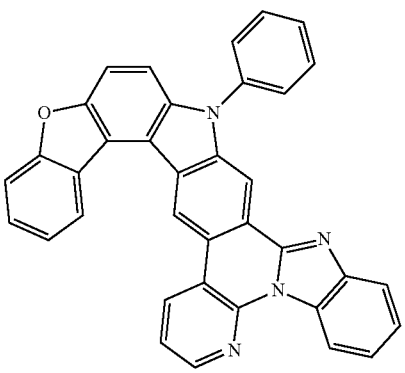
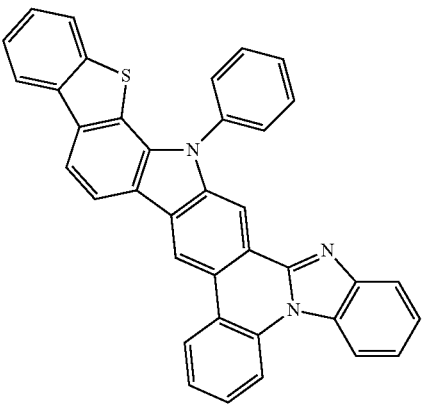
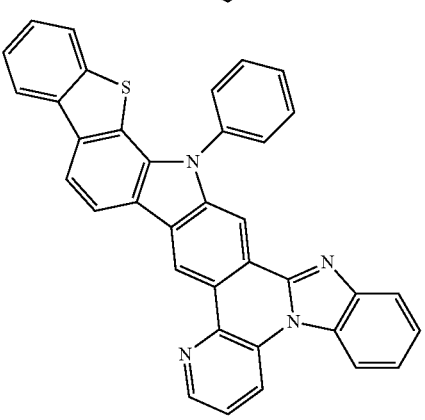
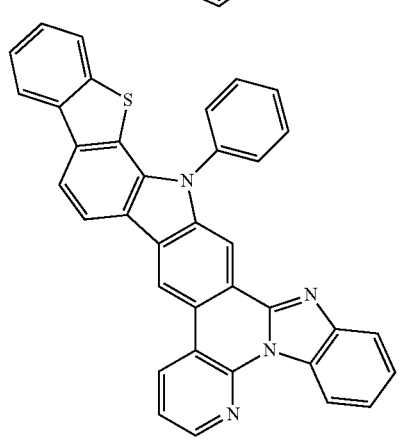

277
-continued
278
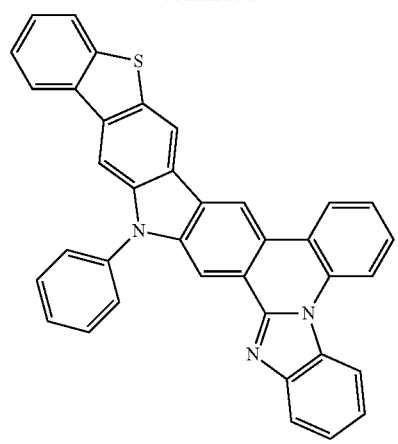
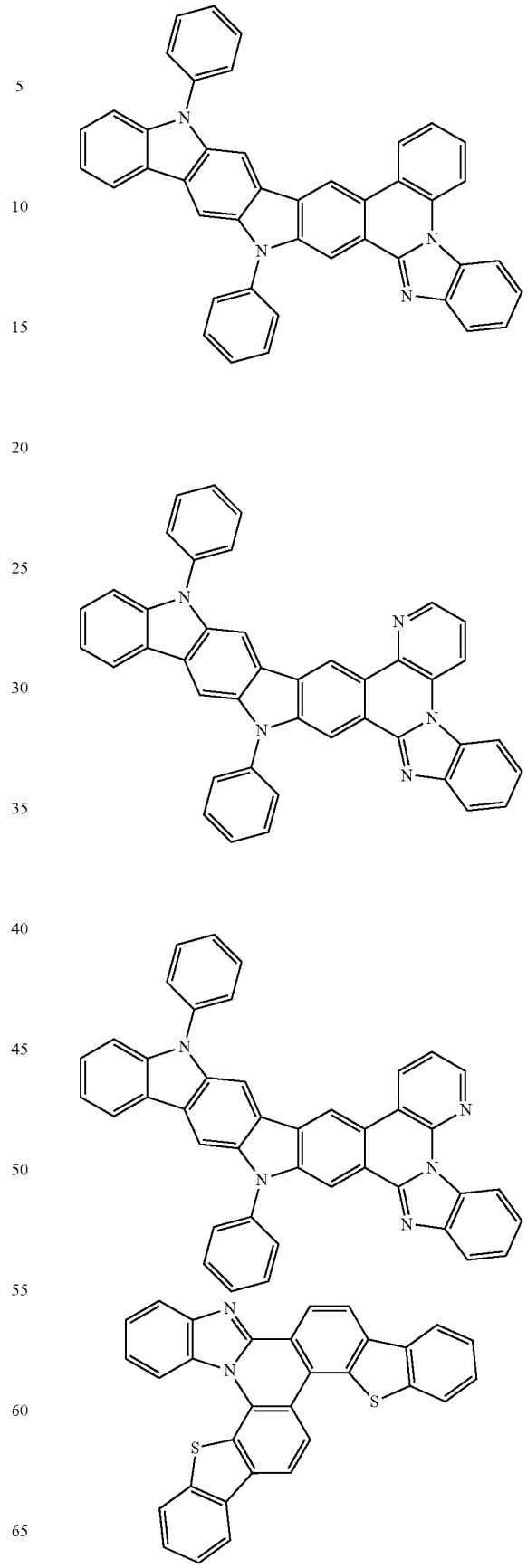

279
-continued
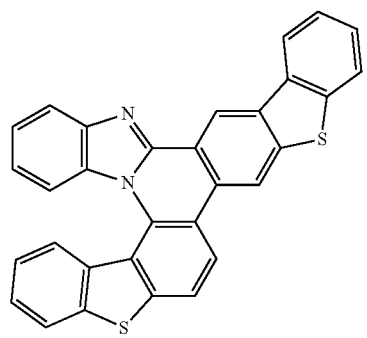
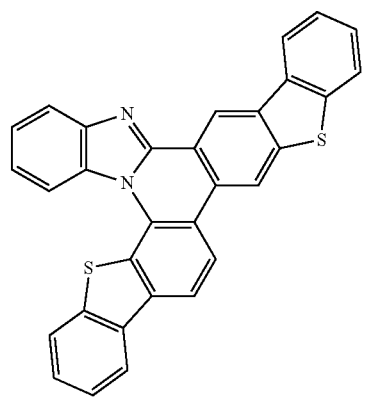
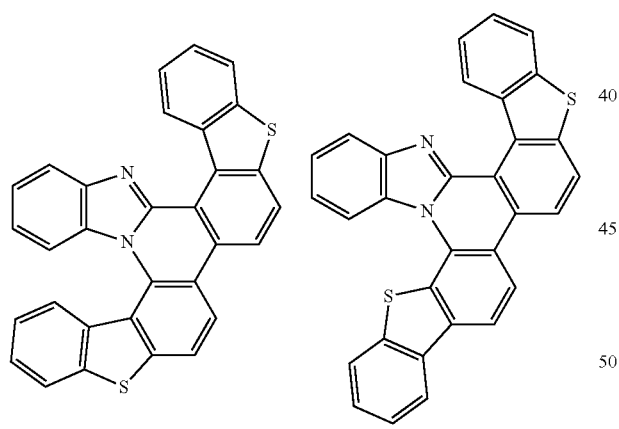
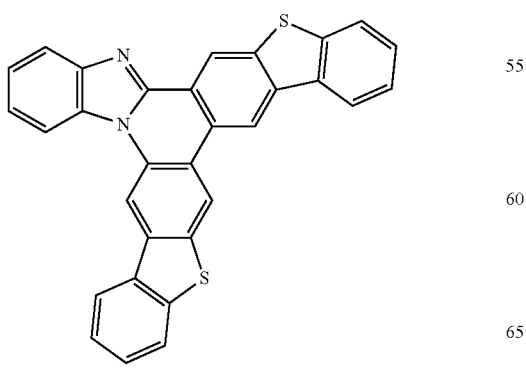
280
-continued
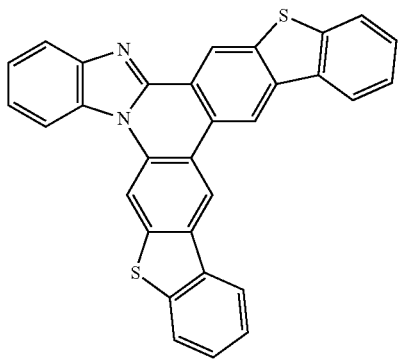
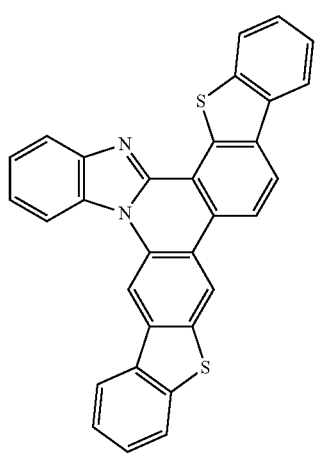
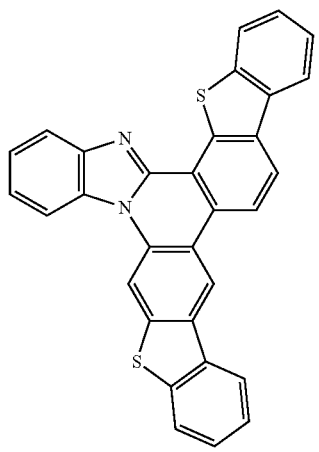
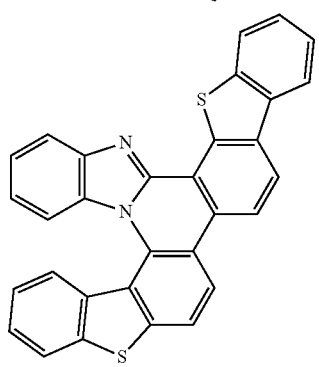

281
-continued
282
-continued
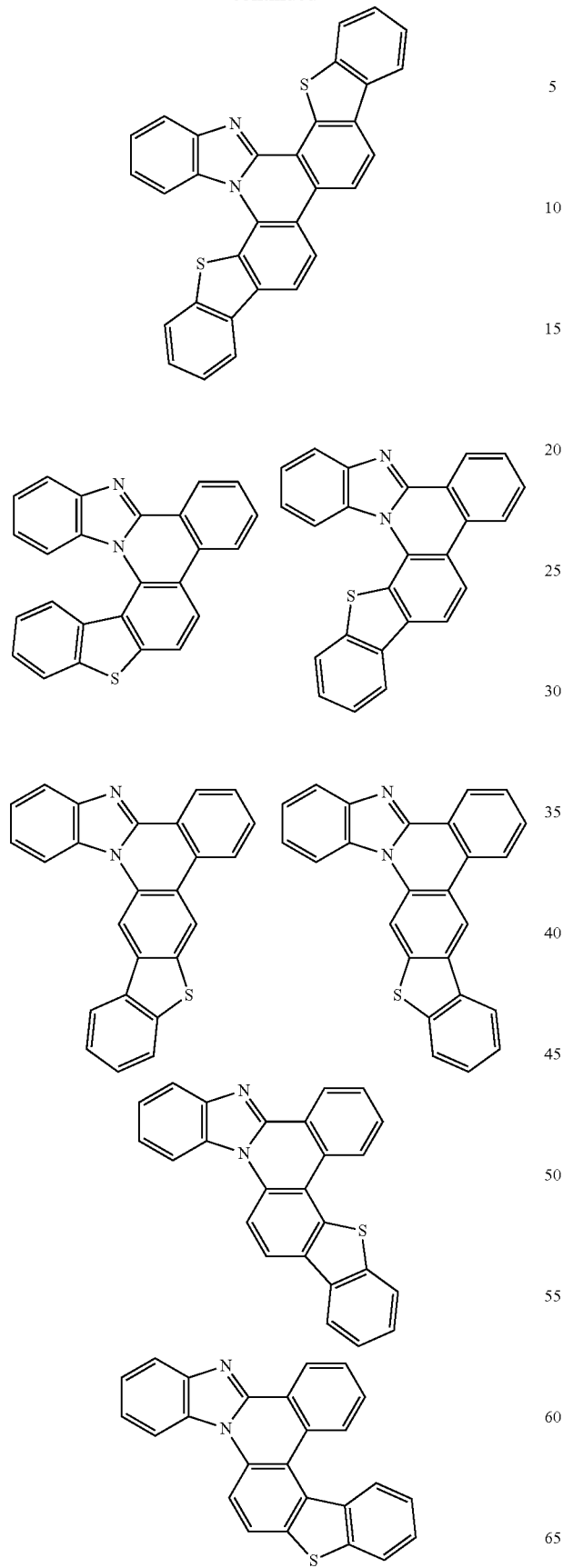
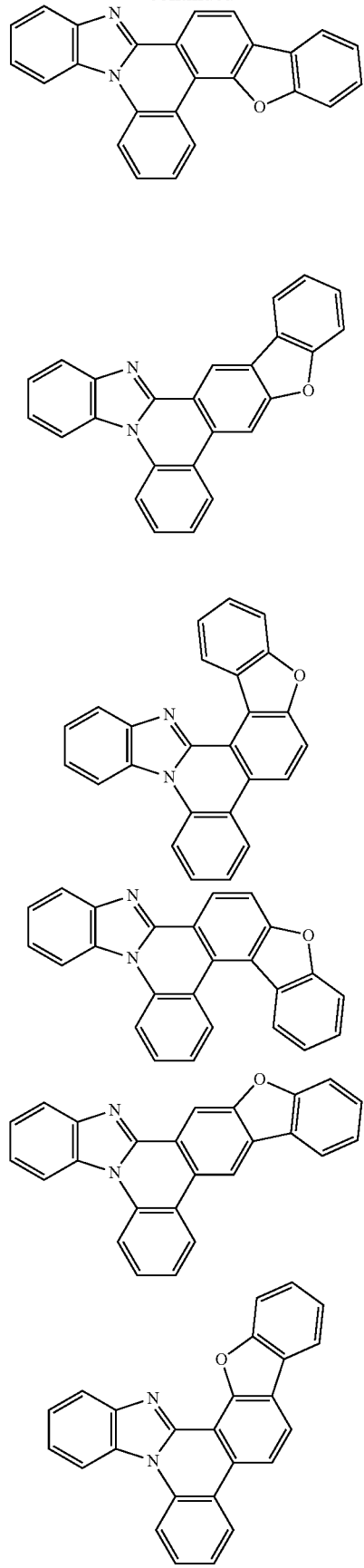

283
-continued
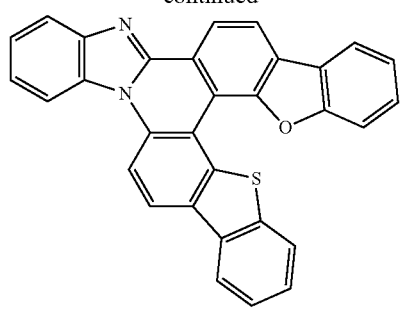
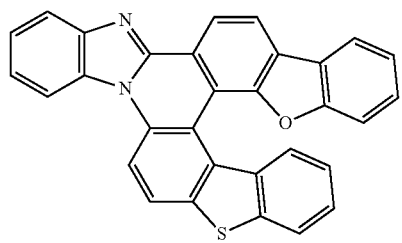
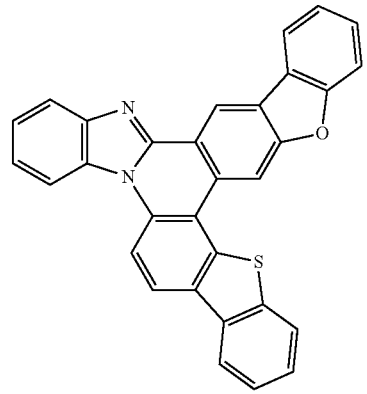
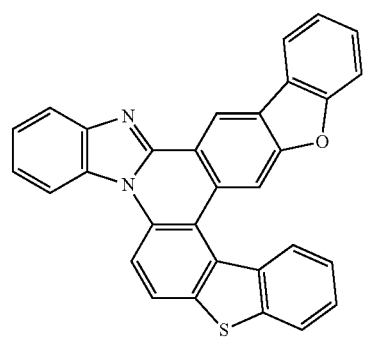
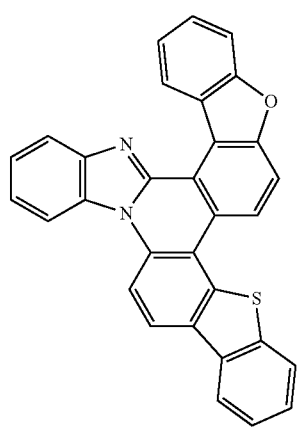
284
-continued
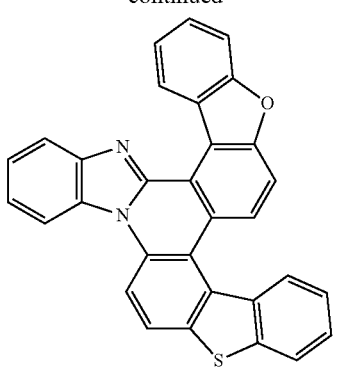
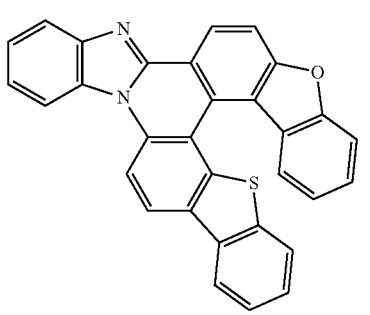
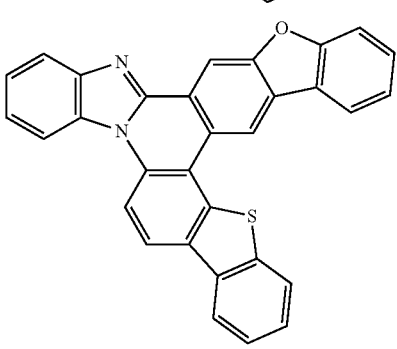
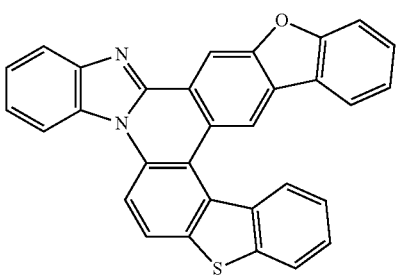
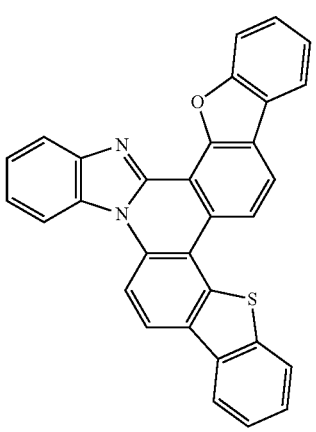

-continued
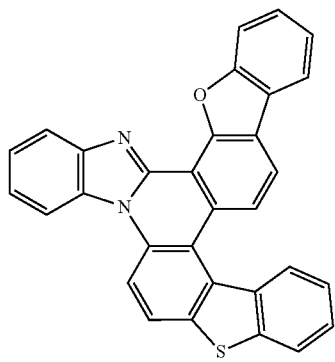
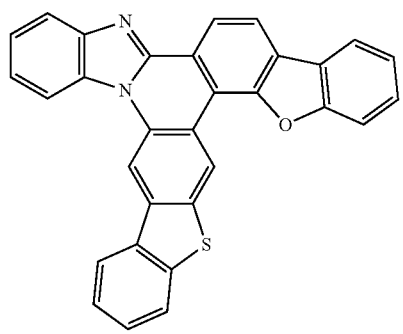
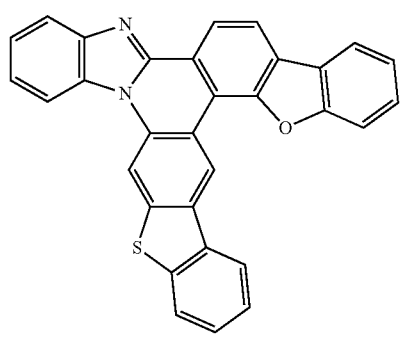
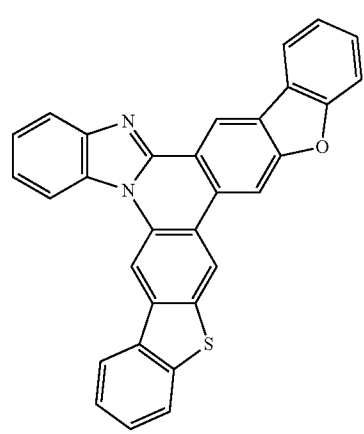
-continued
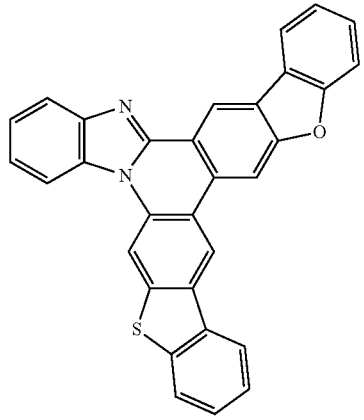
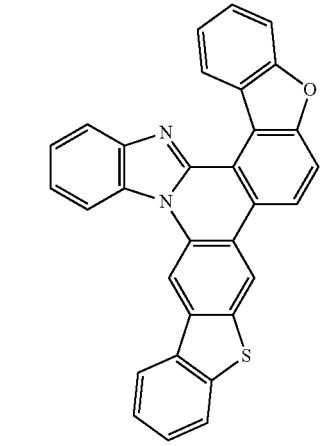
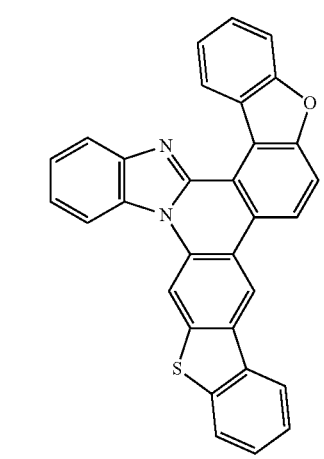
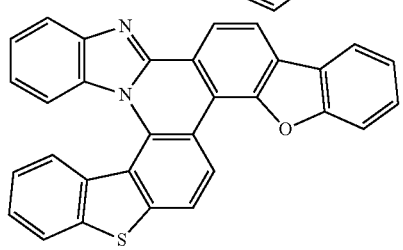

287
-continued
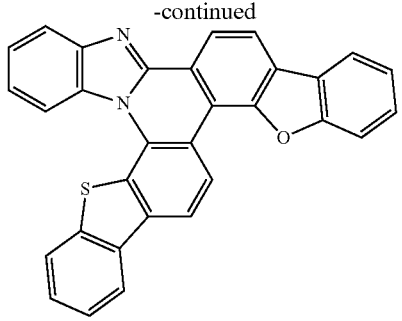
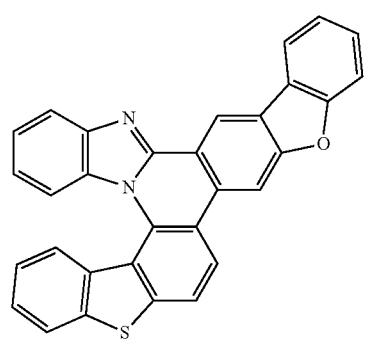
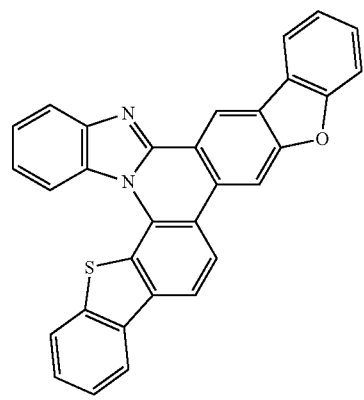
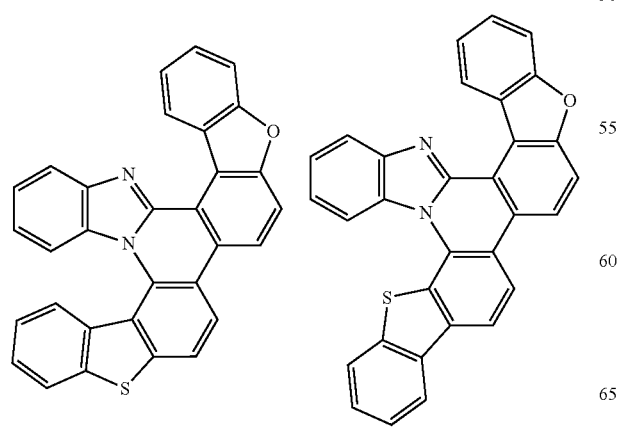
288
-continued
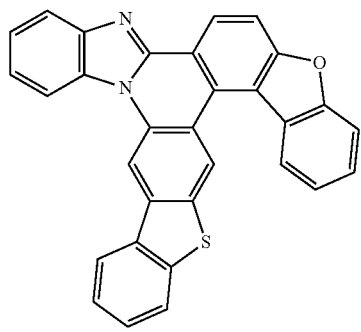
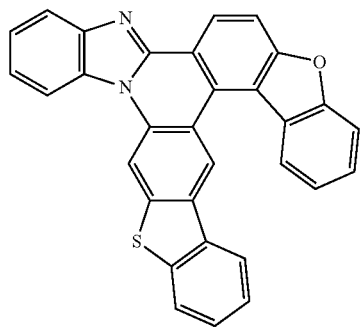
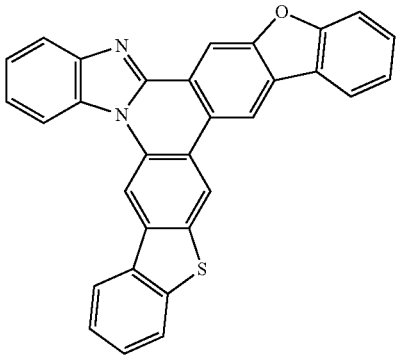
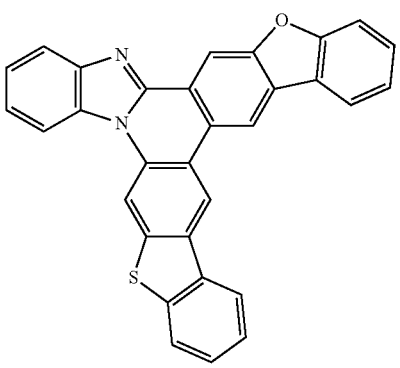

289
-continued
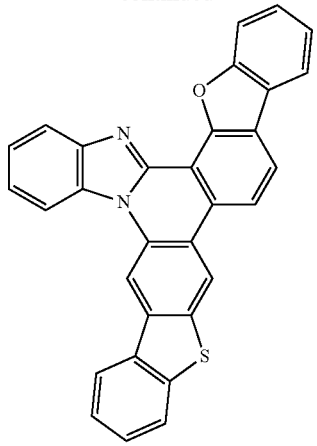
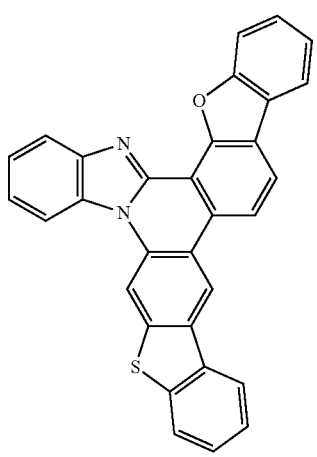
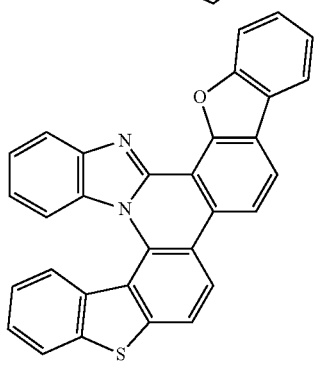
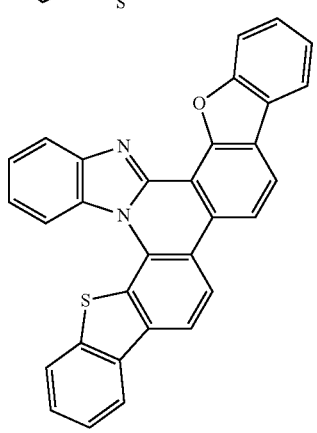
290
-continued
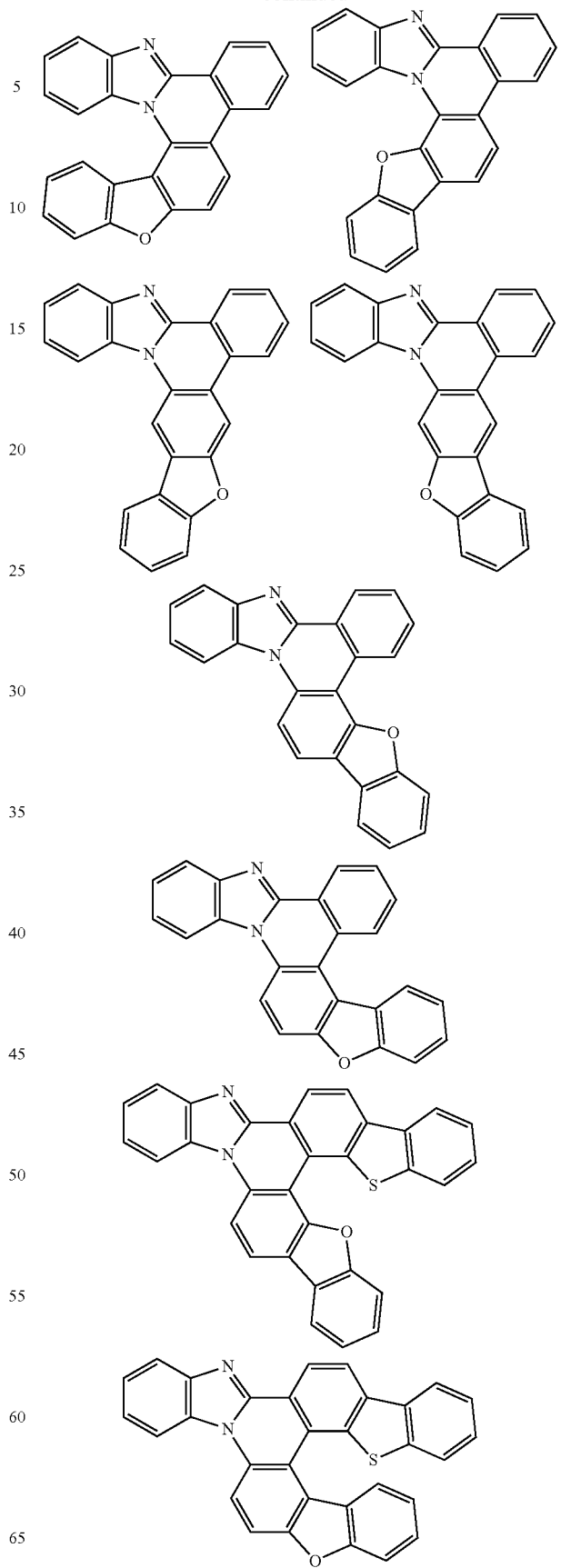

291
-continued
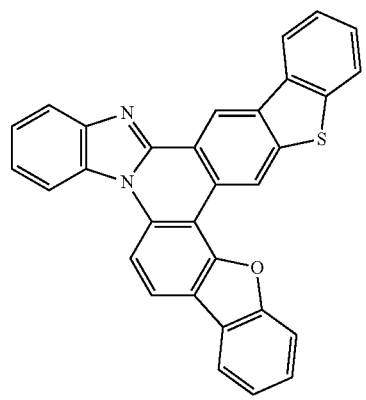
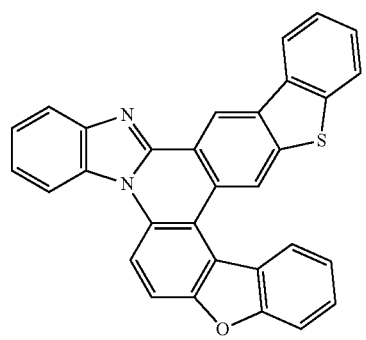
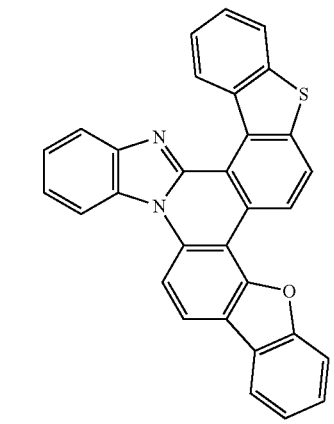
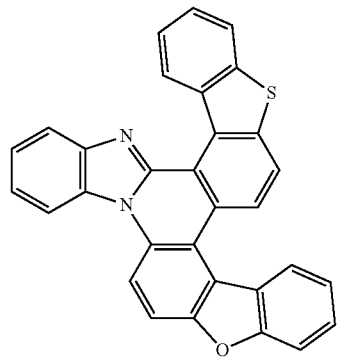
292
-continued
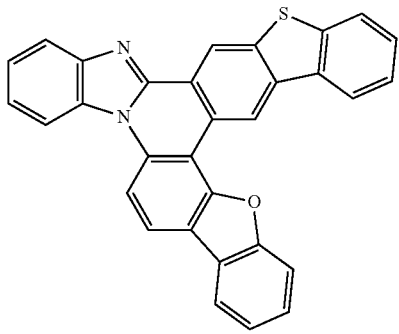
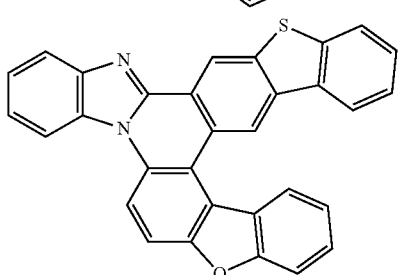
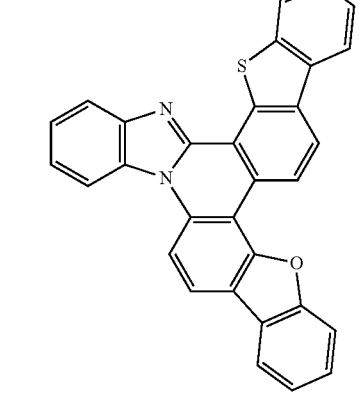
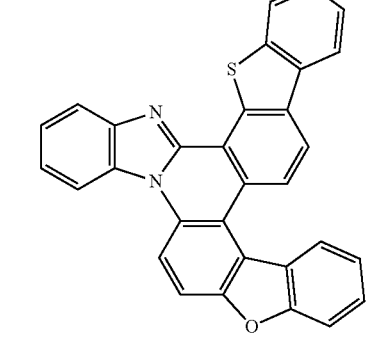
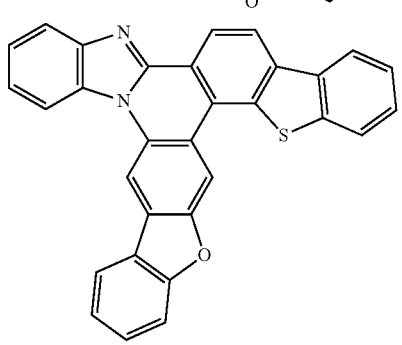

293
-continued
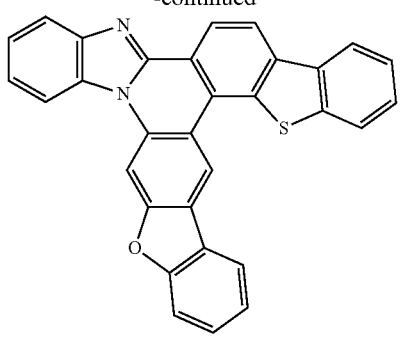
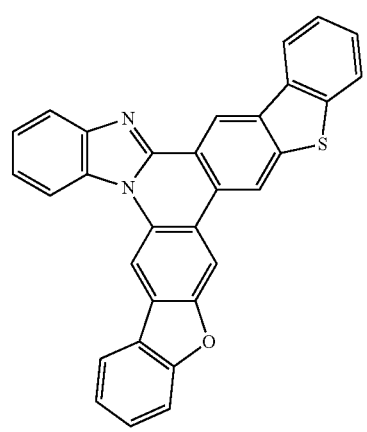
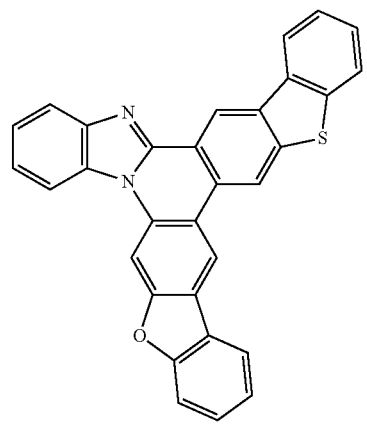
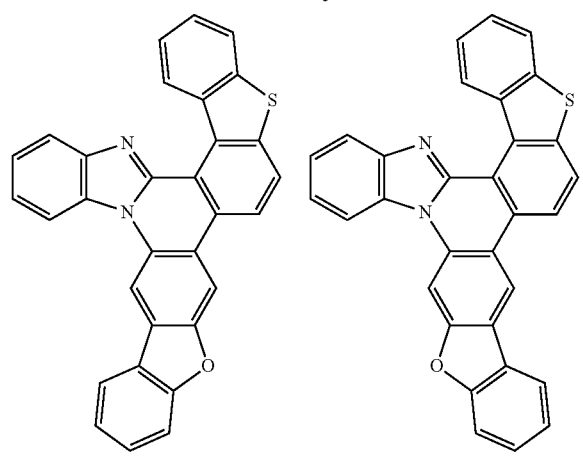
294
-continued
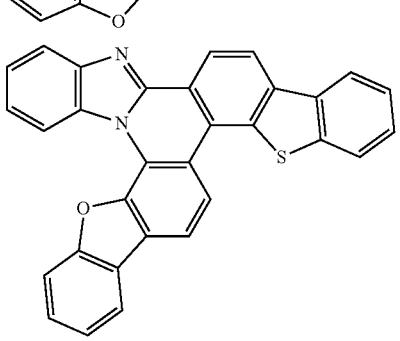
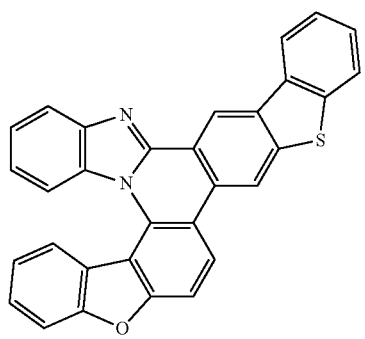
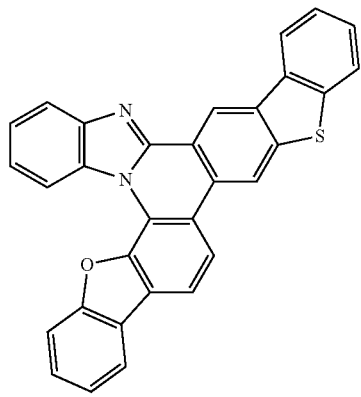
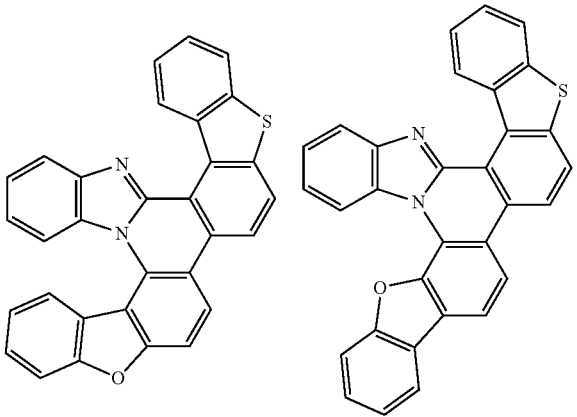

295
-continued
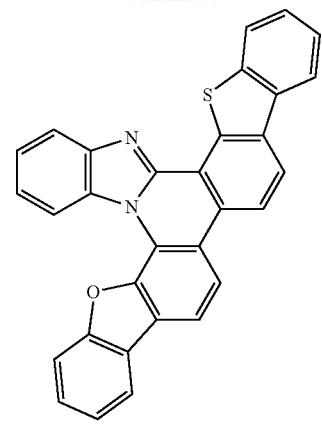
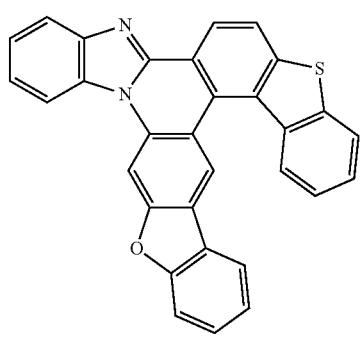
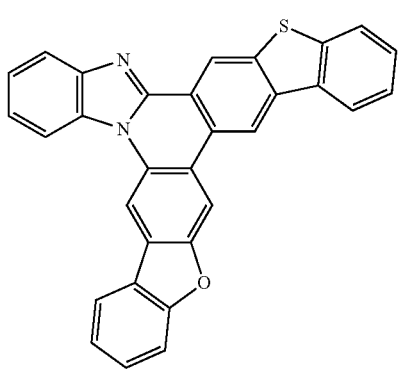
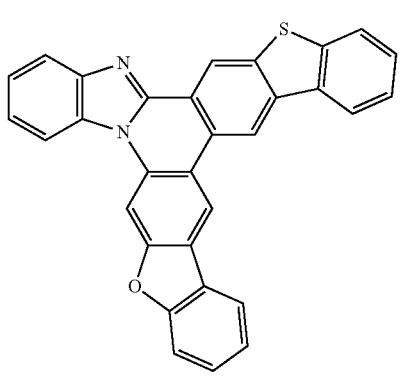
296
-continued
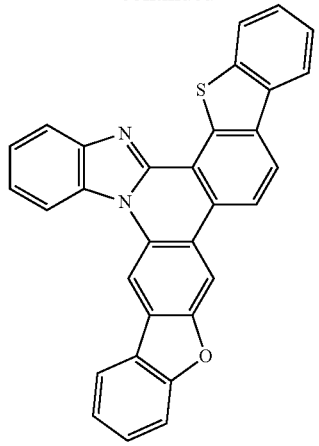
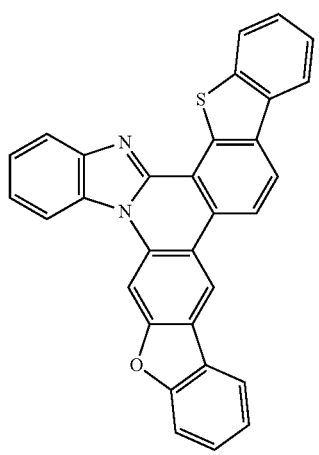
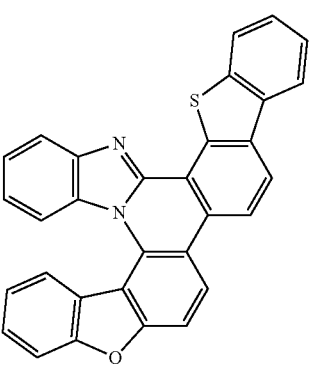
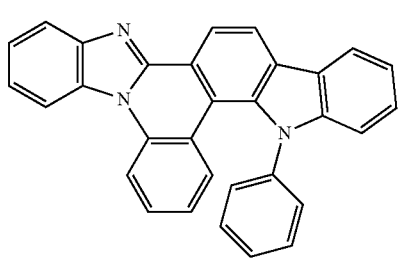

-continued
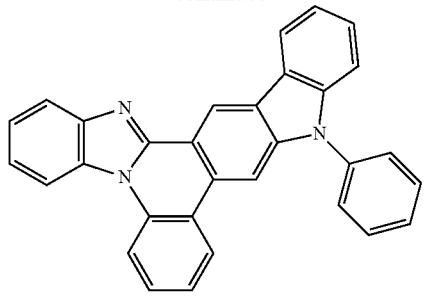
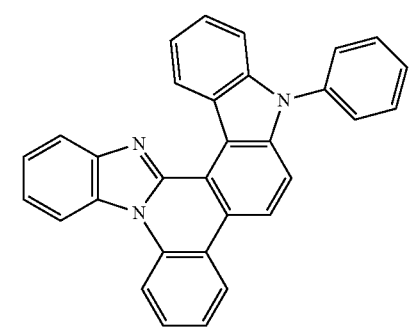
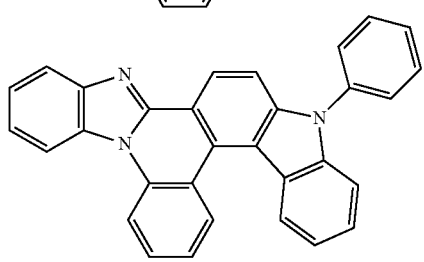
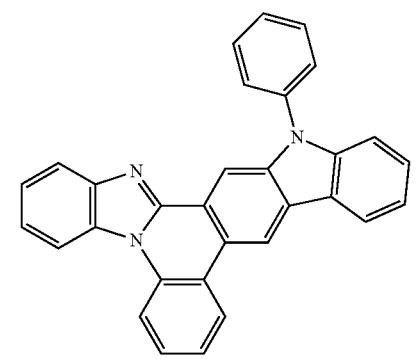
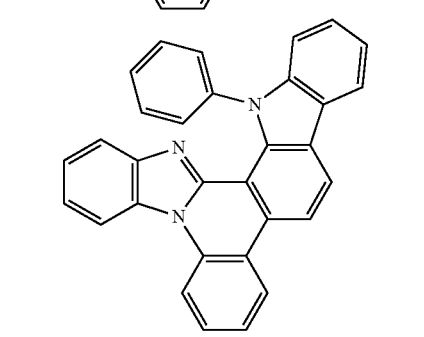
-continued
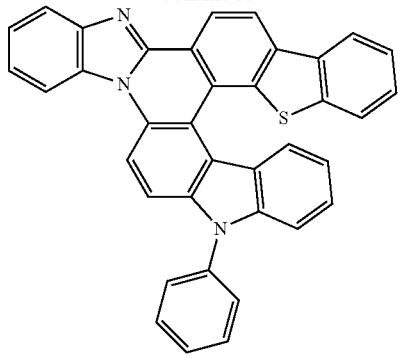
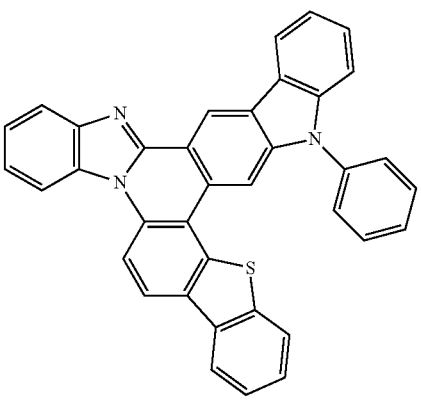
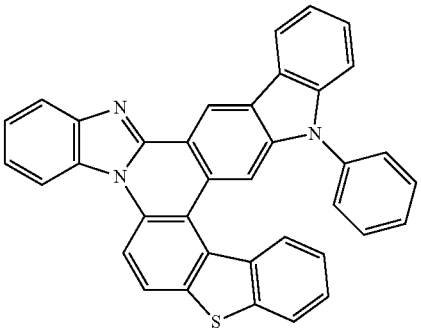
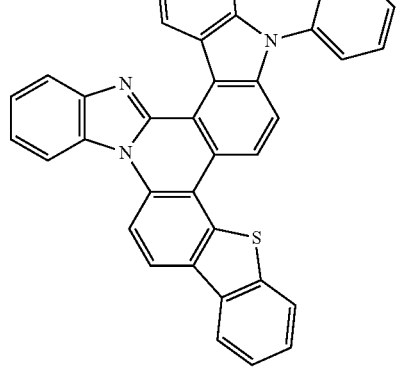

299
-continued
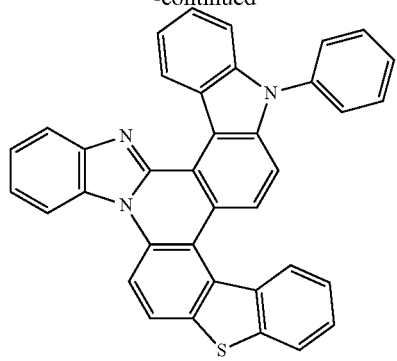
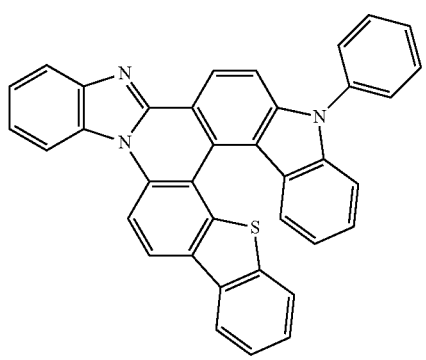
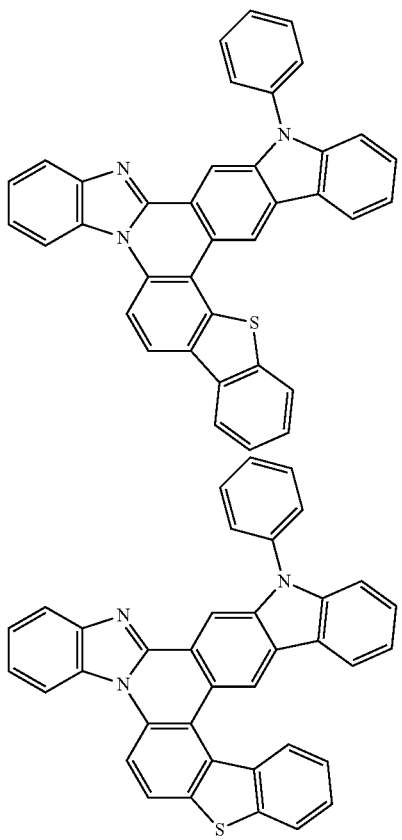
300
-continued
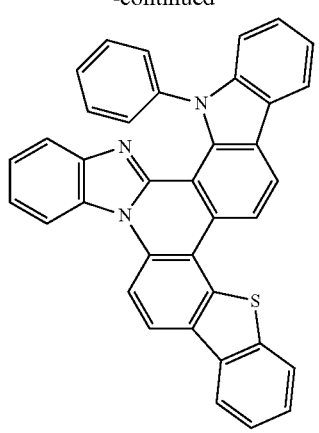
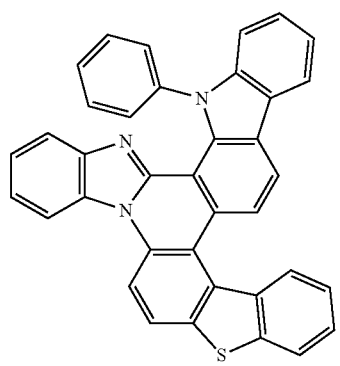
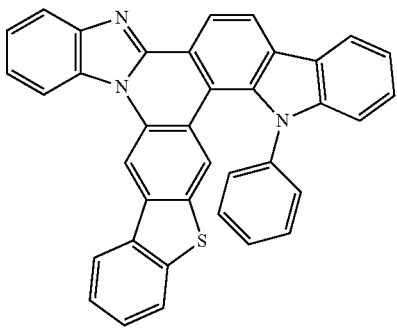
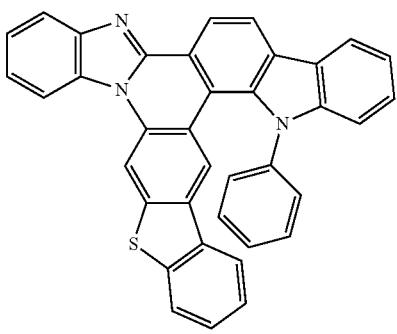

301
-continued
302
-continued
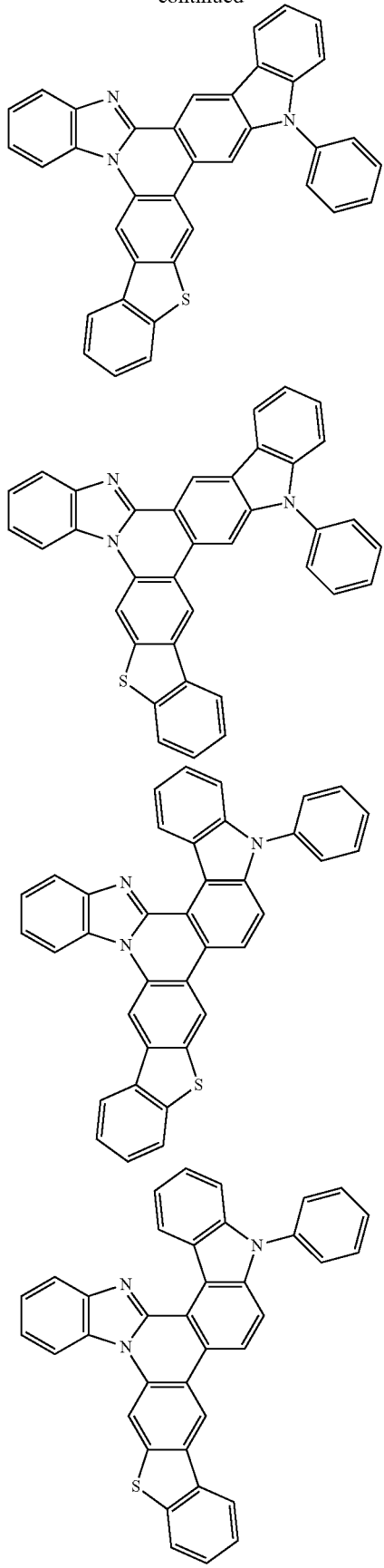
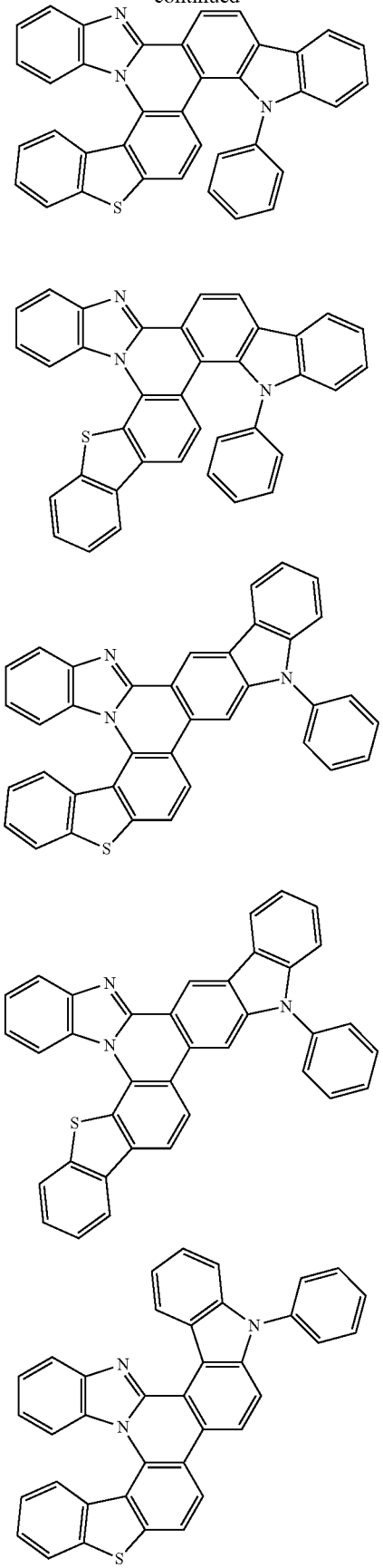

303
-continued
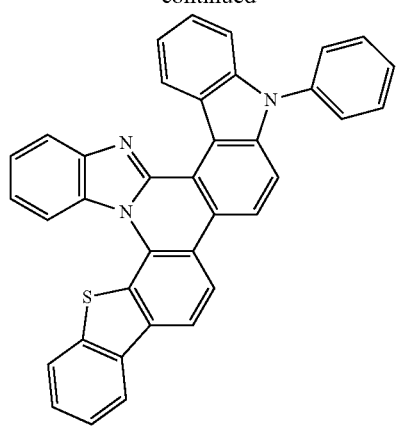
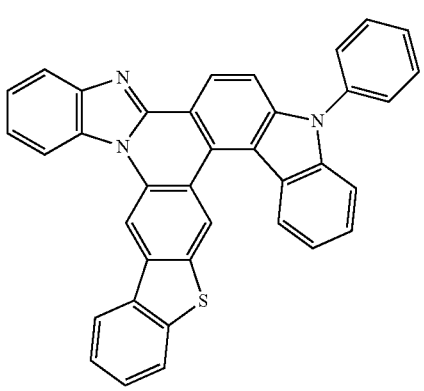
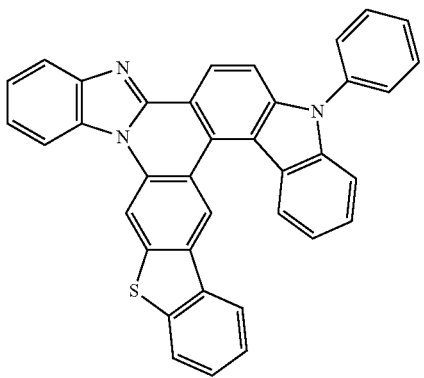
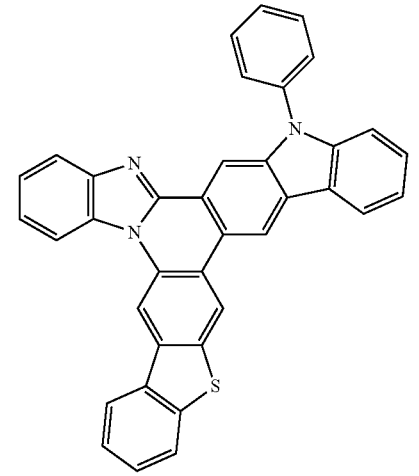
304
-continued
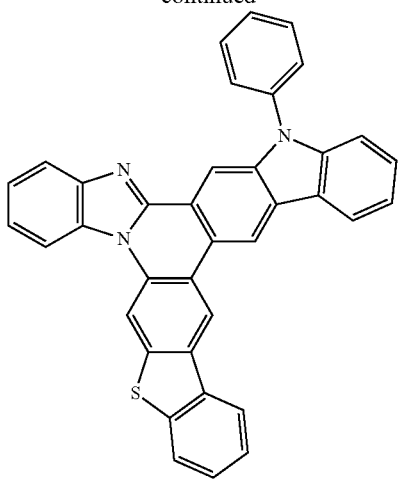
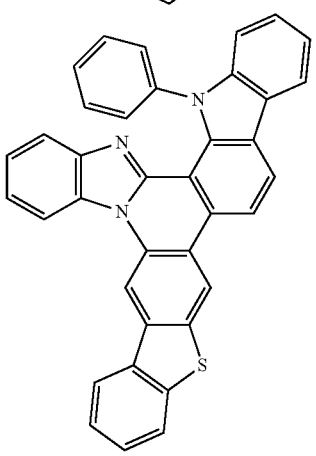
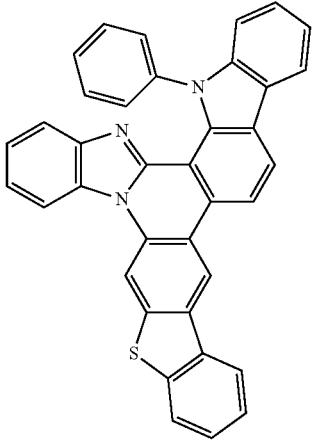
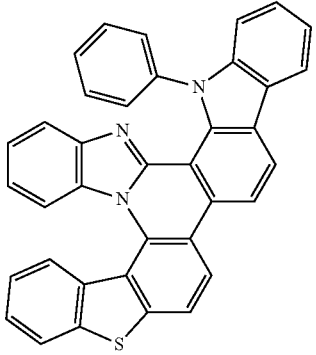

305
-continued
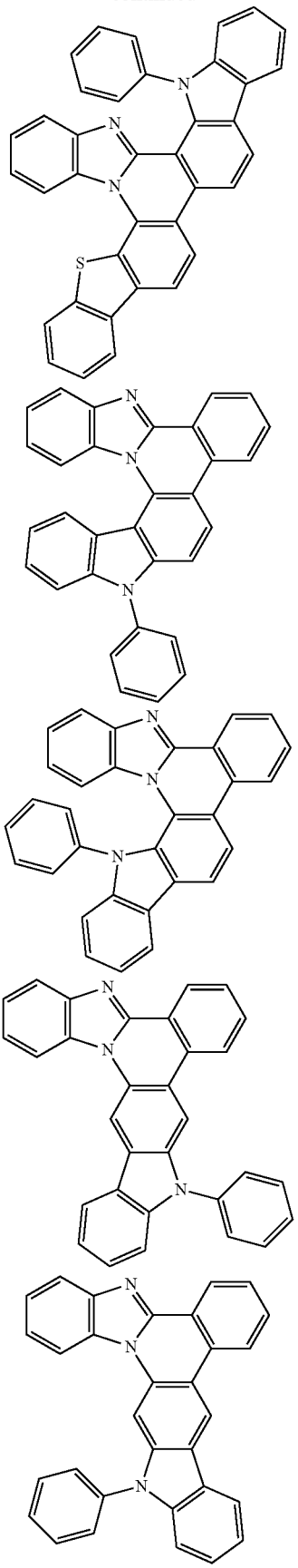
306
-continued
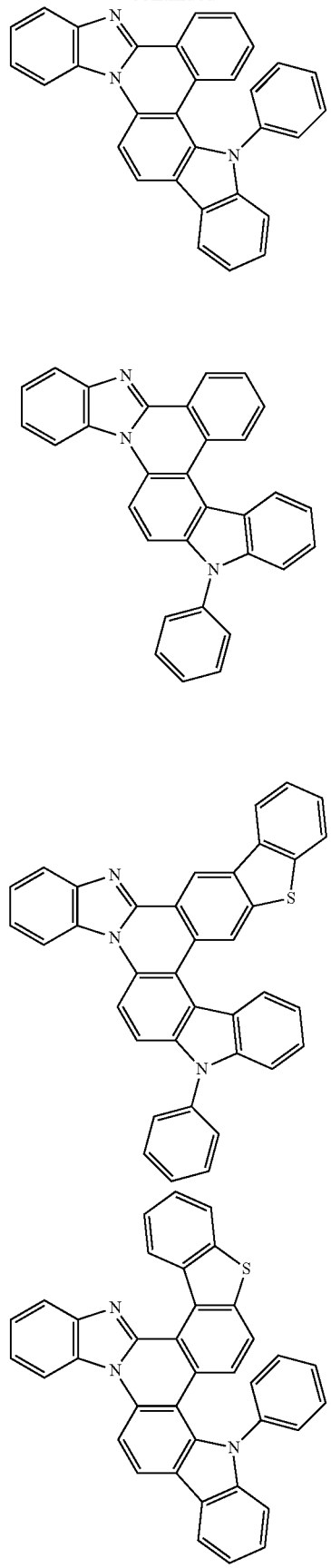

307
-continued
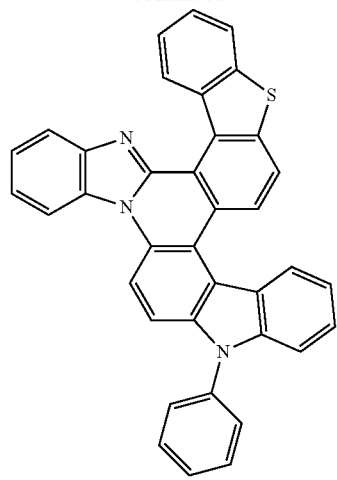
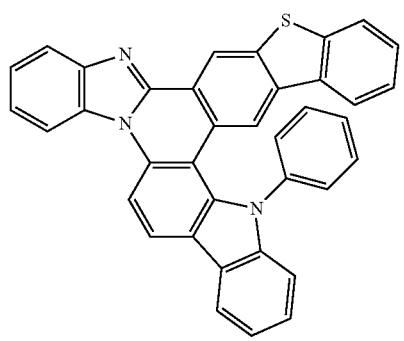
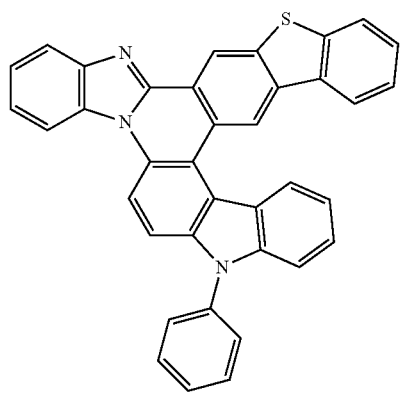
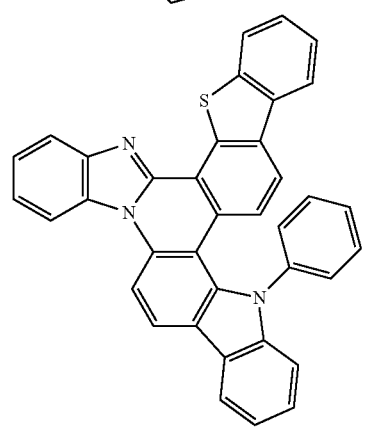
308
-continued
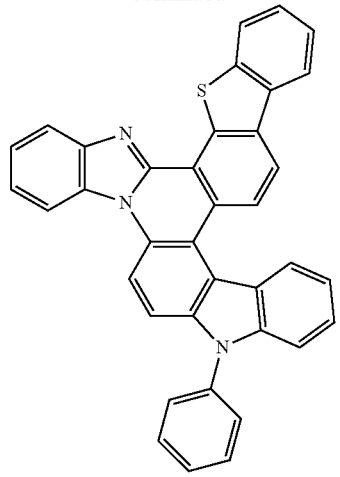
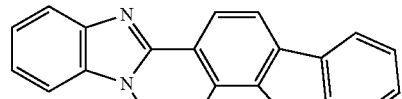
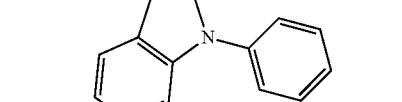
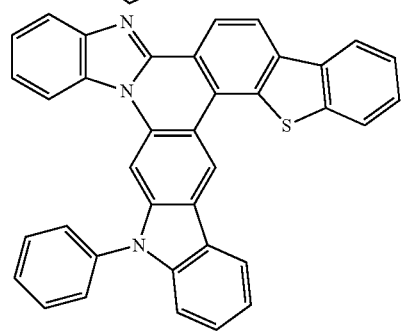
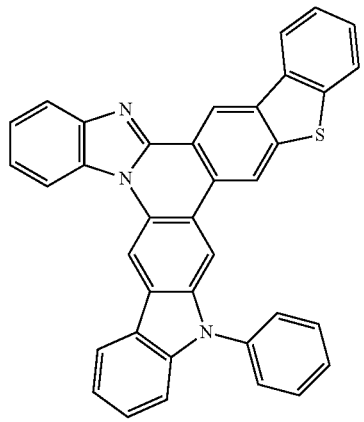

309
-continued
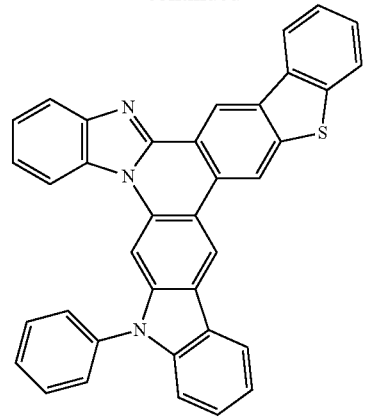
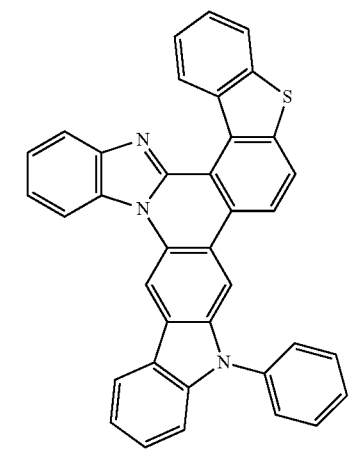
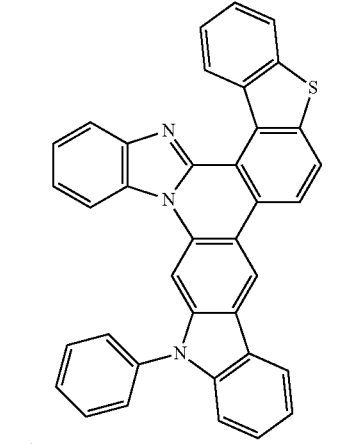
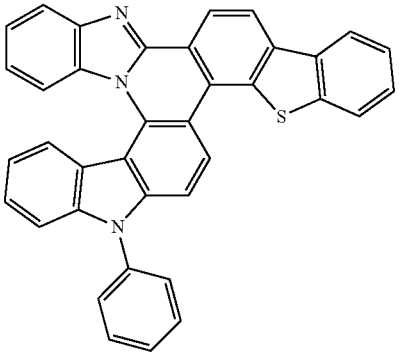
310
-continued
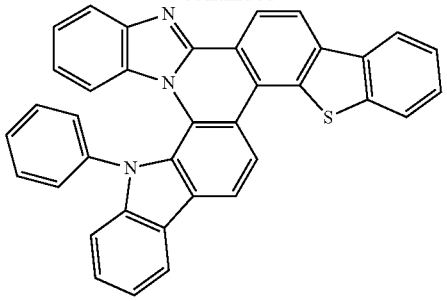
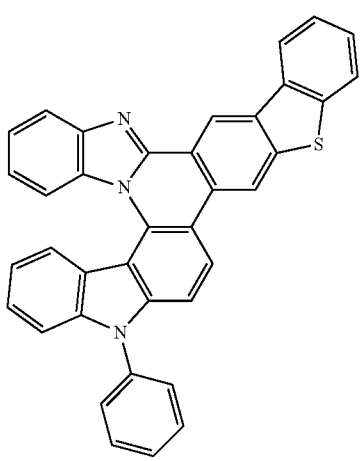
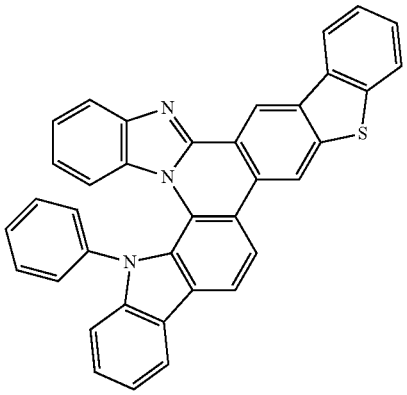
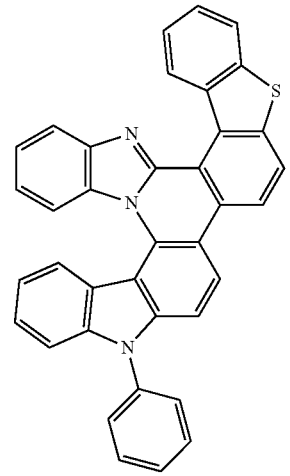

311
-continued
312
-continued
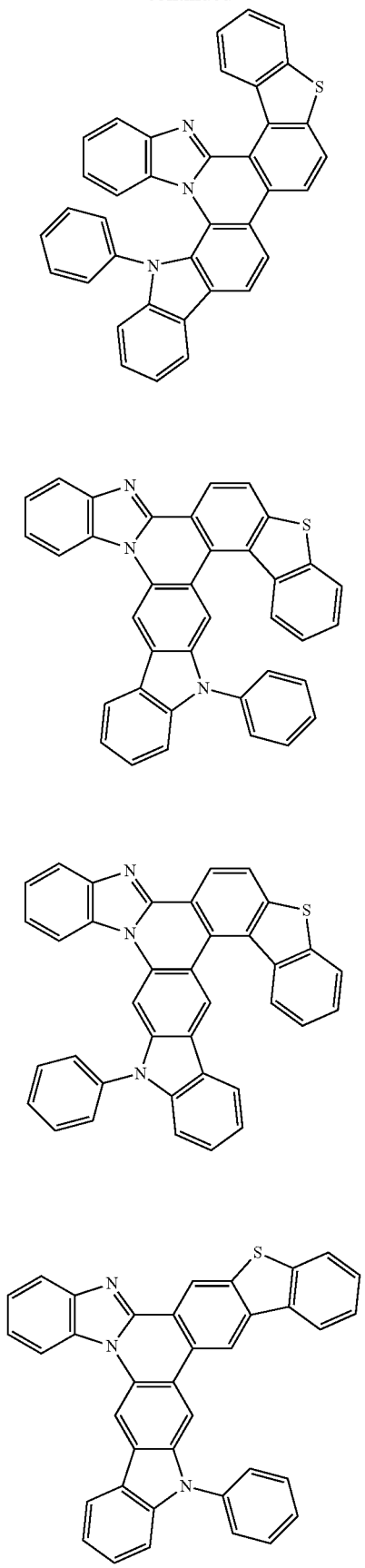
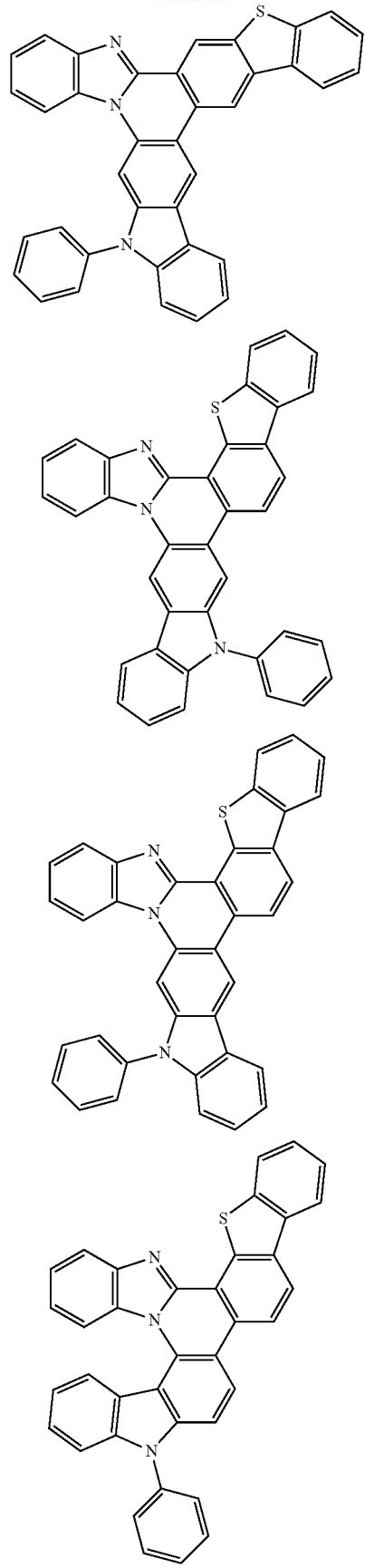

313
-continued
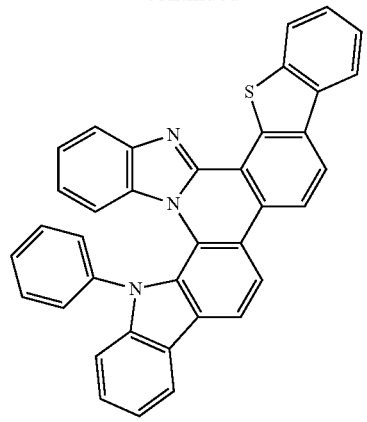
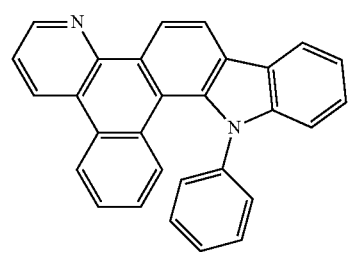
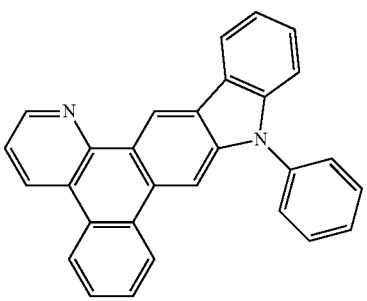
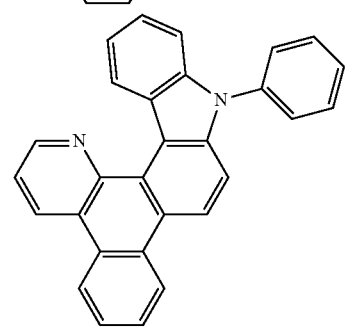
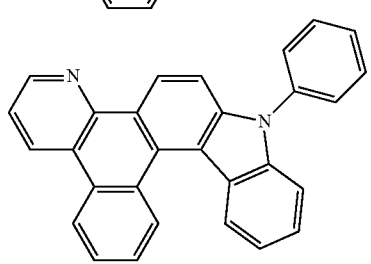
314
-continued
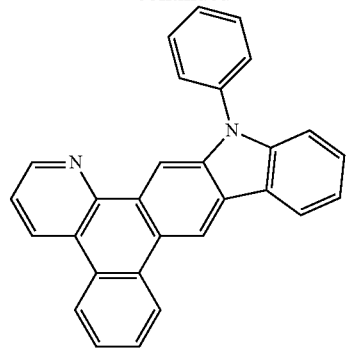
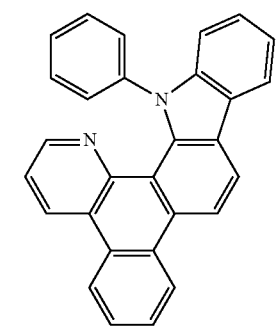
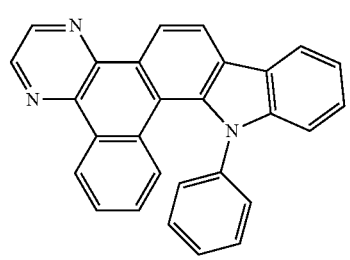
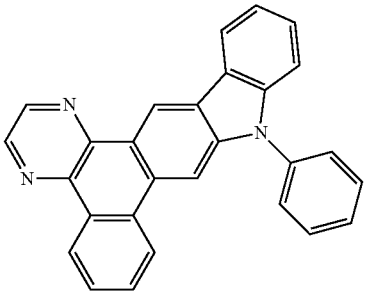
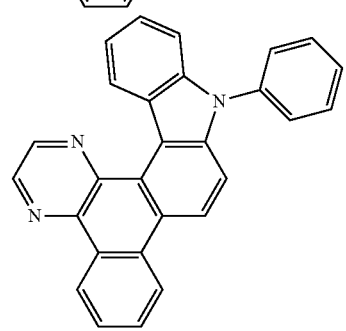

315
-continued
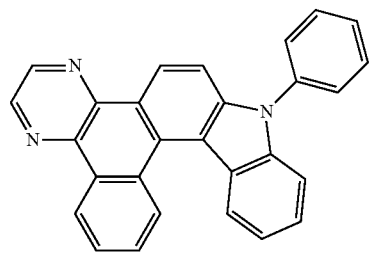
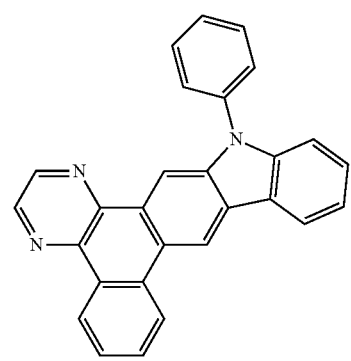
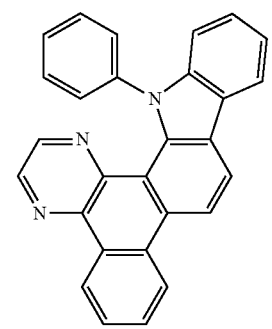
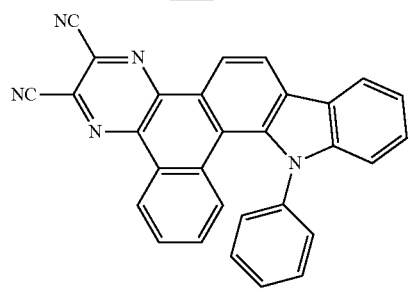
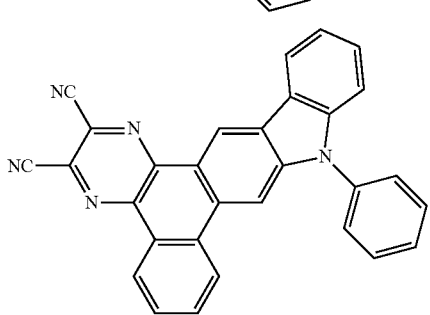
316
-continued
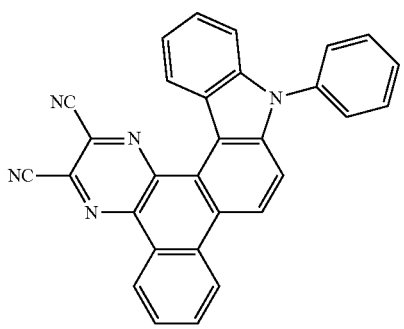
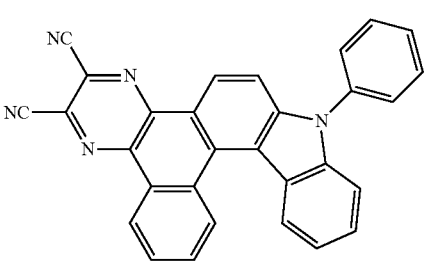
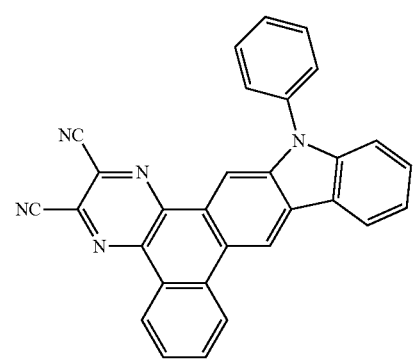
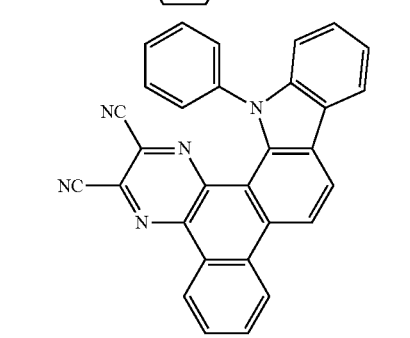
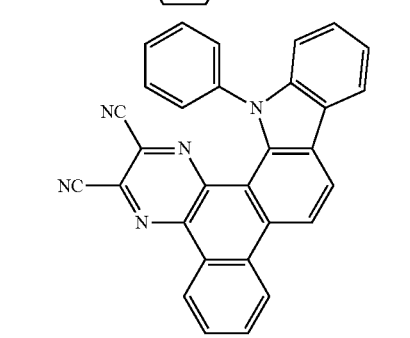

317
-continued
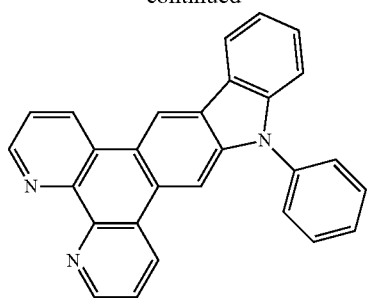
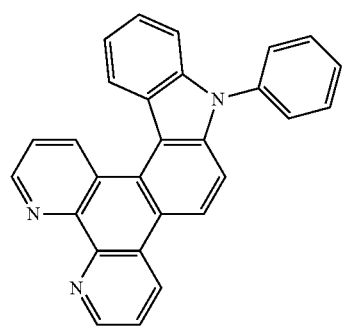
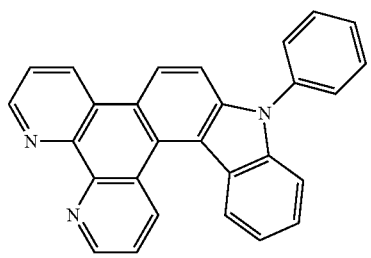
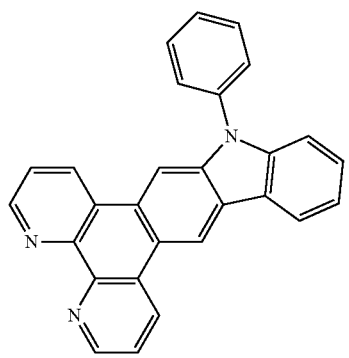
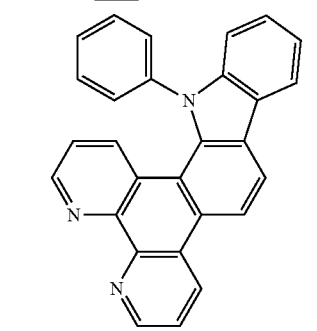
318
-continued
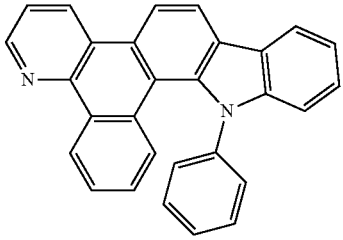
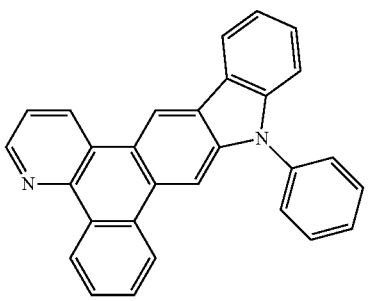
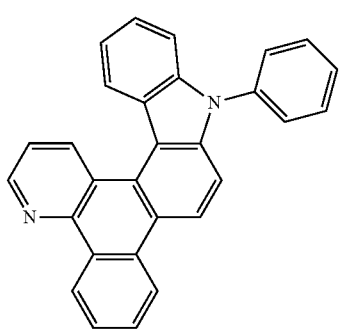
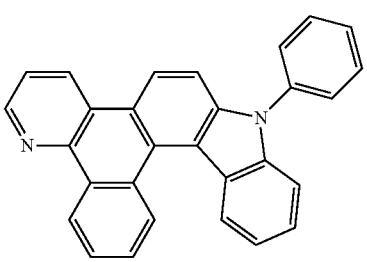
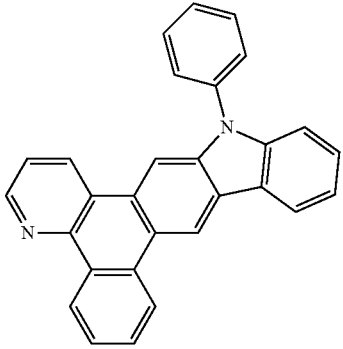

319
-continued
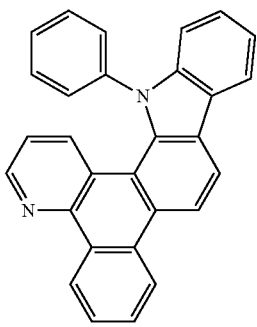
320
-continued
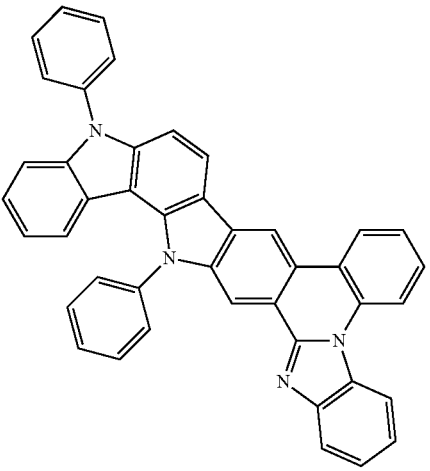
3. The compound of claim 2, wherein the compound is represented by one of the following structures:
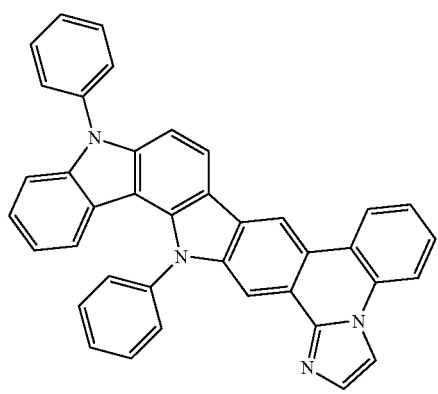
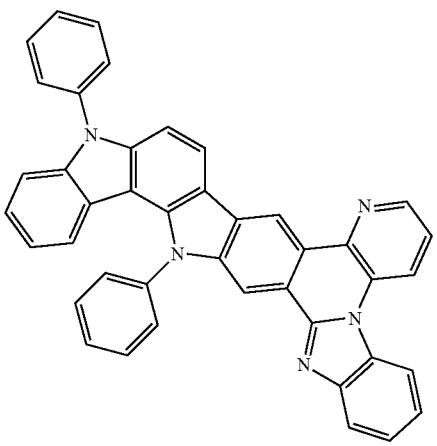
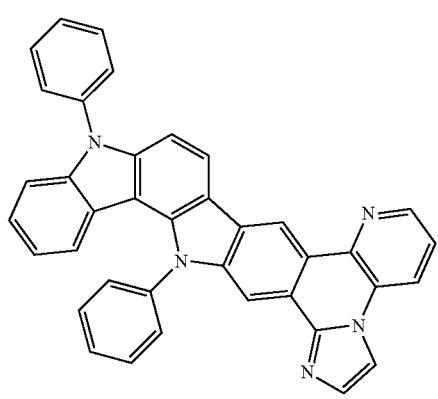
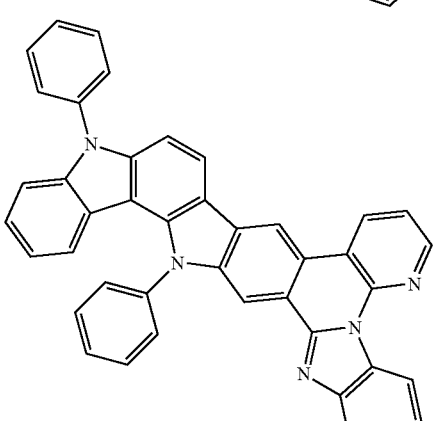
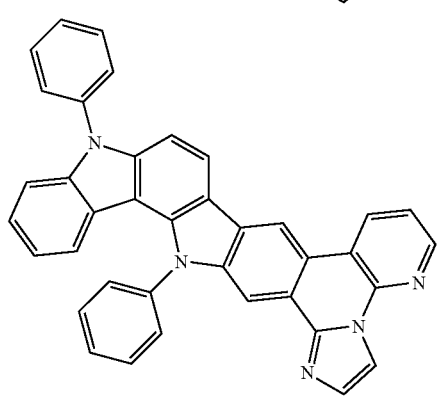
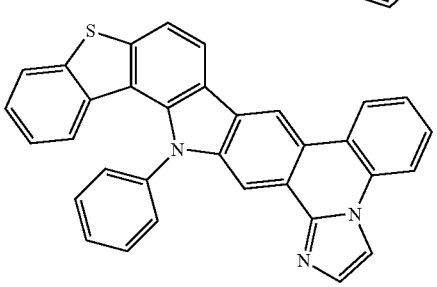

321
-continued
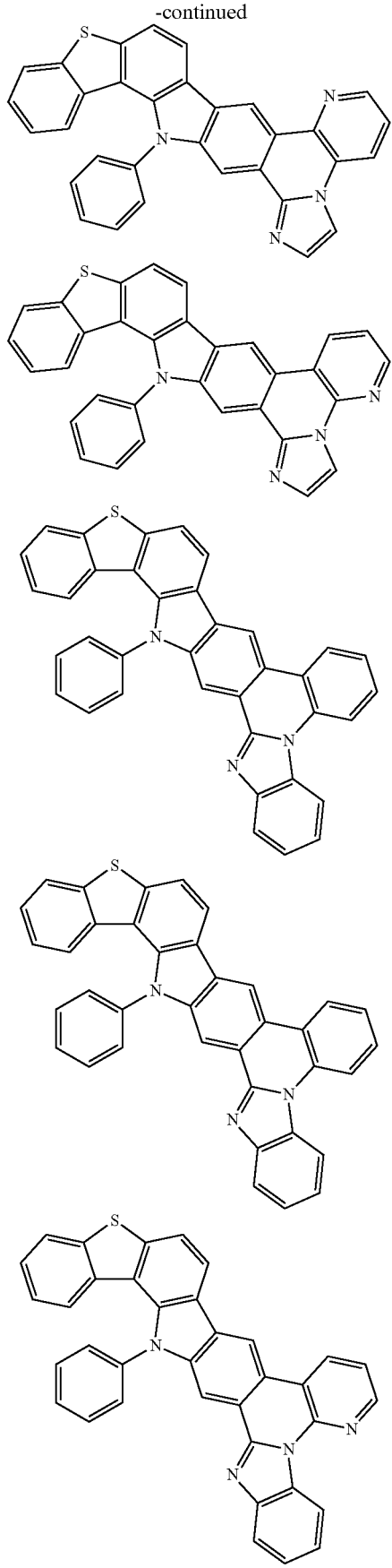
322
-continued
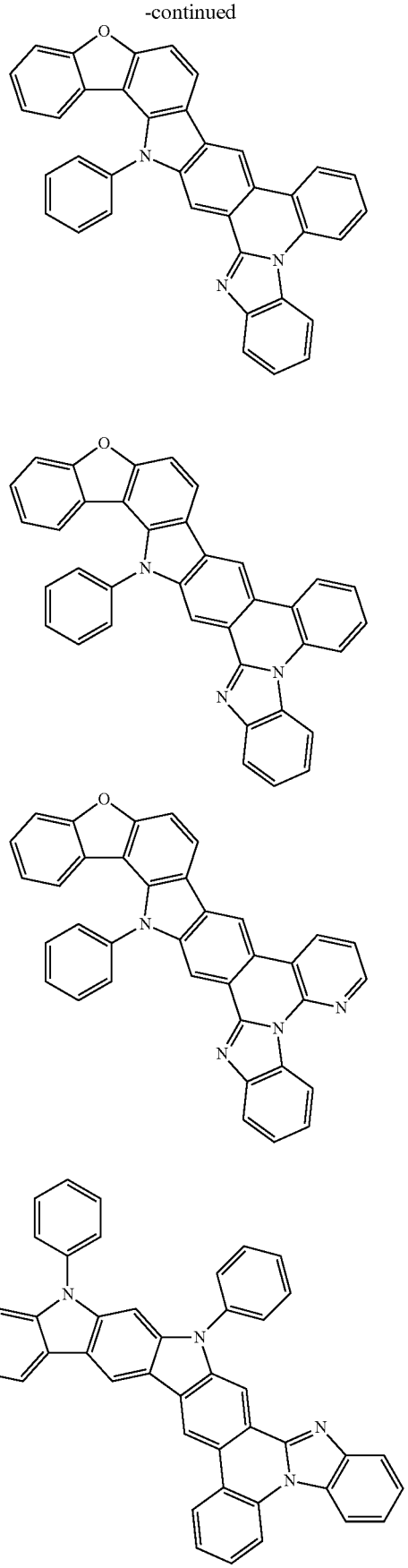

323
-continued
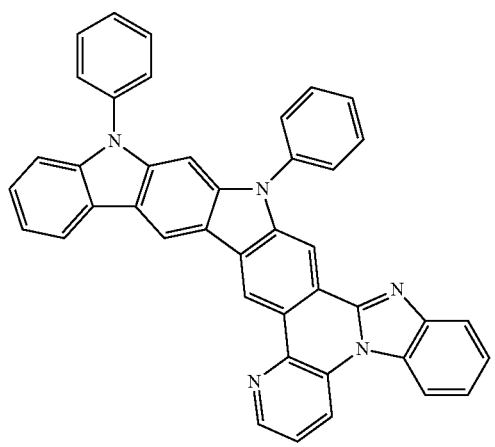
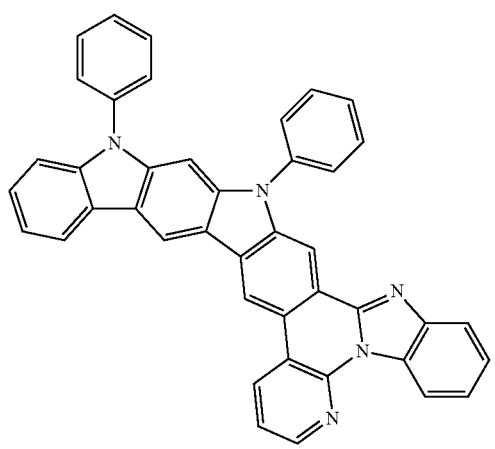
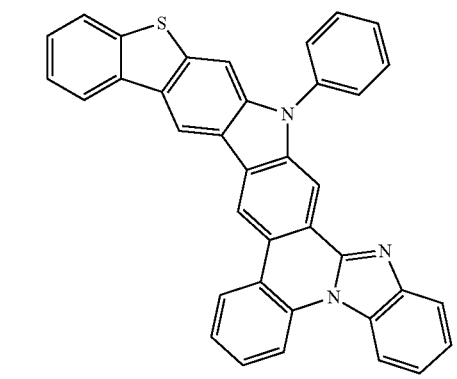
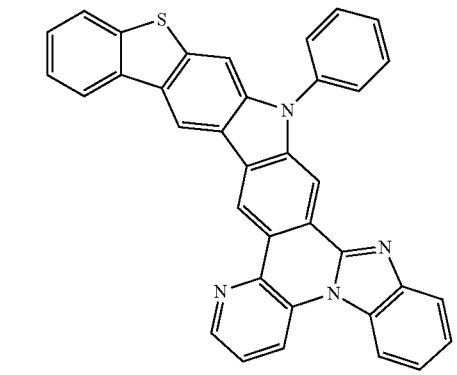
324
-continued
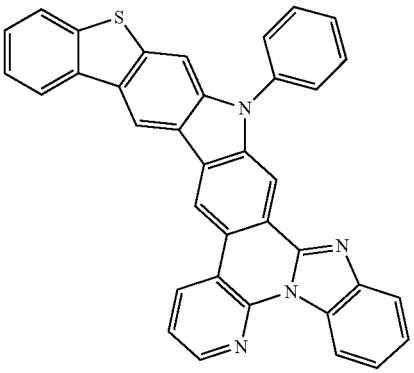
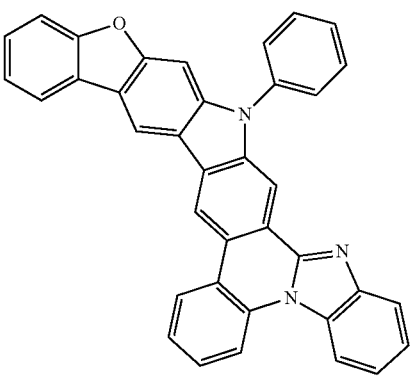
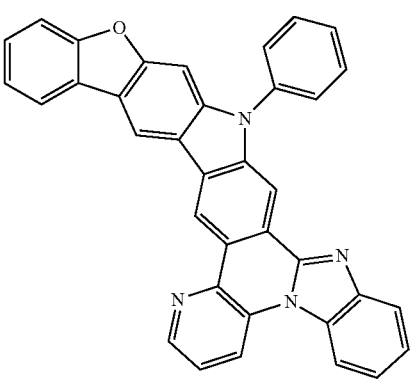
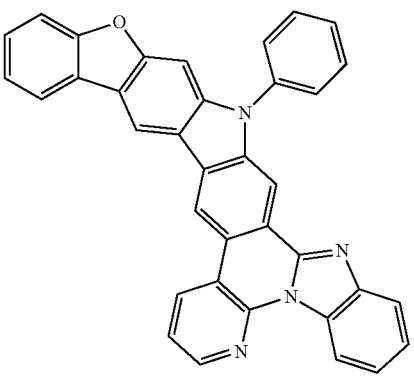

-continued
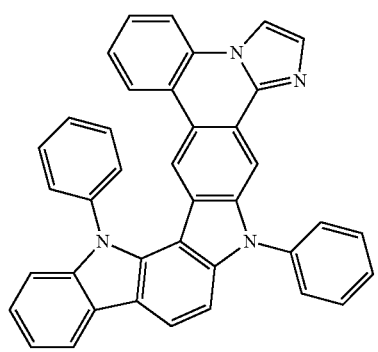
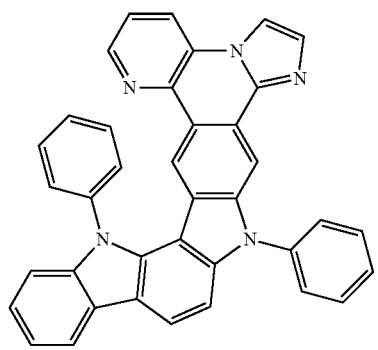
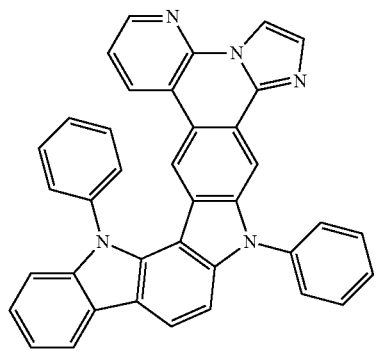
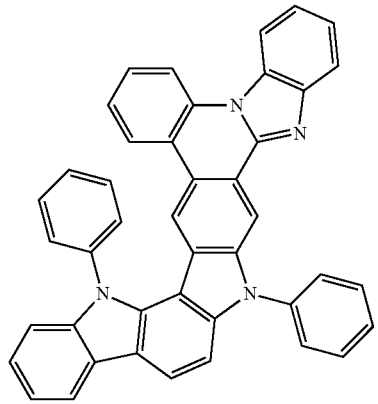
-continued
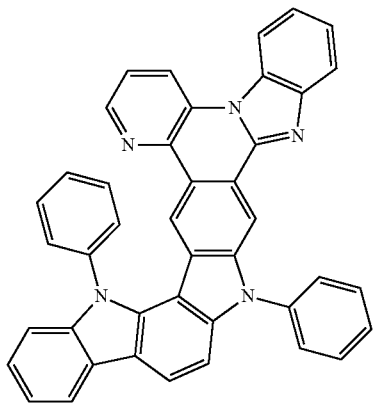
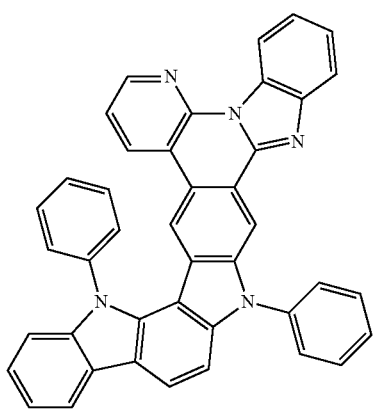
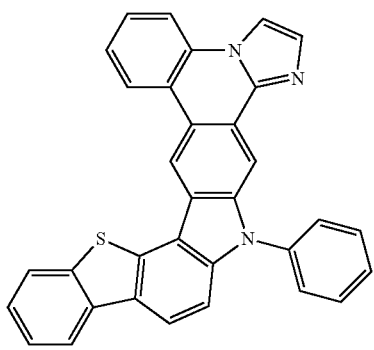
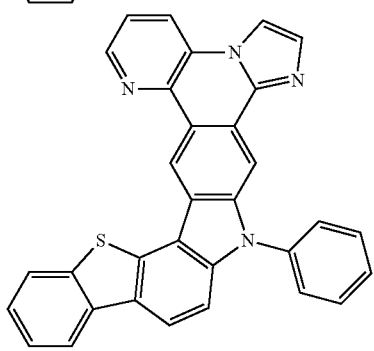

327
-continued
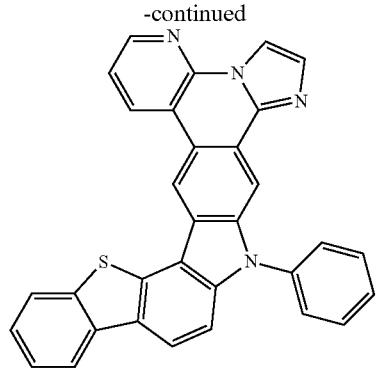
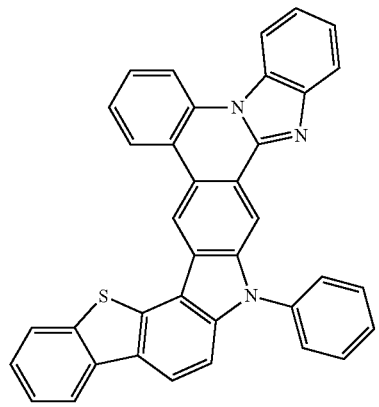
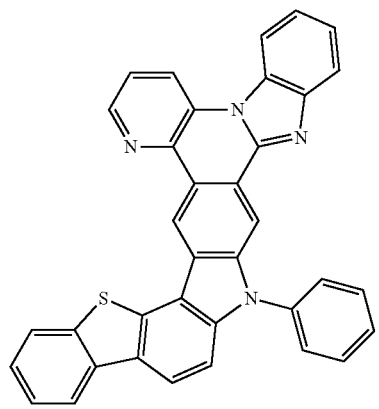
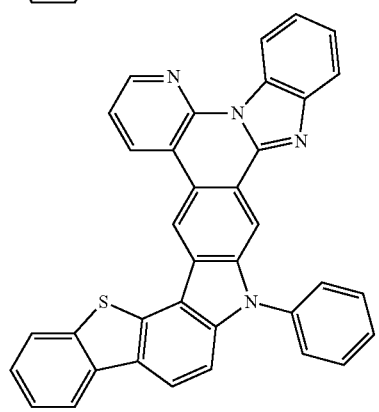
328
-continued
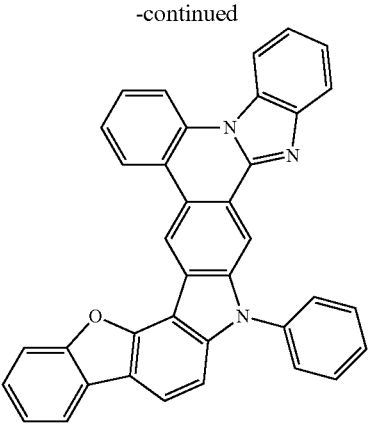
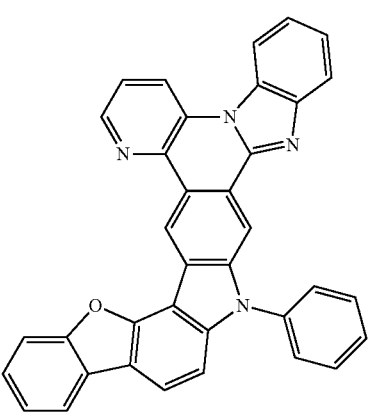
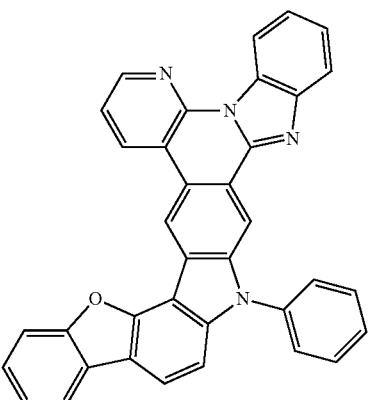
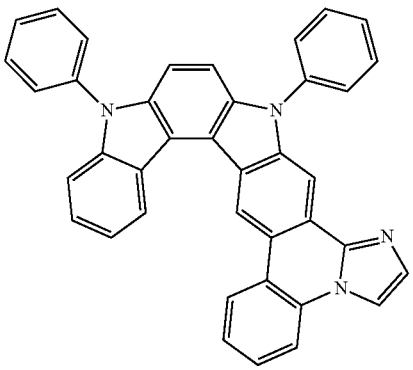

329
-continued
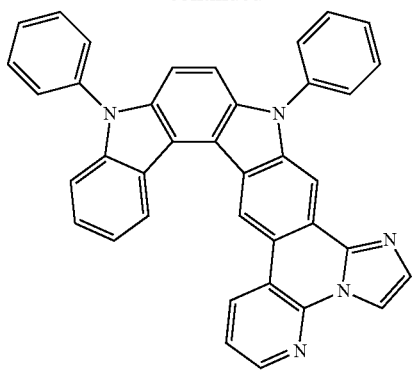
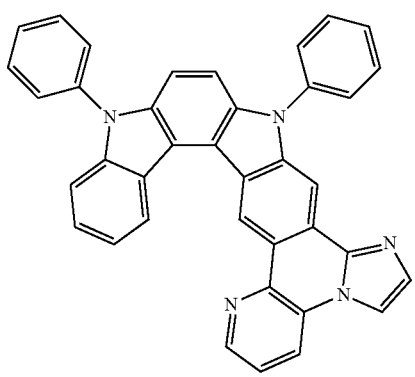
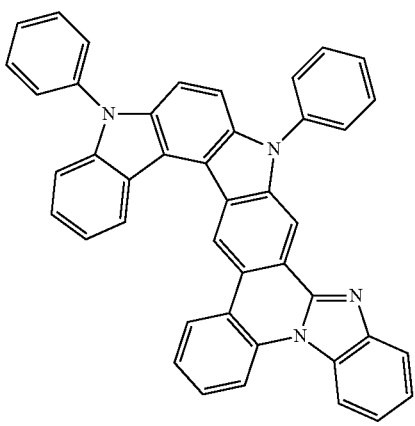
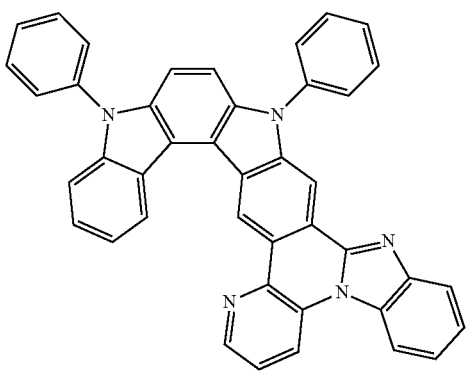
330
-continued
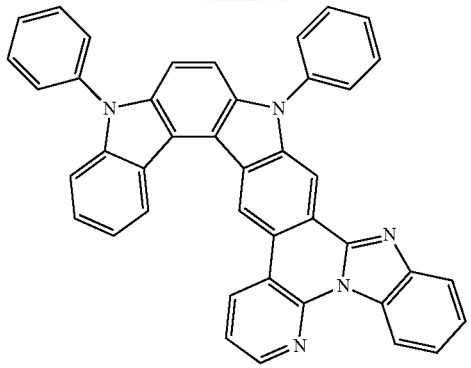
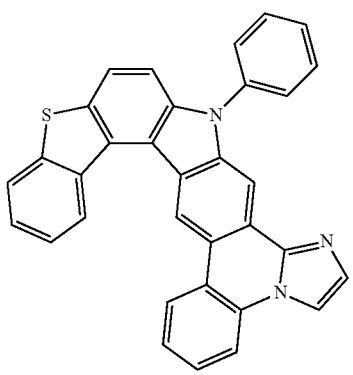
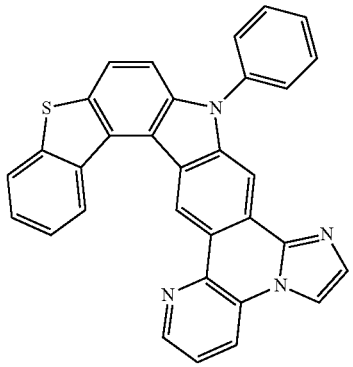
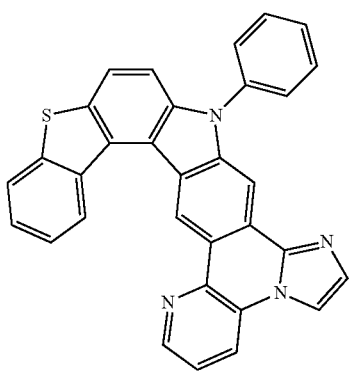

331
-continued
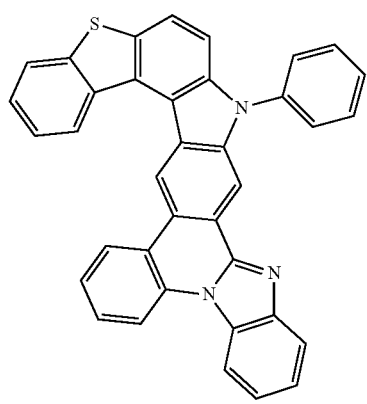
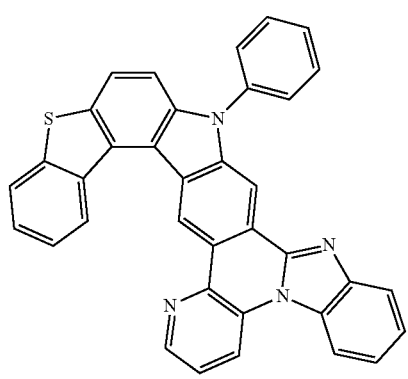
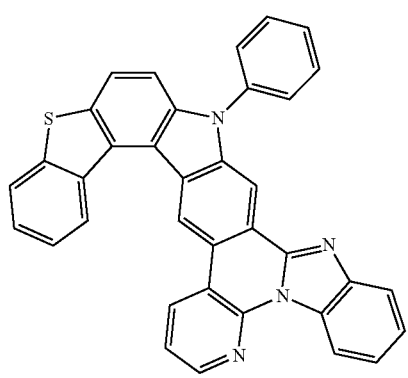
332
-continued
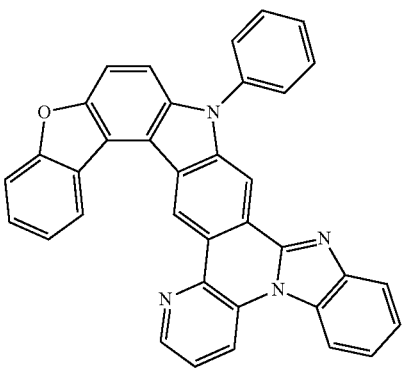
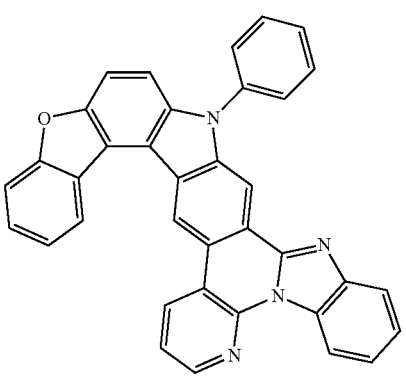
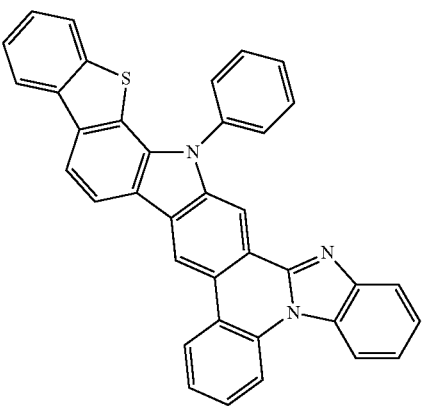
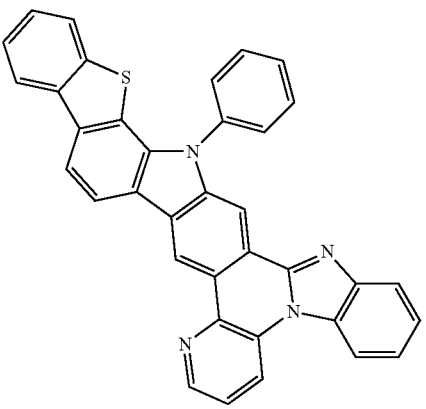

-continued
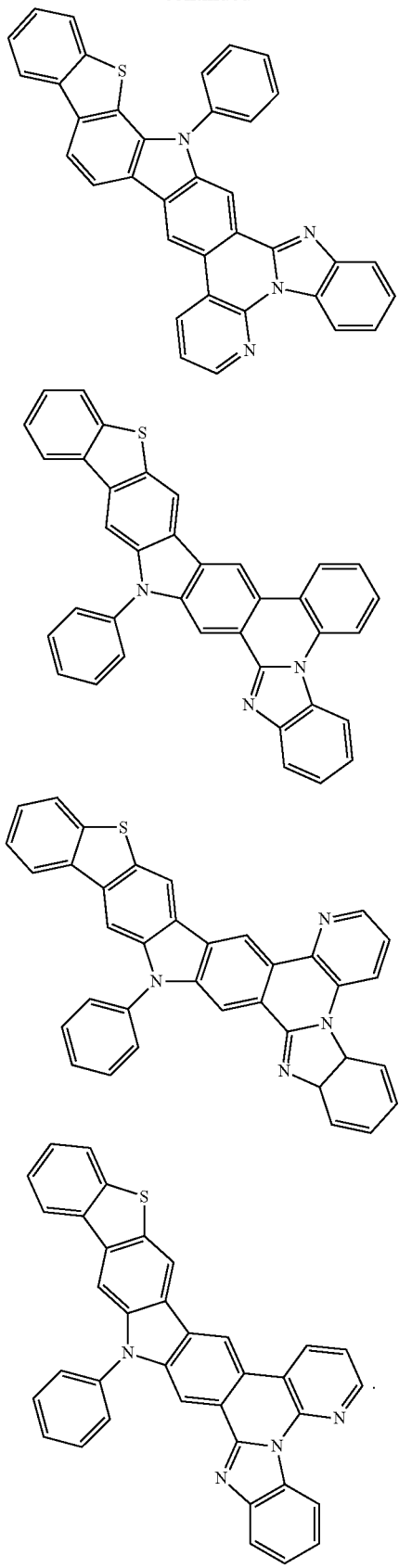
4. The compound of claim 2, wherein the compound is represented by one of the following structures:
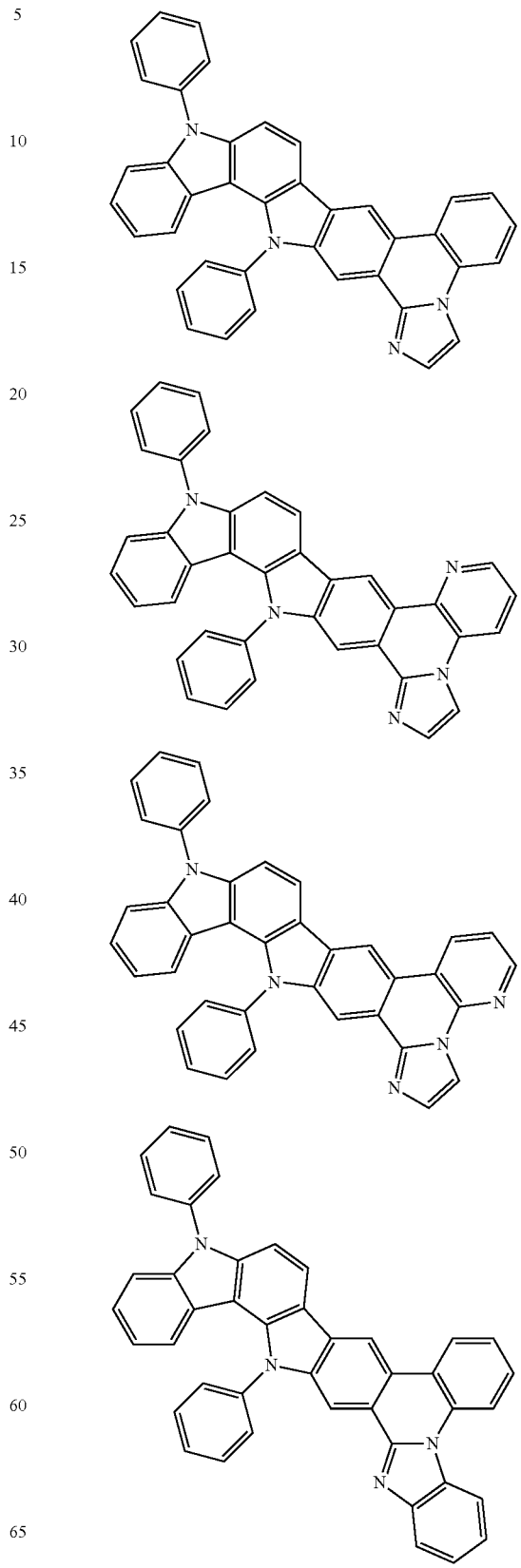

335
-continued
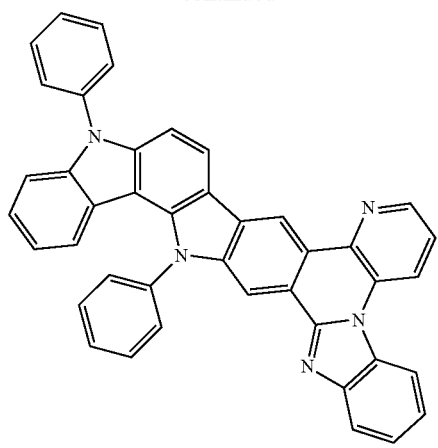
336
-continued
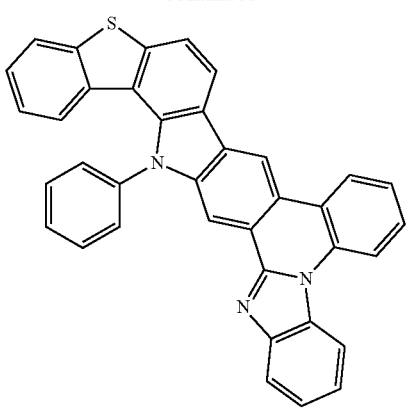
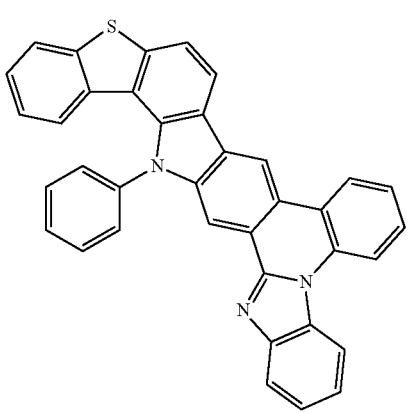
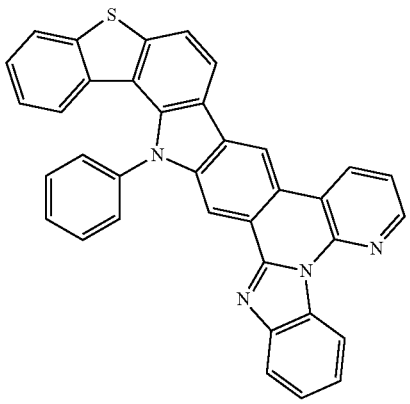
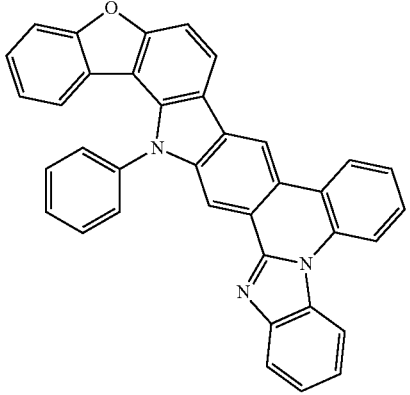

337
-continued
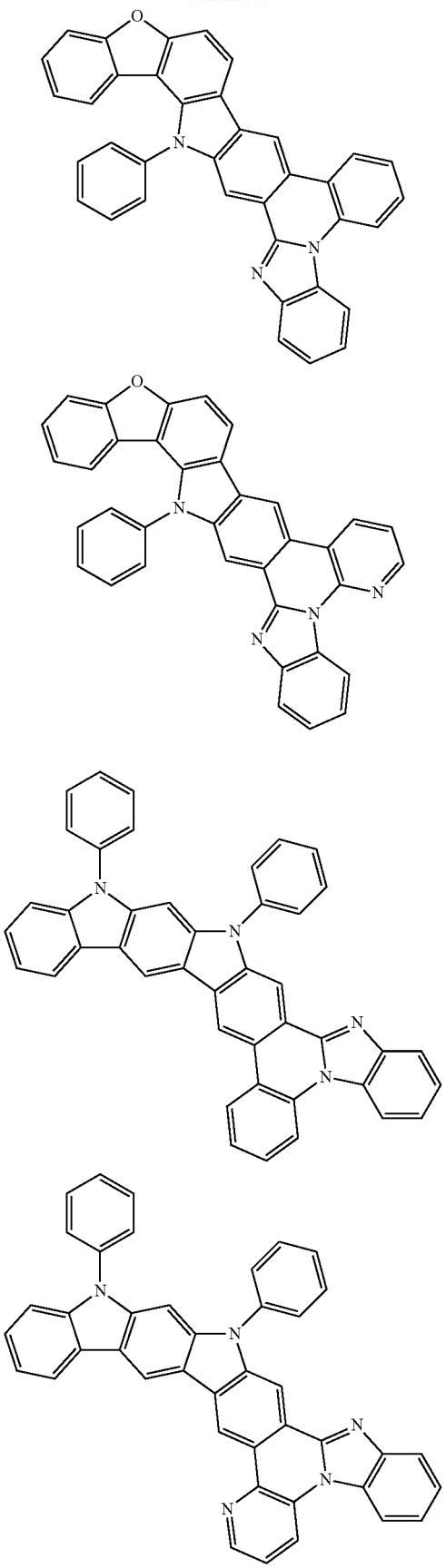
338
-continued
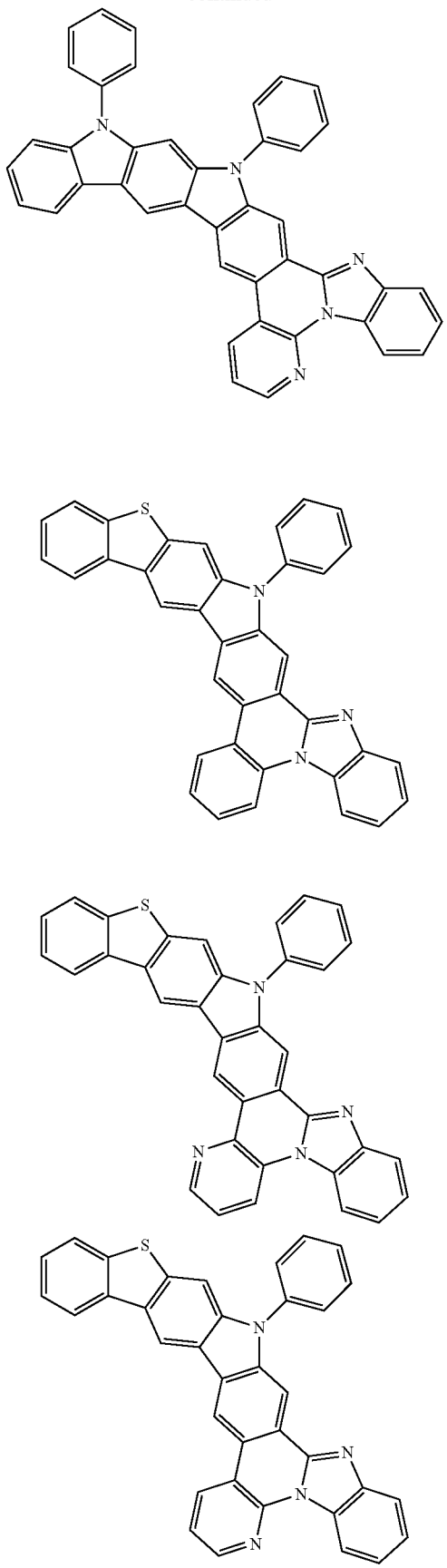

339
-continued
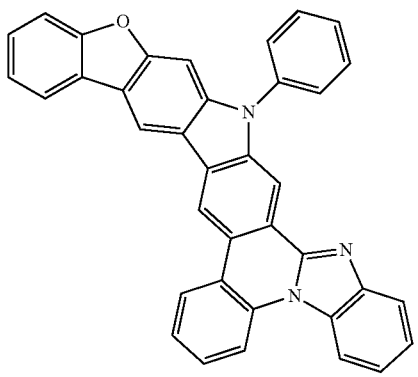
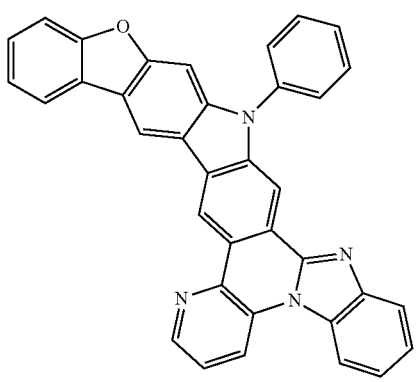
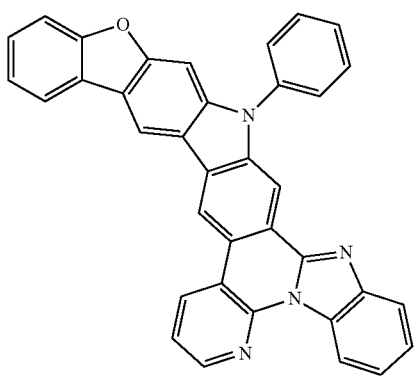
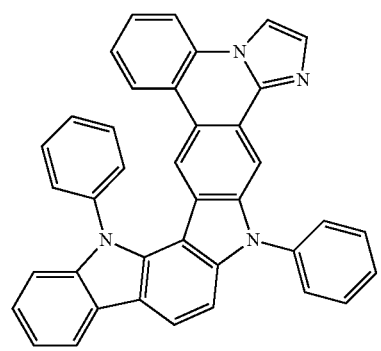
340
-continued
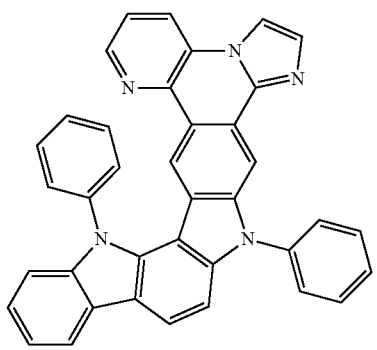
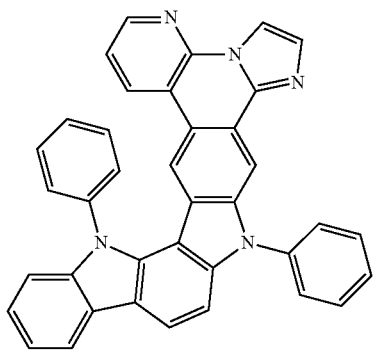
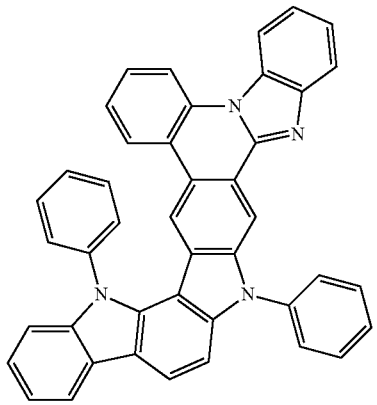
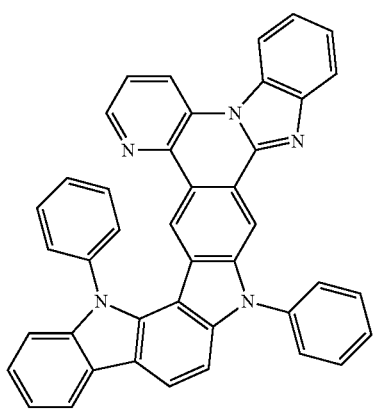

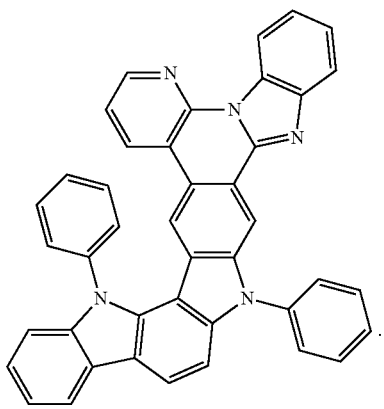
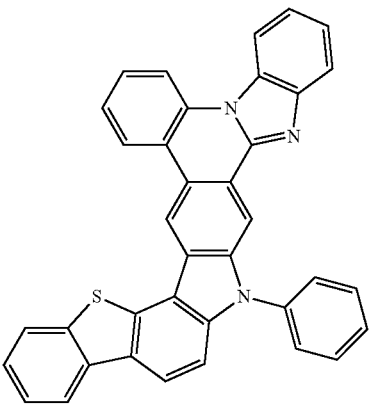
5. The compound of claim 2, wherein the compound is represented by one of the following structures:
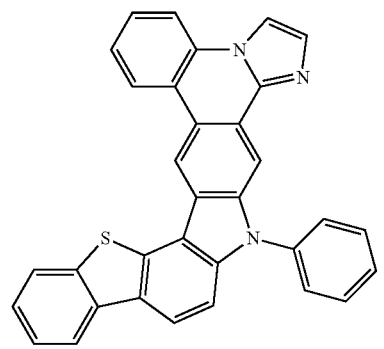
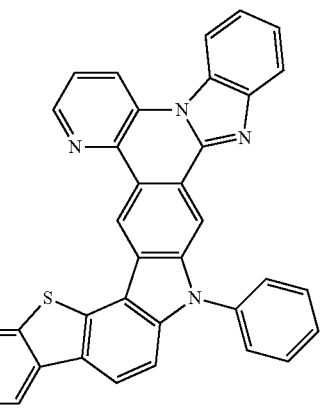
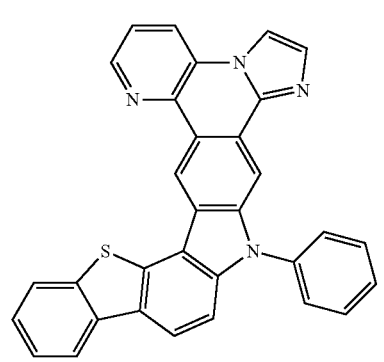
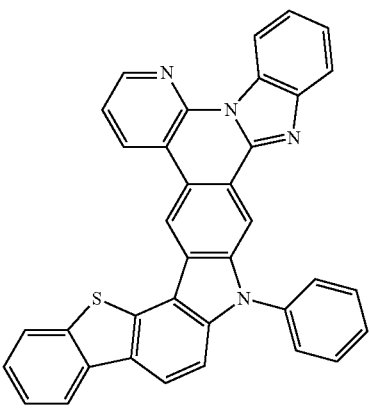
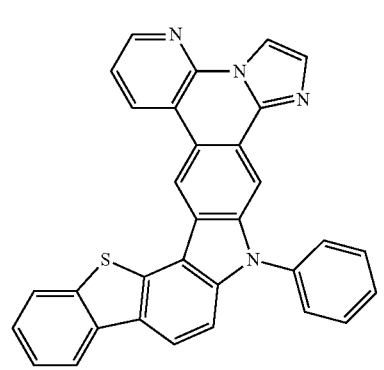
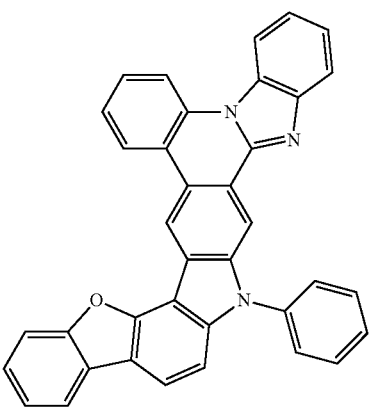

343
-continued
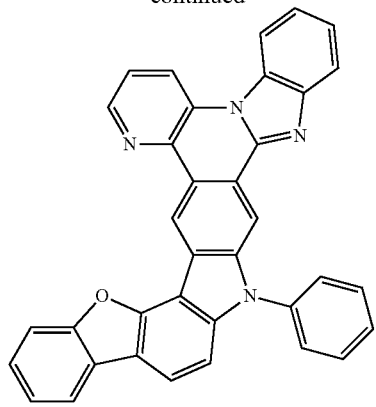
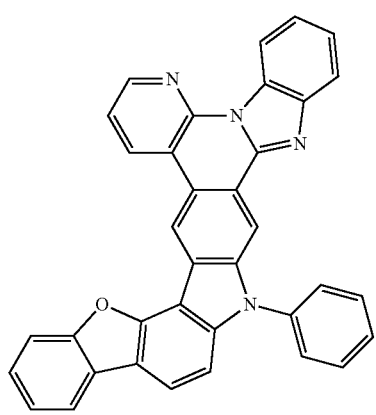
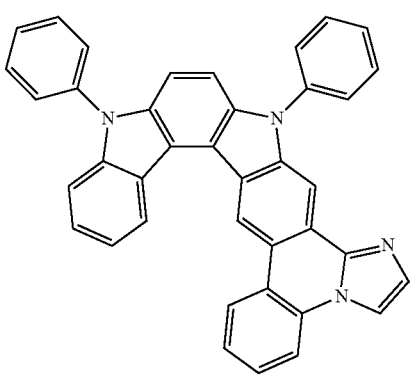
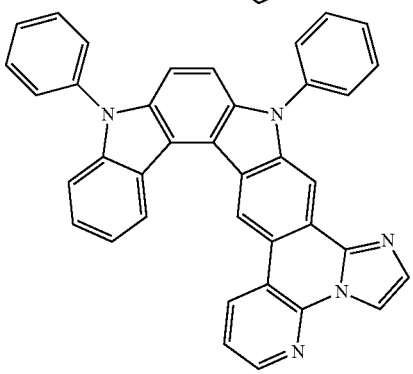
344
-continued
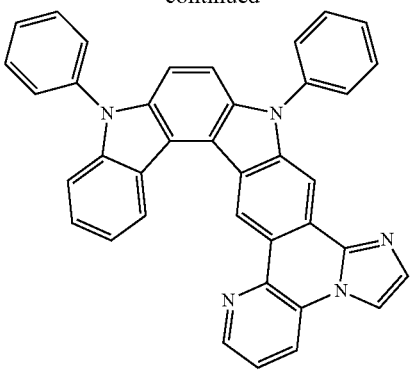
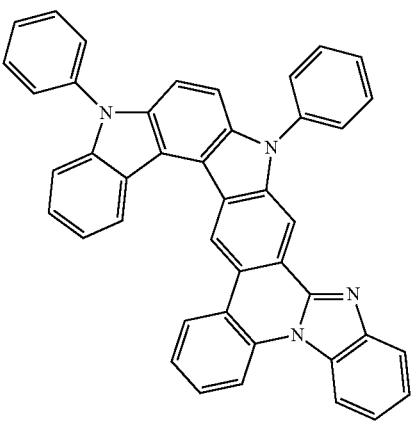
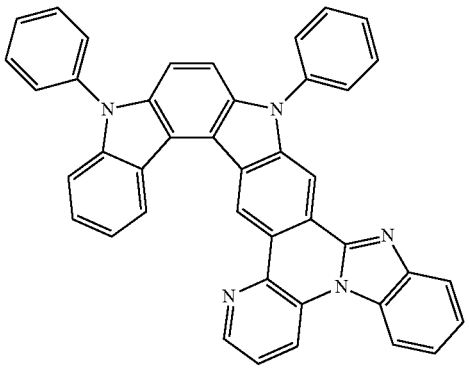
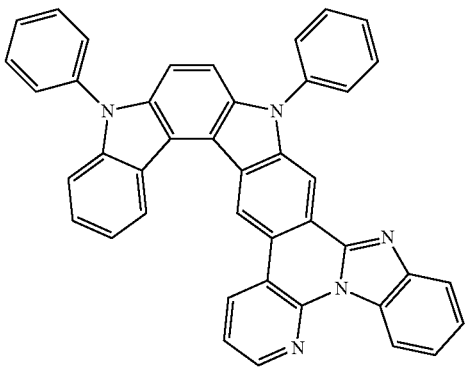

345
-continued
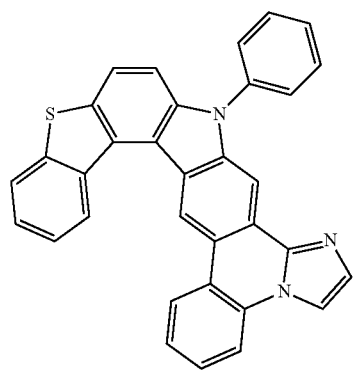
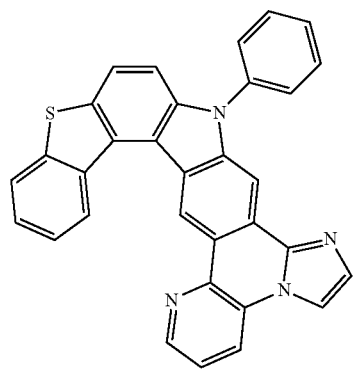
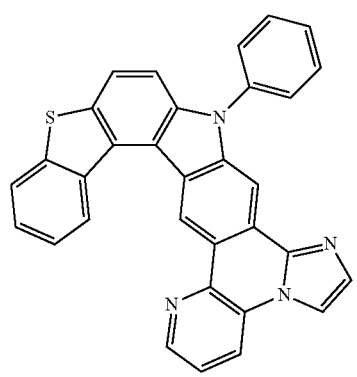
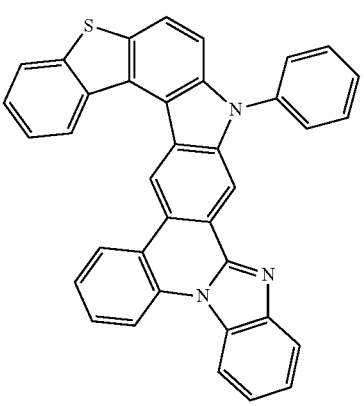
346
-continued
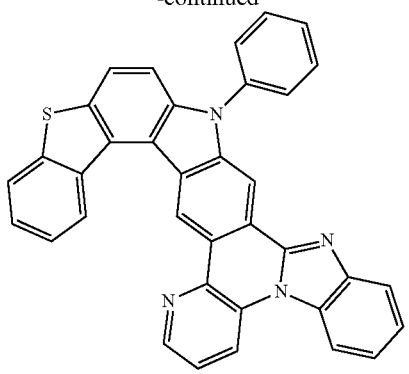
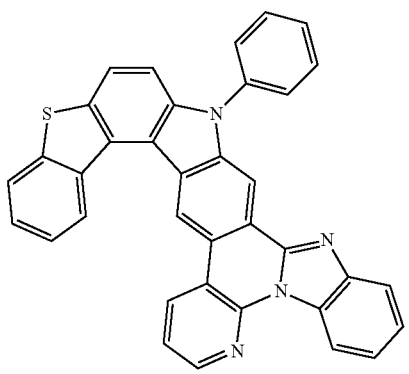
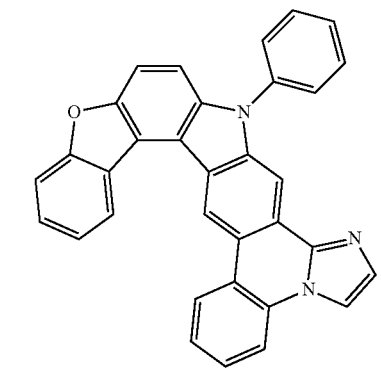
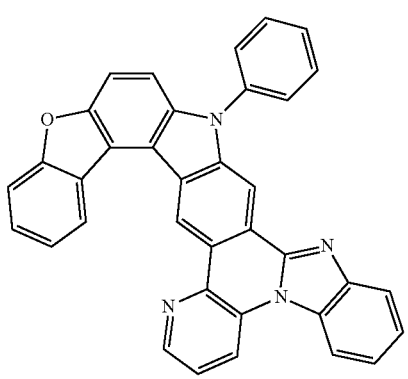

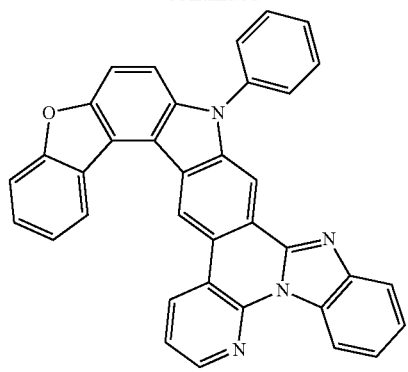
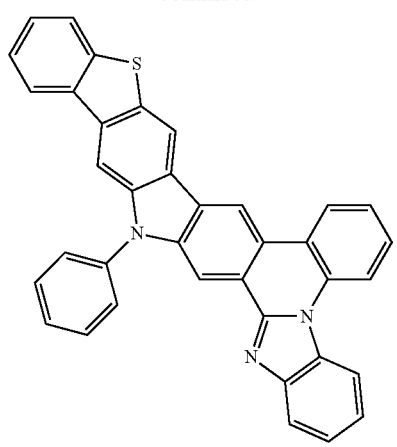
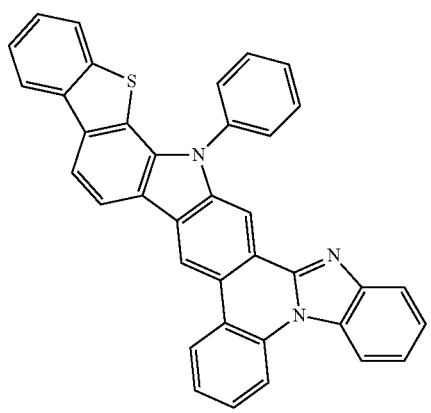
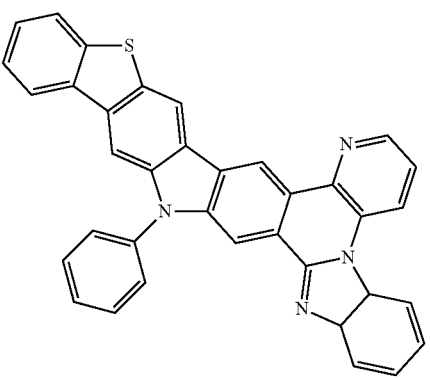
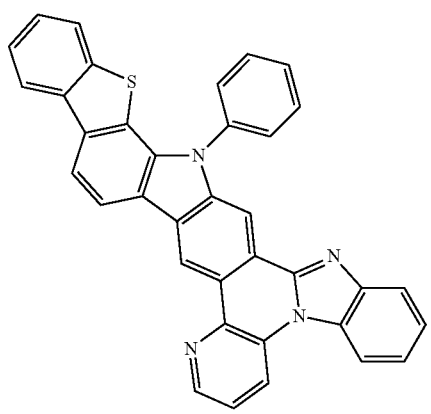
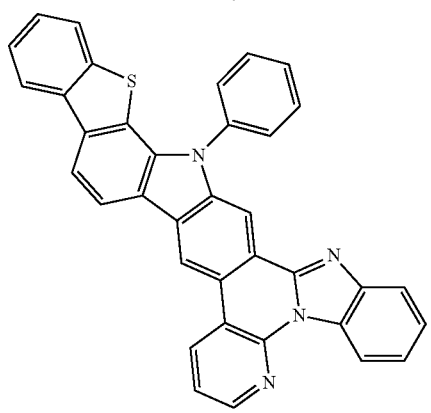
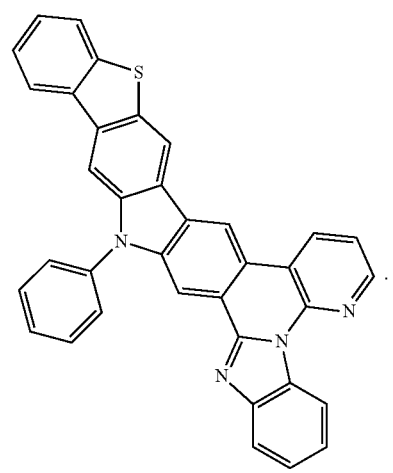

6. The compound of claim 2, wherein the compound is represented by one of the following structures:
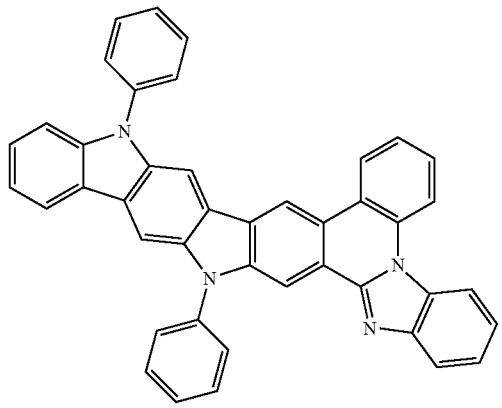
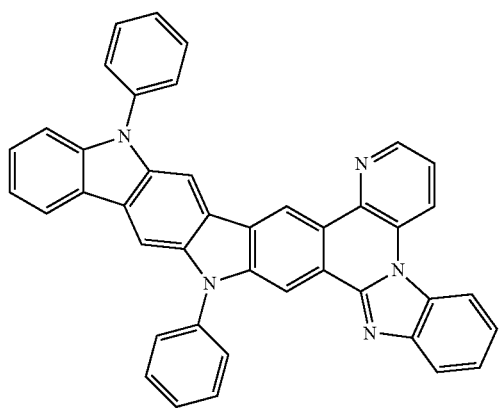
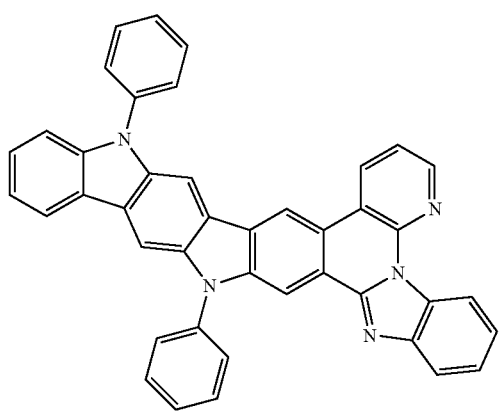
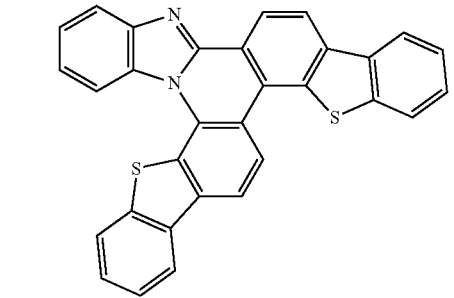
-continued
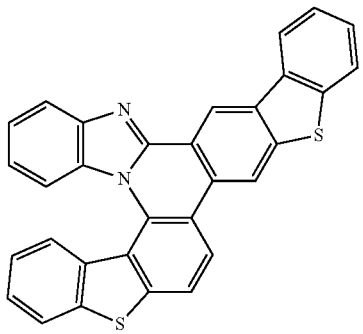
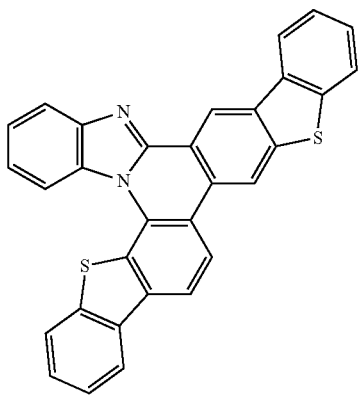
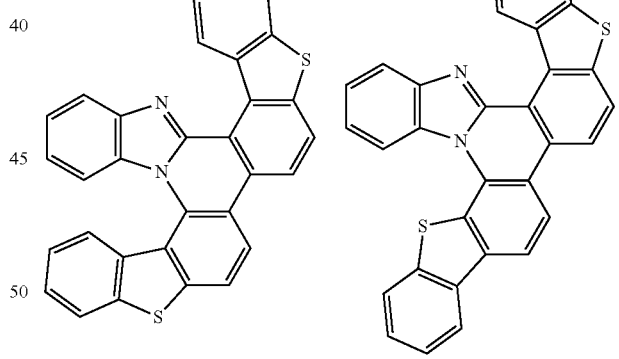
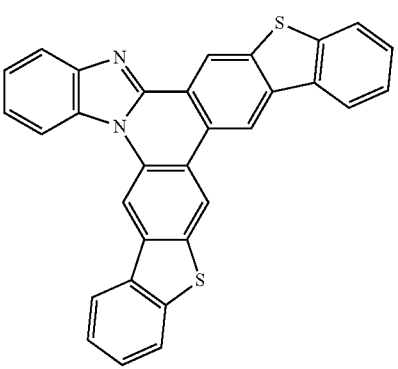

351
-continued
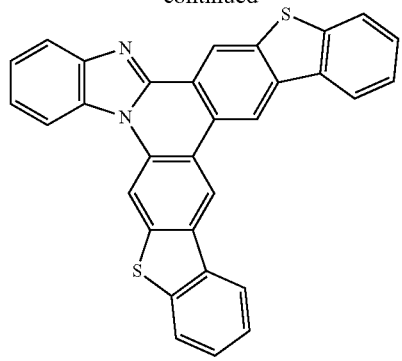
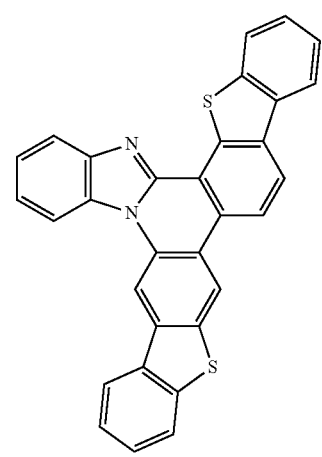
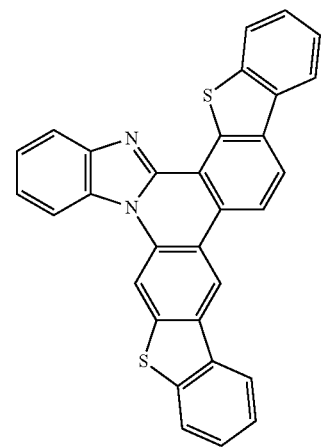
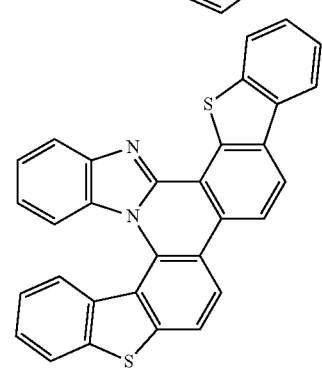
352
-continued
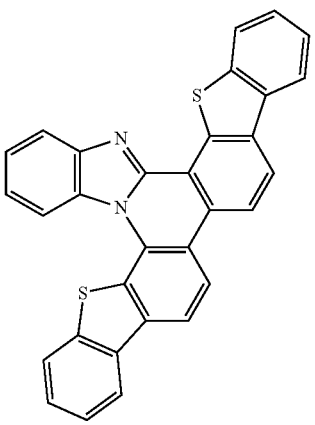
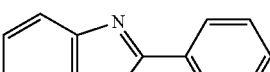
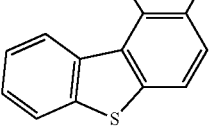
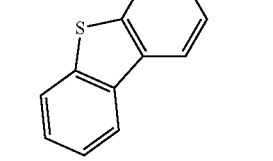
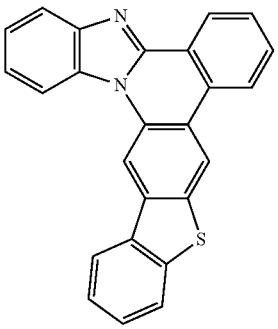
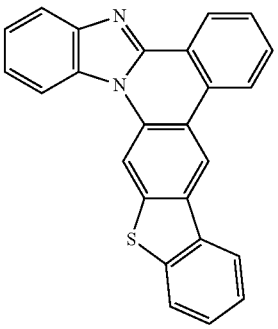

353
-continued
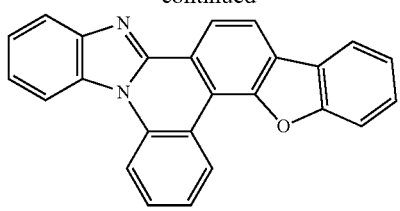
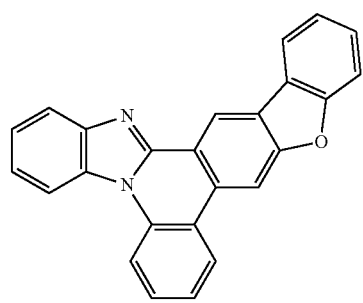
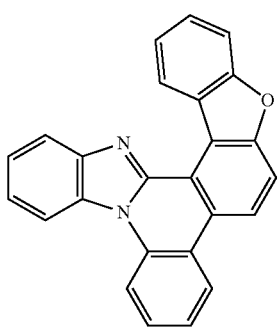
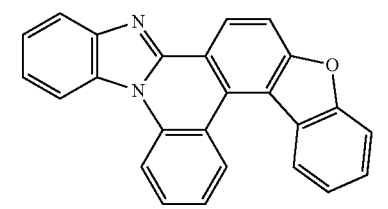
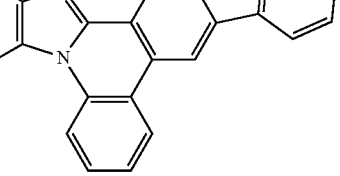
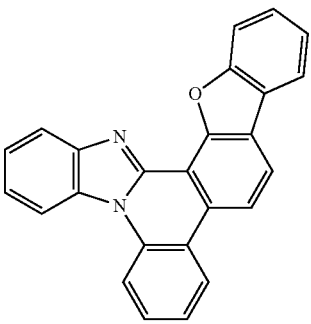
354
-continued
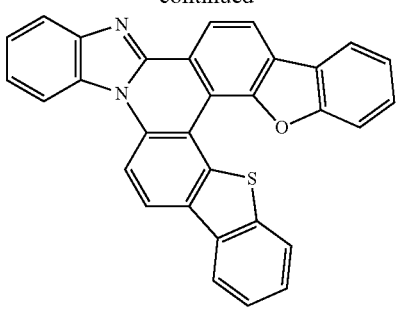
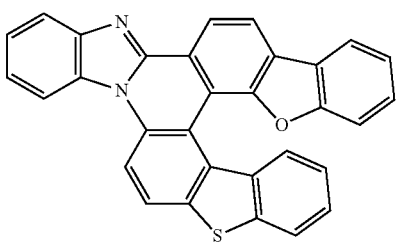
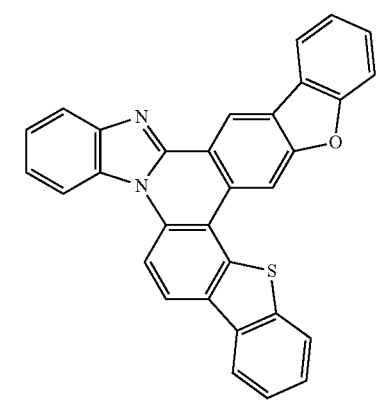
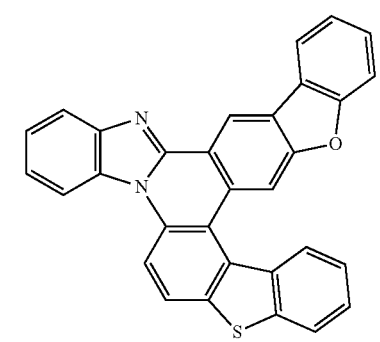
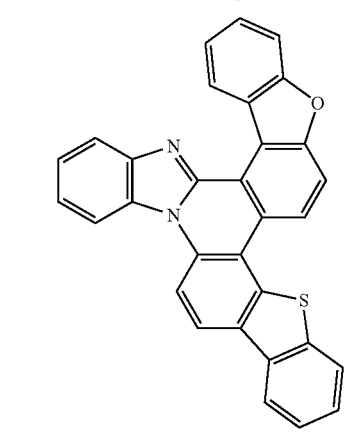

355
-continued
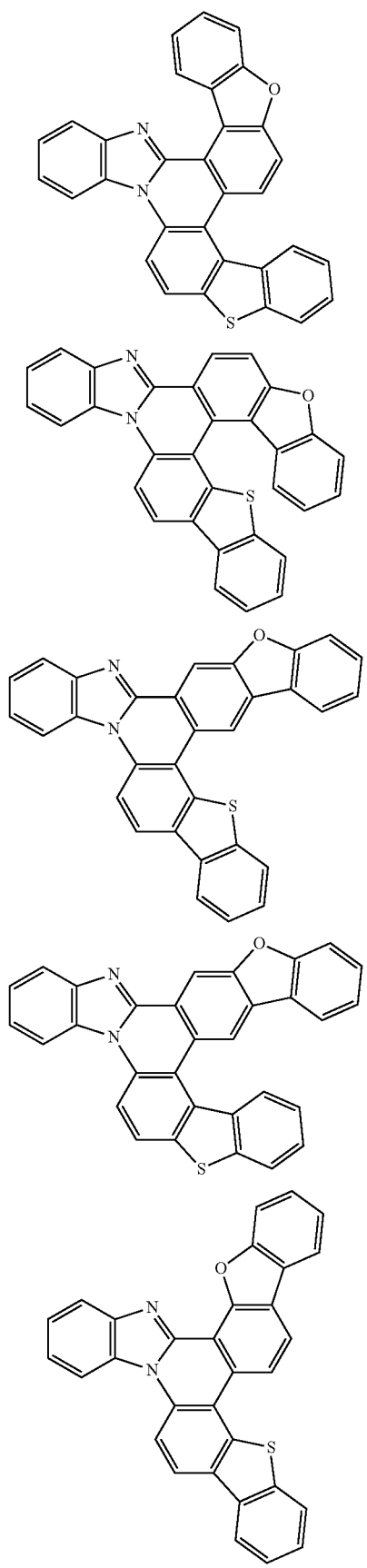
356
-continued
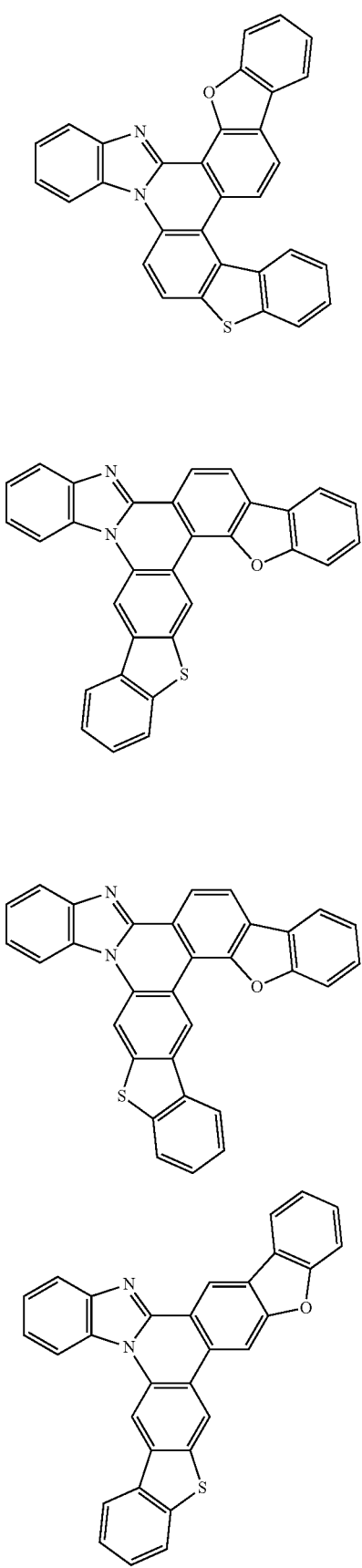

357
-continued
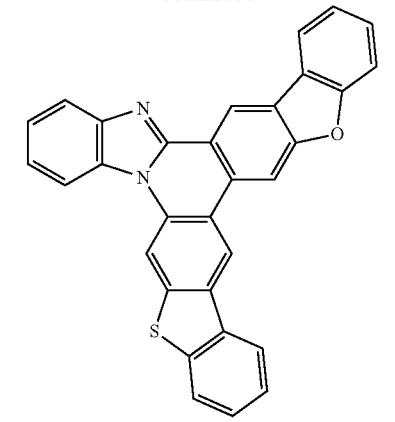
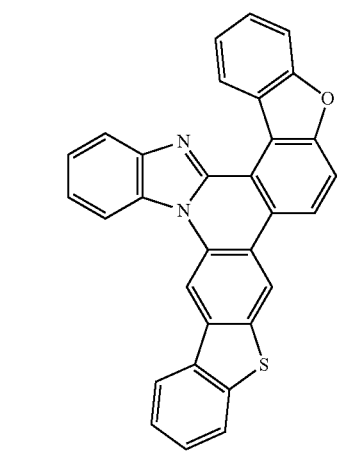
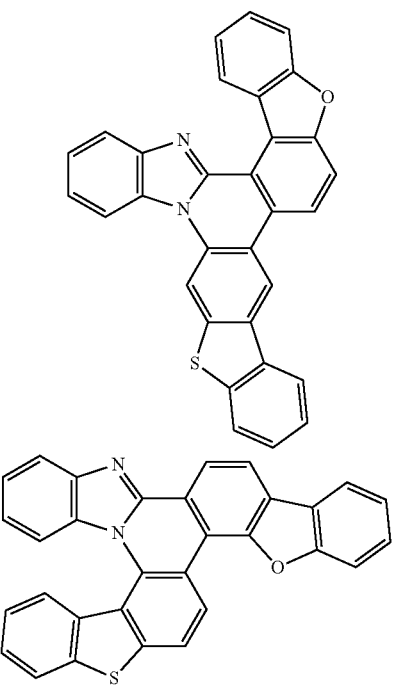
358
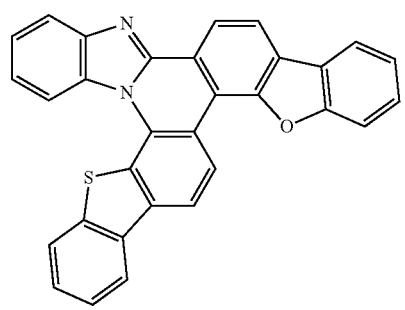
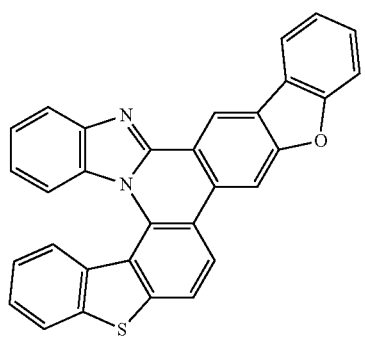
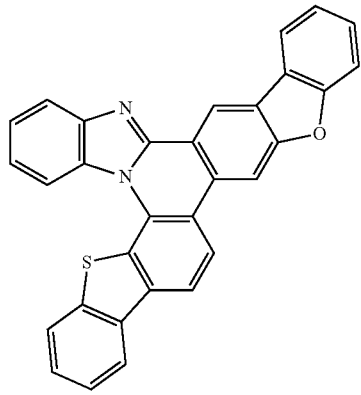
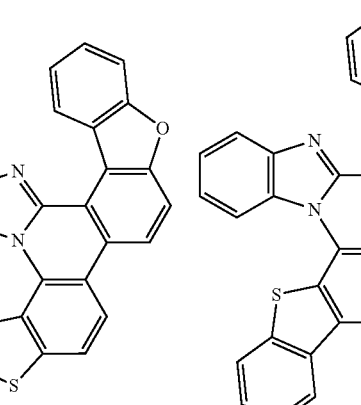

359
-continued
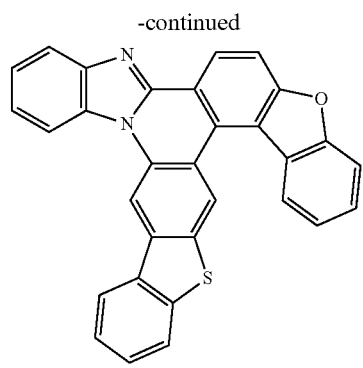
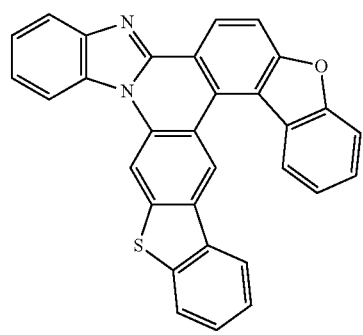
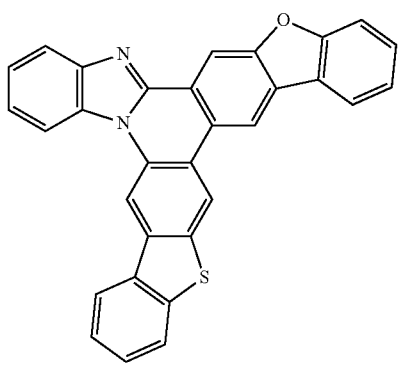
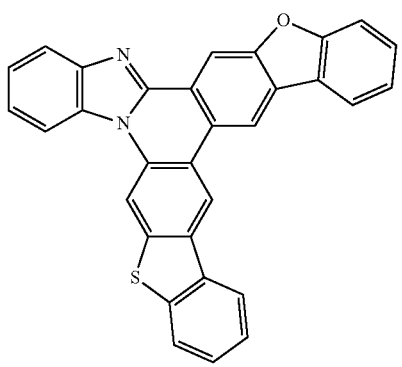
360
-continued
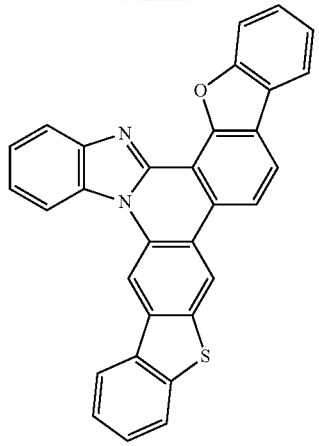
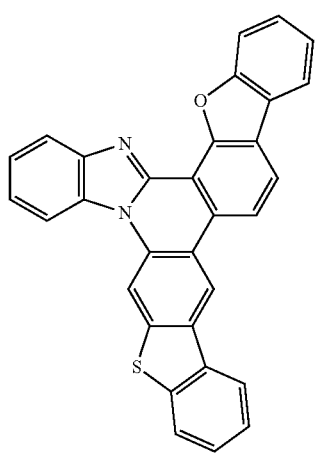
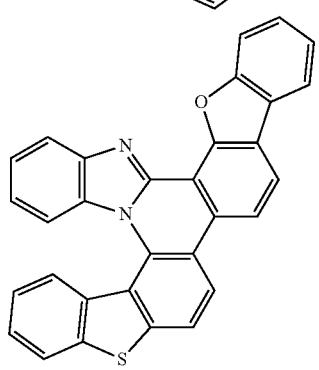
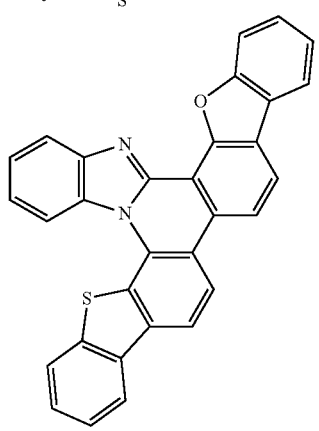

361
-continued
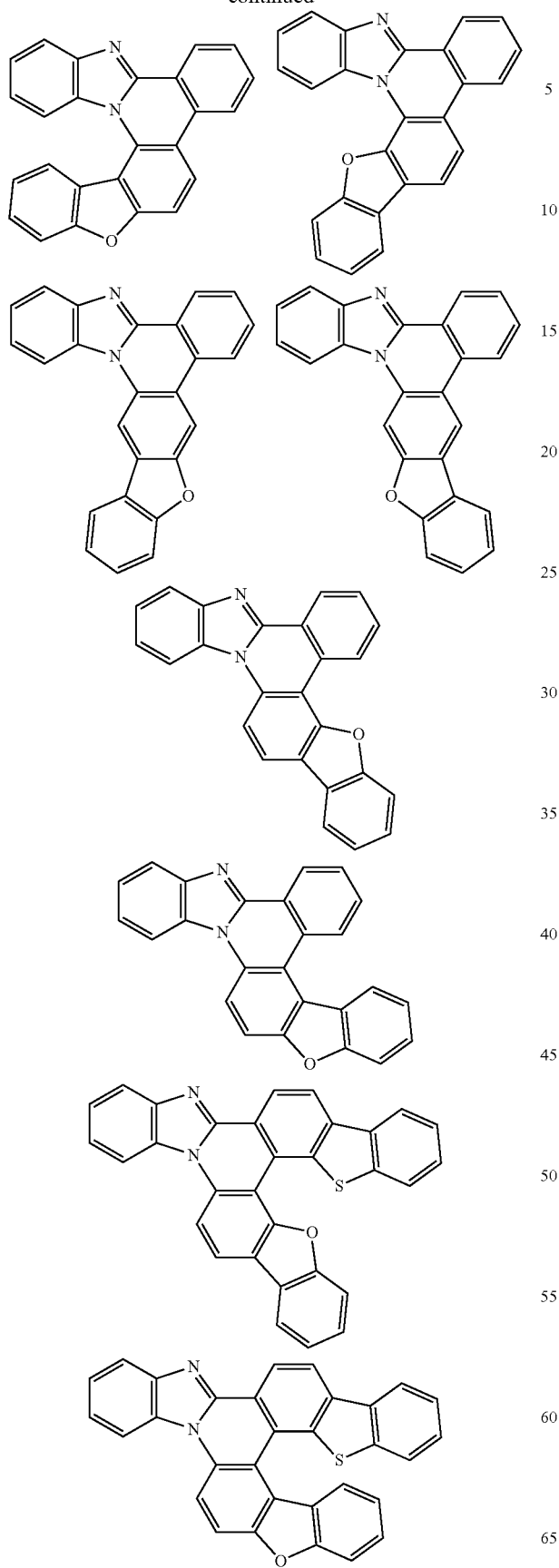
362
-continued
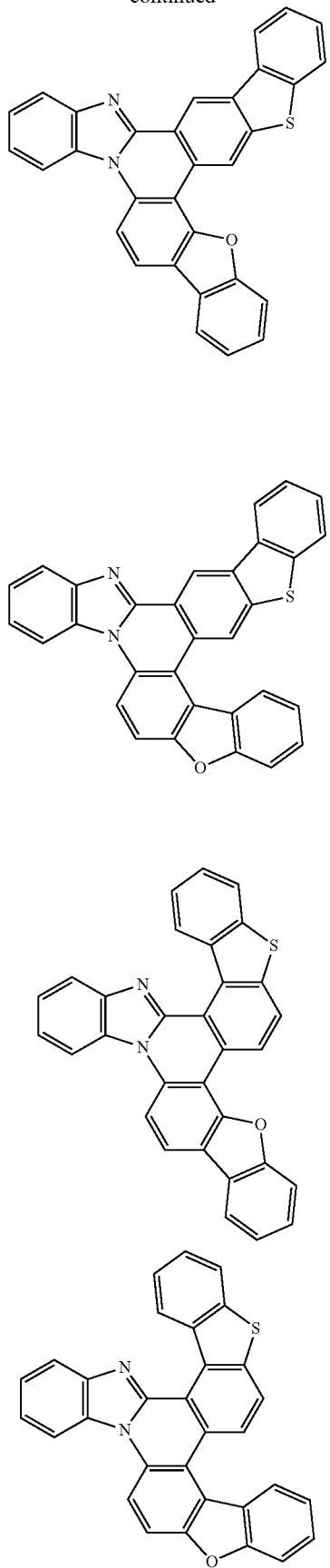

363
-continued
364
-continued
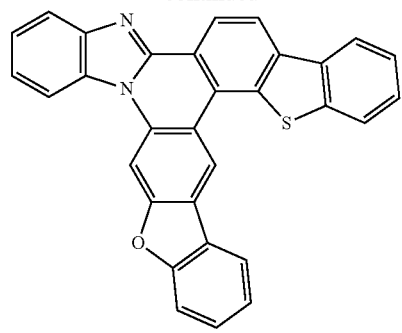
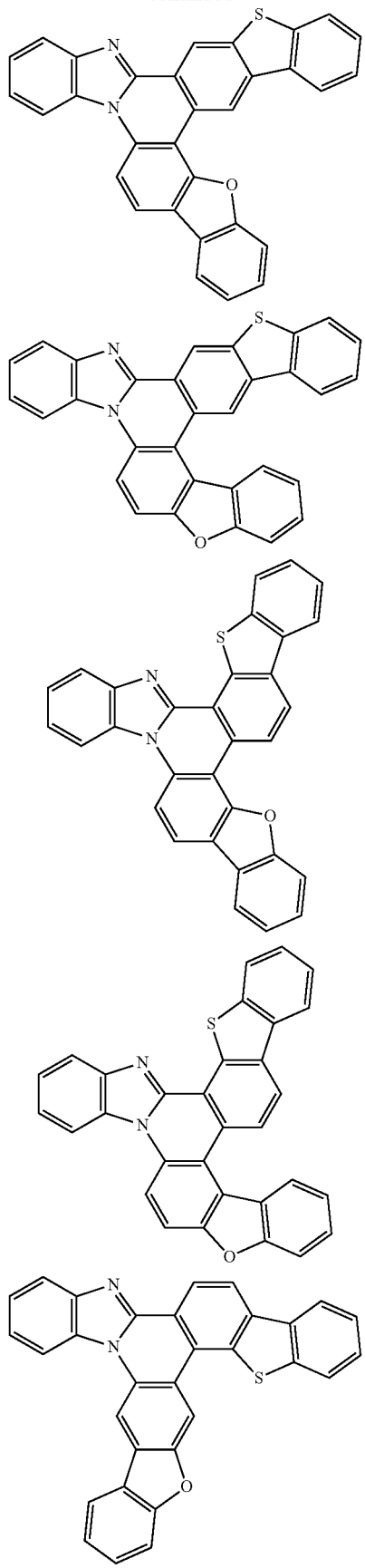
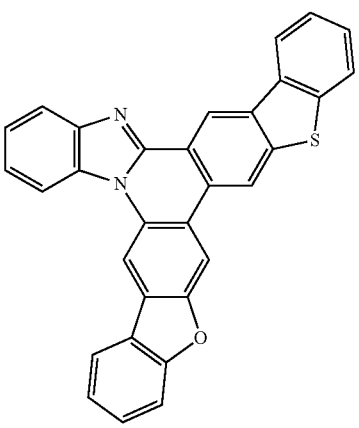
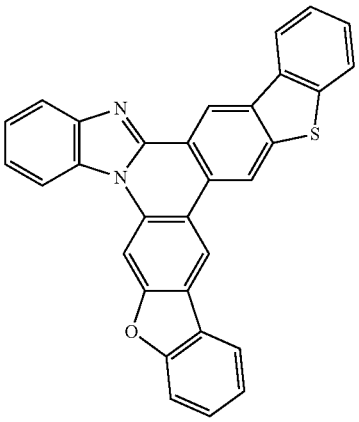
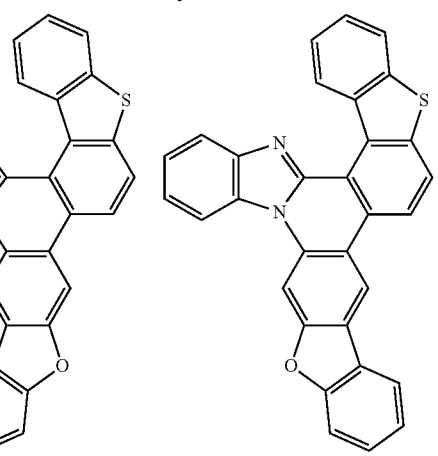

365
-continued
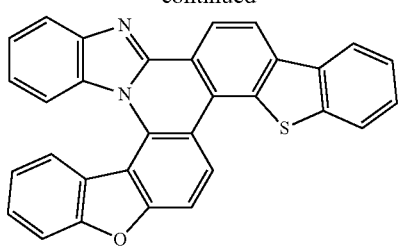
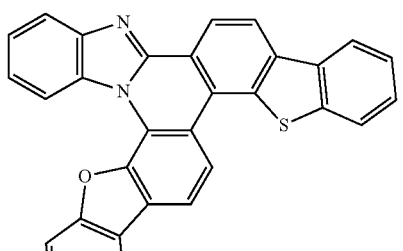
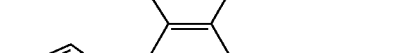
 
366
-continued
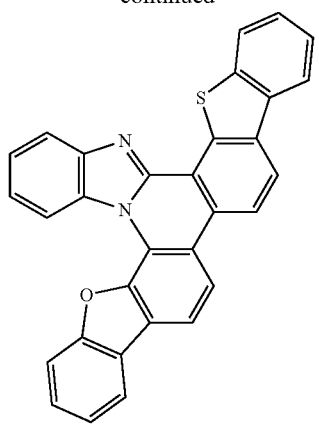
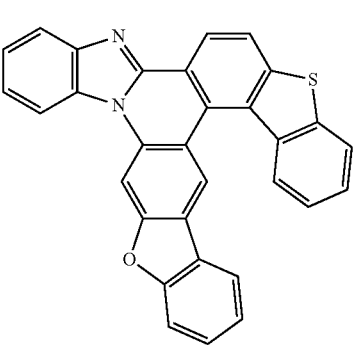
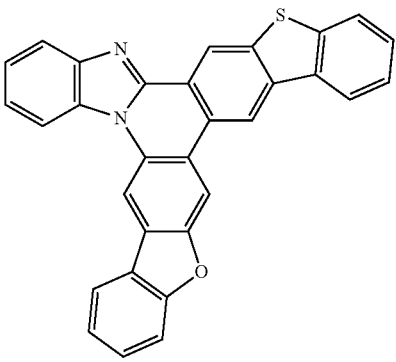
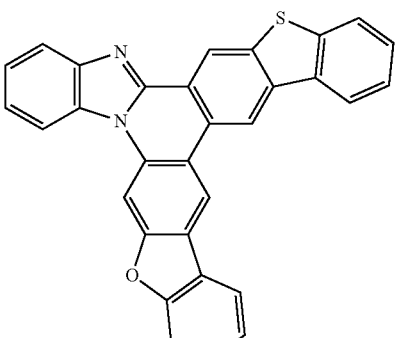

-continued
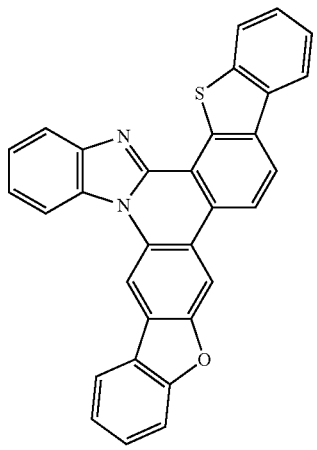
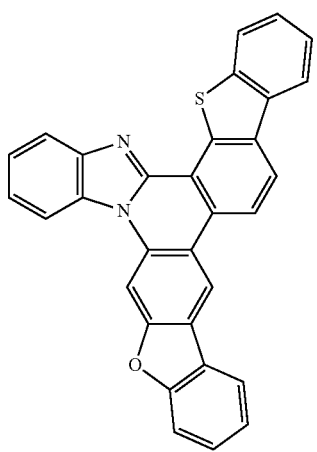
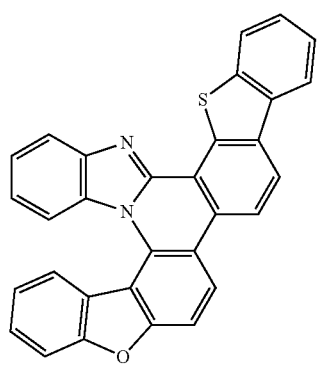
7. The compound of claim 2, wherein the compound is represented by one of the following structures:
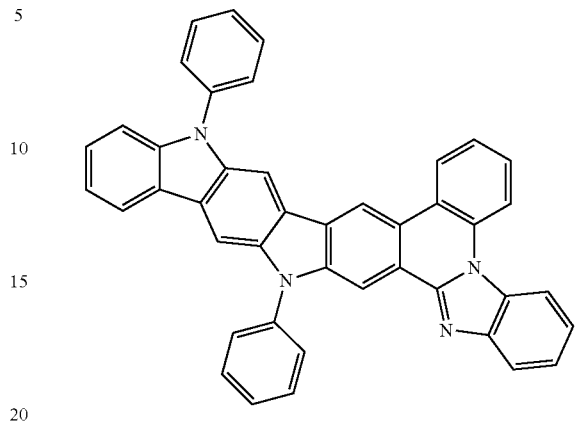
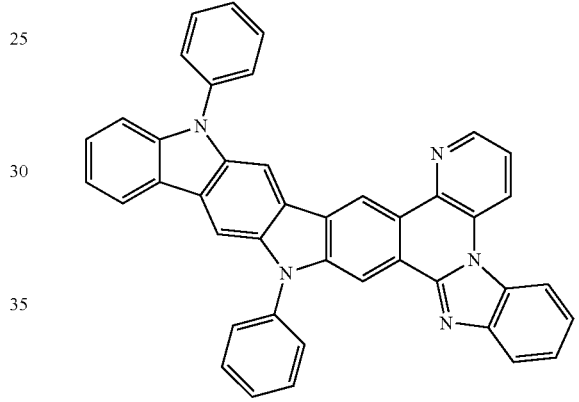
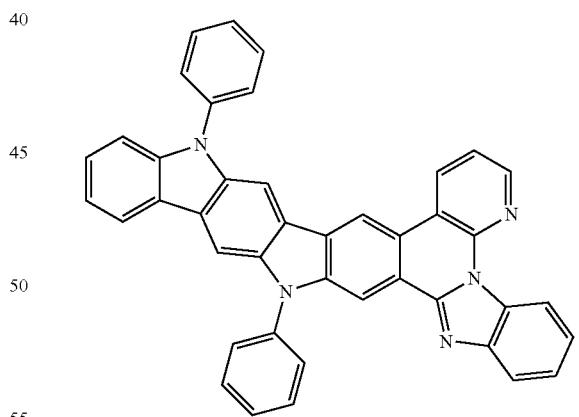
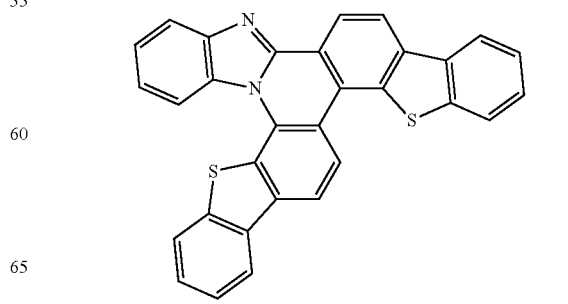

369
-continued
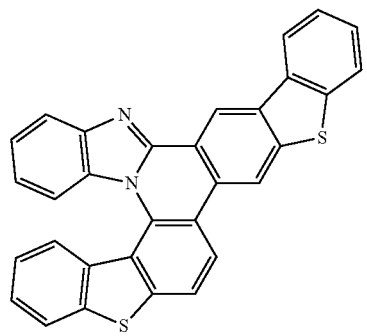
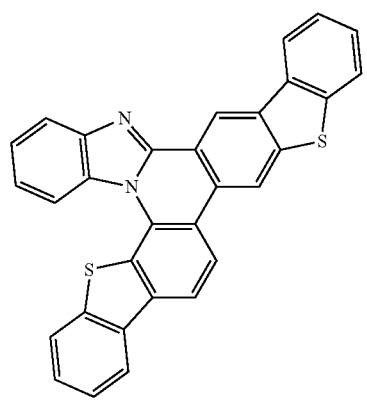
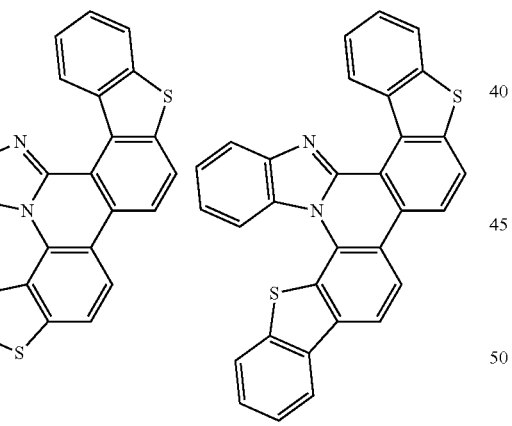
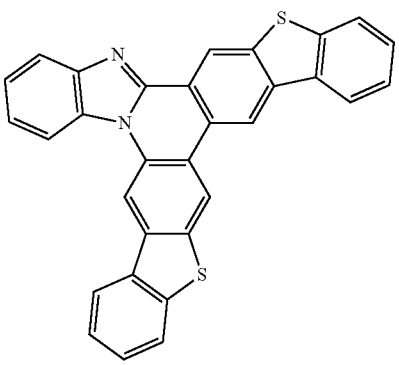
370
-continued
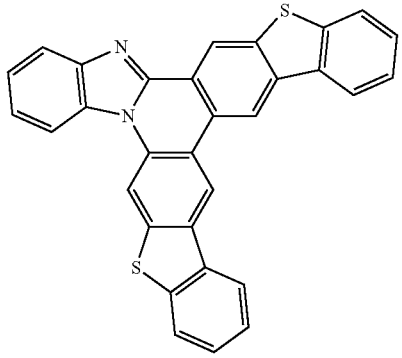
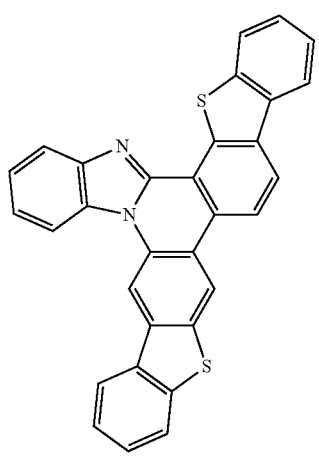
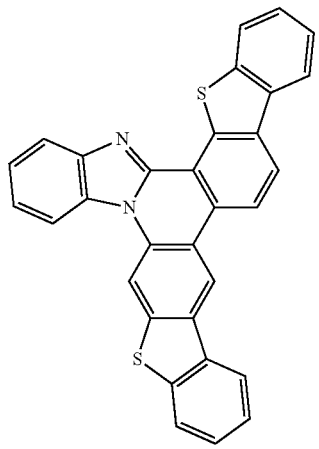
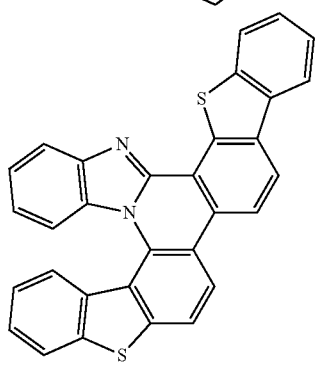

371
-continued
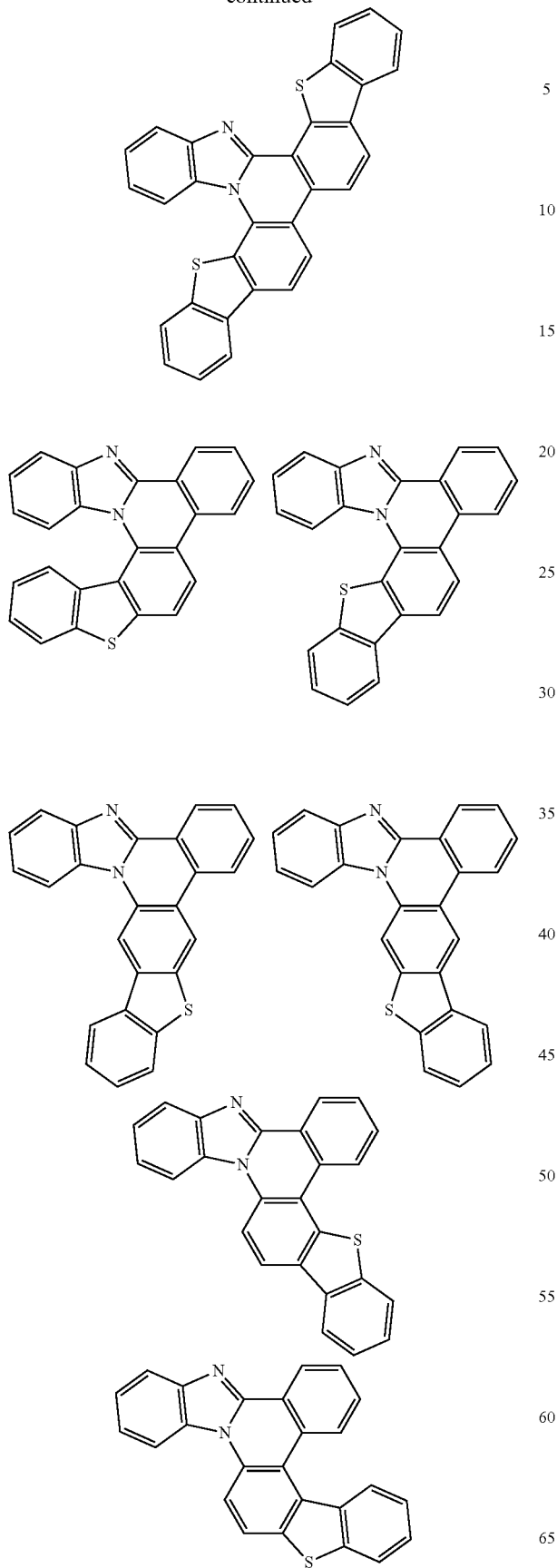
372
-continued
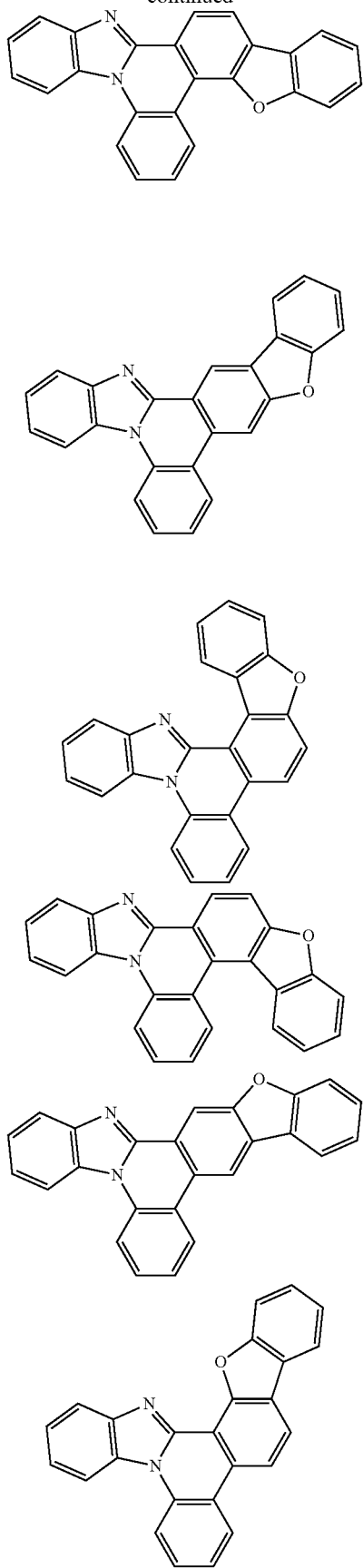

373
-continued
374
-continued
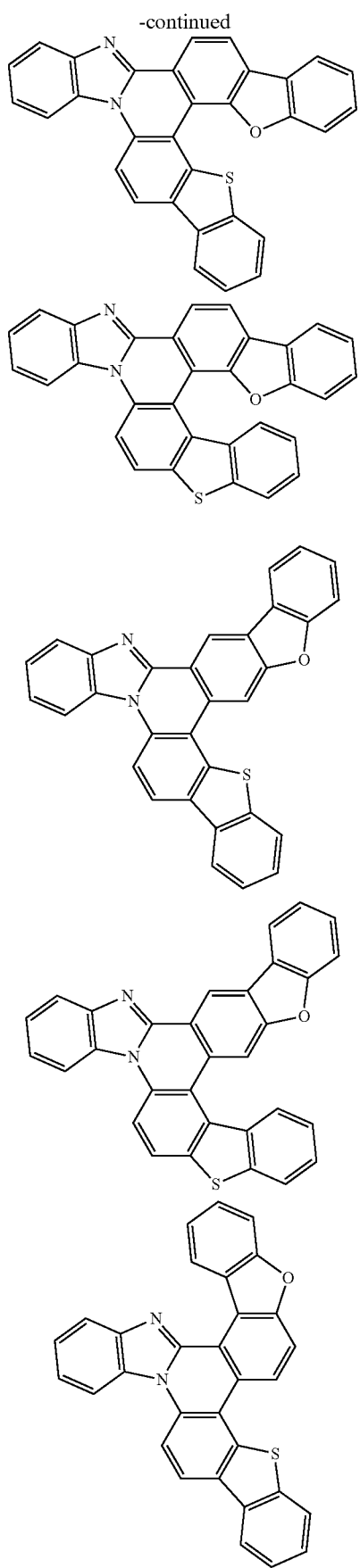
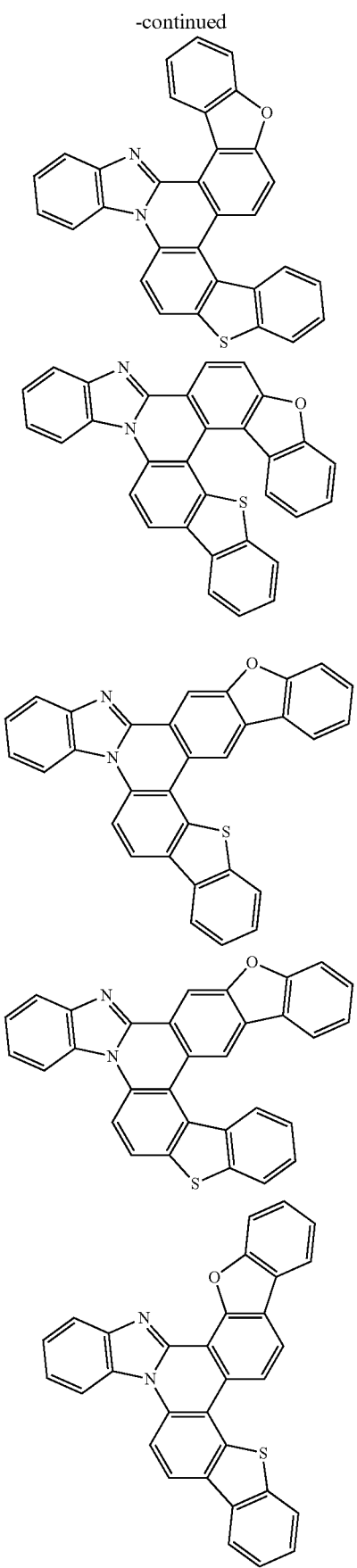

-continued
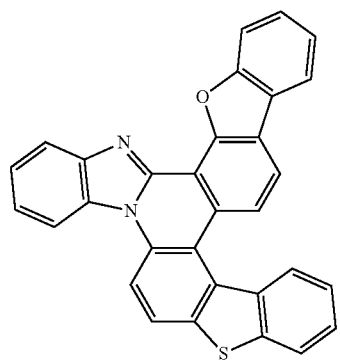
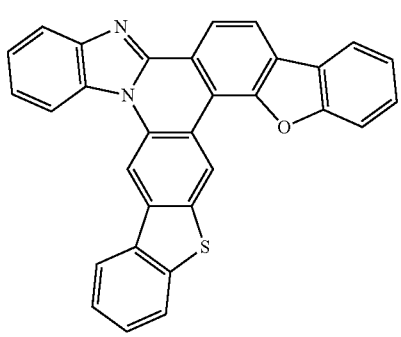
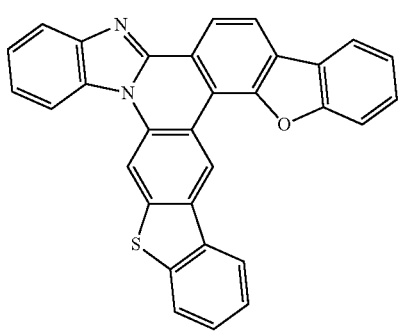
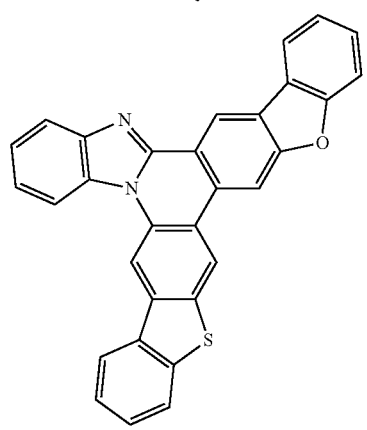
-continued
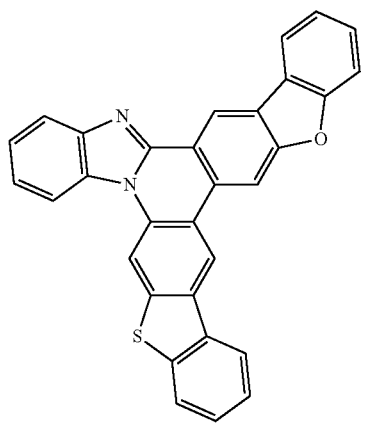
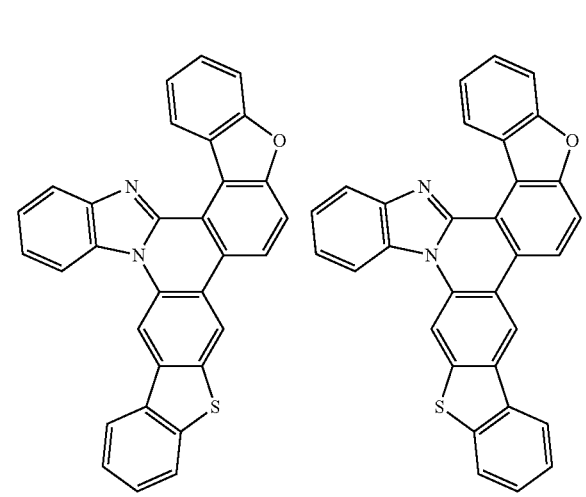
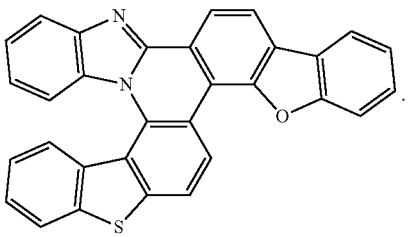
8. The compound of claim 2, wherein the compound is represented by one of the following structures:
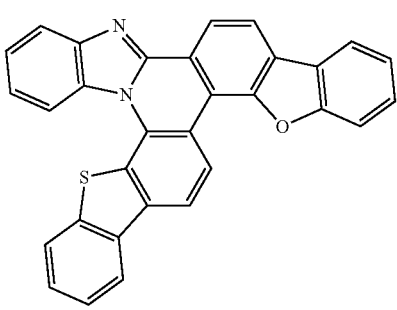

377
-continued
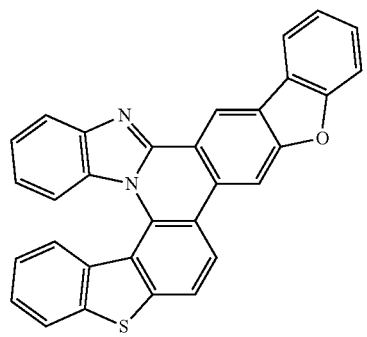
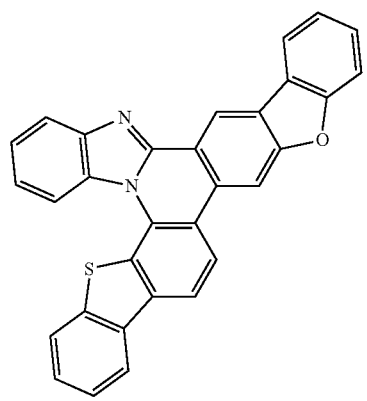
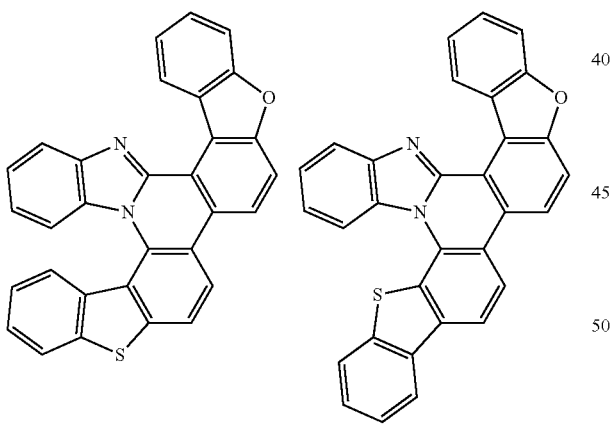
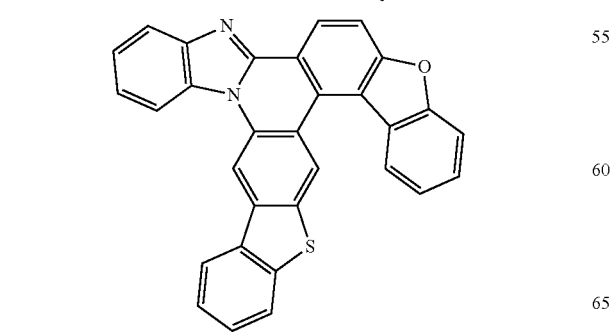
378
-continued
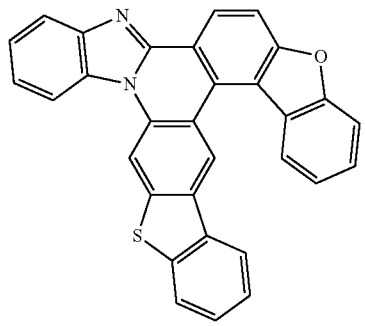
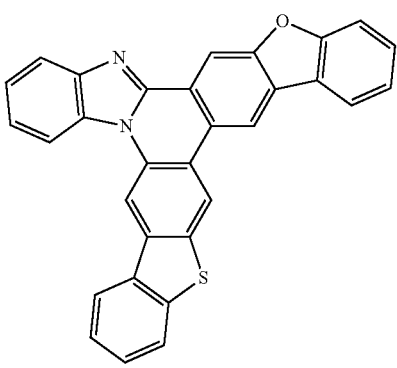
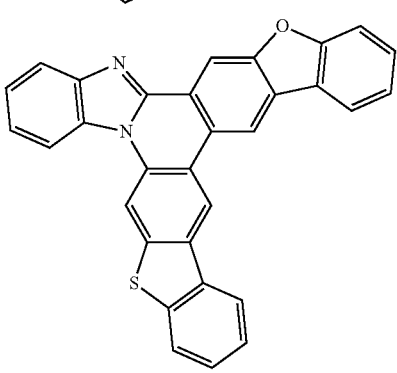
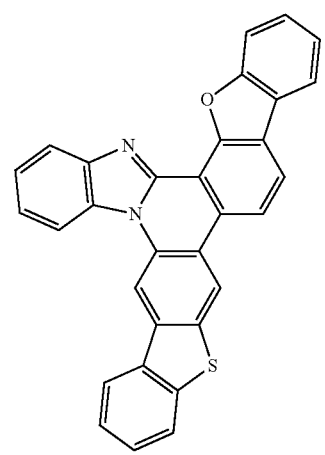

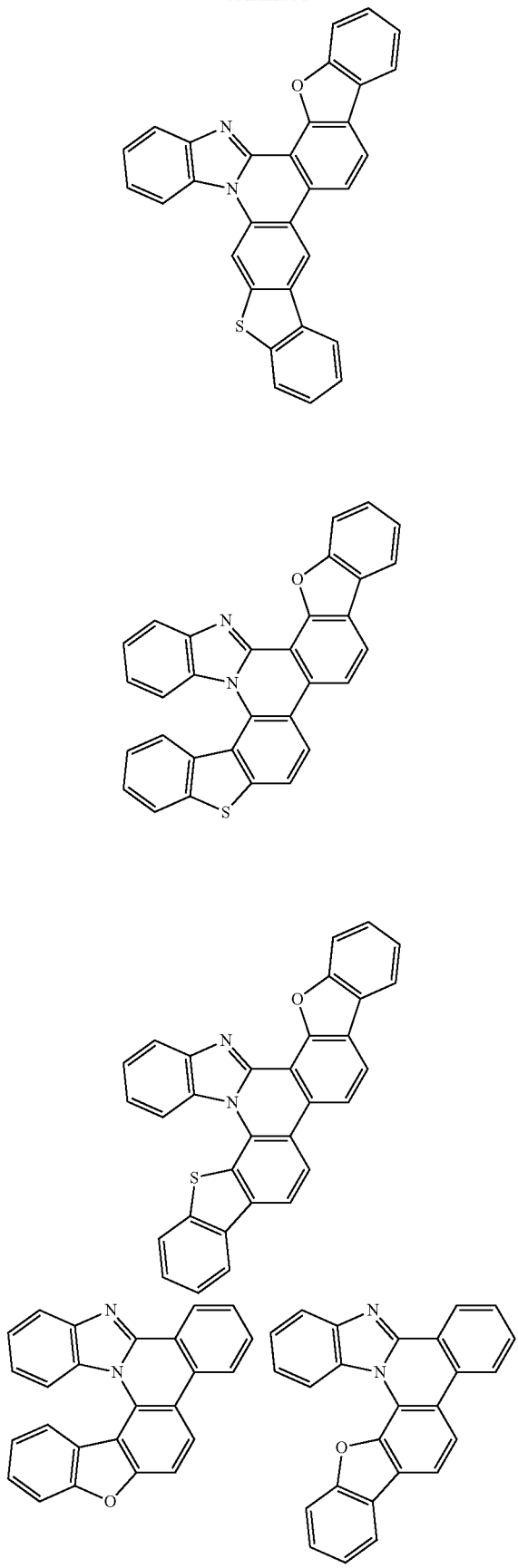
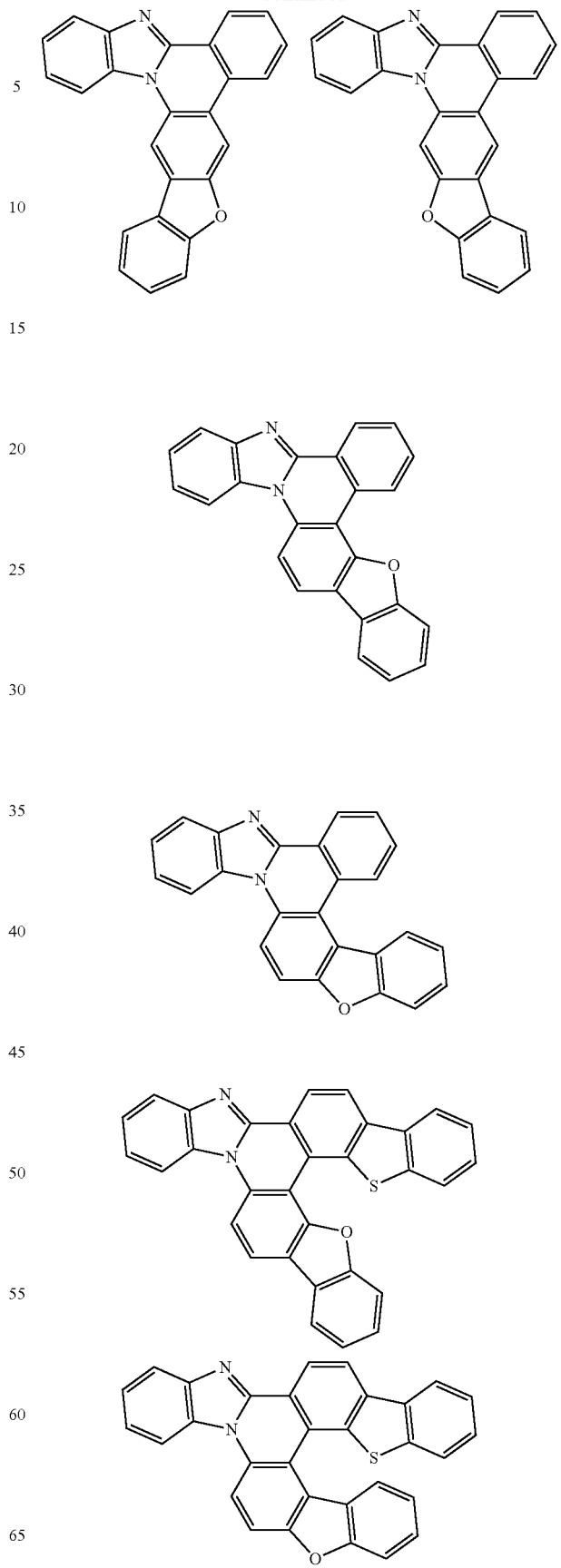

381
-continued
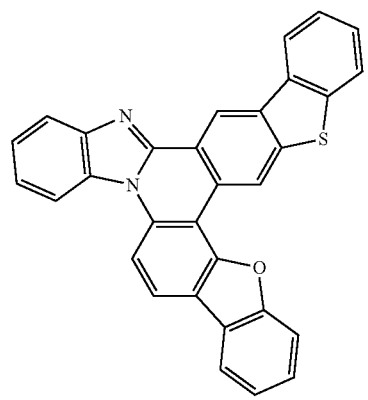
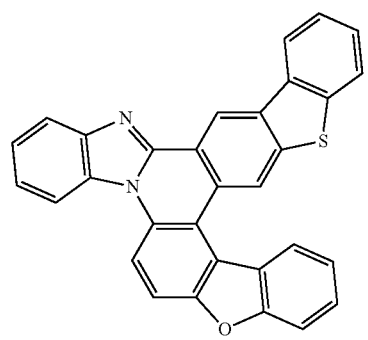
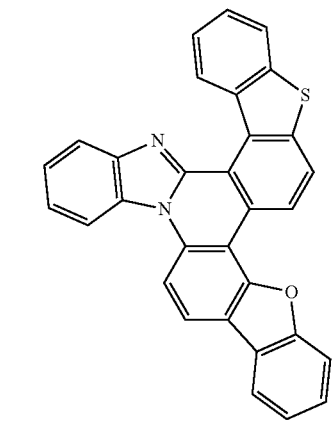
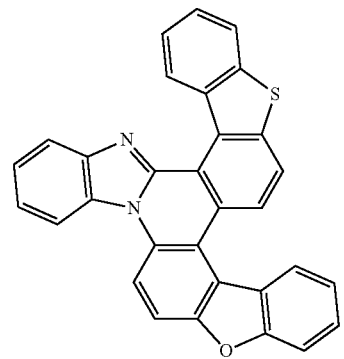
382
-continued
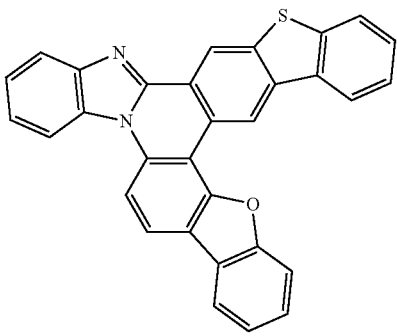
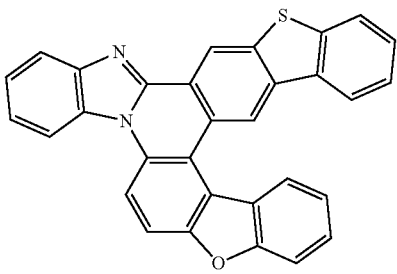
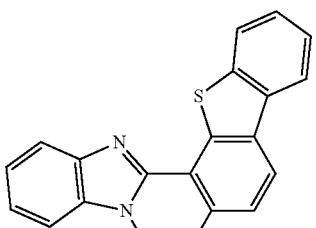
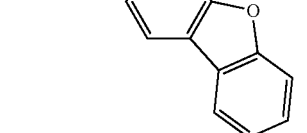
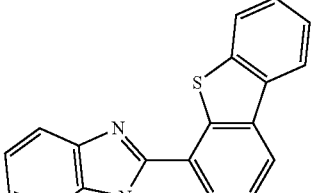
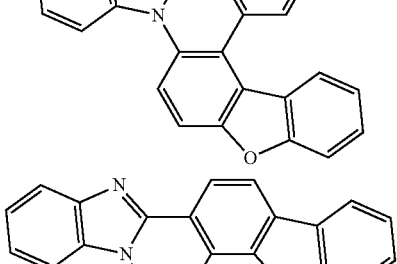
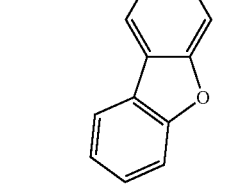

383
-continued
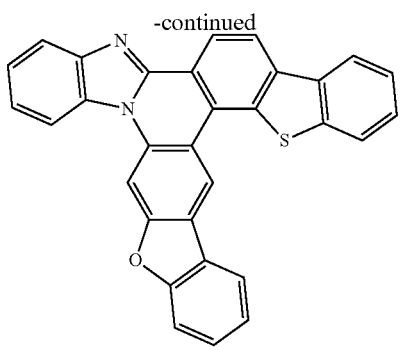
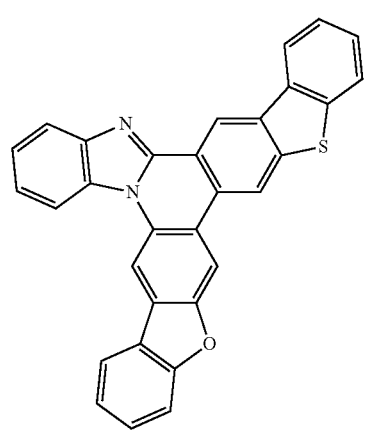
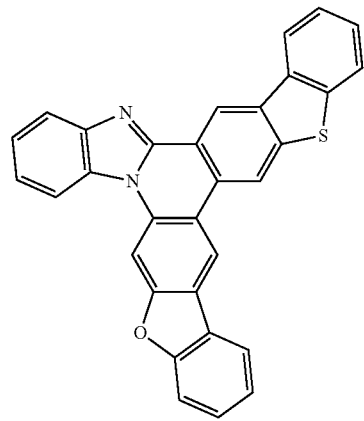
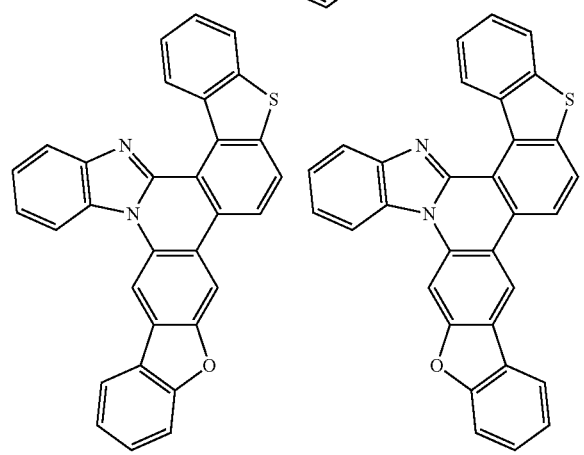
384
-continued
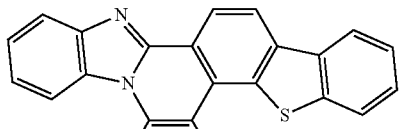
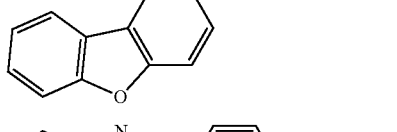
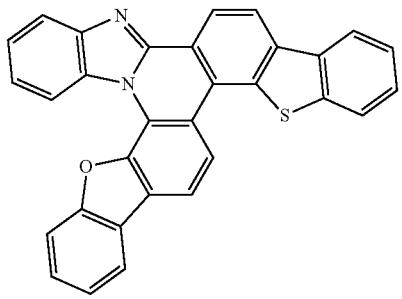
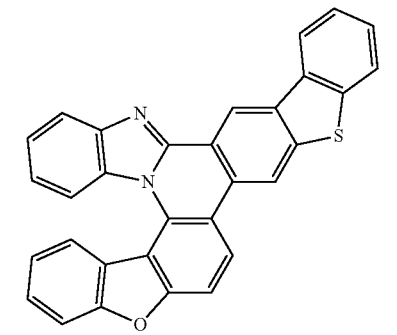
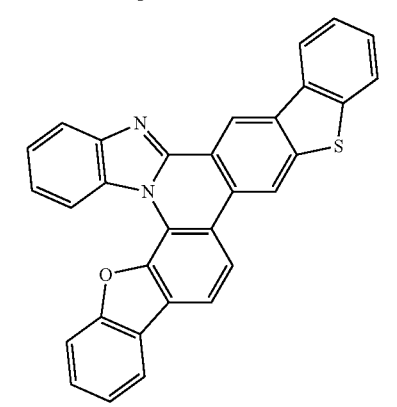

-continued
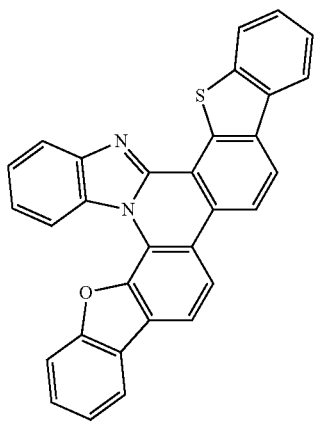
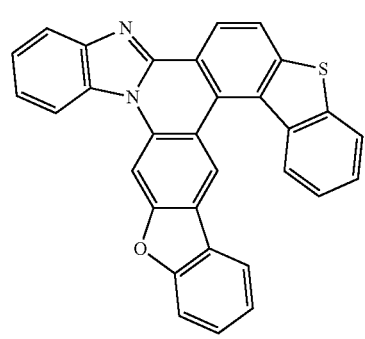
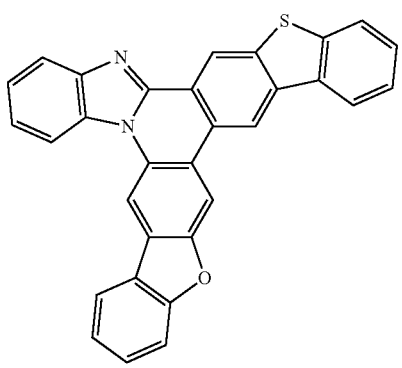
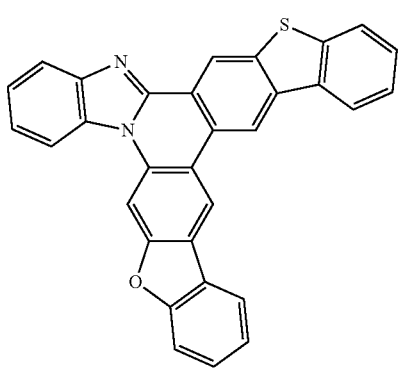
-continued
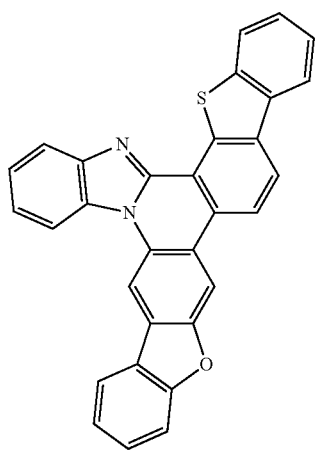
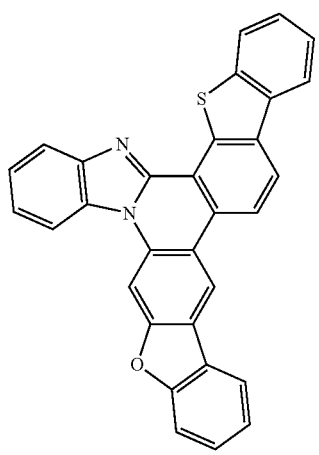
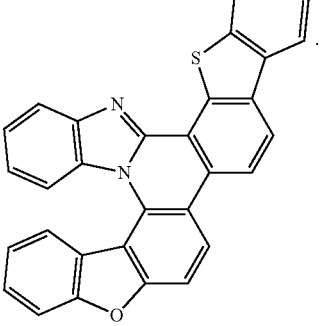
9. The compound of claim 2, wherein the compound is represented by one of the following structures:
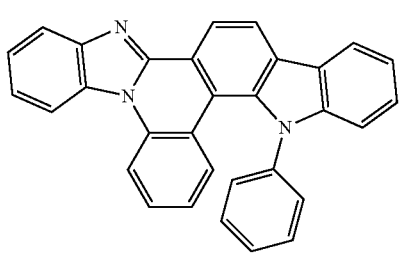

387
-continued
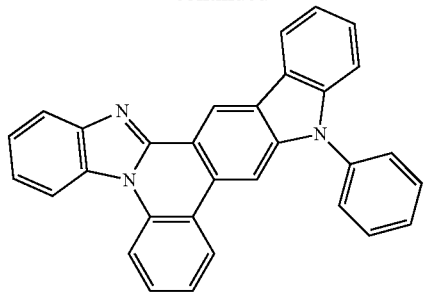
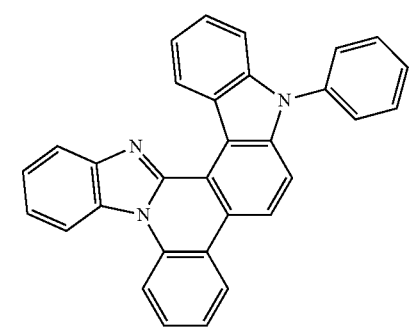
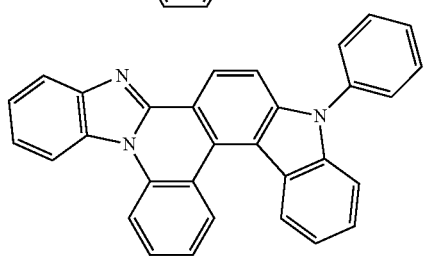
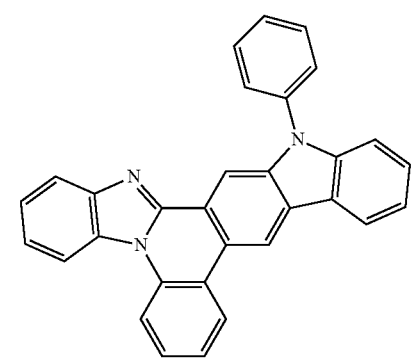
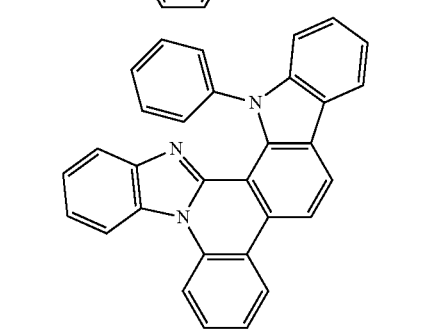
388
-continued
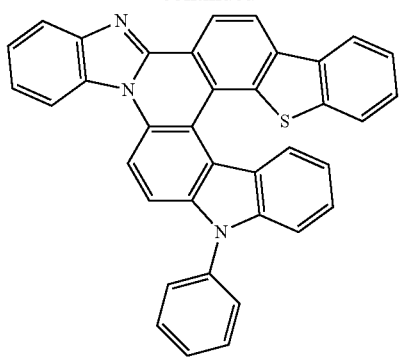 [SMILES: c1ccc(-n2c3ccccc3c3c4c5c(ccc6c7ccccc7sc65)c5nc6ccccc6n5c4ccc32)cc1]
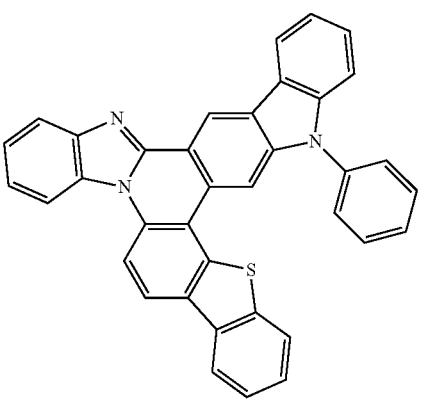
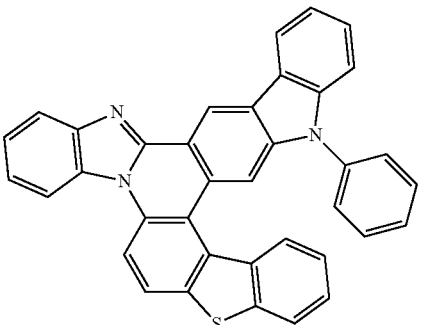
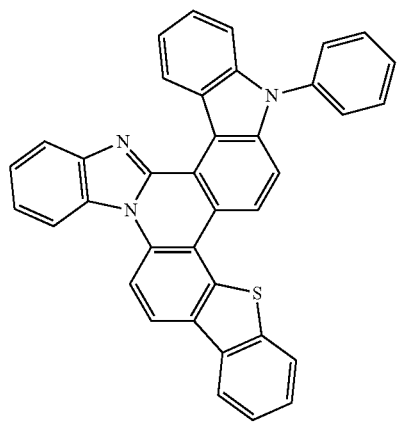

389
-continued
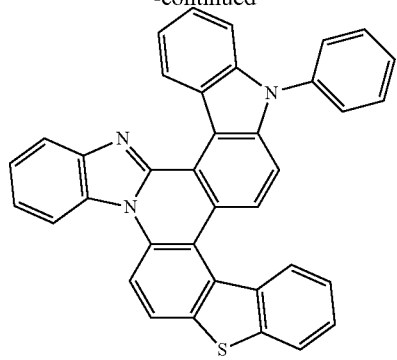
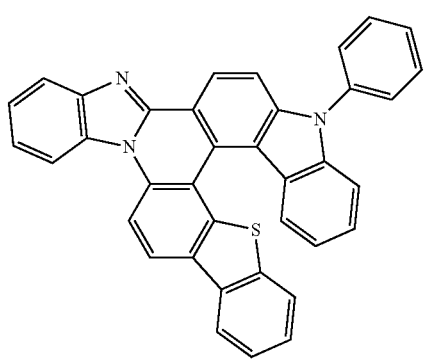
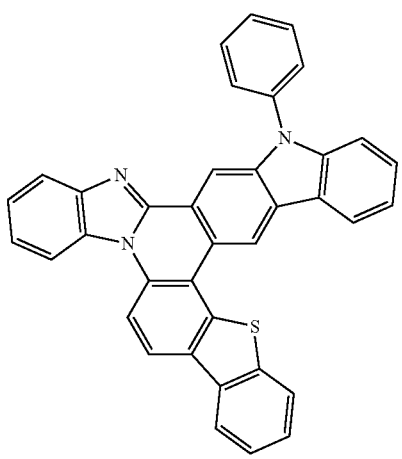
390
-continued
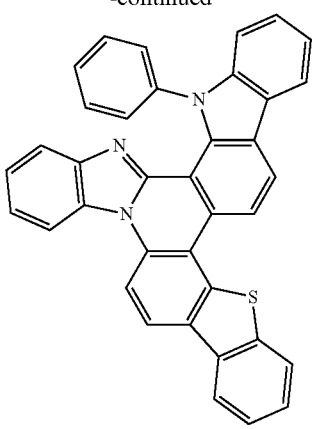
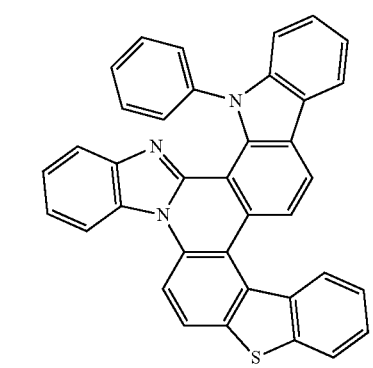
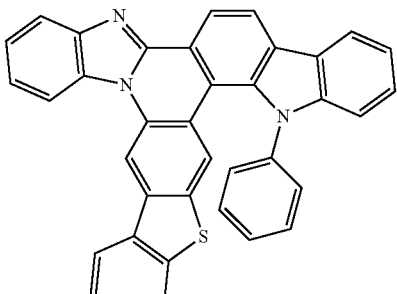
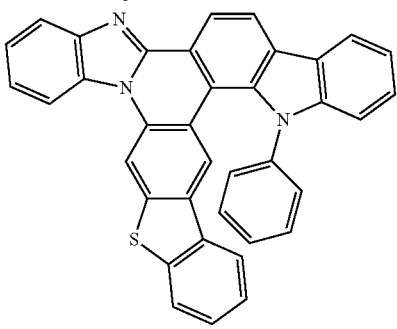

391
-continued
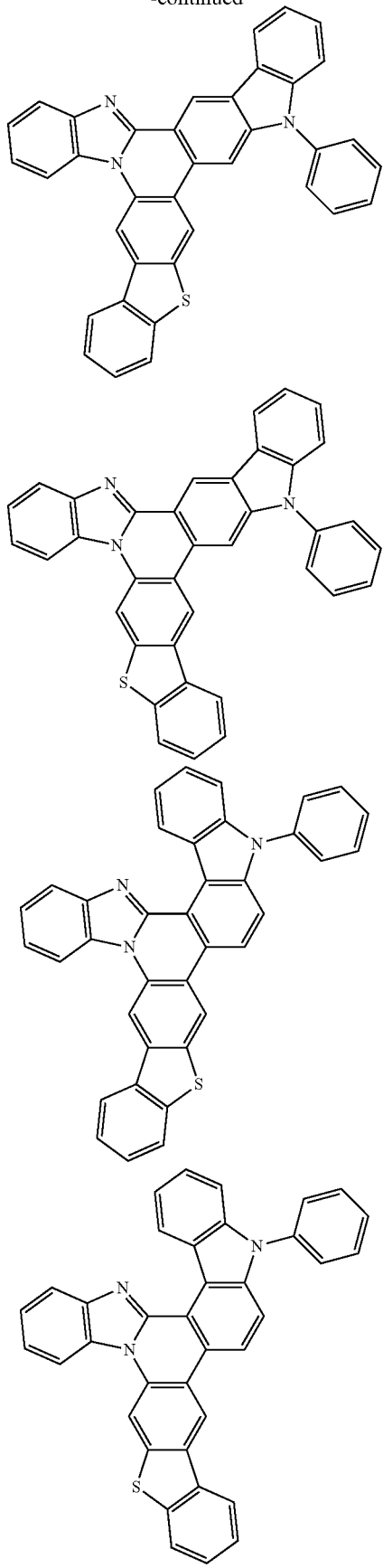
392
-continued
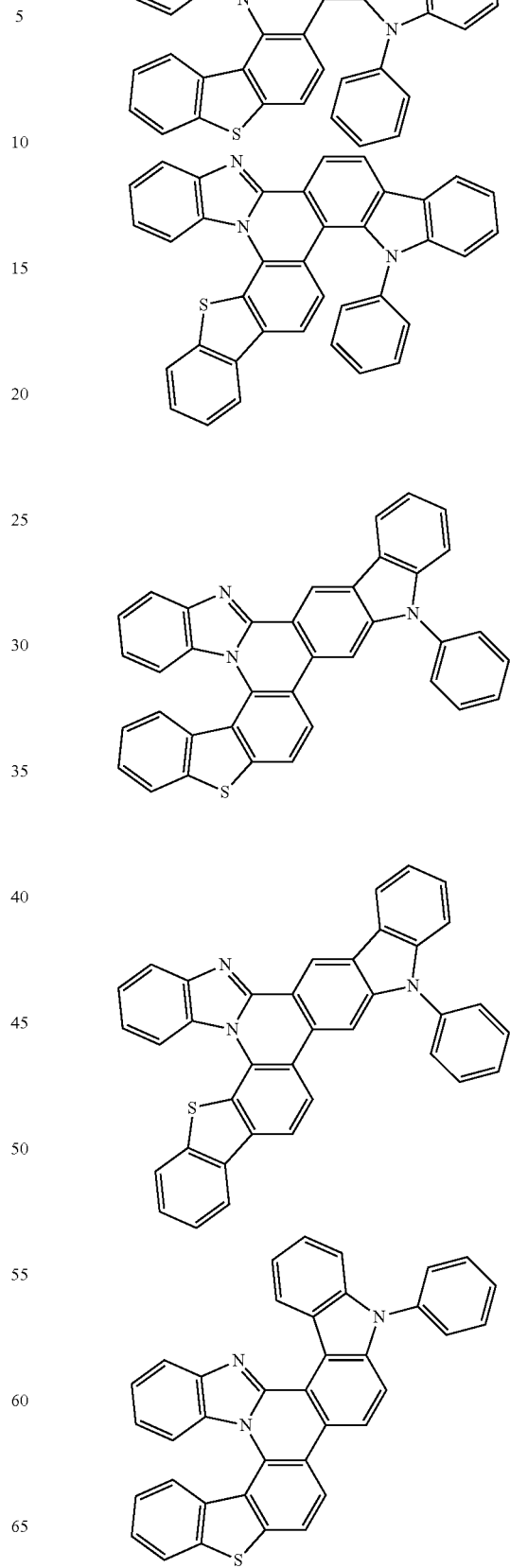

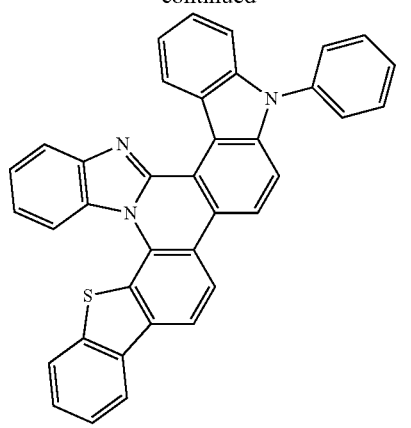
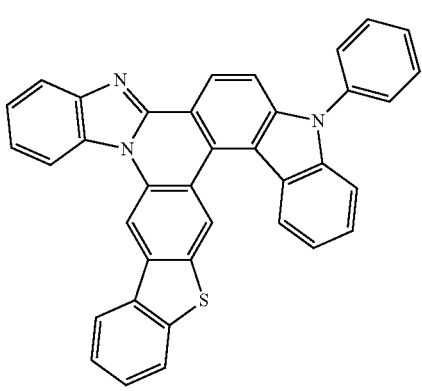
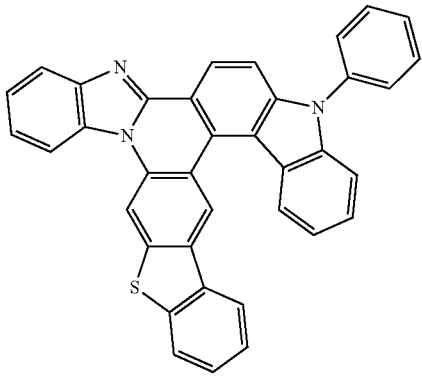
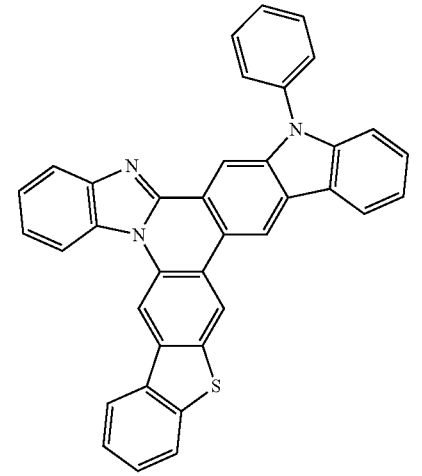
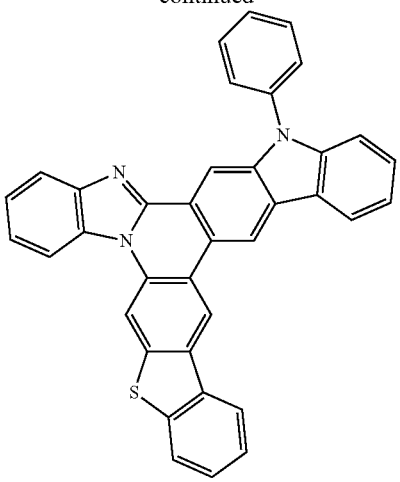
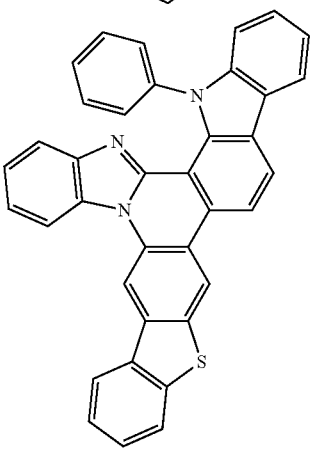
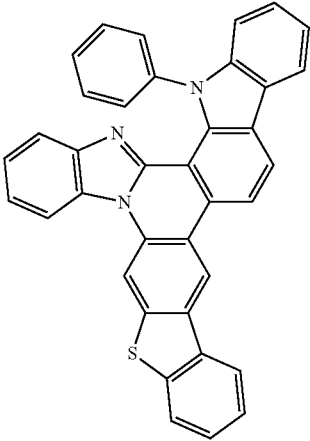
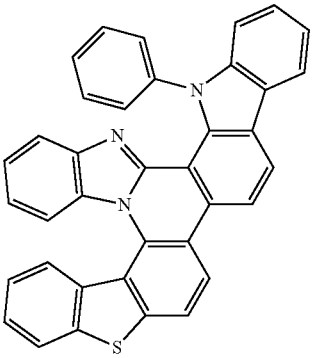

395
-continued
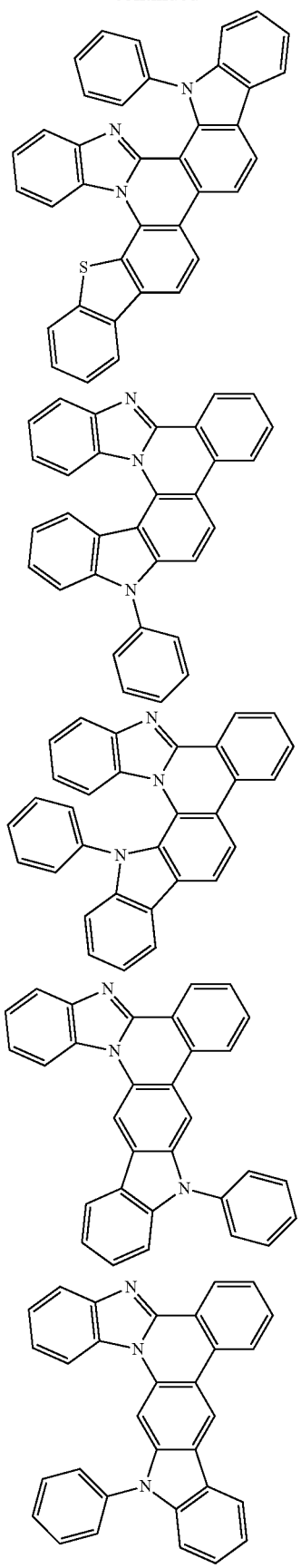
396
-continued
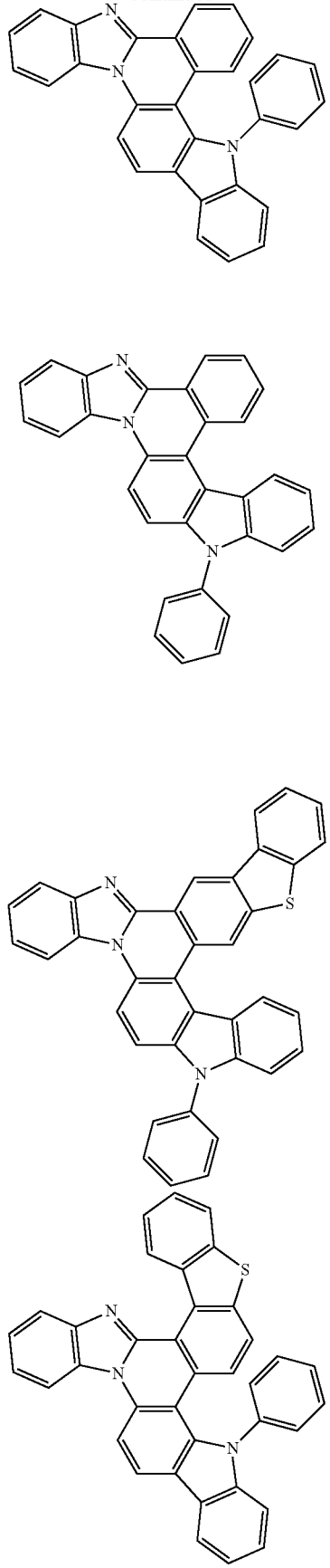

397
-continued
398
-continued
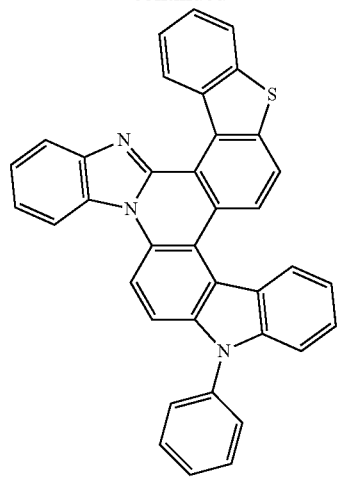
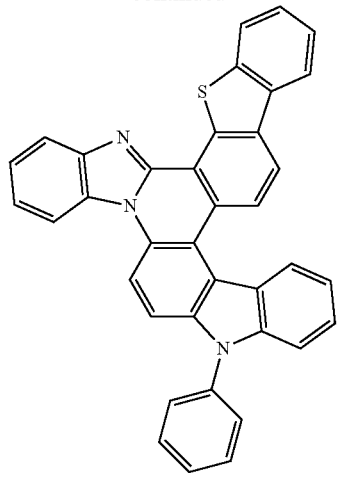
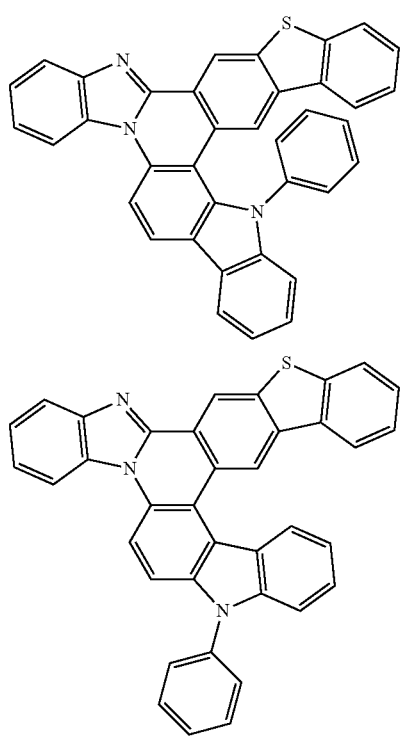
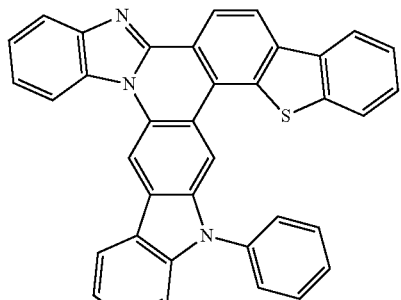
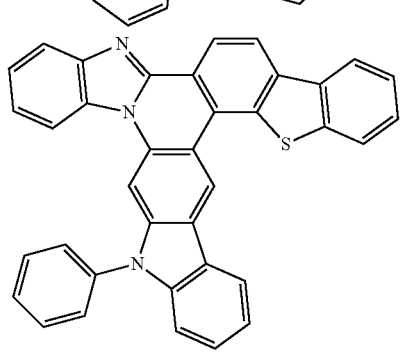
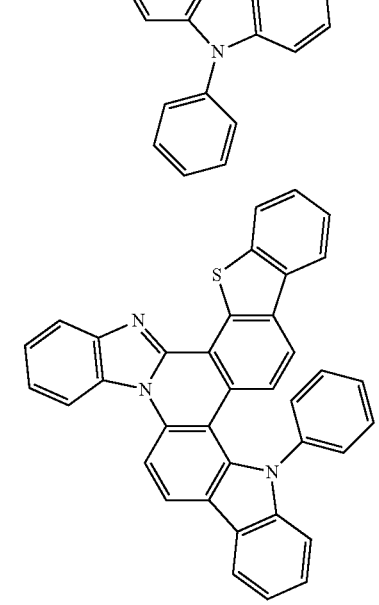
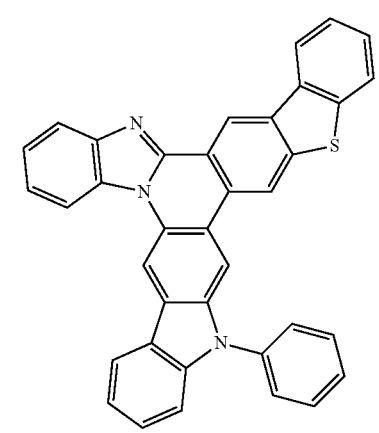

-continued
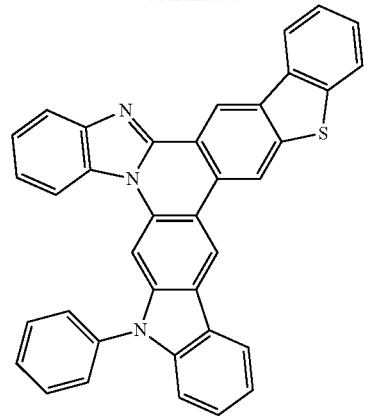
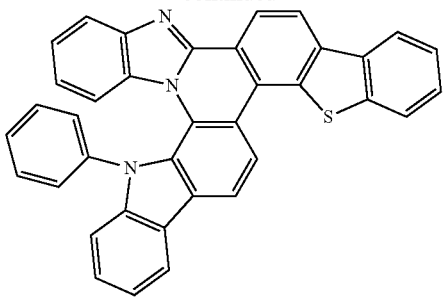
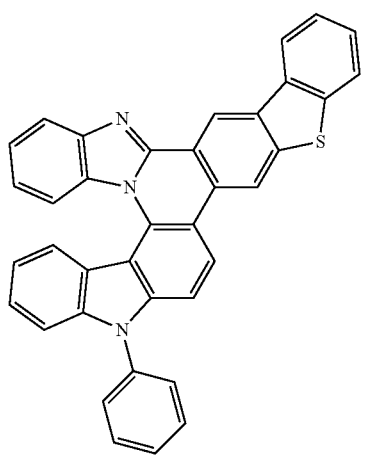
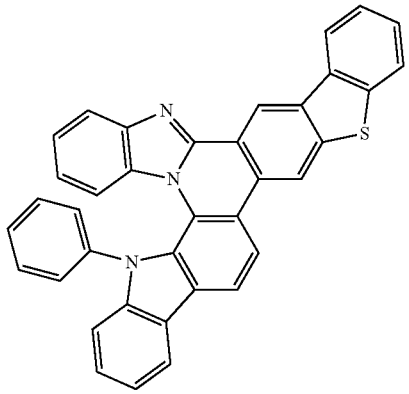
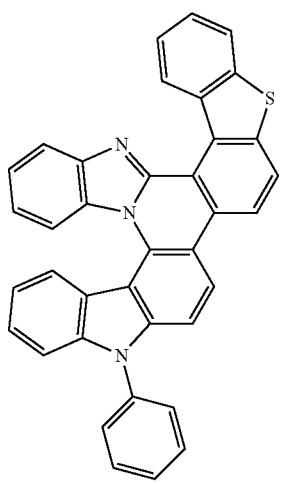

401
-continued
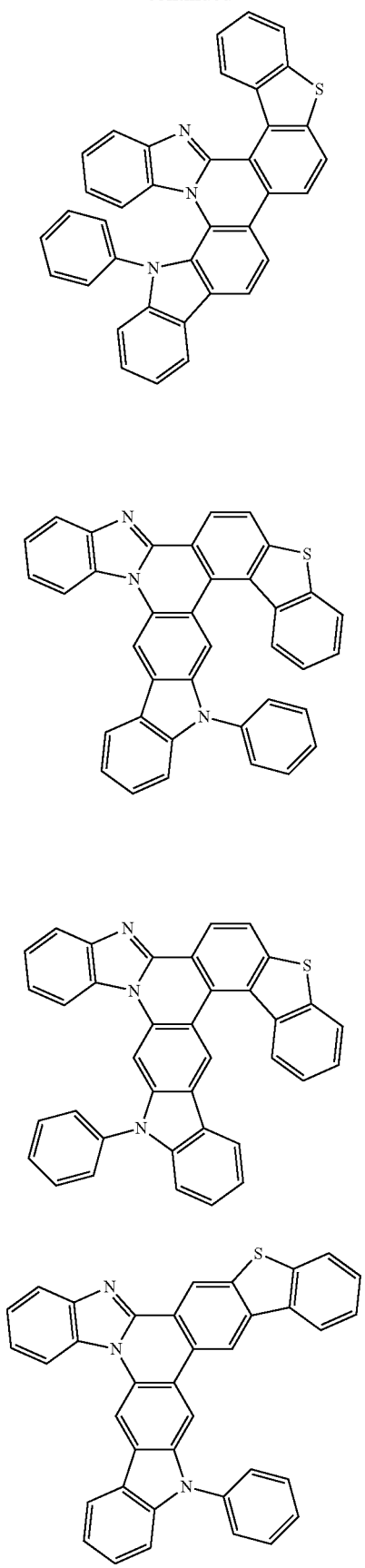
402
-continued
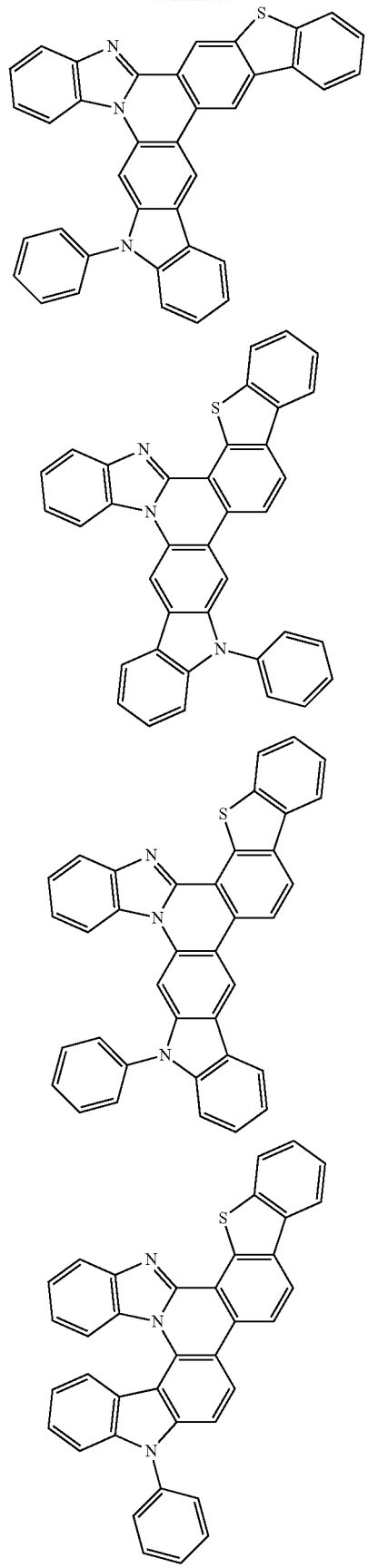

403
-continued
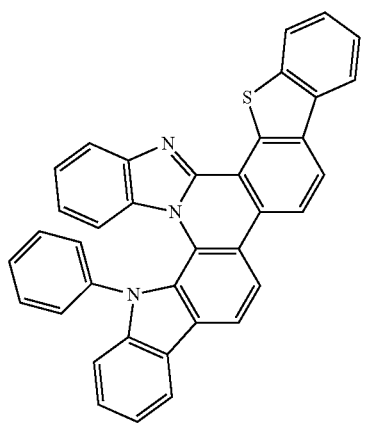
10. The compound of claim 2, wherein the compound is represented by one of the following structures:
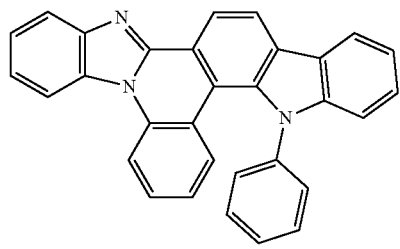
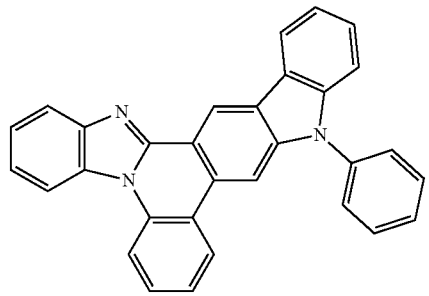
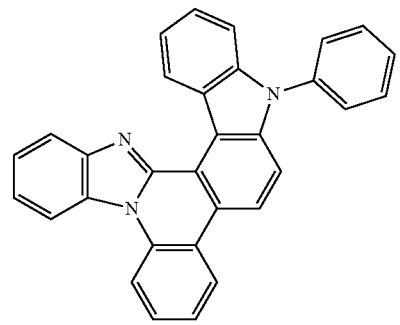
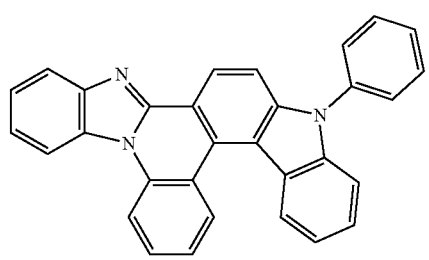
404
-continued
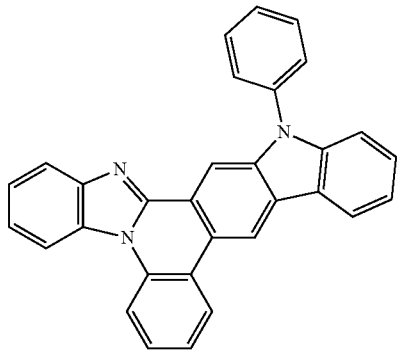
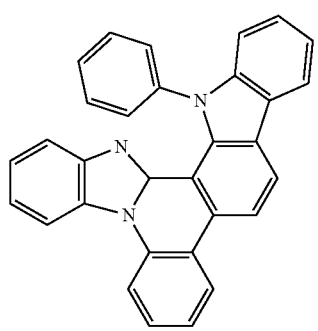
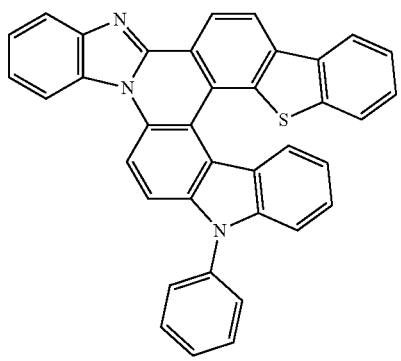
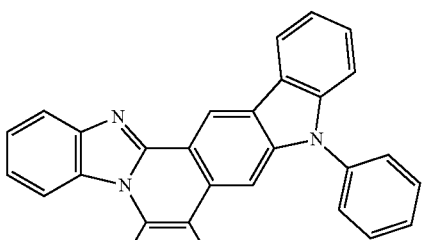
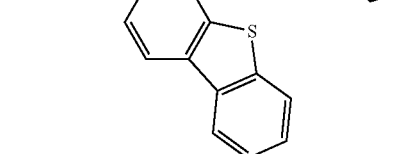

405
-continued
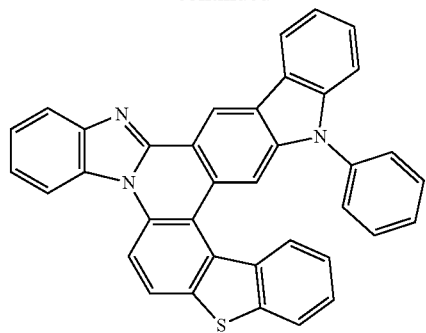
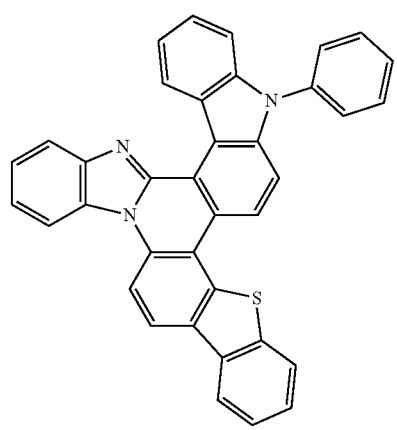
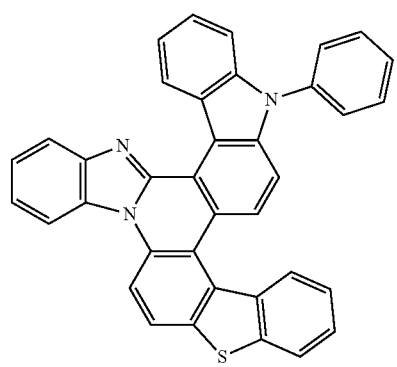
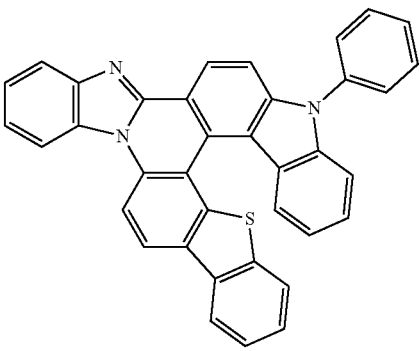
406
-continued
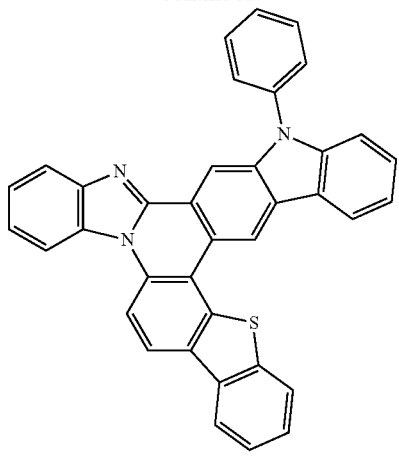
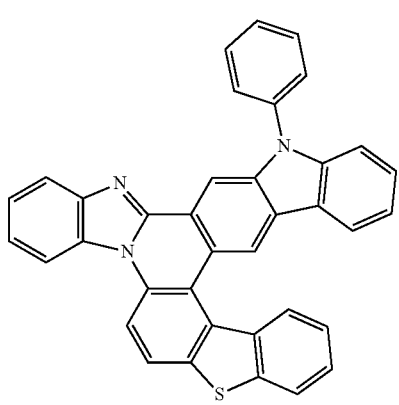
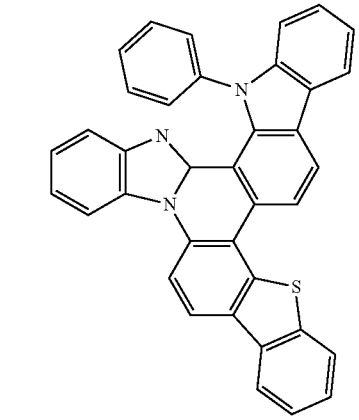
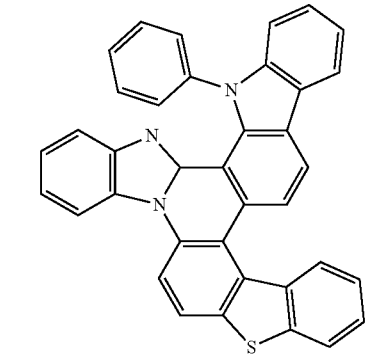

407
-continued
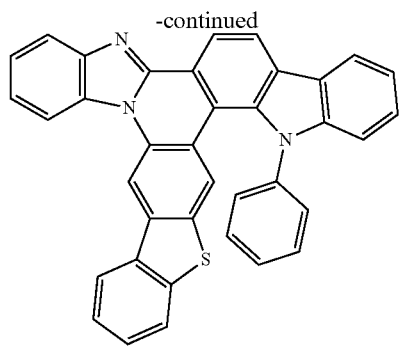
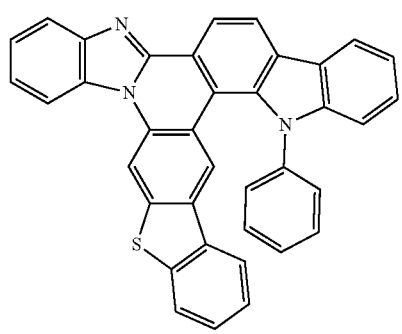
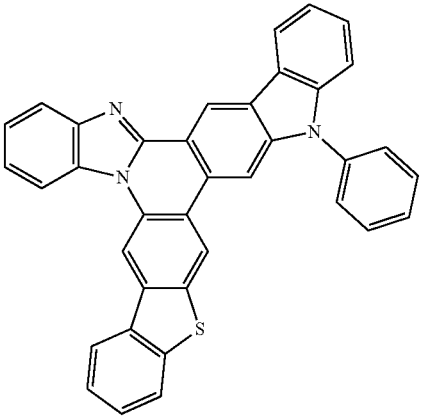
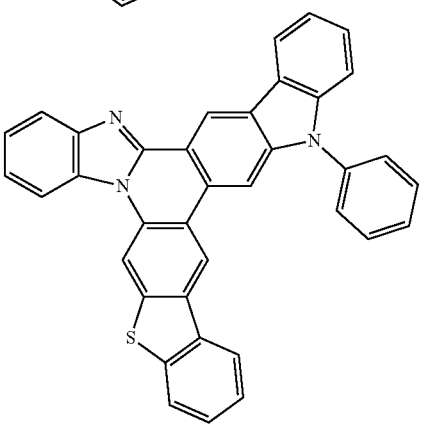
408
-continued
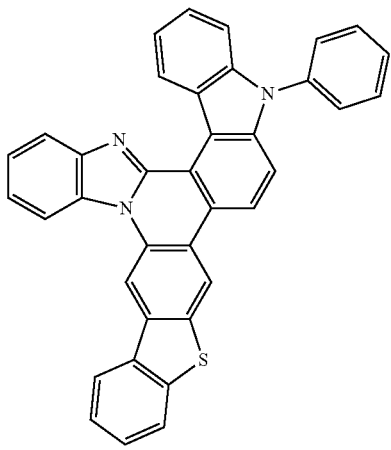
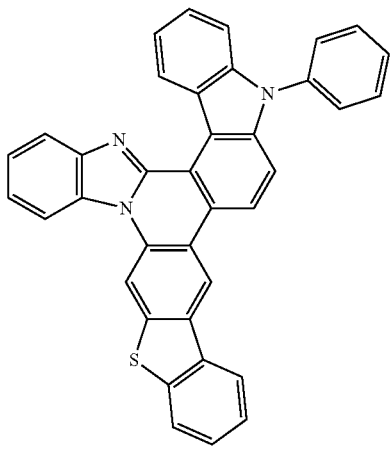
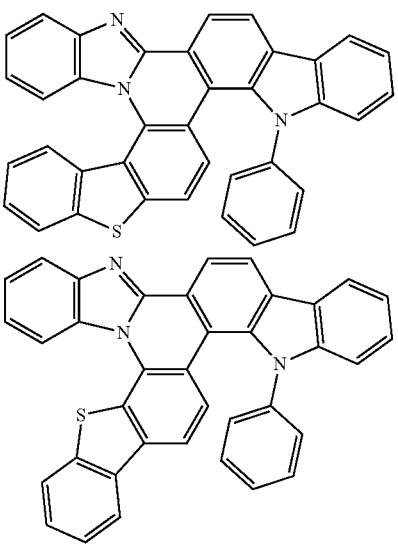

409
-continued
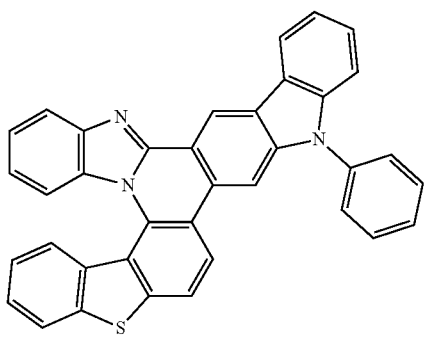
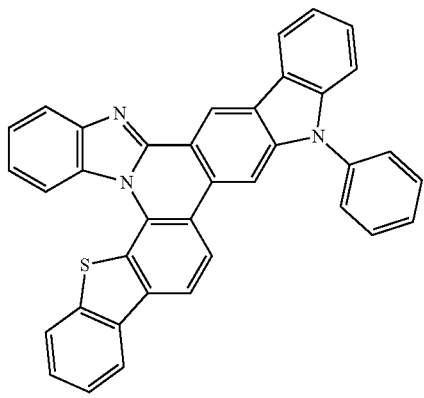
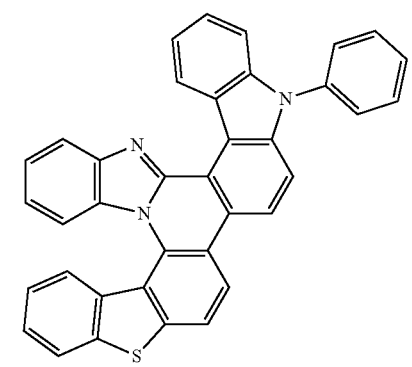
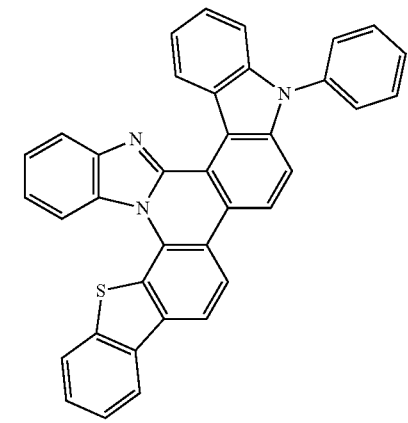
410
-continued
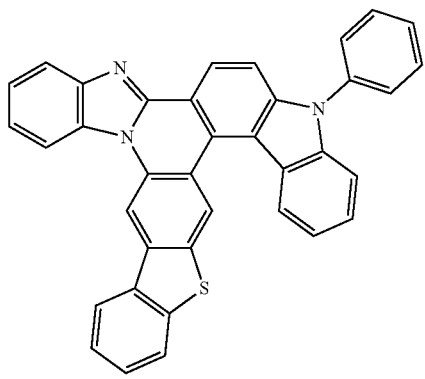
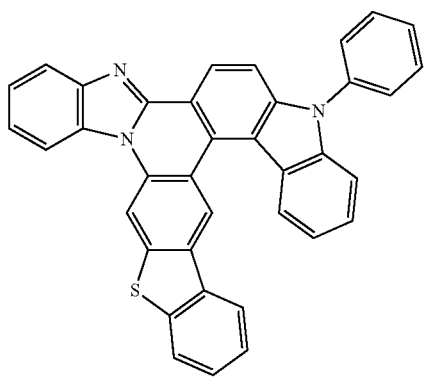
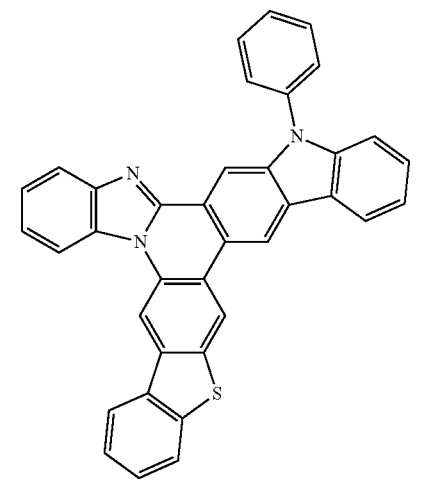
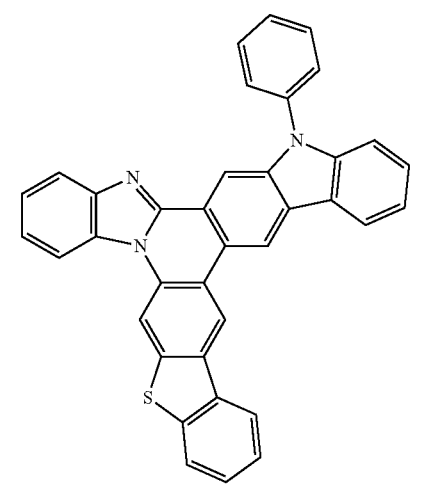

411
-continued
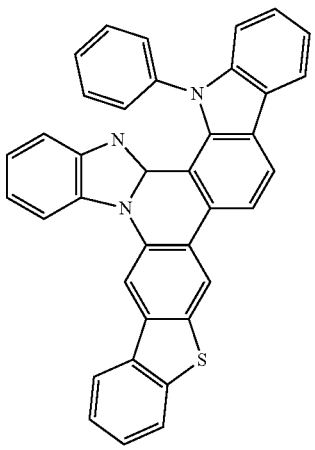
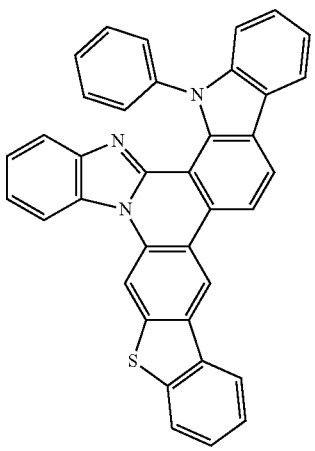
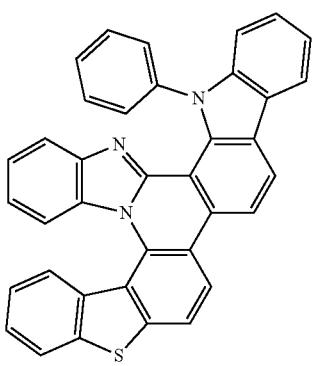
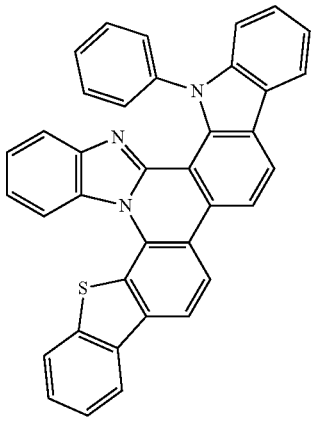
412
-continued
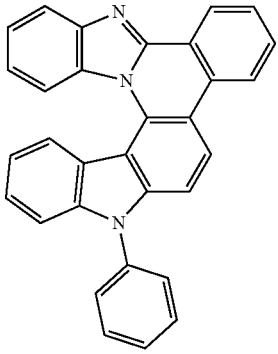
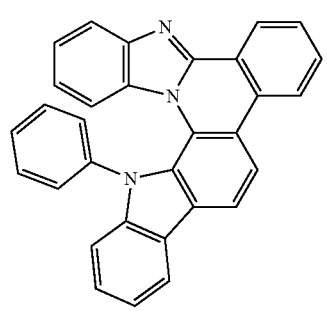
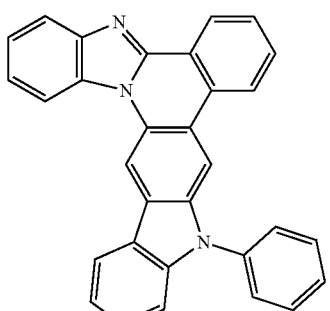
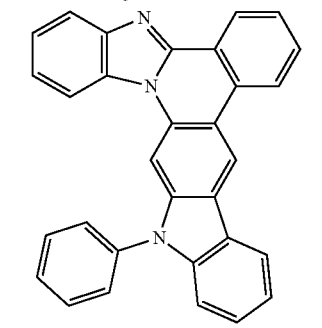
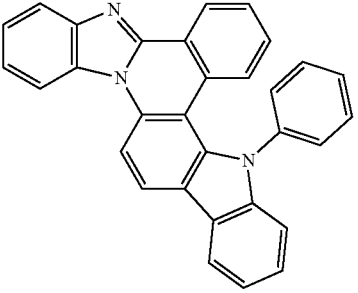

413
-continued
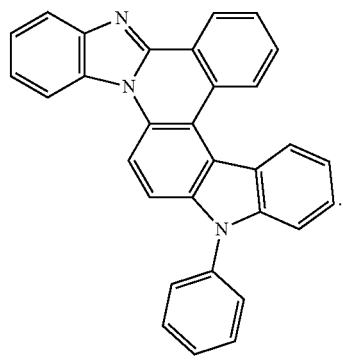
11. The compound of claim 2, wherein the compound is represented by one of the following structures:
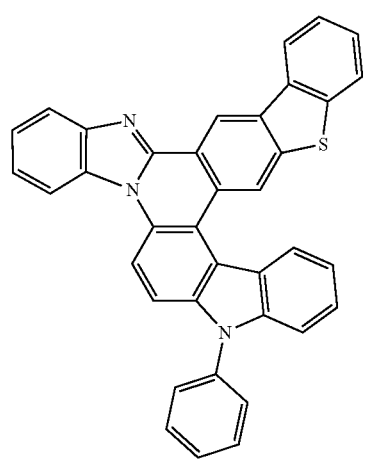
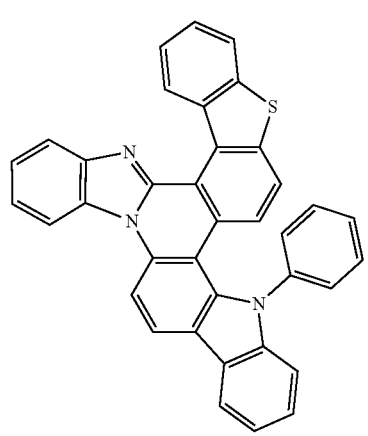
414
-continued
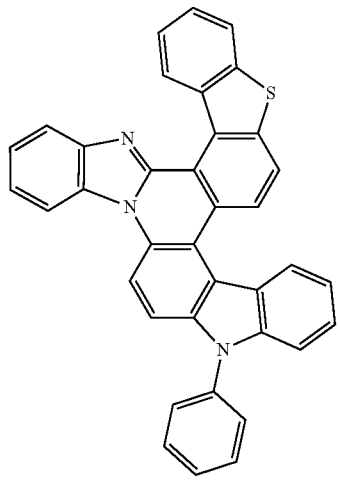
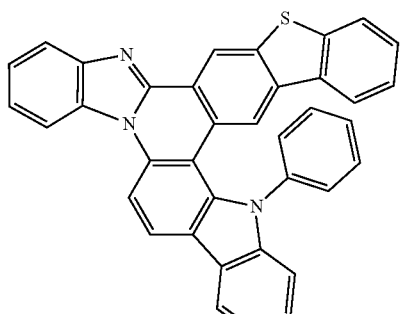
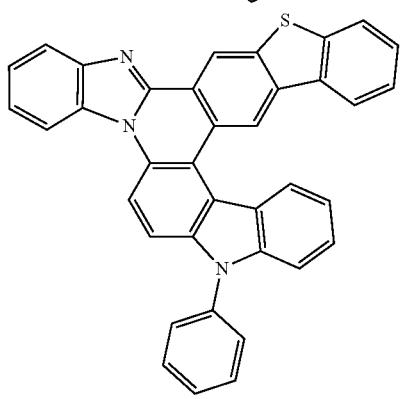

415
-continued
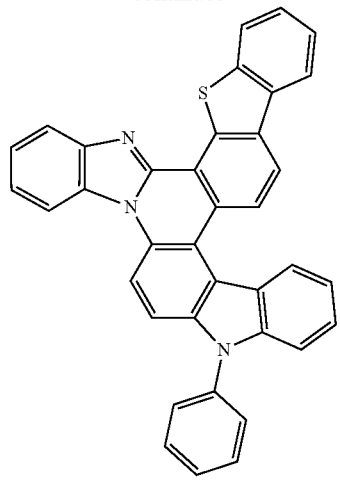
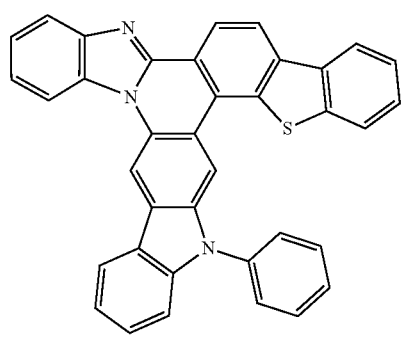
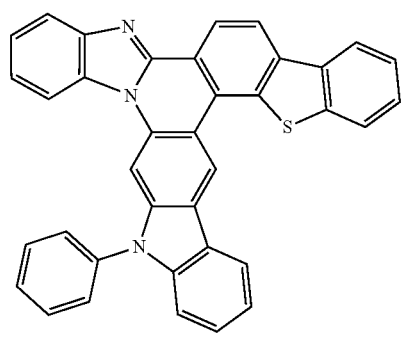
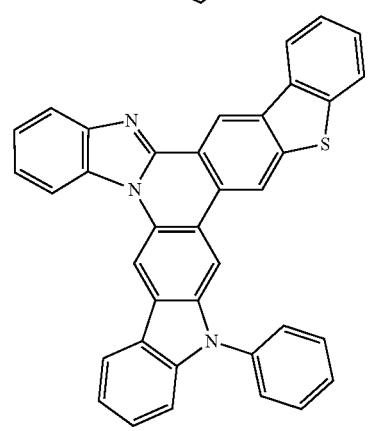
416
-continued
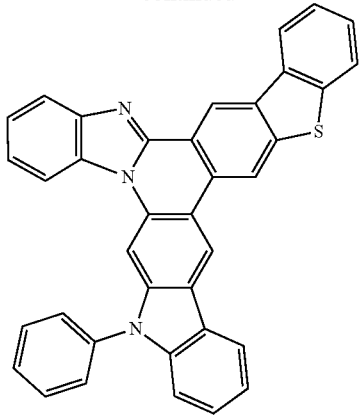
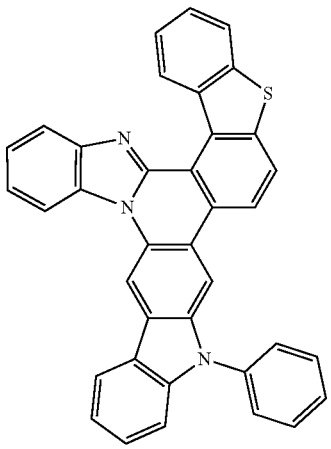
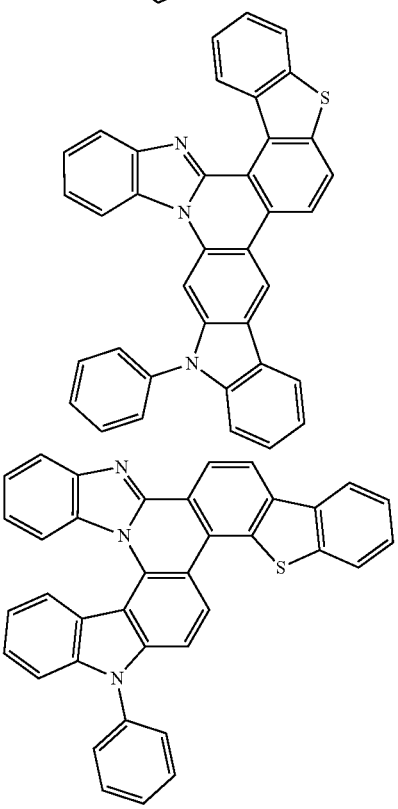

| 417 -continued | 418 -continued |
|---|---|
| 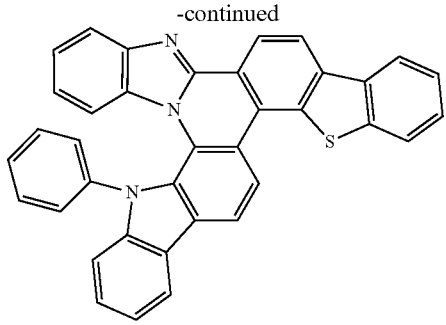 | 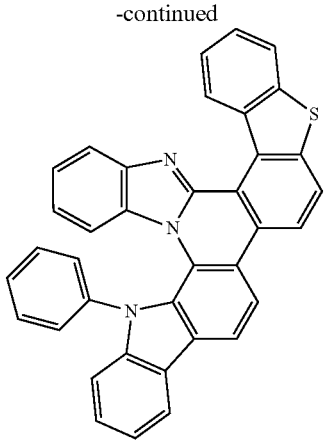 |
| 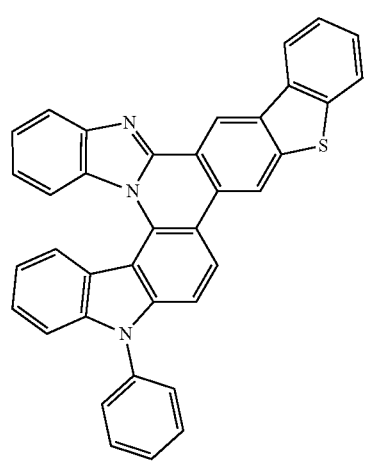 | 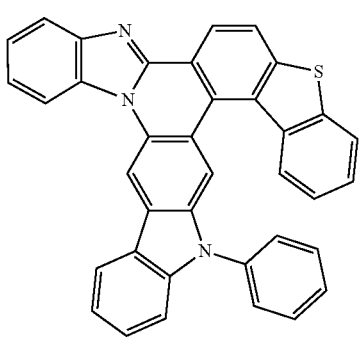 |
| 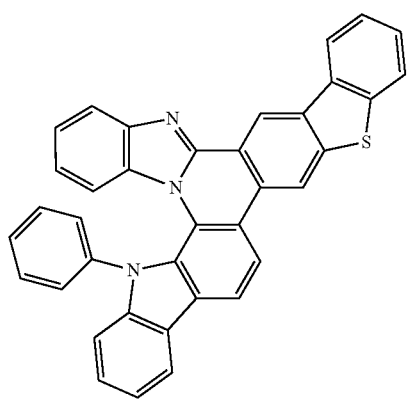 | 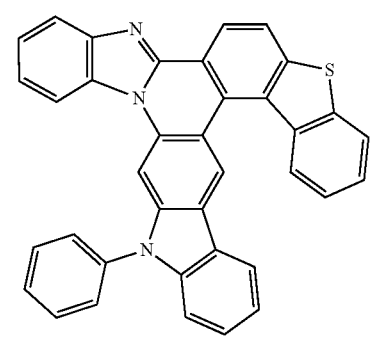 |
| 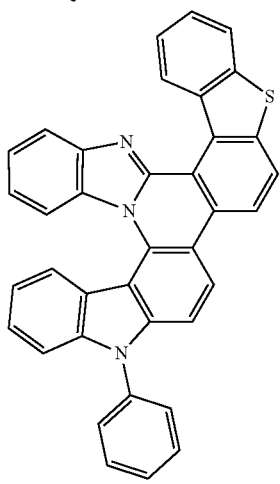 | 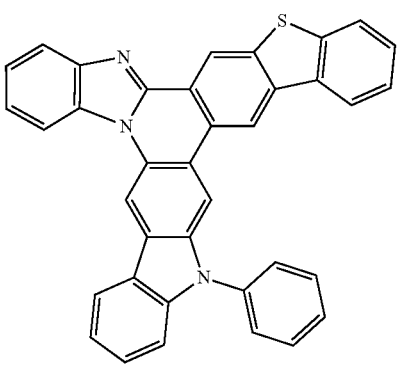 |

419
-continued
420
-continued
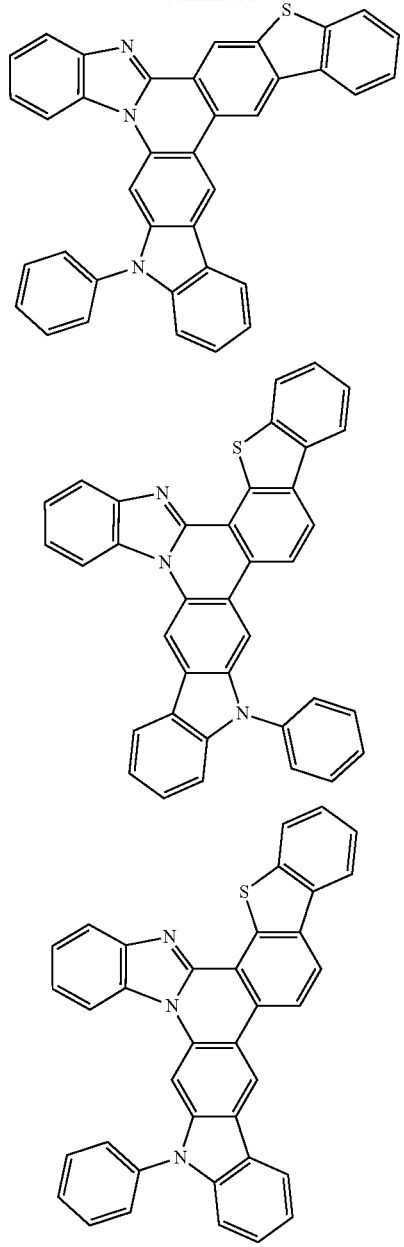
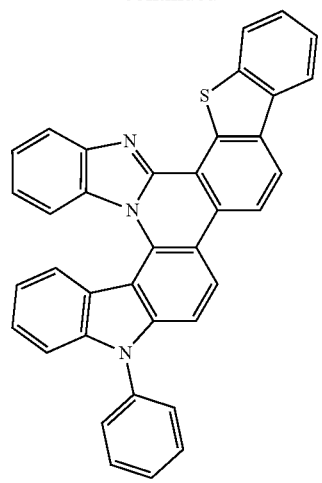
12. An organic light emitting device comprising at least one compound of claim 2.
* * * * *